(12) United States Patent
Amano et al.

(10) Patent No.: US 9,233,767 B2
(45) Date of Patent: Jan. 12, 2016

(54) MEDICINE INSPECTION DEVICE, AND MEDICINE PACKAGING DEVICE

(71) Applicant: YUYAMA MFG. CO., LTD., Toyonaka-shi, Osaka (JP)

(72) Inventors: Hirokazu Amano, Toyonaka (JP); Koji Ito, Toyonaka (JP); Hiromichi Tsuda, Toyonaka (JP); Yasuyuki Yoshikawa, Toyonaka (JP); Keigo Nakamura, Toyonaka (JP); Dai Shimizube, Toyonaka (JP)

(73) Assignee: YUYAMA MFG. CO., LTD., Toyonaka-shi (JP)

( * ) Notice: Subject to any disclaimer, the term of this patent is extended or adjusted under 35 U.S.C. 154(b) by 337 days.

(21) Appl. No.: 13/895,335

(22) Filed: May 15, 2013

(65) Prior Publication Data

US 2014/0002631 A1    Jan. 2, 2014

Related U.S. Application Data

(63) Continuation of application No. 13/885,674, filed as application No. PCT/JP2012/061332 on Apr. 27, 2012, now Pat. No. 8,943,779.

(30) Foreign Application Priority Data

Apr. 28, 2011 (JP) ................................. 2011-100731
Sep. 28, 2011 (JP) ................................. 2011-213116
Dec. 16, 2011 (JP) ................................. 2011-276455

(51) Int. Cl.
  *B65B 5/10* (2006.01)
  *B65B 57/10* (2006.01)
  (Continued)

(52) U.S. Cl.
  CPC ................ *B65B 5/103* (2013.01); *B65B 57/10* (2013.01); *G01N 21/9508* (2013.01); *G07F 9/026* (2013.01); *G07F 17/0092* (2013.01); *H04N 7/18* (2013.01)

(58) Field of Classification Search
  CPC .......... B65B 5/103; B65B 9/08; B65B 57/10; A61J 7/0084; A61J 3/00; A61J 2205/40; A61J 3/06; A61J 3/07; A61J 7/02; H04N 7/18; G01N 21/9508; G06F 19/3462; G06T 7/0008; G06T 2207/30168
  USPC ................... 53/52–54, 494, 501, 64, 65, 167; 348/86, 92; 356/432–435; 378/57; 382/141, 143, 152, 199, 256
  See application file for complete search history.

(56) References Cited

U.S. PATENT DOCUMENTS 4,791,655 A * 12/1988 Nagata et al. .................... 378/57
6,324,253 B1 * 11/2001 Yuyama et al. ................. 53/501
(Continued)

FOREIGN PATENT DOCUMENTS

| JP | 59-1333 A | 1/1984 |
| JP | 7-200770 A | 8/1995 |

(Continued)

*Primary Examiner* — Stephen F Gerrity
(74) *Attorney, Agent, or Firm* — Masuvalley & Partners

(57) ABSTRACT

A medicine inspection device includes: an inspection unit on which a medicine for inspection is disposed, the medicine being contained in a sachet; an imaging unit capable of photographing the sachet disposed on the inspection unit; and a medicine information detector capable of detecting at least either of a quantity or type of the medicine based on an image obtained by the imaging unit. The inspection unit includes a backlight with illumination areas located dottedly per predetermined pitch which is capable of illuminating the sachet from backside when photographing. The medicine information detector is further configured to implement: a basic image acquisition process for acquiring a basic image; an inspection area defining process for defining the area of inspection; an inspection image acquisition process for acquiring the inspection image; and an image inspection process for performing image inspection.

33 Claims, 77 Drawing Sheets

(51) Int. Cl.
*G01N 21/95* (2006.01)
*H04N 7/18* (2006.01)
*G07F 9/02* (2006.01)
*G07F 17/00* (2006.01)

(56) References Cited

U.S. PATENT DOCUMENTS

| | | | |
|---|---|---|---|
| 6,330,351 B1* | 12/2001 | Yasunaga | 382/141 |
| 7,166,856 B2* | 1/2007 | Cho et al. | 382/141 |
| 8,929,641 B2* | 1/2015 | Braun et al. | 382/143 |
| 2006/0213816 A1* | 9/2006 | Jorritsma | 209/576 |
| 2006/0271237 A1* | 11/2006 | Kim | 700/226 |
| 2007/0000805 A1* | 1/2007 | Van Den Brink | 206/531 |
| 2007/0150092 A1* | 6/2007 | Ohmura et al. | 700/231 |
| 2009/0055116 A1* | 2/2009 | Chen et al. | 702/82 |
| 2010/0045976 A1* | 2/2010 | Jorritsma | 356/240.1 |
| 2010/0170206 A1* | 7/2010 | Kim | 53/525 |
| 2010/0175352 A1* | 7/2010 | Soloman | 53/52 |
| 2010/0175968 A1* | 7/2010 | Yagyu et al. | 198/761 |
| 2010/0192523 A1* | 8/2010 | Stoeckel et al. | 382/143 |
| 2010/0206978 A1* | 8/2010 | Van den Brink | 242/531 |
| 2010/0214560 A1* | 8/2010 | Yagyu et al. | 356/237.1 |
| 2012/0201434 A1* | 8/2012 | Natali et al. | 382/128 |

FOREIGN PATENT DOCUMENTS

| | | |
|---|---|---|
| JP | 8-322913 A | 12/1996 |
| JP | 2004-269008 A | 9/2004 |
| JP | 4652480 B | 3/2011 |

* cited by examiner

Cut at SL4

Cut at SL2

Cut at DL

Cut at SL1

Cut at SL3

FIG. 65A

■ Collation Result ■
2011/10/13 20:59:48   OK
0000000001
Taro Yuyama
Taro Yuyama
3 times After each meal
30 days
Quantity OK Medicine Package Count 90/90
Collation OK Medicine Package Count 90/90

Checker : Administrator

FIG. 65B

■ Collation Result ■
2011/10/02 13:04:48   【N G】
0000000002
NG list
NG list
1 time After breakfast
6 days
Quantity OK Medicine Package Count 90/90
Collation OK Medicine Package Count 90/90

|        | Quantity | Collation |                  |
|--------|----------|-----------|------------------|
| Sachet 1 | ×      | NG        | (Insufficient)   |
| Sachet 2 | ×      | NG        | (Excess)         |
| Sachet 3 | ＊      | NG        | (Unknown)        |
| Sachet 4 | ○      | NG        | (Color mismatch) |
| Sachet 5 | ○      | NG        | (Unknown)        |
| Sachet 6 | ○      |           | Similar exists   |

Checker : Administrator

FIG. 65C

■ Collation Result ■
2011/09/29 22:34:56   OK
0000000001
Taro Yuyama
Taro Yuyama
3 times After each meal
3 days
Quantity OK Medicine Package Count 9/9
Collation OK Medicine Package Count 9/9

Checker : Administrator

MEDICINE INSPECTION DEVICE, AND MEDICINE PACKAGING DEVICE

This application claims priority under 35 U.S.C. §120 as a continuation of U.S. patent application Ser. No. 13/885,674, filed May 15, 2013, which is the national phase entry under 35 U.S.C. §371 of International Application No. PCT/JP2012/61332, filed on Apr. 27, 2012, which claims priority under 35 U.S.C. §119 to Japanese Patent Application No. JP 2011-100731, filed on Apr. 28, 2011, Japanese Patent Application No. JP 2011-213116, filed on Sep. 28, 2011 and Japanese Patent Application No. JP 2011-276455, filed on Dec. 16, 2011, the contents of which are hereby incorporated by reference in their entirety for all purposes.

TECHNICAL FIELD

The present invention relates to a medicine inspection device to inspect the quantity of a medicine, and a medicine packaging device equipped with the medicine inspection device.

BACKGROUND ART

Conventionally, medicine dispensing devices such as the one disclosed in the Japanese Patent Application Publication No. 1995-200770 (hereinafter Patent document 1) are available. In the medicine dispensing device disclosed in Patent document 1, solid medicine in form of granular, capsule or the like can be packaged in one package at a time with a packaging paper and supplied. Further, the medicine dispensing device of Patent document 1 has a configuration, wherein solid medicine is imaged in a state of packaged in the packaging paper, and based on the obtained image, the quantity of the solid medicine can be inspected.

Because the medicine dispensing device according to the Patent document 1 images solid medicine packaged in a packaging paper, it is likely that the imaging is done in a state wherein many solid medicines piled up or in contact with each other in the packaging paper. When inspection of the quantity is done based on such an image, there is a high possibility that multiple solid medicines may get misidentified as a single mass, and the quantity of the solid medicines cannot be accurately determined.

Therefore, the object of the present invention is to provide a medicine inspection device in which proper inspection of the quantity of solid medicine is possible without occurrence of inspection failures due to overlap or contact of the solid medicines or the existence of a packaging paper, and a medicine dispensing device equipped with such a medicine inspection device.

SUMMARY OF THE INVENTION

The medicine inspection device according to one embodiment of the present invention includes:
  an inspection unit on which a medicine for inspection is disposed;
  a vibrator to impart vibration to the medicine disposed on the inspection unit;
  a shooting means capable of photographing the medicine disposed on the inspection unit;
  a medicine information detector that can detect the medicine quantity or the type or both based on an image obtained by the shooting means; and
  a distribution detector that can detect a distribution of the medicine on the inspection unit based on the image acquired by the shooting means, and in which the vibrator is configured to operate based on a result of detection by the distribution detector.

In the medicine inspection device of the present invention, the distribution (location and/or amount) of the medicine in the inspection unit is detected by the distribution detector, and based on the result of the detection, the vibrator is operated. With this, it is possible to prevent solid medicine for inspection from piling up, contacting, or standing upright, and the inspection accuracy of a medicine by medicine information detector can be improved.

The medicine inspection device according to another embodiment of the present invention, includes:
  an inspection unit on which a medicine for inspection is disposed;
  a vibrator to impart vibration to the medicine disposed on said inspection unit;
  a shooting means capable of photographing the medicine disposed on the inspection unit;
  a medicine information detector capable of detecting at least either of a quantity or type of the medicine based on an image obtained by the shooting means; and
  a distribution detector configured to detect a distribution of the medicine on the inspection unit based on the image obtained by the shooting means. The inspection unit includes a plurality of inspection areas, and the vibrator is provided such that it is possible to provide vibration separately in each inspection area. The medicine inspection device of the present invention is characterized by operating the vibrator so as to provide vibration in the inspection areas chosen based on the detection result of the distribution detector.

In the medicine inspection device according to the present invention, based on an image of the medicine disposed in the inspection unit taken by the shooting means, the distribution condition of the medicine in the inspection unit is detected by the distribution detector, and vibration is provided to those inspection areas selected in response to the distribution condition. Therefore, in the medicine inspection device according to the present invention, it is possible to provide vibrations to the exact medicines that are piled up or standing, or in contact with each other. With this, with the medicine dispersed on the inspection unit, it becomes possible to detect the medicine quantity or the type or both by the medicine information detector, and it is extremely effective especially when inspecting a medicine that is packaged in the packaging paper. Therefore, according to the medicine inspection device of the present invention, there will be no inspection failure regardless of piling up or contact of the medicine, or presence or absence of package by the packaging paper, and it becomes possible properly detect either the medicine quantity or the type or both.

Regarding the medicine inspection device of the present invention described above, the medicine for inspection may also be supplied in a state wherein each prescription is packaged separately in a translucent packaging paper.

As explained above, in the medicine inspection device according to the present invention, it is possible to provide vibration in appropriate inspection areas by the vibrator based on the distribution condition of a medicine, and therefore, tentatively even if the medicine to be inspected is packaged in a packaging paper, it is possible to disperse the medicine so as to be suitable for inspection. Therefore, according to the medicine inspection device of the present invention, even medicine that has been packaged by each dose by a packaging paper, there will be no inspection failure, and accurate inspection can be carried out.

In the above-mentioned medicine inspection device of the present invention, it is preferable that the vibrator imparts vibration in preference to the inspection area containing more medicines than other areas.

In the medicine inspection device of the present invention, vibration is generated preferentially in the inspection areas containing a large amount of medicine than in other inspection areas, and therefore, even if the medicines are piled up, in an upright state, or in contact with each other, these medicines can be smoothly and definitely separated, and dispersed into a fallen state. Therefore, in the medicine inspection device of the present invention, there will be no inspection failure due to the medicines that are piled up or in contact with each other, or in upright state etc.

In the medicine inspection device of the present invention provided based on similar knowledge, it is further preferable that the vibrator impart vibration to an inspection area having the largest number of medicines, and does not impart vibration in other inspection areas.

In the medicine inspection device of the present invention, it is believed that, in the inspection area having the largest amount of medicines, there is a high probability that the medicine is unevenly distributed, and medicines are overlapped with other medicines, in contact with other medicines, or in an upright state. Based on such a concern, in the medicine inspection device of the present invention, it is made such that vibration is generated in an inspection area having the largest amount of medicines, and vibration is not generated in other inspection areas. With this, even if there are medicines overlapped with other medicines, in contact with other medicines, or in an upright state, these medicines can be smoothly and surely separated and dispersed into a fallen state. Therefore, in the medicine inspection device of the present invention, there will be no inspection failure due to existence of medicine in upright state, a piled up state or in contact with each other.

Here, in case a medicine is unevenly distributed in a predetermined inspection area, it is preferable that the inspection area for operating the vibrator be chosen by taking into account the distribution condition, and apply vibration. On the other hand, in case the medicine is already well-dispersed even without application of vibration, and is in a state wherein accurate inspection is possible, it is possible to not only improve the inspection speed by performing the inspection without application of vibration, but also to achieve a rather high accuracy of inspection. Therefore, it is preferable to provide a configuration for accurately judging the need for generating the vibration and appropriately applying vibration based on the result of the judgment.

The medicine inspection device of the present invention provided based on this knowledge includes a vibration controller that can determine the need for generating vibration based on the distribution condition of medicine in the inspection unit detected by the distribution detector, and that can control the operation of the vibrator based on the determined result. In the medicine inspection device of the present invention, in case the generation of vibration is determined to be necessary by the vibration controller, vibration is generated by the vibrator, and after that, the medicine quantity or type or both can be detected by the medicine information detector based on an image taken by the shooting means. In the medicine inspection device of the present invention, in case the generation of vibration is determined to be unnecessary by the vibration controller, the medicine quantity or type or both can be detected by the medicine information detector based on an image taken by the shooting means without generating vibration by the vibrator.

The medicine inspection device of the present invention is provided with a vibration controller that determines the necessity for vibration generation based on the distribution condition of medicine in the inspection unit, and the vibrator can be operated based on this determined result. With this, the medicine inspection device of the present invention can appropriately provide vibration when there is a need to disperse the medicine, and perform an accurate inspection. Also, in the medicine inspection device of the present invention, it is designed that vibration is not generated if vibration is determined to be unnecessary, and the inspection is performed based on an image captured by the shooting means, and therefore, the inspection speed and the inspection accuracy of the medicine can be further improved.

In the medicine inspection device of the present invention, it is preferable that the vibrator is provided with a leaf spring, and that vibration is generated by the elastic force of the leaf spring, and such leaf springs are provided in each inspection area.

According to this configuration, by vibrating the leaf spring provided in each inspection area, it becomes possible to provide vibration precisely to a medicine existing in an inspection area to which vibration is to be provided.

In the medicine inspection device of the present invention, among the leaf springs, it is further preferable that the leaf spring corresponding to an inspection area determined as not to impart vibration is held down and is made departed from a packaging paper.

According to this configuration, it becomes possible to prevent applying vibration to the medicine in an inspection area that needs to be a non-vibration state, and to disperse the medicine more precisely and improve the inspection accuracy.

In the medicine inspection device of the present invention, it is preferable that the leaf spring includes a fixed part at one end fixed to another member and a free end at another end, and the vibrator includes a shock imparting means to impart a shock to the free end of the leaf spring, and the fixed part is provided in a position departed from the inspection area.

In the medicine inspection device of the present invention, by impacting the free end of a leaf spring by the shock imparting means, it is possible to vibrate the leaf spring corresponding to an inspection area to be vibrated, and to disperse the medicine. By providing impact once or several times intermittently to the free end, the vibration provided to a leaf spring becomes a free or gradually attenuated vibration after the impact application, and unlike a mechanical vibration adding mechanism that always provides constant vibration, it is possible to provide an even more appropriate dispersion effect.

Here, as mentioned above, when vibrating a leaf spring by applying impact to the free end section, the vibration in the fixed part side tends to be smaller than the other section. Based on such knowledge, the fixed part is provided at a position away from the inspection area in the medicine inspection device of the present invention. Therefore, in the medicine inspection device of the present invention, it is possible to generate adequate vibration to disperse medicine even in the fixed section of a leaf spring similarly to the free end section.

In the medicine inspection device of the present invention, it is preferable to include a lighting device encompassing the inspection area or a virtual area conceivable in a position departed vertically from the inspection area, and being capable of emitting light in an outer side of the inspection area or the virtual area.

In the medicine inspection device of the present invention, a lighting device capable of emitting light so as to surround the inspection area or an imaginary virtual area at a location separated in the vertical direction from the inspection area, and therefore, a medicine disposed in the inspection unit can be photographed by the shooting means in an externally illuminated state. With this, it becomes possible to photograph a medicine in a state wherein the outline can be clearly captured. Therefore, in the medicine inspection device of the present invention, by processing an image obtained by the shooting means with a medicine information detector, it becomes possible to precisely detect either the medicine quantity or type or both.

Further, in the medicine inspection device of the present invention, it is preferable to install a diffusion light emitting device capable of generating diffusion light and being provided above the inspection unit.

According to this configuration, a medicine disposed on the inspection unit can be illuminated without creating a shadow, and it is possible to clearly capture the outline of the medicine, marking on the surface, the printed characters or the like. With this, the detection accuracy of the quantity or type of a medicine can be further improved.

In the medicine inspection device of the present invention, it is preferable that the lighting device includes a plurality of light emitting diodes disposed so as to surround the inspection area or the virtual area, and the optical axis of the light emitting diodes is directed towards the inspection area.

In the medicine inspection device of the present invention, light emitting diodes are used as the light source of the lighting device and their optical axes are directed towards the inspection areas, and therefore, it is possible to irradiate a high intensity light precisely onto a medicine disposed in an inspection area. Therefore, in the medicine inspection device of the present invention, it becomes possible to obtain an image clearly capturing the outline of a medicine disposed in an inspection area, and to further improve the inspection accuracy.

In the medicine inspection device of the present invention, it is preferable to provide a lighting device having a light emitting diode as a light source and being provided in a position departed vertically from the inspection area, the light emitting diode being provided outside of virtual area conceivable in a position departed vertically from the inspection area, and a light axis of the light emitting diode being directed to the inspection area.

In the medicine inspection device of the present invention, a lighting device is provided in a vertical direction with respect to the inspection area, and the light emitting diodes that function as the light source in this lighting device will emit light obliquely from an upper direction towards the inspection area. With this, a medicine disposed in an inspection area is illuminated, the medicine is photographed in a state wherein the outline can be captured clearly, and either the medicine quantity or type or both can be clearly captured by the medicine information detector. Thus, according to the present invention, the inspection accuracy of the medicine inspection device can be further improved.

In the medicine inspection device of the present invention, it is preferable to provide a prescription information acquisition means for acquiring at least one of information regarding a quantity based on a prescription regarding a medicine for inspection (legitimate prescription quantity) or a medicine type based on the prescription (legitimate prescription medicine type); and a collation means for collating the prescription information with detected information acquired by the prescription information detector.

According to this configuration, by comparing the detected information obtained by the medicine information detector with the prescription information, it is possible to accurately find out whether the type or quantity of the medicine is consistent with the legitimate ones.

In the medicine inspection device of the present invention, it is preferable that medicines are supplied as a continuous array of sachets formed by packaging one dose of the medicine per sachet in a packaging paper and aligning the sachets in form of a strip, and each sachet is able to be inspected one by one, and it is preferable that the medicine inspection device further includes: a prescription information acquisition means capable of capturing the prescription information based on an information medium if an information medium has been provided to the continuous array of sachets to capture at least one of information regarding the prescribed quantity or prescribed type of the medicine for inspection; and a collation means for collating the prescription information obtained by the prescription information acquisition means with detected information acquired by the medicine information detector.

In the medicine inspection device of the present invention, it is possible to accurately and smoothly capture the prescription information based on the information medium attached to a continuous body of sachets made by packaging the medicine in a continuous packaging paper, and the inspection speed and inspection accuracy can be further improved.

The medicine inspection device of the present invention may be connected to a medicine packaging device, the medicine packaging device including: a medicine supplier capable of supplying a medicine according to prescription; a medicine preparation means capable of storing a medicine supplied by the medicine supplier by one dose and of dispensing the medicine; a packaging means for packaging each done of medicine supplied from the medicine preparation means; and an outlet for discharging a medicine packaged by the packaging means. Also, the medicine inspection device of the present invention may further include a connector for connecting with the outlet.

By making it possible for the medicine inspection device of the present invention to be connected to the medicine packaging device, the operations starting from packaging of medicine till inspection can be coordinated with the medicine packaging device, and executed as one series of operations. Further, the medicine inspection device of the present invention can be also used as a device that operates integrally in cooperation by providing a connector for connecting to the outlet intended for extracting the medicine packaged in the medicine packaging device, and using it together with the medicine packaging device. Therefore, according to the medicine inspection device of the present invention, the operational efficiency and speed involved in the packaging and inspection of a medicine can be improved furthermore.

The medicine inspection device of the present invention may have a configuration in which medicines are supplied as a continuous array of sachets formed by packaging one dose of the medicine per sachet in a packaging paper and aligning the sachets in form of a strip, and each sachet is able to be inspected one by one, and the medicine inspection device may further include a transportation means for delivering the continuous array of sachets to the inspection unit while oscillating it in the horizontal direction.

By adopting such a configuration, even if the medicine is assumed to have been sealed in a sachet in an upright state, or in contact with other medicines etc., the medicine will fall and be dispersed by the time it reaches the inspection unit because of the oscillation in the horizontal direction provided by the transportation means. Therefore, according to the present invention, the possibility of applying vibration to the inspection unit can be kept to a minimum so that the time required for inspection operation can be furthermore shortened.

Here, when vibrating a sachet by operating the transportation means as described above, if a sachet is heavy because a large quantity of medicines are packaged in a sachet or the like, the continuous body of sachets may slip on the transportation means, and may not be oscillated well. Thus, it is possible that a sachet may not be positioned in a correct inspection position after the vibration, and an accurate imaging and inspection may not be performed.

To resolve such a problem, it is preferable that the medicine inspection device of the present invention has a configuration in which medicines are supplied as a continuous array of sachets formed by packaging one dose of the medicine per sachet in a packaging paper and aligning the sachets in form of a strip, and each sachet is able to be inspected one by one, and the medicine inspection device further includes: an introduction unit for introducing the continuous array of sachets; a transportation means for delivering the continuous array of sachets introduced from the introduction unit; and an ejection unit for ejecting the continuous array having passed through the inspection unit, wherein a fixing device capable of stopping a movement of the continuous array of sachets by the transportation means to a transportation direction is provided in the introduction unit or in the ejection unit or in both, and when oscillating the continuous array of sachets in the horizontal direction, at least one end of the continuous array of sachets is fixable by the fixing device.

By adopting such a configuration, by fixing one end of the continuous body of sachets by the fixing device, it becomes possible to avoid slipping of the continuous body of sachets on the transportation means, and make it vibrate with certainty. With this, it becomes possible to sustain the function of disposing a sachet in an original correct inspection position.

In the medicine inspection device described above, it is preferable that the fixing device is configured to sandwich the continuous array of sachets.

By adopting such a configuration, the slipping of the continuous array of sachets during vibration operation can be surely prevented.

Here, in vibrating a continuous body of sachets as described above, if the continuous body of sachets is fixed by the fixing device, excessive stress may get applied to the continuous body of sachets and may result in damaging it in some cases if the fixing is not done at a proper location considering the vibration direction.

Based on the above knowledge, in case of the medicine inspection device of the present invention described above, it is preferable to have a configuration in which, when vibrating the continuous body of sachets first to the introduction unit in performing the vibration operation with the help of the transportation means for vibrating the continuous body of sachets in a horizontal direction, the continuous body of sachets is fixed by the fixing device provided in the introduction unit, and the fixing of the continuous body of sachets by the fixing device provided in the ejection unit is released; and when vibrating the continuous body of sachets first to the ejection unit, the continuous body of sachets is fixed by the fixing device provided in the ejection unit, and the fixing of the continuous body of sachets by the fixing device provided in the introduction unit is released.

As described above, when vibrating a continuous body of sachets, if the fixing location by the fixing device is determined according to the direction of vibration of the initial movement, it is possible to surely prevent excessive stress from applying to the continuous body of sachets, and the continuous body of sachets from being damaged.

Further, the medicine inspection device of the present invention may have a configuration wherein medicines are supplied as a continuous array of sachets formed by packaging one dose of the medicine per sachet in a packaging paper and aligning the sachets in form of a strip, and each sachet is able to be inspected one by one, and the medicine inspection device further includes: a transportation means for transferring the continuous array of sachets to the inspection unit; and an upright-state elimination means provided in an upstream side of the transportation direction of the continuous array of sachets with respect to the inspection unit, wherein the upright-state elimination means has an arm configured to oscillate along a surface of the continuous array of sachets passing through a transportation route of the transportation means.

In the medicine inspection device of the present invention, when conveying a continuous body of sachets by the transportation means, the arm of the upright-state elimination means disposed in the upstream of the inspection unit vibrates along the surface of the continuous body of sachets. With this, the medicine stored in each sachet gets pushed by the arm and falls down, and reaches the inspection unit in a dispersed state. Therefore, in the medicine inspection device of the present invention, the possibility of applying vibration to the inspection unit to disperse medicine can be kept to a minimum, and the time required for inspection operation can be furthermore shortened.

The medicine inspection device of the present invention may have a configuration in which medicines are supplied as a continuous array of sachets formed by packaging one dose of the medicine per sachet in a packaging paper and aligning the sachets in form of a strip, and each sachet is able to be inspected one by one, and the medicine inspection device includes: a transportation means for transferring the continuous array of sachets to the inspection unit; and an upright-state elimination means provided in an upstream side of the transportation direction of the continuous array of sachets with respect to the inspection unit. Also, the upright-state elimination means may include: a spindle provided above a transportation route of the transportation means and along width direction of transportation route; an arm equipped so that the arm is capable of oscillate around the spindle; and a bias means for biasing the arm towards the transportation path so as to let the arm contact with a continuous array of sachets on the transportation path.

In the medicine inspection device of the present invention, the arm is provided to the spindle, which is provided in the upper area of the conveyance path so as to be transverse to the conveyance path, such that it can oscillate. Therefore, when a continuous body of sachets passes the conveyance path, the arm oscillates along the surface of the continuous body of sachets. With this, the medicine contained in each sachet is pushed by the arm and falls, and becomes dispersed within the sachet. Therefore, in the medicine inspection device of the present invention, dispersion of the medicine within a sachet is accelerated before the sachet reaches the inspection unit, and the need for dispersing the medicine by vibration in the inspection unit can be made minimum. With this, it also becomes possible to further reduce the time required for the inspection operation.

In the medicine inspection device of the present invention, it is also possible to have a configuration in which the arm includes a roller capable of contacting a surface of the continuous array of sachets, and the roller is provided substantially all along a width direction of the transportation route formed by the transportation means.

When adopting such a configuration, approximately the whole surface region of each sachet is tracked by the roller, and a medicine that is in an upright state inside a sachet will assume a fallen state. Therefore, by adopting the configuration described above, a medicine contained inside a sachet can reliably assume a fallen state before reaching the inspection unit, and deterioration in inspection accuracy due to feeding a medicine in upright state can be prevented.

The medicine inspection device of the present invention may also have a configuration, wherein the arm provided in the upright-state elimination means includes a contact part capable of contacting a surface of the continuous array of sachets, and the contact part includes: an introduction-side inclined surface inclining toward an introduction part; an ejection-side inclined surface inclining toward an ejection part; and a medicine leveling unit provided in a boundary between the introduction-side inclined surface and the ejection-side inclined surface, wherein the medicine leveling unit includes: a spindle provided along a ridge line formed by the introduction-side inclined surface and the ejection-side inclined surface; and a bead member equipped so as to be able to oscillate with respect to the spindle.

According to the present invention, by providing an ejection-side inclined surface and an introduction-side inclined surface, when transporting a continuous body of sachets from the introduction unit side towards the dispense side (forward direction) by the transportation means, and even when transporting the sachets on the opposite direction, the continuous body of sachets can be prevented from climbing on the upright-state elimination means. Also, by further providing a medicine leveling unit of the present invention, it becomes possible for the bead member to come in good contact with the medicine while moving in the axial direction, and the bead member can overturn any medicine in an upright state, and makes the medicine easy to be inspected.

The medicine inspection device of the present invention may have a configuration in which, medicines are supplied as a continuous array of sachets formed by packaging one dose of the medicine per sachet in a packaging paper and aligning the sachets in form of a strip, and each sachet is able to be inspected one by one, and the medicine inspection device includes: a transportation means for transferring the continuous array of sachets to the inspection unit; and an upright-state elimination means provided in an upstream side of the transportation direction of the continuous array of sachets with respect to the inspection unit, and capable of overturning a medicine that is in an upright state inside a sachet by contacting the surface of the continuous body of sachets, and wherein if a detection result obtained by the medicine information detection means for each sachet in the continuous array of sachets and the prescription information for the sachet are different, the sachet for which the detection information differs from the prescription information is sent in the reverse direction by the upright-state elimination means and the continuous array of sachets is reciprocated in a range in which the upright-state elimination means contacts with the surface of the sachet.

According to this configuration, in case the upright state of the medicine is the cause for the discrepancy between the detection result obtained by the medicine information detector and the prescription information, it is possible to solve the upright state of medicine by the upright-state elimination means, and to perform a re-inspection. With this, the inspection accuracy can be further improved.

In the medicine inspection device of the present invention, in case a detection result obtained by the medicine information detector is different from the prescription information, and only for the case in which the detection result obtained by the medicine information detector is different from the prescription information, it is possible to run a continuous body of sachets in a reverse direction up to the upright-state elimination means. With this, it becomes possible to enhance the inspection accuracy of the medicine inspection device and to accelerate the inspection speed.

It is preferable that the medicine inspection device of the present invention described above is provided with: an introduction unit for introducing the continuous array of sachets; a transportation means for delivering the continuous array of sachets introduced from the introduction unit; and an ejection unit for ejecting the continuous array having passed through the inspection unit, and wherein a contact unit that can contact the surface of a continuous body of sachets is provided on the arm, wherein the arm is provided with a contact unit capable of touching the surface of a continuous array of sachets, and the contact unit consists of an introduction side inclined surface inclining towards the introduction unit, and a dispense side inclined surface inclining towards the ejection unit, and the angle between the conveyance path of the transportation means and the introduction side inclined surface, and the angle between the conveyance path and the dispense side inclined surface are acute angles.

According to such a configuration, a continuous body of sachets can be prevented from climbing onto the upright-state elimination means when the continuous body of sachets is conveyed by a transportation means from the introduction unit in the direction of the dispense side (forward direction), as well as when it is conveyed in a opposite direction. With this, according to the present invention, it becomes possible to smoothly convey a continuous body of sachets both in forward and reverse directions. Therefore, according to the present invention, it is possible to accommodate even the operation of transporting a continuous body of sachets in the reverse direction without any problem.

Here, in the medicine inspection device of the present invention described above, as a method of supplying a continuous body of sachets to be inspected in the state of predetermined position with respect to the inspection unit, a method may be considered in which from the instant a continuous body of sachets is detected by a sensor provided near the introduction unit, the continuous body of sachets is conveyed only by a distance equal to the gap between the sensor and the inspection unit. However, when introducing a continuous body of sachets into a device, if an operator delays withdrawing the hand etc., a situation may be expected that even if the transportation means is operated so as to move only by a distance equal to the gap between the sensor and inspection unit following detection of a continuous body of sachets by an upstream sensor, it may still not be possible to feed a continuous body of sachets with good accuracy to the inspection unit.

When such a situation is expected, it is desirable that the medicine inspection device has a configuration, wherein medicines are supplied as a continuous array of sachets formed by packaging one dose of the medicine per sachet in a packaging paper and aligning the sachets in form of a strip, and each sachet is able to be inspected one by one, and the medicine inspection device includes:

a transportation means for transferring the continuous array of sachets to the inspection unit; an upstream-side sensor provided in upstream side of the transportation direction of the transportation means with respect to the inspection unit; and a downstream-side sensor provided in downstream side of the transportation direction of the transportation means with respect to the inspection unit, wherein when introducing the continuous array of sachets, the continuous array of sachets is transported by the transportation means through a location of the upstream-side sensor and the inspection unit toward a location of the downstream sensor, and on condition that the continuous array of sachets is detected by the downstream-side sensor, the transportation means is configured to reverse a transportation direction of the continuous array of sachets by the transportation means and let the continuous array for inspection to reach the inspection unit.

By adopting such a configuration, even if an operator momentarily delays withdrawing the hand etc., a sachet can be fed to the inspection unit with adequate positional accuracy. With this, the inspection accuracy can be further improved.

The medicine inspection device of the present invention may have a configuration, wherein medicines are supplied as a continuous array of sachets formed by packaging one dose of the medicine per sachet in a packaging paper and aligning the sachets in form of a strip, and each sachet is able to be inspected one by one, and the medicine inspection device includes: a transportation means for transferring the continuous array of sachets to the inspection unit; and an upright-state elimination means provided in an upstream side of the transportation direction of the continuous array of sachets with respect to the inspection unit and capable of oscillating along a surface of the continuous array of sachets, wherein the continuous array of sachets is transported to the inspection unit while being oscillated in horizontal direction, and the upright-state elimination means is configured to fall down a medicine packaged in the sachet in an upright state during a transportation process to the inspection unit.

When using such a configuration, the effect of conveying a continuous body of sachets while oscillating in the horizontal direction is coupled with the effect of an upright-state elimination means installed in the conveyance path towards the inspection unit, the medicine packed in each sachet is definitely supplied in a fallen state to the inspection unit. With this, it becomes possible to minimize a decrease in inspection accuracy due to supplying of a medicine in an upright state.

Here, when supplying a sachet in the form of a continuous body of sachets comprised of a continuous body of sachets in which each dose of a medicine is packaged as described above, there is a possibility that a continuous body of sachets may get damaged or cut because tensile forces greater than the strength of the continuous body of sachets acts due to the effect of such as a force exerted by transporting the continuous body of sachets to the inspection unit, and a force exerted when the continuous body of sachets is suspended or pulled towards medicine dispensing device or outside the inspection device. Therefore, when supplying sachets in the form a continuous body of sachets, it is desirable to take appropriate measures so that such a situation does not occur.

Therefore, the medicine inspection device of the present invention provided based on the knowledge includes an introduction unit for introducing a continuous array of sachets formed by packaging one dose of the medicine per sachet in a packaging paper and aligning the sachets in form of a strip, and each sachet is able to be inspected one by one by supplying the continuous array of sachets introduced from the introduction unit to the inspection unit, wherein the introduction unit includes an introduction unit oscillation member capable of oscillating vertically and biased toward an upper direction, and the continuous array of sachet supplied from the introduction unit is configured to pass above the introduction unit oscillation member.

When adopting such a configuration, when forces such as acting force due to conveying of the continuous body of sachets towards the inspection unit, or a force acting due to suspending of the continuous body of sachets etc., are acting, it is possible to prevent an excessively large force from acting on the continuous body of sachets by oscillating the introduction unit oscillating member. With this, a damage or breakage of a continuous body of sachets can be prevented.

It is preferable that the medicine inspection device of the present invention has a configuration wherein medicines are supplied as a continuous array of sachets formed by packaging one dose of the medicine per sachet in a packaging paper and aligning the sachets in form of a strip, and each sachet is able to be inspected one by one, wherein each of the sachets is sealed with a longitudinal seal part along a width direction of the continuous array of sachets and a lateral seal part along a longer direction of the continuous array of sachets, and wherein the medicine inspection device includes: a transportation means for conveying a continuous body of sachets to the inspection unit; and a transfer guide disposed on the side of the transportation means, wherein the transfer guide is provided with a guide roller biased towards the conveyance path and the continuous body of sachets can be conveyed by the transportation means in a state in which a force is applied to the lateral sealing part by the guide roller.

By adopting such a configuration, it becomes possible to smoothly convey a continuous body of sachets by transportation means, and to prevent passage of guide roller on a medicine packaged in a sachet.

It is preferable that, in the medicine inspection device of the present invention, the transfer guide is provided with a support arm formed so as to extend in the direction of transport direction by the transportation means and to surface-contact the surface of a continuous body of sachets passing over the conveyance path, and a guide roller is installed in the middle of the length direction of the support arm.

By adopting such a configuration, irrespective of whether a continuous body of sachets is moved in the forward direction or reverse direction by the transportation means, the continuous body of sachets can be prevented from climbing onto the transfer guide. Therefore, according to the present invention, even the operation of transporting a continuous body of sachets in the reverse direction can be accommodated without any problem.

Here, in order to properly carry out the inspection of a medicine packaged in a sachet, the sachet shall be preferably disposed in a proper position in the inspection unit. In case sachets are supplied in the form of a continuous body of sachets wherein several sachets are joined, if a sachet is not positioned accurately with respect to the inspection unit, there may be a possibility that a medicine inside a sachet cannot be identified, or a failure such as a medicine in a sachet that is adjacent to a sachet to be inspected being accidentally detected. Therefore, when a medicine to be inspected is supplied as a sachet in the form of a continuous body of sachets, it is preferable to have a configuration wherein each sachet can be disposed with a high positioning accuracy.

Thereupon, the medicine inspection device of the present invention provided based on the knowledge has a configuration wherein medicines are supplied as a continuous array of sachets formed by packaging one dose of the medicine per sachet in a packaging paper and aligning the sachets in form of a strip, and each sachet is able to be inspected one by one, wherein each of the sachets is sealed with a longitudinal seal part along a width direction of the continuous array of sachets and a lateral seal part along a longer direction of the continuous array of sachets, and a boundary is formed between longitudinal seal parts of neighboring sachets in the continuous array of sachets, and wherein the medicine inspection device further includes: an imaging means for detecting position provided so as to be able to photograph the longitudinal seal part located at both sides of the boundary in a longer direction of the continuous array of sachets, the imaging means capable of photographing the supplied continuous array of sachets in a predetermined position: a longitudinal seal position detecting means capable of obtaining a location information of each longitudinal seal part appearing in an image area photographed by the imaging means for detecting position; a boundary position detection means capable of deriving position of the boundary by calculating an intermediate value of position information of each of longitudinal seal parts detected by the longitudinal seal position detecting means; and a position identification means for identifying position of sachet with respect to the inspection unit based on position of the boundary derived by the boundary position detection means.

In the medicine inspection device of the present invention, the positional information of each longitudinal seal part contained in an image photographed by the imaging means for detecting position is detected by longitudinal seal position detecting means, and from the intermediate value of this positional information, the boundary of two continuous sachets can be identified. Therefore, in the medicine inspection device of the present invention, based on the identified result of boundary position of sachets, it is possible to perform positioning of a sachet to be inspected, and thereby achieve an improvement in the inspection accuracy.

Further, the imaging means for detecting position used in the present invention may be same as a shooting means (hereafter also referred to as 'imaging means for medicine imaging') provided for photographing the medicine disposed in the inspection unit, or may also be different from the shooting means for medicine imaging. If the imaging means for detecting position is same as the shooting means for medicine imaging, it becomes possible to simplify the device configuration. If the imaging means for detecting position is provided separately from the shooting means for medicine imaging, the position of a longitudinal sealing part can be detected in any position, and the flexibility of device design will improve.

The medicine inspection device of the present invention has a configuration wherein a medicine is supplied in form of continuous array of sachets in which a plurality of sachets are aligned in form of a strip and each of the sachets is formed by sealing packaging paper, and a longitudinal seal part is provided at least between neighboring sachets, and a dot-shaped seal trace is formed in the longitudinal seal part, and each sachet is able to be inspected one by one, and wherein the medicine inspection device further includes: a boundary position detection means capable of deriving a position of the boundary, wherein the boundary position detection means is configured to derive the position of the boundary by implementing: an outline detection process for detecting an outline present in an image area of the sachets photographed by the shooting means; an outline expansion process for expanding a detected area surrounded by an outline detected by the outline detection process toward outside in a predetermined amount; a longitudinal seal area detection process for detecting a longitudinal area, the longitudinal area being an area comprising a plurality of detected areas which is mutually overlapped by expansion in an image after the outline expansion process, and the longitudinal area elongating along a longitudinal seal direction; and a boundary position derivation process for deriving an intermediate position of the longitudinal seal area as a position of the boundary.

In the medicine inspection device of the present invention, by detecting the longitudinal sealing area as described above, the region where a continuous body of sachets was vertically sealed can be identified, and the boundary position of the adjoining sachet can be identified.

In the present invention, by expanding an outline towards the outside of a detection area by an outline expansion process and mutually overlapping a plurality of detection areas, it is possible to improve the accuracy of identifying whether the outline and detection area detected in the outline detection process is due to dot-shaped seal mark of the longitudinal sealing part or due to a medicine.

That is, a detection area corresponding to seal mark of a longitudinal sealing part is a series of areas (corresponding to longitudinal sealing region) overlapped by the outline expansion process and extending in the width direction (longitudinal sealing direction) of a continuous body of sachets. On the other hand, when the outline expansion process is executed, though the area of detection for the medicine expands into a shape that approximates the exterior shape of the medicine, it is usually thought it will not become a region of shape like the longitudinal seal region extending in the width direction of the continuous body of sachets.

In light of such a characteristic, in the present invention, by performing an outline expansion process in addition to outline detection process, it has been made possible to accurately detect the longitudinal sealing part even under the presence of medicine, and therefore, it becomes possible to detect the position of a longitudinal sealed region (longitudinal sealing region) with excellent accuracy. Therefore, in the medicine inspection device of the present invention, the position of the boundary formed between the sachets can be detected with very high accuracy.

It is preferable that the medicine inspection device of the present invention described above has a configuration wherein a content image removal process is implemented before the longitudinal seal area detection process and content packaged in packaging paper is recognized based on luminance information and/or color information of an image for deriving a position of the boundary and image information corresponding to the content is removed.

According to the present invention, it is configured such that a content in a sachet is identified based on the brightness information and/or color information of an image used for deriving the position of the boundary, the section where the content is present is excluded, and then the operation for deriving the boundary position is executed, and therefore, the possibility of erroneously detecting the outline of the content as the outline of the longitudinal sealing part can be minimized. With this, the detection accuracy of boundary formed between adjacent sachets can be further improved.

Further, the medicine inspection device of the present invention may have a configuration wherein medicines are supplied as a continuous array of sachets formed by packaging one dose of the medicine per sachet in a packaging paper and aligning the sachets in form of a strip, and each sachet is able to be inspected one by one, wherein each of the sachets is sealed with a longitudinal seal part along a width direction of the continuous array of sachets and a lateral seal part along a longer direction of the continuous array of sachets, and a boundary is formed between longitudinal seal parts of neighboring sachets in the continuous array of sachets, the medicine inspection device further includes a boundary position detection means capable of deriving position of the boundary, wherein the boundary position detection means is configured to implement: a longitudinal edge detection process for detecting the longitudinal edge, the longitudinal edge being an outline elongating longitudinally in an image area of the sachets photographed by the shooting means; a longitudinal edge selection process for selecting a longitudinal edge longer than a predetermined length from the longitudinal edge derived from the longitudinal edge detection process; an edge area recognition process for recognizing an area where a distance between longitudinal edges selected by the longitudinal edge selection process is equal to or shorter than a predetermined distance set based on a width of longitudinal seal part; and a boundary position recognition process for recognizing a central part of the edge area recognized by the edge area recognition process as a boundary position between the longitudinal seal parts.

In the medicine inspection device of the present invention, a longitudinal sealing part and a boundary formed between longitudinal sealing parts can be detected as a vertical edge that extends in the vertical direction and exceeds a predetermined length, and the boundary can be derived by focusing on the unique characteristic of the continuous body of sachets in which the longitudinal edge corresponding to the longitudinal sealing part and boundary is located within a predetermined interval. Due to focusing on such a characteristic, compared to the case of deriving the boundary by a simple image analysis, the boundary position can be derived easily and accurately.

Here, when processing a large number of prescriptions together, the case of packaging a medicine in the form of so-called continuous prescriptions etc., the medicines are also packed wherein a medicine is packaged as a series of former-dose sachets and sachets of latter-dose sachets. Further, when packaging a medicine in such a packaging form, empty sachets in which the medicine is not packaged may be provided in the middle section of the continuous body of sachets. Furthermore, when an empty sachet is formed, distinguishing mark such as bar code may also be attached on an empty sachet.

As described above, when empty sachets are formed in the middle of a continuous body of sachets, in order to maintain the inspection operation of the medicine with good accuracy, a medicine-containing sachet that is formed next to an empty sachet should be sent to the inspection unit and must be positioned with good accuracy. Therefore, when adopting a medicine inspection device configuration wherein it is possible to supply a continuous body of sachets provided with empty sachets, it is preferable to take a measure to improve the positioning accuracy of a sachet containing medicine adjacent to an empty sachet (that is, existing on the downstream of the empty sachet) with respect to the inspection unit.

The medicine inspection device of the present invention provided based on the knowledge has a configuration wherein medicines are supplied as a continuous array of sachets formed by packaging one dose of the medicine per sachet in a packaging paper and aligning the sachets in form of a strip; a vacant sachet not containing medicine is provided in an intermediate part of the continuous array of sachets; an identification mark is put on a predetermined position of the vacant sachet; and each sachet is able to be inspected one by one, and the medicine inspection device further includes an identification mark recognition means capable of recognizing the identification mark having arrived at a predetermined readout position present in the inspection unit or an upstream side of supply direction of the continuous array of sachets from the inspection unit, wherein a sachet containing medicine and positioned in a downstream side of the vacant sachet is locatable against the inspection unit based on the recognition position where the identification mark is recognized by the identification mark recognition means.

In the medicine inspection device of the present invention, by having an identified position in which an identification mark, which is provided on an empty sachet formed in the middle of a continuous body of sachets, is identified by identification mark recognition means as a reference, it is possible to perform positioning of a sachet containing medicine following an empty sachet and the inspection unit with excellent accuracy. Therefore, in the medicine inspection device of the present invention, even for a case of such as forming empty sachet in the middle of a continuous body of sachets for continuous prescription etc., with regard to a medicine-filled sachet existing in the downstream of the empty sachet, it becomes possible to avoid lowering in the inspection accuracy due to a reduction in the positioning accuracy with the inspection unit.

The medicine inspection device of the present invention has a configuration of including: an inspection unit on which a medicine for inspection is disposed, the medicine being contained in a sachet; a shooting means capable of photographing the sachet disposed on the inspection unit; and a medicine information detector capable of detecting at least either of a quantity or type of the medicine based on an image obtained by the shooting means; wherein the inspection unit comprises a backlight capable of illuminating the sachet from backside when photographing, the backlight comprising illumination areas located dottedly per predetermined pitch, and wherein the medicine information detector is configured to implement: a basic image acquisition process for acquiring a basic image for medicine inspection based on a back lit image photographed by illuminating the packaging paper from behind by the backlight; an inspection area defining process for defining the area for inspection by executing a exclusion process of excluding the dot-shaped translucent region contained in the basic image obtained in the basic image acquisition process; an inspection image acquisition process for acquiring the inspection image by extracting an area corresponding to the area for inspection from a back unlit image obtained by photographing same region as the back lit image in a state where the backlight is unlit; and an image inspection process for performing image inspection to detect the medicine quantity or type or both based on the inspection image.

In the medicine inspection device of the present invention, in the basic image acquisition process, a basic image is acquired for medicine inspection on the basis of a back lit image obtained by photographing a sachet disposed in the inspection unit in an illuminated state by the backlight. Here, the backlight used in the present invention can emit light in a dot-shape. Therefore, in a basic image, a region where the medicine is assumed to be present is photographed as a shadow in the basic image, and the other region is photographed as a region where the light is transmitted in a dot-shape (translucent region). Also, in the present invention, the inspection area defining process includes a process wherein a region through which the dot shaped light is transmitted is excluded from the basic image, and the remaining area is identified as the region for inspection. Thus, by executing basic image acquisition process and inspection area defining process, it is possible to narrow down a region where the medicine is assumed to be present as a region for inspection. With this, it becomes possible to minimize the execution load of the image inspection process, and thereby improve the detection speed of the type and/or quantity of a medicine through image inspection.

It is preferable that the medicine inspection device of the present invention described above has a configuration wherein the backlight comprises a light source, and a mesh member disposed between the light source and the sachet and having perforations through which light passes through at each predetermined pitch.

According to such a configuration, it becomes possible to easily and reliably emit light in dot shape at every predetermined pitch over the entire illumination area.

More often, information such as name of the prescribed patient, dosage method of the medicine etc., is printed as characters or patterns on the packaging paper in which a medicine is packaged. When a sachet having printings on the packaging paper is supplied for inspection, the characters or the like that are printed on the packaging paper coexist in the basic image, and differentiation of medicine present region and printed area may become difficult. Therefore, when supplying a medicine in a printed packaging paper is assumed, it is desirable to devise measures so that a medicine present region and printed area can be easily and reliably differentiated.

Therefore, the medicine inspection device of the present invention provided based on the above knowledge has a configuration wherein a medicine packaged in a printed packaging paper is able to be supplied for the inspection unit as a medicine for inspection, and the medicine information detection means is capable of executing an image processing to vary size of a region surrounded by outline in the basic image, and as a result of such image processing if a continuous region is formed wherein a region surrounded by the outline is contiguous, the medicine information detection means is capable of executing a printed area exclusion process for excluding an area containing the said continuous region as printed area from the inspection region.

In case where printing has been done on a packaging paper as described above, in the basic image obtained by photographing the packaging paper by emitting light in a dot pattern with the backlight, the light is blocked in a region where the medicine is present thereby forming a shadow, and it is photographed such that the outline of the outer edge of the medicine can be recognized. On the other hand, as for the area that has printings on the packaging paper (print area), it is photographed in a state where the outline can be captured similarly to the shadow in the basic image, but the area is photographed in a state where the light is transmitted in a dot pattern. That is, in the print area, the section through which the light is transmitted in a dot pattern (translucent region) is photographed such that the outer edge of translucent region is captured as an outline.

If an outline contained in the basic image is expanded by image processing, the translucent region aligned in dot pattern in the basic image join and form a series of regions (contiguous region). Therefore, a contiguous region formed by executing image processing for varying (expanding or contracting) the outline in the basic image can be considered as a print area.

The present invention is provided focusing on such a phenomenon. In the present invention, when a contiguous region is detected by the expansion or contraction of a region surrounded by outline in the basic image, a region containing this contiguous region is considered as a printed area on the packaging paper (print area), and therefore, this region is excluded from the inspection area. Therefore, in the medicine inspection device of the present invention, even when a packaging paper that is printed with such as characters etc., is supplied, the medicine quantity or type or both can be derived accurately and rapidly without any interference by the printing.

The medicine inspection device of the present invention includes: an inspection unit on which a medicine for inspection is disposed, the medicine being contained in a sachet; a shooting means capable of photographing the sachet disposed on the inspection unit; and a medicine information detector capable of detecting at least either of a quantity or type of the medicine based on an image obtained by the shooting means; wherein the inspection unit includes a backlight capable of illuminating the sachet from backside when photographing, the backlight including illumination areas located dottedly per predetermined pitch, and wherein the medicine information detector is configured to implement: a basic image acquisition process for acquiring a basic image for medicine inspection based on a back lit image photographed by illuminating the packaging paper from behind by the backlight; a gray scale image acquisition process for acquiring a gray scale image by gray-scaling the basic image; a gray morphology treatment process, wherein at least one channel image from among the basic R channel image, basic G channel image and basic B channel image that were obtained by RGB resolution of the basic image is subjected to a gray morphology treatment to be acquired as an image for identifying a region for exclusion; an inspection region defining process for defining the area for inspection by executing a exclusion process of excluding a region for exclusion determined by the image for identifying a region for exclusion to the gray scale image; an inspection image acquisition process for acquiring the inspection image by extracting an area corresponding to the area for inspection from a back unlit image obtained by photographing same region as the back lit image in a state where the backlight is unlit; and an image inspection process for performing image inspection to detect the medicine quantity or type or both based on the inspection image.

According to this configuration, the probability of a printed area on a sachet getting included in an image for inspection can be minimized. With this, the inspection accuracy and inspection speed for the medicine can be improved.

Here, in the medicine inspection device of the present invention described above, when executing the image inspection process, it is necessary to extract the outline of the medicine present in the image used for inspection. Here, in cases when the background color of the basic image processed image obtained by processing the basic image and the color of the medicine are same, derivation of outline of a medicine may be difficult by only using the basic image processed image.

The medicine inspection device of the present invention provided in order to solve such a problem has a configuration wherein in the image inspection process, a contour of a medicine existing in a sachet is able to be identified by executing composite image edge extraction process to extract an edge contained in a composite image formed by superposing a basic image processed image obtained through an exclusion process in which a dotted translucent region in a basic image acquired in the basic image acquisition process, a brightness map image showing a distribution of brightness in the back unlit image, and a saturation map image showing a distribution of the saturation component in the back unlit image in the image inspection process.

As in the present invention, by using a composite image obtained by superposing a basic image processed image, a brightness map image and a saturation map image, it is also possible to extract the outline of a medicine from the perspective of brightness and saturation. Thus, even if the background color of the basic image processed image is same as color of a medicine, it is possible to not only accurately and smoothly derive the outline of the medicine, but also improve the image inspection accuracy.

The medicine inspection device of the present invention may have a configuration wherein the image inspection process is configured to execute: an acquisition of a basic image processed image wherein an inspection area contained in the basic image has been extracted; an acquisition of a HSV resolution image for inspection comprising at least one from among a back unlit H channel image, a back unlit S channel image and a back unlit V channel image that were obtained by a HSV resolution of the back unlit image; and an acquisition of a single channel image for inspection comprising at least one from among a back unlit R channel image, a back unlit G channel image and a back unlit B channel image that were obtained by an RGB resolution of the back unlit image, wherein the image inspection process is also configured to execute composite image edge extraction process to extract an edge contained in a composite image formed by superposing the basic image processed image, the HSV resolution image for inspection and the single channel image for inspection in order to identify a contour of a medicine existing in a sachet.

In the image inspection device of the present invention, in addition to the basic image processed image, it is also possible to extract the edge of a medicine corresponding to outer edge of medicine from the perspective of HSV resolution image for inspection and single channel image for inspection, and to identify the contour of a medicine. Thus, it becomes possible to further improve the identification accuracy of the outline of a medicine, and quickly execute the inspection of the medicine with high accuracy.

Furthermore, the medicine inspection device of the present invention may have a configuration wherein, when acquiring the HSV resolution image for inspection, a back unlit H channel image is selected as a HSV resolution image for inspection on a condition that a background color of the sachet during acquisition of the basic image and a color of the medicine packaged in the sachet are similar, and a back unlit S channel image is selected as a HSV resolution image for inspection on a condition that a background color of the sachet and a color of the medicine packaged in the sachet are different.

In the present invention, an HSV image for inspection is acquired considering the relation between the color of a medicine and the background color. Specifically, if a medicine is of same color as background color, because of a high possibility of the difference in hue between the medicine and the background getting manifested strongly, the back unlit H channel image is chosen as a HSV resolution image for inspection. On the other hand, if a medicine is of a color that is different from the background color, because of a possibility of the difference in saturation getting manifested strongly, the back unlit S channel image is chosen as an HSV resolution image for inspection. Therefore, according to the present invention, the identification accuracy of contour of a medicine and the inspection accuracy of the medicine can be further improved.

The medicine inspection device of the present invention may have a configuration wherein when acquiring the single channel image for inspection, from among a back unlit R channel image, back unlit G channel image and back unlit B channel image that were obtained by RGB resolution of the back unlit image, the image having highest contrast between the inspection area and the non-inspection area is selected as a single channel image for inspection.

The present invention reflects the results of extensive studies by the inventors that led to a finding that, by selecting an image having the highest contrast between inspection area and non-inspection area from among the back unlit R channel image, back unlit G channel image and back unlit B channel image, the detection accuracy of the edge corresponding to the contour of a medicine can be improved. Thus, by focusing on the contrast between inspection area and non-inspection area according to the present invention, and selecting that with highest contract as a single channel image for inspection, the identification accuracy of contour of a medicine and the inspection accuracy of the medicine can be further improved.

It is desirable that the medicine inspection device of the present invention described above has a configuration wherein a composite image edge extraction process is executed on condition that the background color of the sachet during acquisition of the basic image and the color of the medicine packaged in the sachet are similar.

The composite image edge extraction process, as described above, is optimal when the background color of the basic image and the color of the medicine are of similar color. Therefore, according to the present invention, the accuracy of image inspection can be further improved.

It is desirable that the medicine inspection device of the present invention described above has a configuration wherein the backlight is configured to generate red light or a light of a longer wavelength than red.

In the present invention, since red light or a light having a wavelength longer than the wavelength of red is generated and used, the light generated by the backlight has a high linearity. Therefore, in the medicine inspection device of the present invention, the region where a medicine exists and the outline of the medicine can be clearly recognized in the basic image.

In addition, even for a case where a packaging paper has printings as described above, it is possible to ensure that the light generated by a backlight is transmitted through the print area. Therefore, as explained above, when executing a process for excluding a print area based on the section through which the light in dot pattern (transmission area) is transmitted in the basic image, by using a backlight capable of generating red light or a light having a high linearity that has a wavelength longer than red, it becomes possible to not only improve the exclusion accuracy of excluding a print area from the inspection area, but also to improve the inspection accuracy of a medicine.

It is preferable that the medicine inspection device of the present invention described above further includes: a medicine present area defining means for determining the medicine present area in a medicine region identification image obtained by photographing a sachet disposed in the inspection unit with the shooting means; and a foreign object detection process for detecting a foreign object existing in the sachet based on an image for position recognition containing position signs provided with coordinates for each predetermined pitch, and a basic image acquired by the medicine information detector; wherein the foreign object detection process is configured to implement: an object existence area coordinate extraction process for extracting a position coordinates existing in a region determined by the inspection area defining process by superposing the image for position recognition and basic image, a medicine coordinates group derivation process for extracting position coordinates existing inside a medicine-existing area defined by the medicine present area defining means by superposing an image for medicine area determination and the basic image; and a foreign object determination process for judging a presence of a foreign object in coordinate position on condition that coordinates that are different from the medicine area coordinates group are existing in the object existence area coordinates group.

In the medicine inspection device of the present invention, by executing an object existence area coordinate extraction process, an area where items such as medicines etc. exist can be obtained as a coordinates group (object existence area coordinates group) from the outline contained in a basic image. In addition, by separately executing a medicine coordinate group derivation process, an area where a medicine exists can be obtained as a coordinates group (medicine area coordinates group). In the medicine inspection device of the present invention, in the foreign object determination treatment process, it is checked whether the object existence area coordinates group and the medicine area coordinates group are identical, and if not so, it is inferred that a foreign object other than the medicine is present inside the sachet. Therefore, according to the medicine inspection device of the present invention, not only the inspection of the quantity or type of a medicine, but the co-existence of a foreign object other than medicine can be reliably detected.

It is preferable that the medicine inspection device of the present invention has a configuration wherein in the inspection area defining process, an expansion process is executed for expanding an area remained after an execution of elimination process by a predetermined amount towards the outside.

In the present invention, in the inspection area defining process, the expansion process is performed after the elimination process, and therefore, an accidental elimination of a medicine-existing area from the inspection area due to exclusion process can be prevented. With this, the accuracy of medicine inspection can be further improved.

The medicine inspection device of the present invention has a configuration wherein an image of a medicine provided on the inspection unit is able to be clipped by use of a back lit image obtained by photographing with the imaging means in a irradiated state wherein the inspection unit is irradiated by the backlight and a back unlit image obtained by photographing by the imaging means in a back non-irradiated state wherein the inspection unit is not irradiated by the backlight, and an image of medicine provided on an inspection unit is able to be obtained by: acquiring a back lit binary image by binarization of a back lit RGB resolution image comprising at least one from among the back lit R channel image, back lit G channel image and back lit B channel image obtained from the RGB resolution of the back lit image, assuming an intensity distribution of medicine and the back lit image in the said back lit binary image to be a Gaussian distribution, deriving mean value Mm and standard deviation σm of the intensity distribution corresponding to the medicine, and the mean value Mb and standard deviation σb of the intensity distribution corresponding to the back image; creating a mask for medicine image clipping for masking a region of an intensity higher than the intensity Mm+3σm on condition that Mm+3σm≥Mb−3σb; creating a mask for medicine image clipping for masking a region of an intensity higher than the intensity Mb−3σb on condition that Mm+3σm<Mb−3σb; and clipping a back unlit image based on the mask for medicine image clipping.

The present inventors, as a result of extensive studies, discovered that the region corresponding to the medicine in the back lit binary image that is obtained by binarizing the back lit RGB resolution image, and the brightness distribution of the region corresponding to the background can be approximated to Gaussian distribution. The inventors further discovered that the brightness of a region corresponding to the medicine is lower than the brightness of a region corresponding to the background, and have mutually different characteristics.

Based on the findings, in the present invention, the mean value Mm of the brightness distribution and standard deviation σm for a region corresponding to the medicine, and the mean value Mb of the brightness distribution and the standard deviation σb for a region corresponding to the background image are derived, and based on their values, the region corresponding to the medicine is identified. That is, with Mm+3 σm≥Mb−3 σb as a condition, a medicine image cut-out mask is formed to mask a region whose brightness is greater than brightness Mm+3 σm, and with Mm+3 σm<Mb−3 σb as a condition, a medicine image cut-out mask is formed to mask a region that has brightness greater than brightness Mb−3 σb. By cutting out a back unlit image based on the medicine image cut-out mask set as above, the image of a medicine disposed in the inspection unit can be acquired without leak, and inspection accuracy can be improved even more.

In the medicine inspection device of the present invention described above, it is preferable to further include a photographing jig comprising a translucent stage, wherein the photographing jig with the medicine to be photographed disposed on the stage is moved to the inspection unit, a contour line of the medicine is derived based on the back lit image obtained by photographing with the shooting means in an irradiation state where the stage is irradiated by the backlight, in the back unlit image obtained by photographing the jig disposed in the inspection unit by the imaging means in a non-irradiated state wherein the stage is not irradiated by the backlight, the device is able to construct a contour image database by accumulating appearance images showing external appearance of the medicine obtained by clipping a region corresponding to a region surrounded by the contour line of the medicine derived based on the back lit image.

In the present invention, in the back lit image photographed in an irradiated state, since a medicine is photographed as a shadow, it is possible to distinctly and reliably detect the outline of a medicine. In contrast to this, in an image where a back unlit image was acquired separately by photographing in a back unlit state, it will be different from the back lit image, and for a medicine that was clearly included, the outline may not be evident. In the present invention, based on the back lit image, a region for cutting out the image of a medicine is defined by the outline, and a section corresponding to the region surrounded by the outline is cutout from the back unlit image. Accordingly, a region in the back unlit image where a medicine is included can be cutout properly (i.e. neither more nor less). Therefore, according to the present invention, a vivid contour image of a medicine can be acquired easily and with high accuracy, and a contour image database can be created.

In the medicine inspection device of the present invention described above, it is desirable that the stage includes a plurality of imaging zones associated with each side of a medicine, and a medicine is arranged in each imaging area such that a side associated with each imaging area is orienting towards the imaging means, and by using a back lit image and back unlit image obtained when the imaging jig is moved to the inspection unit, a database is created by storing a contour image of each side of the medicine.

According to such a configuration, the contour image of each side of a medicine can be photographed at once, and a contour image database can be created.

In the medicine inspection device of the present invention described above, it is desirable that an installation guide is provided in stage to facilitate disposing a medicine in a predetermined location, and size of the installation guide is smaller than presumed size of a medicine and foreign object.

By installing positioning guides in a stage according to the present invention, when photographing a medicine for the purpose of creating a contour image database, a medicine can be guided to be placed in an appropriate place. Also, by setting size of the positioning guides to be smaller than the size of the medicine and a substance thought to be a foreign object as in present invention, in an image photographed for construction of a contour image database, identification of positioning guide and medicine becomes easy, and an imaging processing can be executed to prevent a positioning guide from getting imaged in the contour image of the medicine.

In the medicine inspection device of the present invention described above, it is preferable that a color of the stage is white.

By making the color of the stage white as in the present invention, for example, even for medicines that are of green color or of dark color such as black color etc., in an image photographed for contour image acquisition, the stage and the medicine can be clearly distinguished. With this, the contour image of a medicine can be acquired easily and accurately, and thereby the accuracy of the contour image database can be improved.

In the medicine inspection device of the present invention described above, it is desirable that the shooting means includes imaging means for back lit image for imaging a back lit image, and an imaging means for back unlit image for imaging a back unlit image.

In the medicine inspection device of the present invention, a shooting means for back lit image and a shooting means for back unlit image are provided separately. With this, the back lit image and back unlit image can be acquired under optimal conditions. Thus, according to the present invention, a better contour image database can be created with more clear and appropriate contour images.

In the medicine inspection device of the present invention described above, it is desirable to include a medicine database for inspection in which master contour images showing at least the shapes of medicines that is able to be inspected are stored, wherein the device is capable of carrying out image inspection by matching an outside shape inspection image with a contour image of the medicine present in a sachet, and among the master contour images registered in the medicine database for inspection, by dividing a master contour image showing a complete shape of the medicine by a dividing line passing through middle of the medicine area corresponding to the medicine as boundary, a master contour image is able to be acquired for a divided medicine obtained by dividing the medicine, and registered in the medicine database for inspection.

According to this configuration, a master contour image for inspection of a tablet medicine divided by such as cutter etc., can be acquired easily and accurately, and create a medicine database for inspection.

Here, in dividing a medicine by such as cutter etc., it is not limited to cutting with a high accuracy without much deviating from the center of the medicine, and it is possible to cut in a position much away from the center but within the range that will not create problem with dosage. It is desirable to easily create an appropriate medicine database for inspection to facilitate inspection without causing any error even for a case when a medicine that has been cut in a position somewhat away from the center exists in a sachet.

To deal with such issue, in the medicine inspection device of the present invention, it is desirable that, with the dividing line as reference, an image obtained by dividing a master contour image with an imaginary quasi-dividing line as boundary at a location separated by a predetermined interval, is able to be added as a master contour image for the divided medicine.

By adopting such a configuration, a master contour image can be easily acquired even for a divided medicine that has been cut at a position slightly away from the center, and registered in the medicine database for inspection. Thus, according to the present invention, the inspection accuracy for the divided medicine can be further improved.

The medicine inspection device of the present invention may have a configuration wherein medicine division groove included in a medicine is identified in the master contour image, and a dividing line is determined on the basis of the medicine division groove contained in the master contour image.

According to this configuration, a divided tablet master contour image for the purpose of creating a medicine database for inspection or contour image database can be easily and accurately acquired.

In the medicine inspection device of the present invention, it is preferable that, after determining the dividing line with reference to the medicine division groove contained in the master contour image, the master contour image is rotated around the center of gravity of a medicine region with reference to the said dividing line, and in a situation where a shape of the medicine region present on one side and a shape of the region that is present on the other side with respect to the dividing line are symmetrical, by dividing the master contour image with the dividing line as reference, a master contour image of the divided medicine is obtained.

According to this configuration, while making the medicine division groove formed in the medicine as reference, the division position of the master contour image due to the dividing line can be slightly corrected. With this, it becomes possible to obtain the master contour image of a divided medicine with still higher accuracy. Moreover, when rotating a master contour image in this invention, it is desirable to rotate by a small angle in both forward and opposite directions using as basis the dividing line around the center of gravity of the of the medicine region.

Further, in the medicine inspection device of the present invention, it is desirable that, by dividing a master contour image depicting a full shape of a medicine by a dividing line as boundary, a master contour image of a divided medicine obtained by dividing the medicine is registered as a contour image of the contour of a divided medicine in a contour image database.

As per the present invention, it becomes possible to use a master contour image of a divided medicine for creating a master contour image database. Therefore, according to the present invention, a need to prepare separate images of a divided medicine for contour image database is eliminated.

In the medicine inspection device of the present invention, it is preferable to include a rectangular guide for setting a divisional line circumscribing a medicine area in the outside shape inspection image is assumed all over the medicine area, passing through the center of the guide for setting a divisional line and perpendicular to the length side of the rectangle of the guide for setting a divisional line is specified as division candidate line, and a medicine region present on one side with the said division candidate line as boundary is defined as medicine region CA, and a medicine region present on the other side is defined as medicine region CB, and a non-overlapping region, formed by flipping the medicine region CA over the medicine region CB with the said division candidate line as boundary, is defined as non-overlapping region CC, and the division candidate line when the said non-overlapping region CC is smallest is specified as a dividing line.

According to this configuration, it becomes possible to specify a dividing line at appropriate place for a medicine of any shape, and obtain a master contour image for the divided medicine. Moreover, the guide for setting the dividing line used in the present invention, for example, can be a rectangle of minimum size that can completely surround the contour of the medicine.

In the medicine inspection device of the present invention, it is desirable to include a side illumination on the side of the inspection unit and away at a location higher than the inspection unit, wherein an optical axis of the side illumination is directed towards the inspection unit in a horizontal direction or upper than the horizontal direction.

According to this configuration, it becomes possible to obtain a vivid image of the medicine disposed in the inspection unit.

It is desirable that the medicine inspection device of the present invention has a configuration wherein medicines are supplied as a continuous array of sachets formed by packaging one dose of the medicine per sachet in a packaging paper and aligning the sachets in form of a strip, and each sachet is able to be inspected one by one, the medicine inspection device further including an introduction unit for introducing the continuous array of sachets, wherein the introduction unit includes: a horizontal portion wherein a continuous body of sachets is able to be disposed in a horizontal state, a sachet detecting sensor capable of detecting a continuous body of sachets present on the horizontal portion, and an introduction failure determining means for determining introduction failure of a continuous body of sachets in the introduction part, and wherein the sachet detecting sensor is provided in both directions with the direction of passage of the continuous body of sachets in the horizontal portion as reference, and on condition that the continuous body of sachets is detected by one of the sachet detecting sensors that are provided on both sides, the introduction failure determining means is configured to judge that an introduction failure of the continuous body of sachets has occurred.

According to this configuration, distortion of the continuous body of sachets can be accurately detected, and inspection failures due to introduction defects of a continuous body of sachets can be prevented. In addition, introduction of a continuous body of sachets in a distorted state towards the inspection unit can be prevented, and such as damage of the continuous body of sachets can be prevented.

The medicine inspection device of the present invention may have a configuration wherein medicines are supplied as a continuous array of sachets formed by packaging one dose of the medicine per sachet in a packaging paper and aligning the sachets in form of a strip, and each sachet is able to be inspected one by one, and is able to show an inspection result, wherein a sachet of the continuous body of sachets is able to be classified based on dosing time, and among a plurality of sachets corresponding to each doing time, a result of inspection for desired sachet is able to be selectively displayed.

According to this configuration, in the results of inspection, it becomes possible to selectively confirm only for the requested ones. With this, the operation of checking of result of inspection by a doctor or pharmacist can be all the more simplified.

A medicine packaging device of the present invention includes: the medicine inspection device of the present invention described above; a medicine feeding means capable of supplying a medicine according to a prescription; and a medication preparation means capable of gathering the medicine supplied from the medicine feeding means for each package and dispensing the medicine; wherein a quantity of medicine dispensed from the medication preparation means is able to be inspected by the medicine inspection device.

In the medicine packaging device of the present invention, a medicine inspection device of the present invention described above is provided, and the quantity of medicine in each package supplied from a medication preparation means can be accurately checked.

According to the present invention, it becomes possible to provide a medicine inspection device capable of properly inspecting the quantity of solid medicines without inspection failures due to the solid medicines being in a overlapped, contacting, upright state or the like, or due to the presence of packaging paper etc., and a medicine dispensing device equipped with such a medicine inspection device.

BRIEF DESCRIPTION OF THE DRAWINGS

The present disclosure is described in conjunction with the appended figures:

FIGS. 65A, 65B, and 65C are illustrating one example of a journal showing the result of inspection.

DETAILED DESCRIPTION OF THE INVENTION

Embodiments of the present invention will be described hereinafter with reference to the accompanying drawings, in which preferred exemplary embodiments of the invention are shown. The ensuing description is not intended to limit the scope, applicability or configuration of the disclosure. Rather, the ensuing description of the preferred exemplary embodiments will provide those skilled in the art with an enabling description for implementing preferred exemplary embodiments of the disclosure. It should be noted that this invention may be embodied in different forms without departing from the spirit and scope of the invention as set forth in the appended claims.

《《 First Embodiment 》》

Next, a medicine inspection device 10 according to one embodiment of the present invention, and a medicine packaging device 100 provided with this medicine inspection device 10 will be described in detail while referring to the diagrams. In the following description, the medicine inspection device 10, which is a characteristic part of this embodiment, will be described first, and subsequently the medicine packaging device 100 will be described. Here, the example shown in this embodiment is just one example of many embodiments that can be assumed with respect to the present invention.

《 Medicine Inspection Device 10 》

Figure 1:
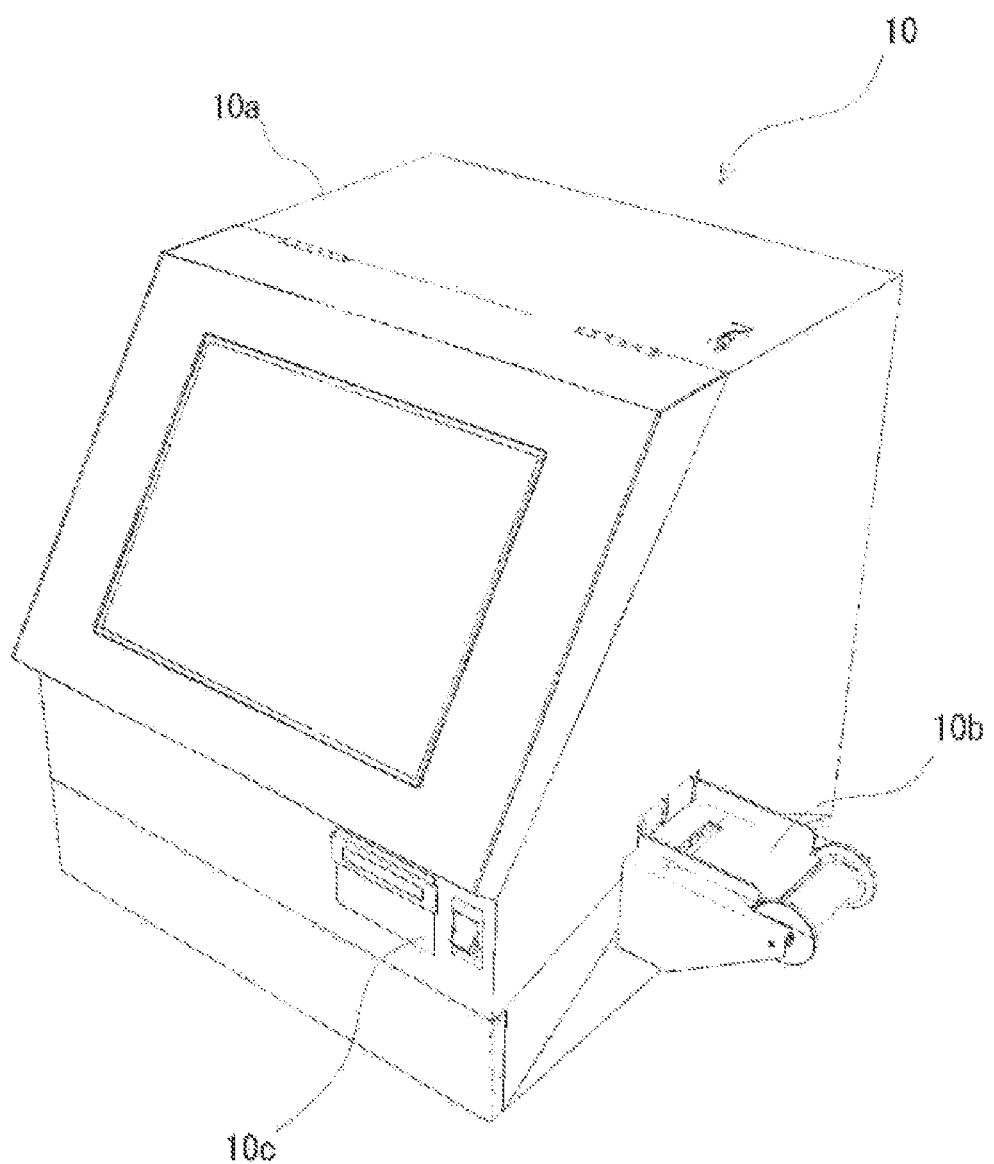
FIG. 1 is a perspective view showing the exterior configuration of a medicine inspection device according to one embodiment of the present invention.
Figure 2:
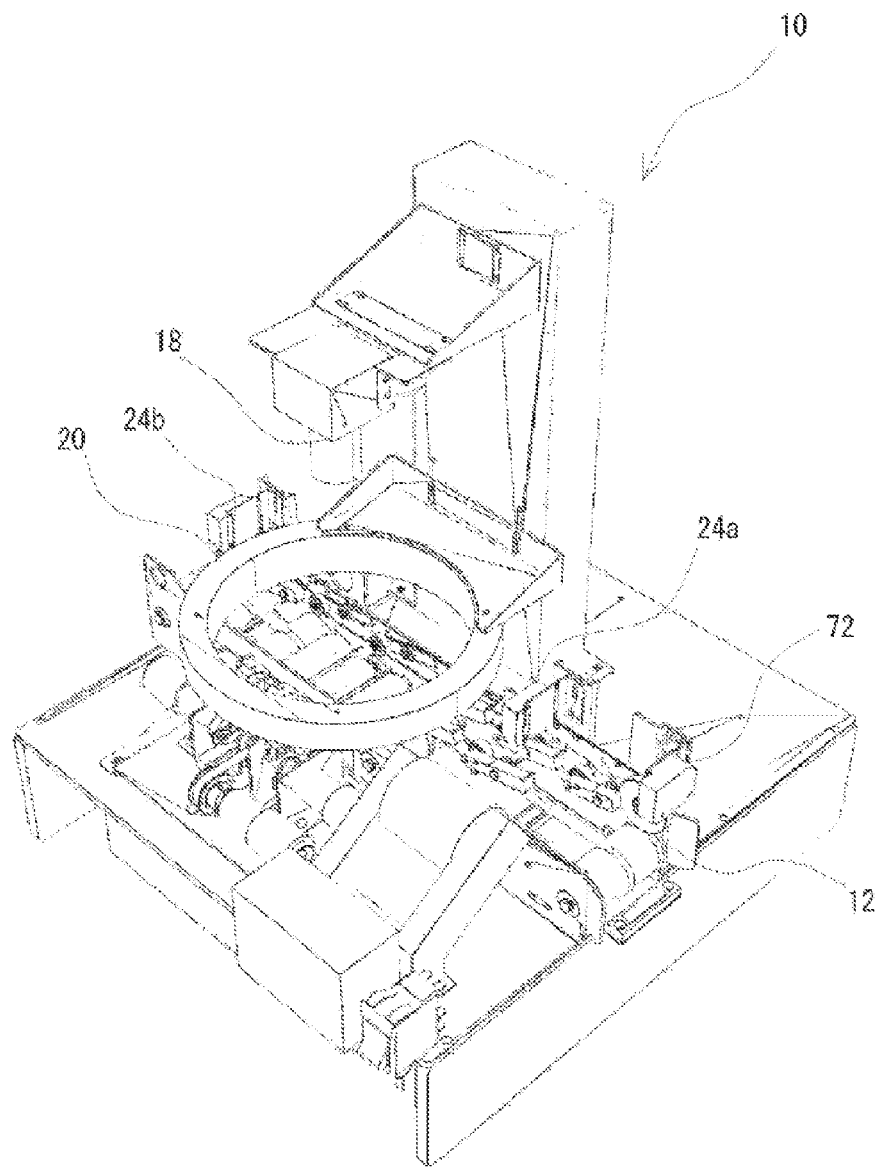
FIG. 2 is a perspective view showing the main parts of the medicine inspection device according to one embodiment of the present invention.
Figure 3:
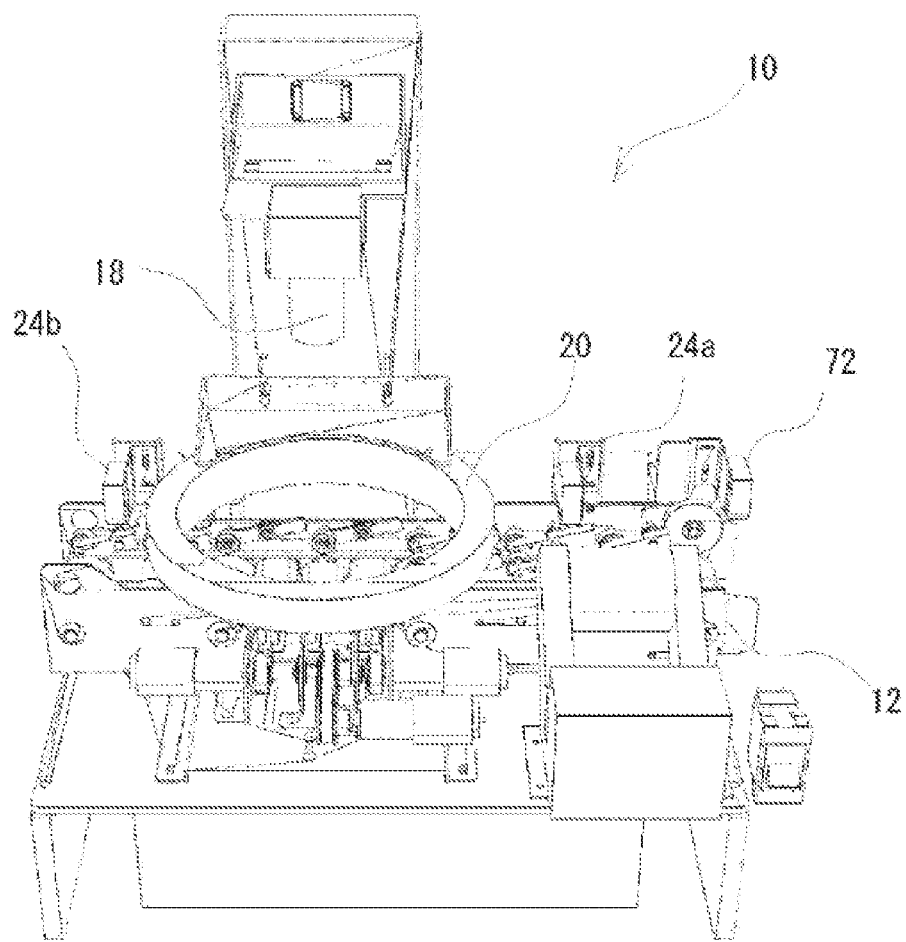
FIG. 3 is a perspective view showing the main parts of the medicine inspection device according to one embodiment of the present invention.
Figure 4:
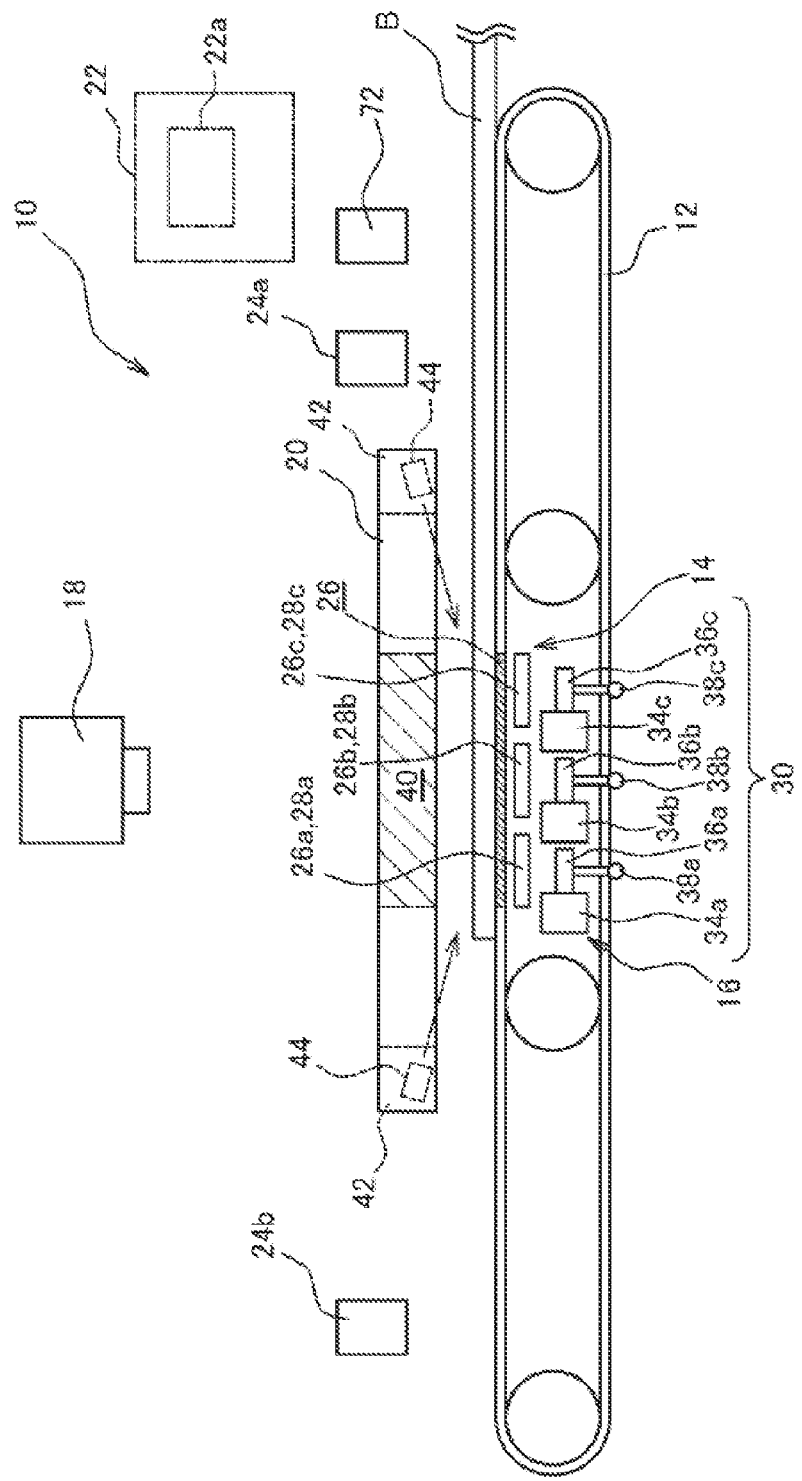
FIG. 4 is a side view schematically showing the main parts of the medicine inspection device according to one embodiment of the present invention.
Figure 5:
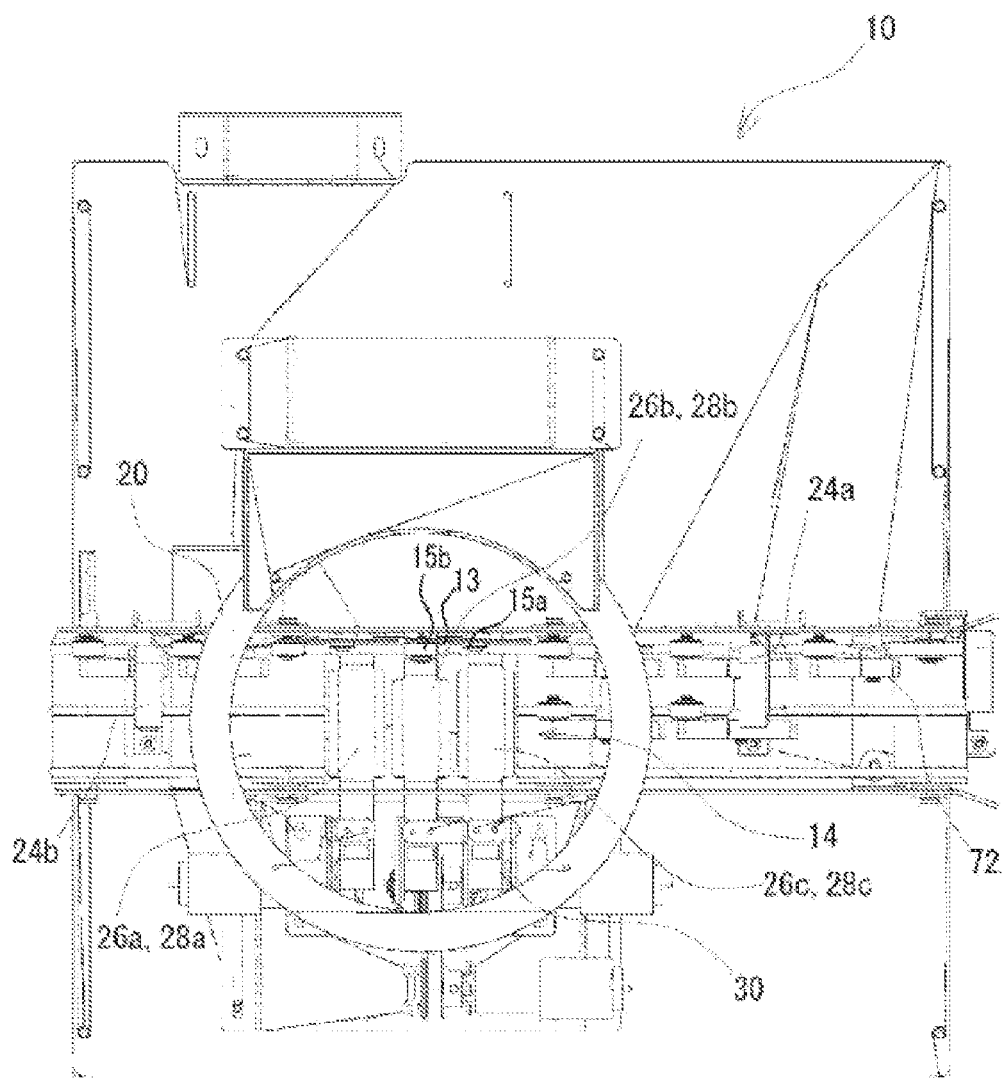
FIG. 5 is a plane view showing the main parts of the medicine inspection device according to one embodiment of the present invention.

The medicine inspection device 10 is a device for inspecting the quantity and type of a medicine to be inspected that is supplied in a state wherein each dose is packaged in a packaging paper. As shown in FIG. 1, the medicine inspection device 10 has an introduction unit 10b provided in the side surface of a casing 10a for introducing a medicine for inspection, and has an operation panel 10c in the front. Medicine is packaged in a translucent packaging paper, and supplied to the medicine inspection device 10 in a state wherein it can be viewed from outside as shown in FIG. 7.

Figure 7:
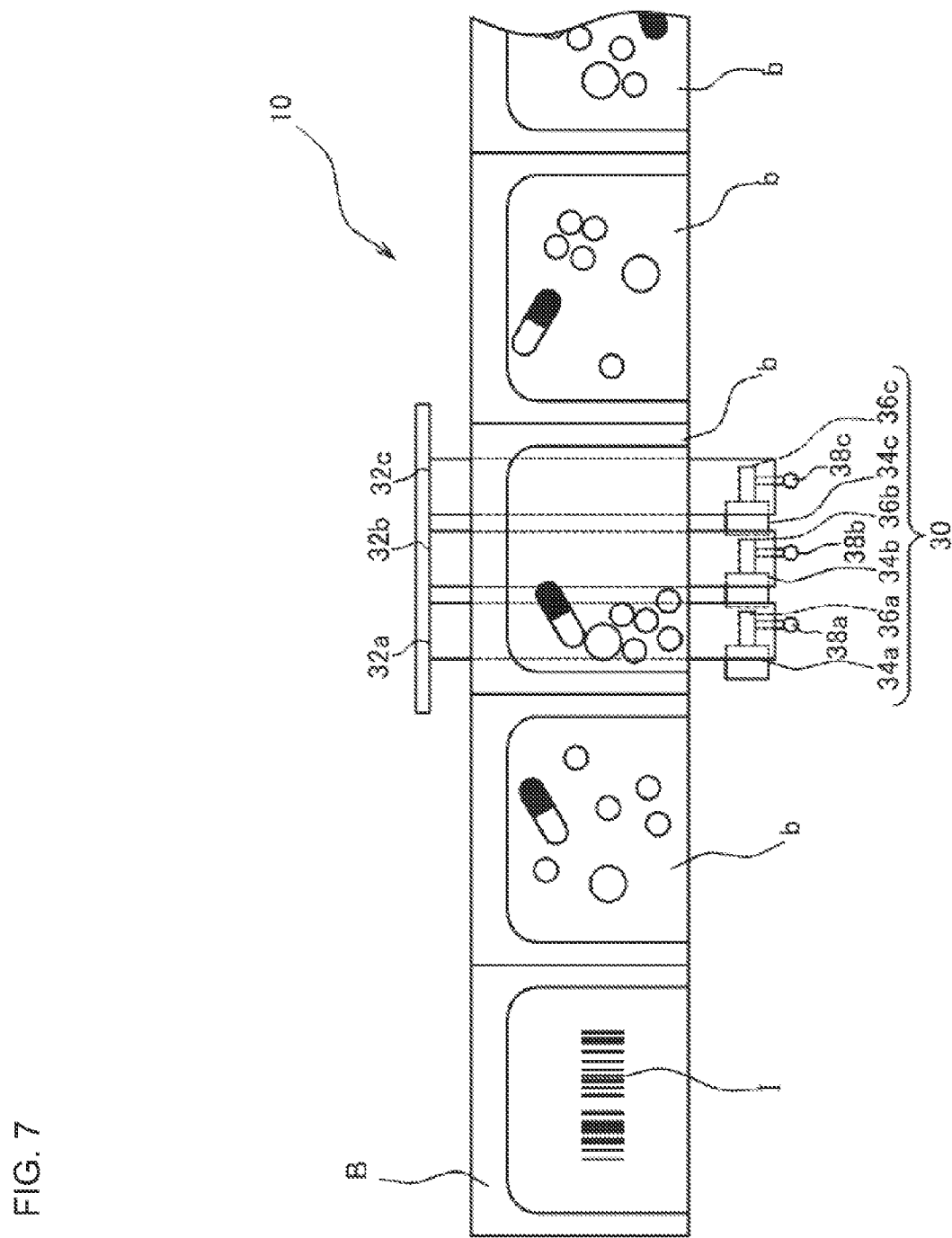
FIG. 7 is a plane view schematically showing a relationship between a continuous body of sachets formed from a packaging paper and an inspection unit etc.

As shown in FIG. 7, medicine is supplied to the medicine inspection device 10 in a state of a continuous body of sachets B wherein a plurality of sachets b, each containing one dose of medicine, are continuously formed. An information medium I associated with prescription information is attached to the beginning of the continuous body of sachets B. As information medium I, conventionally well-known identification signs such as bar code, information recording media such as IC ships, character information and symbols etc., about prescription information can be used. In the present embodiment, a continuous body of sachets B is supplied with a bar code associated with prescription information at the beginning by printing or the like.

As shown in FIG. 2 through FIG. 6, the medicine inspection device 10 is provided with a transportation means 12, inspection unit 14, vibrator 16, shooting means 18, illuminating device 20, control device 22, and etc. Though not illustrated, a filter may be provided in the shooting means for distinguishing various types of information (name of patient, dose time, medicine type etc.) printed on a continuous body of sachets B from the medicine of the continuous body of sachets B. The transportation means 12 is a meant to receive and convey a continuous body of sachets B that is formed by packaging medicine. The transportation means 12 may be formed of conventionally well-known belt conveyor, roller conveyor etc. In this embodiment, a belt conveyor is employed as a transportation means 12. When a continuous body of sachets B formed of a packaging paper is detected by a supply detection means 24a provided in the upstream of the inspection unit in the conveying direction, the transportation means 12 operates under the control of a control device 22, which is described later, and conveys the continuous body of sachets B sequentially in the downstream direction. When the dispense detection means 24b, which is provided in the downstream end, confirms that the end of the continuous body of sachets B has been dispensed beyond the downstream of the inspection unit 14, the operation of the transportation means 12 stops.

The inspection unit 14 is provided approximately in the middle of a conveyance path formed by the transportation means 12. The inspection unit 14 is the part where a medicine conveyed by the transportation means 12 will be positioned. That is, the inspection unit 14 is an area having approximately a size in which one sachet b formed of a packaging paper can fit in. Therefore, by conveying a continuous body of sachets B by the transportation means 12 such that a sachet b arrives on the inspection unit 14, a medicine to be inspected is positioned on the inspection unit 14 in a state packaged in a sachet b (packaging paper).

Here, the inspection unit 14 is divided into a plurality of areas (inspection areas 26) from the upstream side of a direction in which medicine (continuous body of sachets B) is conveyed by the transportation means 12 towards the downstream side. In this embodiment, the inspection unit 14 has been divided into three inspection areas 26a, 26b and 26c from the upstream side toward the downstream side.

The vibrator 16 provides vibrations to the sachet b (medicine) positioned on the inspection unit 14. The vibrator 16 is capable of causing vibrations independently to each inspection area 26a, 26b, and 26c. The vibrator 16 that is employed in this embodiment is provided with leaf springs 28a, 28b, and 28c that function as a source for generating vibrations, and an shock imparting means 30 for imparting impact to the leaf springs 28a, 28b, and 28c.

Figure 6:
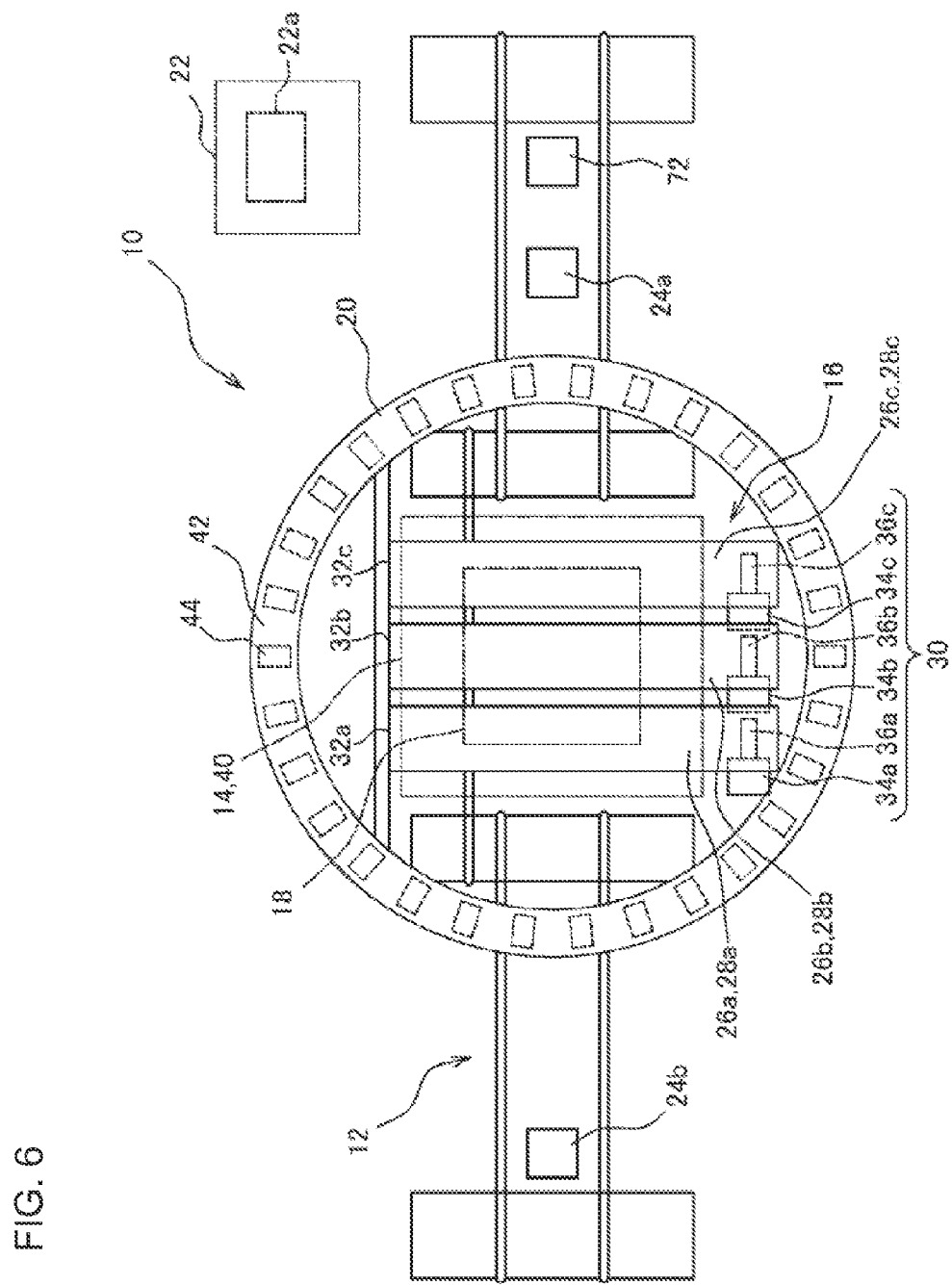
FIG. 6 is a plane view schematically showing the main parts of the medicine inspection device according to one embodiment of the present invention.

Leaf springs 28a, 28b, and 28c are provided for each respective inspection area 26a, 26b, and 26c. The leaf springs 28a, 28b, and 28c are positioned directly below a sachet b (continuous body of sachets B) that reaches the inspection unit 14, and can provide vibrations to the sachet b and the medicine contained therein. The leaf springs 28a, 28b, and 28c are provided orthogonally to the conveying direction of the continuous body of sachets B due to the transportation means 12. As shown in FIG. 6 and FIG. 7, the leaf springs 28a, 28b, and 28c are supported in a cantilever state by fixing the fixing parts 32a, 32b, and 32c provided at one end. The fixing parts 32a, 32b, and 32c are fixed on the side of device main body of the medicine inspection device 10 in positions away from the inspection unit 14 (inspection areas 26a, 26b, and 26c).

The shock imparting means 30 is provided directly below the other end (free end) of the leaf springs 28a, 28b, and 28c. The shock imparting means 30 is comprised of motors 34a, 34b, and 34c, and plectrums 38a, 38b, and 38c integrally mounted with respect to the rotating shafts 36a, 36b, and 36c of the motors 34a, 34b, and 34c, and are provided for each leaf spring 28a, 28b, and 28c (inspection areas 26a, 26b, and 26c) respectively. Each motor 34a, 34b, and 34c can be operated independently. In addition, the plectrums 38a, 38b, and 38c are provided substantially perpendicular to the rotating shafts 36a, 36b, and 36c, and with the rotation of the rotating shafts 36a, 36b, and 36c, an impact can be added through collision against the free ends of the leaf springs 28a, 28b, and 28c. Therefore, the shock imparting means 30 can independently provide impact to each leaf spring 28a, 28b, and 28c (inspection areas 26a, 26b, and 26c), generating vibrations in the upper/lower directions.

The shooting means 18 is intended for photographing a medicine disposed on the inspection unit 14, and is disposed vertically above the inspection unit 14. A lighting device 20 is intended for irradiating the inspection unit 14 when photographing with the shooting means 18, and is disposed vertically above the inspection unit 14 similarly to the shooting means 18.

The lighting device 20 includes a light emitting part 42 of annular shape. The light emitting part 42 emits light with a plurality of light emitting diodes 44 as light source provided in the entire circumference. If an area (virtual area 40) equivalent to the area of the inspection unit 14 is imagined in a vertical direction with respect to the inspection unit 14, the light emitting part 42 is provided so as to surround this virtual area 40. The optical axis of each light emitting diode 44 is directed towards the light emitting part 42. That is, the optical axis of each light emitting diode 44 is directed in radially inward of the light-emitting unit 42 (a direction toward the inside from the outside of the virtual area 40) and in a downward direction. With this, as shown by arrows in FIG. 4, each medicine disposed on the inspection unit 14 in a state packaged by a packaging paper can be obliquely irradiated from above and prominently accentuate the contour of each medicine.

Figure 8:
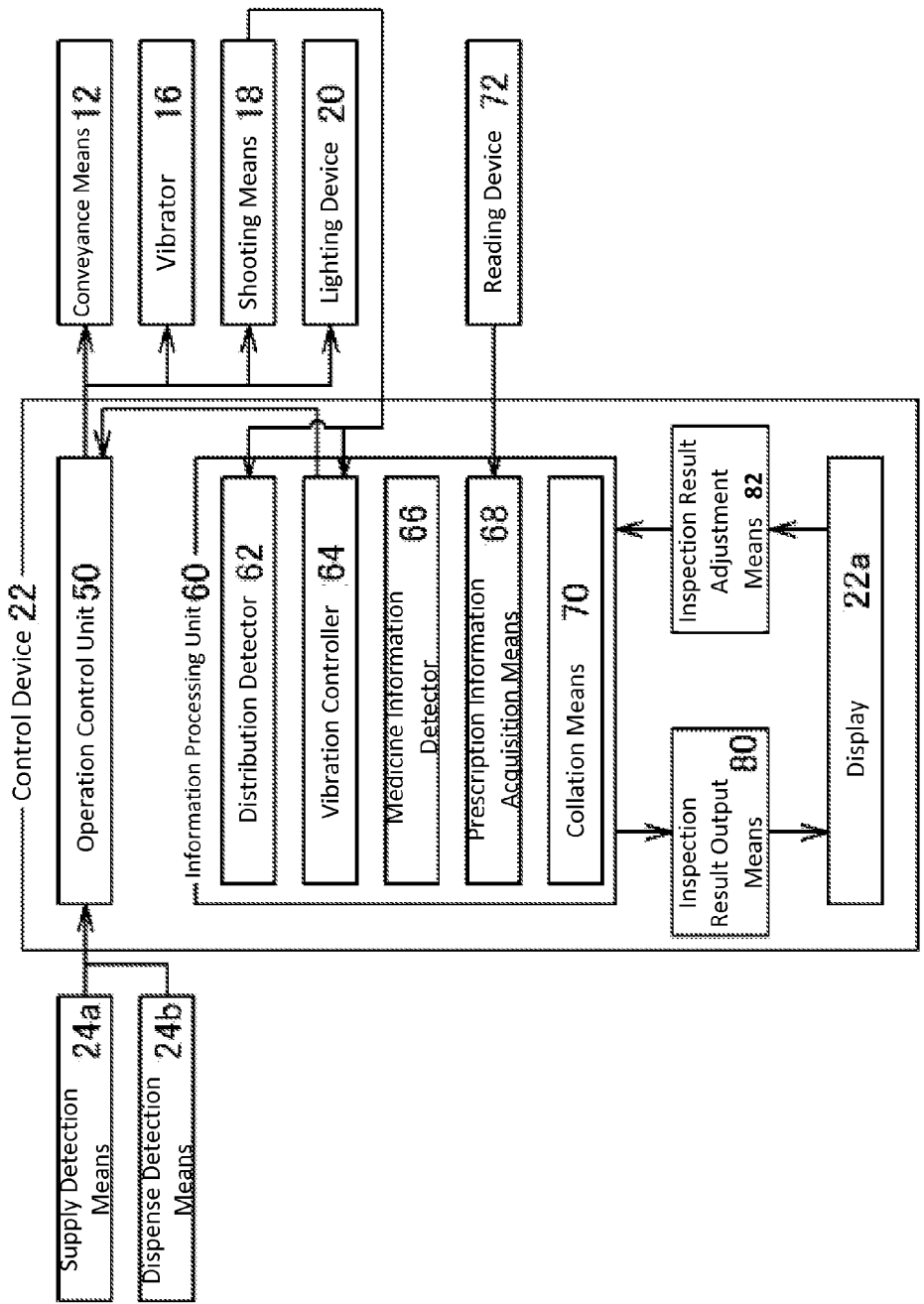
FIG. 8 is a block diagram showing the configuration of a control device.

The control device 22 is provided for the operation of the medicine inspection device 10 and carrying out inspection, and consists of a personal computer, a dedicated board with electronic components etc., and the like. As shown in FIG. 8, the control device 22 includes an operation control unit 50 for controlling the operations of various parts of the medicine inspection device 10, and an information processing unit 60 for performing information processing based on information obtained by the operation of the various parts, and carrying out inspection of medicine contained in each sachet b. An operation control unit 50 controls the operation of transportation means 12, vibrator 16, imaging device 18, and lighting device 20 described above.

When a supply of a continuous body of sachets B formed from a packaging paper is detected by the supply detection means 24a that is provided in the upstream of the inspection unit 14, the operation control unit 50 operates the transportation means 12 and moves the continuous body of sachets B to the inspection unit 14, and each time the inspection operation, which is described later, is completed, it will control the movement by sequentially moving the sachets in the downstream direction by an amount equivalent to one sachet b at a time. Further, after starting the operation of sequentially dispatching the continuous body of sachets B by the transportation means 12, the operation control unit 50 makes sure that all sachets b containing the medicine to be inspected have passed through the inspection unit 14 based on the detection result of the dispense detection means 24b provided in the downstream of the inspection unit 14. Specifically, after a continuous body of sachets B is detected by the dispense detection means 24b, at the instant when the continuous body of sachets B is no longer detected by the dispense detection means 24b, the operation control unit 50 determines that the end section of the continuous body of sachets B has reached the downstream of the inspection unit 14 and that all sachets b have passed through the inspection unit 14. When all sachets b have been confirmed to have passed through the inspection unit 14, the operation control unit 50 stops the operation of the transportation means 12.

When a sachet b containing a medicine to be inspected reaches the inspection unit 14, the operation control unit 50 operates the imaging device 18, and the sachet b disposed in the inspection unit 14 and the medicine packaged therein can be photographed. During the course of photographing by the imaging device 18, the inspection unit 14 can be illuminated by operating the lighting device 20 by the operation control unit 50. Also, based on the command from an information processing unit 60, which is described in detail later, the control section 50 can operate the vibrator 16, and generate vibrations in each inspection area 26a, 26b, and 26c of the inspection unit 14.

The information processing unit 60 includes a distribution detector 62, a vibration controller 64, a medicine information detector 66, a prescription information acquisition means 68 and a collation means 70. Based on the image photographed by the shooting means 18, the distribution detector 62 detects the distribution condition of a medicine packaged in the sachet b that reached the inspection unit 14. The detection result of the distribution detector 62 is forwarded as distribution condition detection information to a vibration need determination means 64. Moreover, the distribution detector 62 may be capable of carrying out a filtering treatment for distinguishing various types of information (patient name, dosage time, medicine type etc.) printed on a continuous body of sachets B from the medicine of the continuous body of sachets B.

On the basis of distribution condition detection information received from the distribution detector 62, the vibration controller 64 determines if there is a need for generating vibrations by the vibrator 16, and based on this judgment result, can control the operation of the vibrator 16. Specifically, on the basis of the distribution information detection information, the vibration controller 64 determines if there is an area where the medicine is unevenly distributed in each of the inspection areas 26a, 26b, and 26c of the inspection unit 14. If the medicine is found to be unevenly distributed, the vibration controller 64 determines that there is a need for operating the vibrator 16, and if the medicine is not found to be unevenly distributed, determines that there is no need for operating the vibrator 16.

If it is determined that there is a need to operate the vibrator 16, the vibration controller 64, on the basis of the uneven distribution condition of the medicine, can determine in which area among the inspection areas 26a, 26b, and 26c vibration needs to generated, and send a command to the operation control unit 50 for operating the vibrator 16. To be more explicit, the vibration controller 64 sends a command to the operation control unit 50 for controlling the operation of the shock imparting means 30 for vibrating the leaf spring, among the leaf springs 28a to 28c, that corresponds to an area having the largest quantity of the medicine among the inspection areas 26a, 26b, and 26c, and not to vibrate the leaf springs corresponding to other areas. With this, the medicine distributed unevenly in any of the inspection areas 26a, 26b, 26c will be moved to other areas, and piling up or contact of medicines can be eliminated.

The medicine information detector 66, on the basis of an image taken by the shooting means 18, identifies the type and quantity of a medicine. When the vibrator 16 is operated as described above, an image taken by means of the shooting means 18 operation is used for identification of type of medicine and number by the medicine information detector 66. Also, if there is no need to operate the vibrator 16, an image taken by the shooting means 18 at the instant a medicine (sachet b) for inspection reaches the inspection unit 14 is used for identification of type of medicine and the number by the medicine information detector 66.

From an image obtained by the shooting means 18, the medicine information detector 66 can identify the types of medicines by a variety of methods. For example, by identifying the shape of the outer edge of a medicine contained in an image obtained by the shooting means 18, the size and shape of the medicine can be determined. Also, based on the color information of a region corresponding to a medicine in the photographed image, the color of the medicine can be determined. The medicine information detector 66, based on a database prepared beforehand of the medicine properties such as medicine type, shape, size, color and etc., can identify the type of a medicine that is under inspection. The medicine information detector 66 can also identify the type of a medicine and the like based on the information that is stamped or printed on the surface of a medicine.

The medicine information detector 66 can identify the quantity of a medicine by a variety of methods from an image obtained by the shooting means 18. For example, the quantity of a medicine can be found out by identifying the outer edge of a medicine contained in an image obtained by the shooting means 18 and counting the number of areas enclosed by the outer edge. In addition, by such as checking how many things of similar size and shape are present in a photographed image, it is also possible to find out the quantity for each type of medicine.

The prescription information acquisition means 68, on the basis of prescription information, can acquire prescription information regarding the type and the quantity of a medicine packaged in each sachet b. In this embodiment, a reading device 72 capable of reading the bar code included at the head section of a continuous body of sachets B, which is a continuous body of sachets b, is provided in the upstream of the transportation means 12 with respect to the inspection unit 14 in the conveying direction. The prescription information acquisition means 68 is capable of accessing an external recording means (not illustrated) in which the prescription information is stored, and based on information media I such as bar code, ID number and the like read by a reading device 72, the prescription information can be acquired from an externally mounted recording device or the like.

The collation means 70 can compare the information relating to the type and the quantity of a medicine detected by the medicine information detector 66 described above with the prescription data acquired from the prescription information acquisition means 68, and verify whether the type and the quantity of a medicine contained in a sachet b is as per the prescription information.

In addition to the configuration described above, the control device 22 is provided with an inspection result output means 80 for outputting the information showing the results of inspection obtained from collation by the collation means 70 to an output device such as a display 22a provided in the control device 22, and an inspection result adjustment means 82 for correcting the results of inspection and the like. In the medicine inspection device 10 of this embodiment, the information that is output from the inspection result output means 80 can be displayed on the display 22a as shown in FIG. 9 and FIG. 10.

Figure 9:
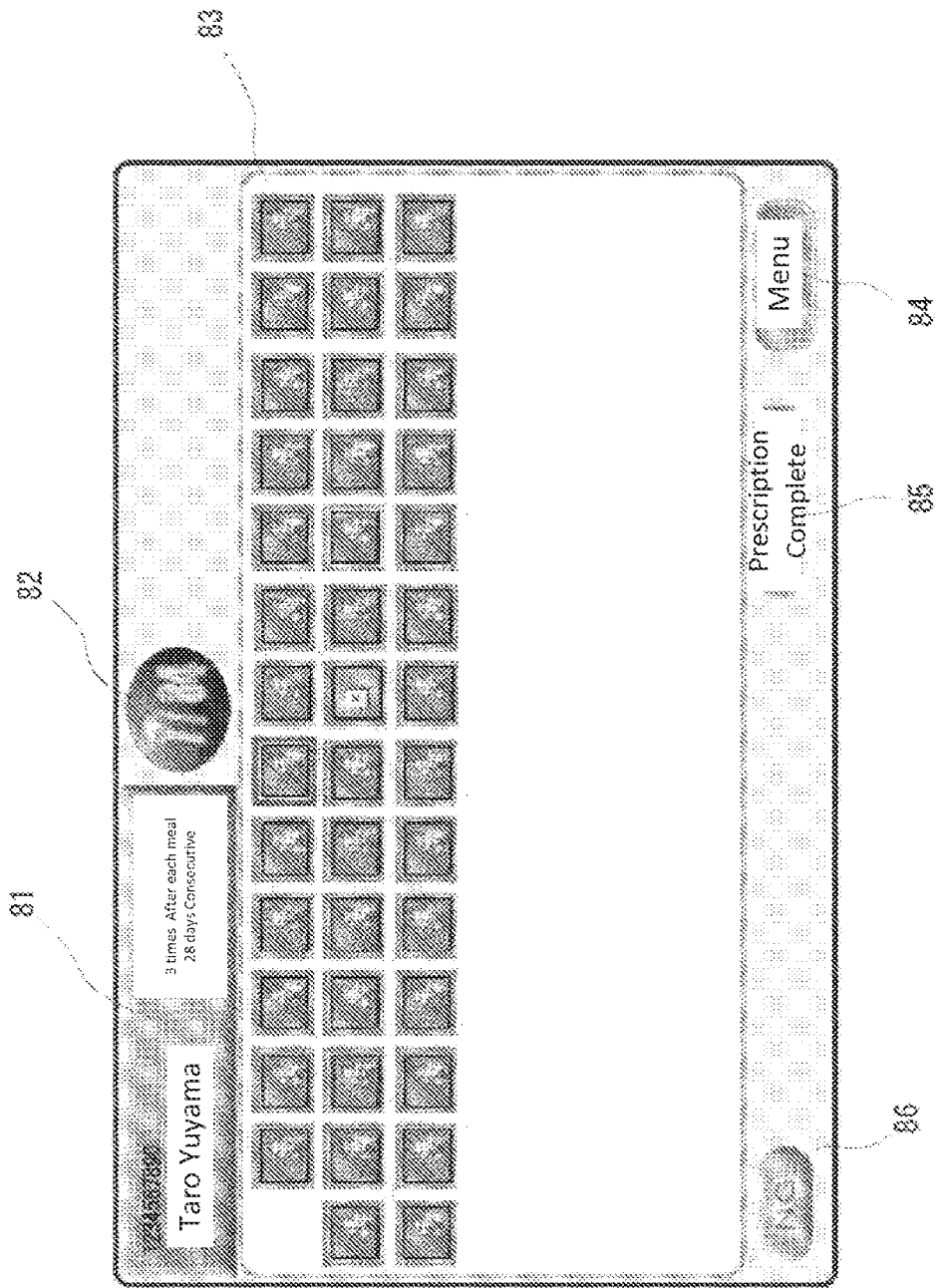
FIG. 9 is an image showing an integrated interface.
Figure 10:
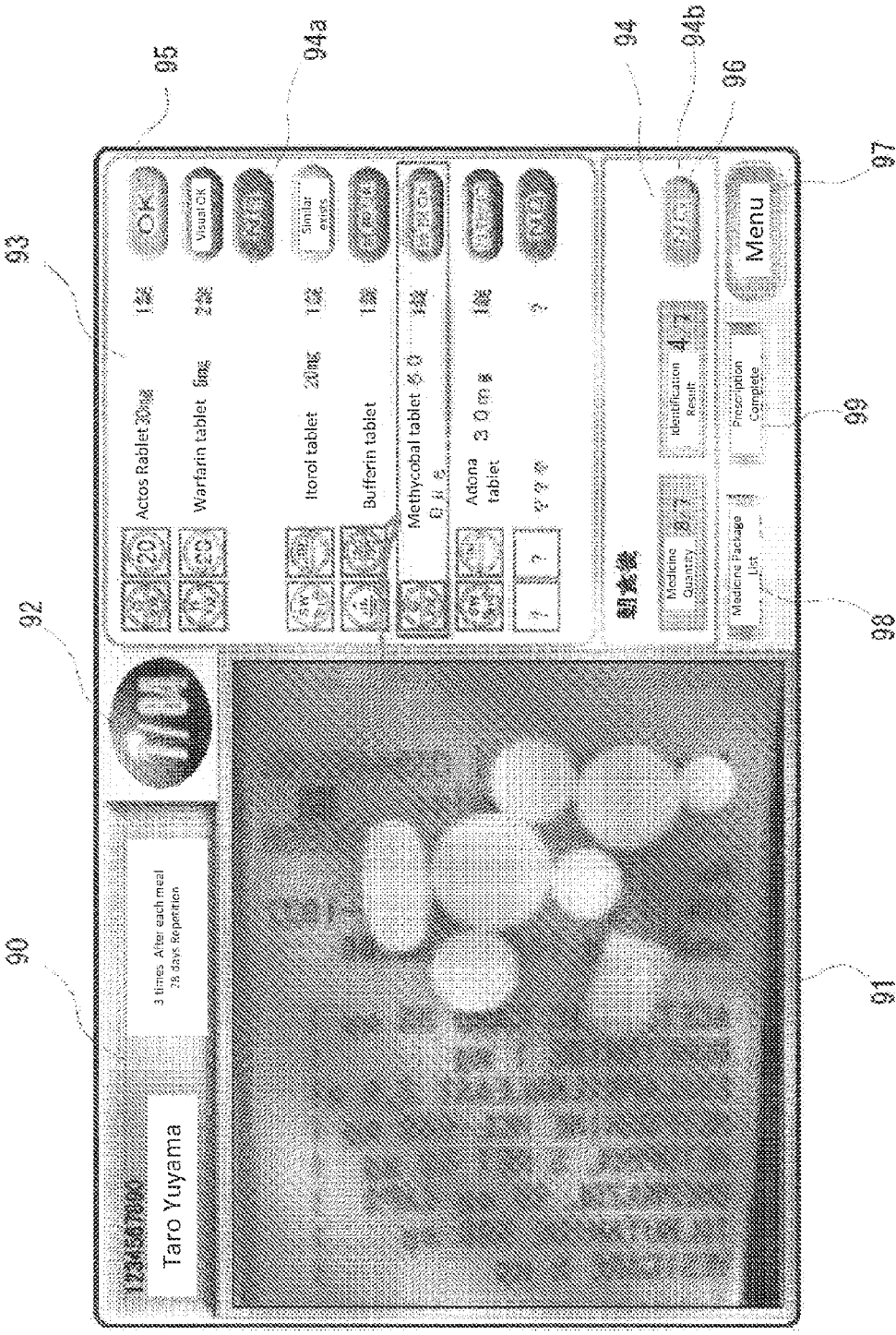
FIG. 10 is an image showing individual interfaces.

A display screen (hereafter also referred to as 'general interface') shown in FIG. 9 shows a list of results of image inspection. In the general interface, display fields displaying various types of information such as prescription attribute information column 81, package identification information column 82, medicine list display column 83 etc., and buttons such as menu button 84, finish button 85, and batch change button 86 etc. are displayed.

In the prescription attribute information column 81, based on the prescription information acquired from a recording device (not illustrated) or the like provided in the medicine packaging unit 120 of the medicine packaging device 100, which is described later in detail, information such as the patient identification information such as a patient name, ID number and the like to whom the inspection medicine is prescribed, the number of packages, number of dosing days of the prescribed medicine and number of doses etc., is displayed. In the package identification information column 82, the position of the currently selected sachet b from the beginning is displayed.

The medicine list display column 83 is a column provided for displaying as thumbnails the images used for carrying out inspection of each sachet b constituting a continuous body of sachets B. In the medicine list display column 83, according to the result of inspection, the thumbnail images can be displayed in a different display format. Specifically, a thumbnail image of a sachet b in which the medicine quantity and type contained therein have been determined to match the prescription information (hereafter also referred to as 'normal sachet b'), and a thumbnail image of a sachet b in which either the quantity or the type or both have been determined to be different from the prescription information (hereafter also referred to as 'defective sachet b'), are enclosed by frames of different colors or lines.

The menu button 84 is a button intended for displaying a list of operational menus. The finish button 85 is a button intended for confirming and finishing a series of inspection results. The batch change button 86 is a button provided for collectively switching between an approval and disapproval of the inspection results of all sachets b displayed in thumbnails. In this embodiment, a touch panel system is used as display 22a, and by touching with a finger the area where various buttons 84, 85 and 86 described above are displayed, various types of operations, which is described later in detail, can be performed.

The display screen shown in FIG. 10 (hereafter also referred to as "individual interface") is an interface displayed by selecting a thumbnail image that is displayed in the medicine list display column 83 in the general interface of FIG. 9. The individual interface displays the details of inspection results of a medicine packaged in a sachet b pertaining to the selected thumbnail image, and they can be suitably edited, etc.

In the individual interface, display columns for displaying various types of information such as a prescription attribute information column 90, image information column 91, package identification information column 92, inspection details information column 93, general inspection information column 94 and etc. are provided. In the inspection details information column 93 and general inspection information column 94, buttons 95 and 96 are displayed for correction, modification, confirmation and the like of respective inspection information. Further, in the individual interface, in addition to the buttons 95 and 96, menu button 97, medicine package list button 98, and prescription finish button 99 etc., are displayed. In the individual interface, by touching with finger the region where various buttons 95, 96, 97, 98 and 99 are displayed, various types of operations, which are described later in detail, can be performed.

To describe various parts of the individual interface more specifically, in the prescription attribute information column 90, similarly to the prescription attribute information column 81 of the general interface described above, displays information such as the patient identification information like name, ID number and etc. of the patient to whom the inspection medicine is prescribed, the number of packages, the number of dosing days of the prescribed medicine and the number of doses etc. In the image information column 91, the image of the selected sachet b used for inspection of the medicine is displayed. In the package identification information column 92, the position of the currently selected sachet b from the beginning is displayed.

In the inspection details information column 93, the inspection information (type and quantity of medicine) about a currently selected sachet b acquired by the medicine information detector 66 is listed together with an image showing the shape of the medicine. Here, the name and quantity of the medicine listed in the inspection details information column 93 is the official prescription information obtained from a recording device provided externally or the like, and the result of the inspection is shown in the form of buttons 95 provided for each medicine. Specifically, the result of verification by the collation means is displayed as 'OK' for a medicine judged to be correctly packaged, and 'NG' for a medicine judged to be incorrectly packaged. In addition, a "Similar exist" is displayed for a medicine that cannot be correctly determined by verification by the collation means 70.

In the inspection details information column 93, when the part displaying the name of the medicine or the part displaying image of the medicine shape is selected by touching, the region corresponding to the medicine selected is explicitly indicated in the image display column 91. Specifically, by enclosing the region corresponding to the selected medicine with a line having a color different from others, or a color that is same as the color of button 95 that is provided for each medicine, etc., the medicine is displayed in a way that it is identifiable from others.

It is possible to correct an inspection result by touching with finger or the like and selecting the buttons 95 displayed in the inspection details information column 93. Specifically, for a medicine for which the inspection result of 'OK' or 'NG' is displayed in button 95, if the operator visually determines that the inspection result is incorrect, the inspection result can be modified by selecting a button 95 for that medicine. When the inspection result is changed from a state of 'NG', the display of the button 90 is switched to a display of 'Visual OK'.

Similarly, when changing from the inspection result of 'OK', the display of the button 95 is switched to a display of 'Visual NG'. Similarly, when 'Similar exists' is displayed on button 95, an operator can switch to 'Visual OK' upon determining that it is a correct medicine based on visual observation, and can also switch to 'Visual NG' upon determining the medicine is incorrect. Further, by selecting the button 96, it is possible to batch convert the inspection results displayed on buttons 95 in detailed information display column 93.

When associating the name of a medicine listed in inspection details information column 93 with the image of the medicine displayed in the image information column 91, use a finger or the like to touch the area where the medicine is displayed in the image information column 91 and move it to the section in the inspection details information column 93 where the name of the medicine is displayed. That is, after using a finger or the like to touch the section in the image information column 91 where the image of the medicine is displayed, by performing the so-called drag-and-drop operation, the name of the medicine and the image of the medicine are associated. With regard to the medicine that was associated in this manner, the display of the button 95 is switched to 'Visual OK'.

As a result of the inspection by medicine information detector 66 and collation means 70 described above, if there is anything that cannot be identified is present in the image, there will be a mention to that in the inspection details information column 93. Specifically, as shown in the example shown in FIG. 10, the medicine name and the quantity are shown by symbols such as '?' mark or characters etc.

In the inspection general information column 94, the quantity of medicine and identification result of the entire selected sachet b are displayed. Specifically, in the general inspection information means 94, a medicine quantity display part 94a showing whether the quantity is as per the prescription information or not, and an identification result display part 94b that displays the quantity of medicine wherein the result of inspection displayed in button 95 is 'OK' or 'Visual OK'. In the example shown in FIG. 10, due the presence of a medicine that is not identifiable, it has been identified that 8 nos. of the medicine were detected in contrast to the quantity of a medicine specified in the prescription information being 7, and therefore, a display as 8/7 is shown in the medicine quantity display part 94a. Further, since 4 medicines for which the result of inspection is 'OK' or 'Visual OK' are present while the quantity of medicine specified in the prescription information is 7, a display of 4/7 is shown in the identification result display part 94b.

The menu button 97, similarly to the menu button 84 described above, is intended for displaying a list of operation menus. The medicine package list button 98 is intended for displaying the general interface described above. The prescription finish button 99 is a button for closing the individual interface. When the prescription finish button 99 is selected, the information of setting changes in the individual interface is saved as inspection information.

《 Medicine Packaging Device 100 》

Figure 11:
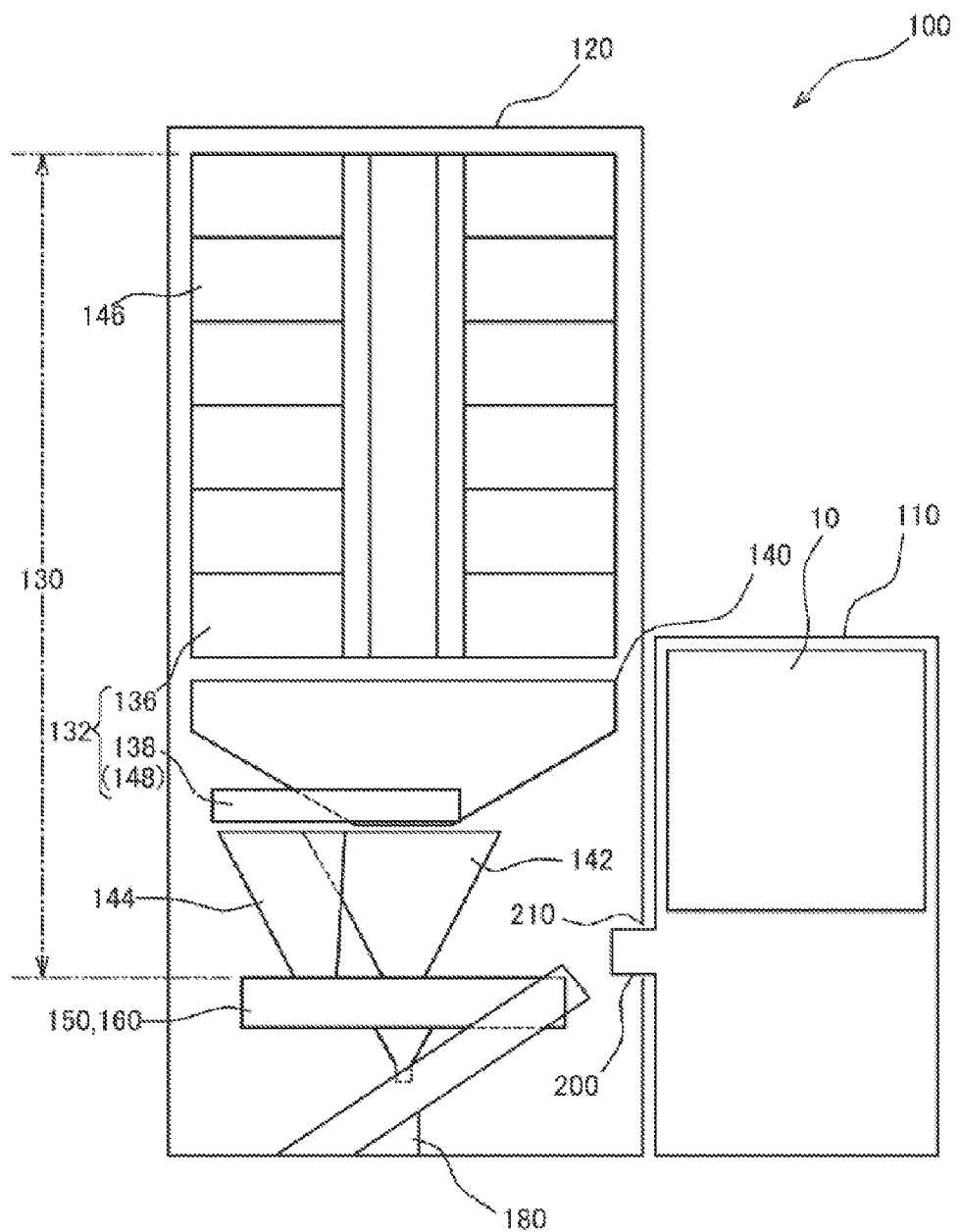
FIG. 11 is an explanatory drawing schematically showing the configuration of a medicine packaging device according to one embodiment of the present invention.

A medicine packaging device 100 is a device capable of dividing and packing medicine as per the input prescription data and dispensing them. As shown in FIG. 11, the medicine packaging device 100 has a medicine inspection part 110 consisting of a medicine inspection device 10 described above, and a medicine packaging part 120 for packaging the medicine. The inside of the body of the medicine packaging part 120 is provided with a medicine supplier 130, a medication preparation means 150, and a medicine packing means 180.

The medicine supplier 130 is provided for storing solid medicine, appropriately dispensing the solid medicine according to the prescription, and supplying to the medicine packing means 180. The medicine supplier 130 includes a feeding part 132. The feeding part 132 has the function of storing the solid medicine, and dispensing the solid medicine as per prescription towards the medication preparation means 150. The medication preparation means 150 has the function of storing the solid medicine supplied from the feeding part 132 per package, and sequentially dispensing towards the medicine packing means 180.

The feeding part 132 has a feeder type feeding part 136 and a manual feeding part 138 as a means for supplying solid medicine. Furthermore, the feeding part 132 is provided with a standby hopper 140, collecting hopper 142, and a manual feed hopper 144, etc. The feeder type feeding part 136 is provided with a plurality of cassette type medicine feeders 146, and a solid medication prepared in advance in each medicine feeder 146 for each medicine type can be dispensed according to the prescription. A standby hopper 140 is disposed below a feeder type feeding part 136. After collecting one package of the solid medicine discharged from each medicine feeder 146, the standby hopper 140 will be able to dispense them at a time. The solid medicine dispensed from the standby hopper 140 is supplied one package at a time to the medicine preparation means 150 via a collection hopper 142 provided below the standby hopper 140.

The manual feeding part 138 is provided separately from the feeder type feeding part 136, and can supply solid medicine to the medicine preparation means 150 similarly to the feeder type feeding part 136.

The medicine preparation means 150 is disposed in the downward direction of the feeding part 132 described above. The medicine preparation means 150 can store one package worth of solid medication received from the medicine supplier 130 via a collection hopper 142 or manual feed hopper 144, and supply them towards the medicine packaging means 180.

The medicine packaging means 180 can form each sachet b by folding a strip-shaped packaging paper prepared beforehand and heat sealing it or the like, and also package in a sachet b one dose worth of medicine that was supplied from the medicine preparation means 150. As a result, a strip of continuous body of sachets B is formed from a continuum of a large number of sachets b. The continuous body of sachets B formed by the medicine packaging means 180 is discharged towards medicine inspection part 110 through an outlet 200 provided in the body of the medicine packaging part 120.

Here, a connecting part 210 that can connect to the outlet 200 of the medicine packaging part 120 is provided to the medicine inspection device 10 constituting the medicine inspection part 110, and the medicine inspection part 110 and medicine packaging part 120 are connected via this connecting part 210. Further, it is configured such that it is possible to introduce a continuous body of sachets B dispensed from the outlet 200 into the medicine inspection part 110 via the connecting part 210, and to feed it to the medicine inspection device 10. Accordingly, in the medicine packaging device 100, when a continuous body of sachets B is formed by the medicine packaging means 180, then, the medicine contained in each sachet b of this continuous body of sachets B can be continuously inspected.

As described above, in the medicine inspection device 10 of this embodiment, based on the image obtained by photographing the medicine disposed on the inspection unit 14 with the shooting means 18, the distribution condition of the medicine in the inspection unit 14 is detected by distribution detector 62, and vibrations are generated in the area where a largest number of medicines exists among the inspection areas 26a to 26. Therefore, even if there is an overlap or contact of medicines, or the medicines are in a upright state in the sachet b supplied from medicine packaging part 120 to medicine inspection device 10, it is possible to disperse and separate the medicines by providing vibrations as well as to make them in a fallen state wherein printed characters or stamping are visible to detect the quantity and type of a medicine by medicine information detector 66. Therefore, even though medicine is packaged by a packaging paper, the medicine inspection device 10 is possible to accurately find out the quantity and type of the medicine.

In the medicine inspection device 10 of this embodiment, the vibrator 16 generates vibration in an area among the inspection areas 26a-26c with a largest quantity of the disposed medicine, and vibration is not generated in the other inspection areas 26a-26c. With this, even if a medicine is sealed inside a sachet b in a state of overlap or contact with other medicines, or sealed in an upright state, such medicines can be smoothly and effectively separated and dispersed. Therefore, in the medicine inspection device 10, it is possible to accurately capture each medicine one by one. Further, by making medicines in a fallen state, it is possible to not only accurately capture the surface of the medicine, but also to accurately capture the characters or symbols printed on the surface. Accordingly, in the medicine inspection device 10, the medicine type can be identified very smoothly and accurately.

This embodiment uses a configuration wherein vibration is generated in an area among the inspection areas 26a to 26c where there is a largest concentration of a medicine, and vibration is not generated in other areas at all, but the present invention is not limited to this, and it is also possible such as to vary the magnitude of the vibration generated in each inspection area 26a to 26c depending on the quantity of the medicine. Specifically, it is also possible to generate maximum vibration in an area among the inspection areas 26a to 26c having a highest distribution of the medicine, minimal vibration in an area having a least medicine quantity, and to generate moderate vibration in an area having moderate distribution of the medicine. In other words, it may be configured such that vibration is provided preferentially in an area among the inspection areas 26a to 26c having more medicine than an area with less quantity of medicine than this.

In the medicine inspection device 10, a need for generating vibration is determined based on the distribution condition of the medicine on the inspection unit 14 detected by the distribution detector 62, and if it is determined by the vibration controller 64 that there is a need for generating vibration, the vibration is generated by the vibrator 16, and then, an image is taken by the shooting means 18 and inspection is carried out based on the image. When it is determined by the vibration controller 64 that there is no need for providing vibration, vibration will not be generated by the vibration means 16, and based on an image photographed by the shooting means 18, inspection will be carried out for the quantity and type of the medicine contained in the sachet b. Thus, in the medicine inspection device 10, since the vibrator 16 is operated only when there is a need for dispersing the medicine, and therefore, it is possible to improve the accuracy of inspection of a medicine, and to minimize the slowing of inspection speed due to the operation of the vibrator 16.

In the medicine inspection device 10 of this embodiment, the vibrator 16 is able to generate vibrations by the elastic force of the leaf springs 28a to 28c, and therefore, the device configuration is extremely simple. Moreover, although an example of a configuration using leaf springs 28a to 28c as a source of vibration of the vibrator 16 was illustrated in this embodiment, the present invention is not limited to this, and they may be substituted by ultrasonic wave vibrator etc., for example. In addition, the vibrator 16 is capable of providing vibrations in a vertical direction by the leaf springs 28a to 28c, but the present invention is not limited to this, and it is also possible to impart vibrations in a direction other than a vertical direction such as a horizontal direction, etc.

The vibrator 16 employed in this embodiment is configured such that, among the leaf springs 28a to 28c, a leaf spring of 28a to 28c provided corresponding to an inspection area of 26a to 26c that is deemed to be in a non-vibrating state is made to be in a non-vibrating state by not imparting impact by the shock imparting means 30, but the present invention is not limited to this. Specifically, it is also possible to provide a push-down means or the like to push down the leaf springs 28a to 28c, and by pushing down the leaf spring, among the leaf springs 28a to 28c, that is in a non-vibrational state by the push-down means or the like, they may be moved away from the packaging paper (sachet b). With such a configuration, it becomes possible to reliably prevent vibration from being applied to the medicine in the region that should be non-vibrational among the inspection areas 26a to 26c, and to disperse the medicine even more accurately, and as a result, the inspection accuracy can be further improved.

In the medicine inspection device 10, the fixing parts 32a to 32c provided at one end of the leaf springs 28a to 28c are fixed at a location away from the inspection areas 26a to 26c. Due to this, the leaf springs 28a to 28c can generate substantially uniform vibrations in any position of the inspection areas 26a to 26c, and the medicine can be smoothly and reliably dispersed on the inspection unit 14.

In the medicine inspection device 10, the leaf springs 28a, 28b, 28c are disposed directly below the sachets b (continuous body of sachets B) that arrive in the inspection unit 14, and they are in direct contact with the sachet b, and vibration can be provided to the sachet b and a medicine packaged therein. Also, vibration generated by the leaf springs 28a to 28c is a decreasing vibration which will freely and gradually decrease after applying an impact by the shock imparting means 30. This vibration is a vibration suited for dispersing medicine unlike a constantly same vibration generated by conventionally known vibration providing mechanism such as ultrasonic vibrators or vibrators. Therefore, in the medicine inspection device 10, even when a medicine is fed in a state where the medicine is unevenly distributed in part of the inspection areas 26a to 26c, due to the dispersion effect by the vibration of the leaf springs 28a to 28c, it can be smoothly dispersed in the entire inspection unit 14 in a substantially uniform manner.

Further, in the medicine inspection device 10, the number of impacts applied to the leaf springs 28a to 28c by the shock imparting means 30 may be one or multiple. Although the medicine inspection device 10 showed an example of applying impact intermittently by plectrums 38a to 38c, which are attached to the rotating shafts 36a to 36c, by operating the motors 32a to 32c as explained above, the present invention is not limited to this, and it is also possible to apply the impact continuously.

In the medicine inspection device 10 of this embodiment, an annular lighting device 20 is provided in a position vertically away from the inspection areas 26a to 26c so as to surround an assumed virtual area 40. The optical axis of light-emitting diodes 44 provided in the light emitting part 42 of the lighting device 20 is directed towards the inspection areas 26a to 26c that are existing below in an oblique direction. Accordingly, it is possible to illuminate a medicine disposed on the inspection unit 14 from outside and to photograph the medicine by the shooting means 18, and to take an image to distinctly capture the contour of the medicine. Therefore, in the medicine inspection device 10, the contour or color of a medicine can be easily and accurately captured when the image obtained from the shooting means 18 is processed by a medicine information detector 66, and therefore inspection failures are minimized.

In this embodiment, a lighting device 20 is positioned vertically away from the inspection areas 26a to 26c, that is, installed at a position away in the same direction from the shooting means 18, but the distance between the inspection areas 26a to 26c and the lighting device 20 is preferably as short as possible. It is also possible to position the lighting device 20 on the sides of inspection areas 26a to 26c. It is also possible to position the lighting device 20 below the inspection areas 26a to 26c, that is, at a position in the opposite direction from the shooting means 18. Even when varying the position of the lighting device 20 in this manner, it is desirable to position the lighting device 20 such that the inspection areas 26a to 26c can be irradiated from outside towards inside in order to acquire an image wherein the contour of a medicine is prominent.

Figure 14:
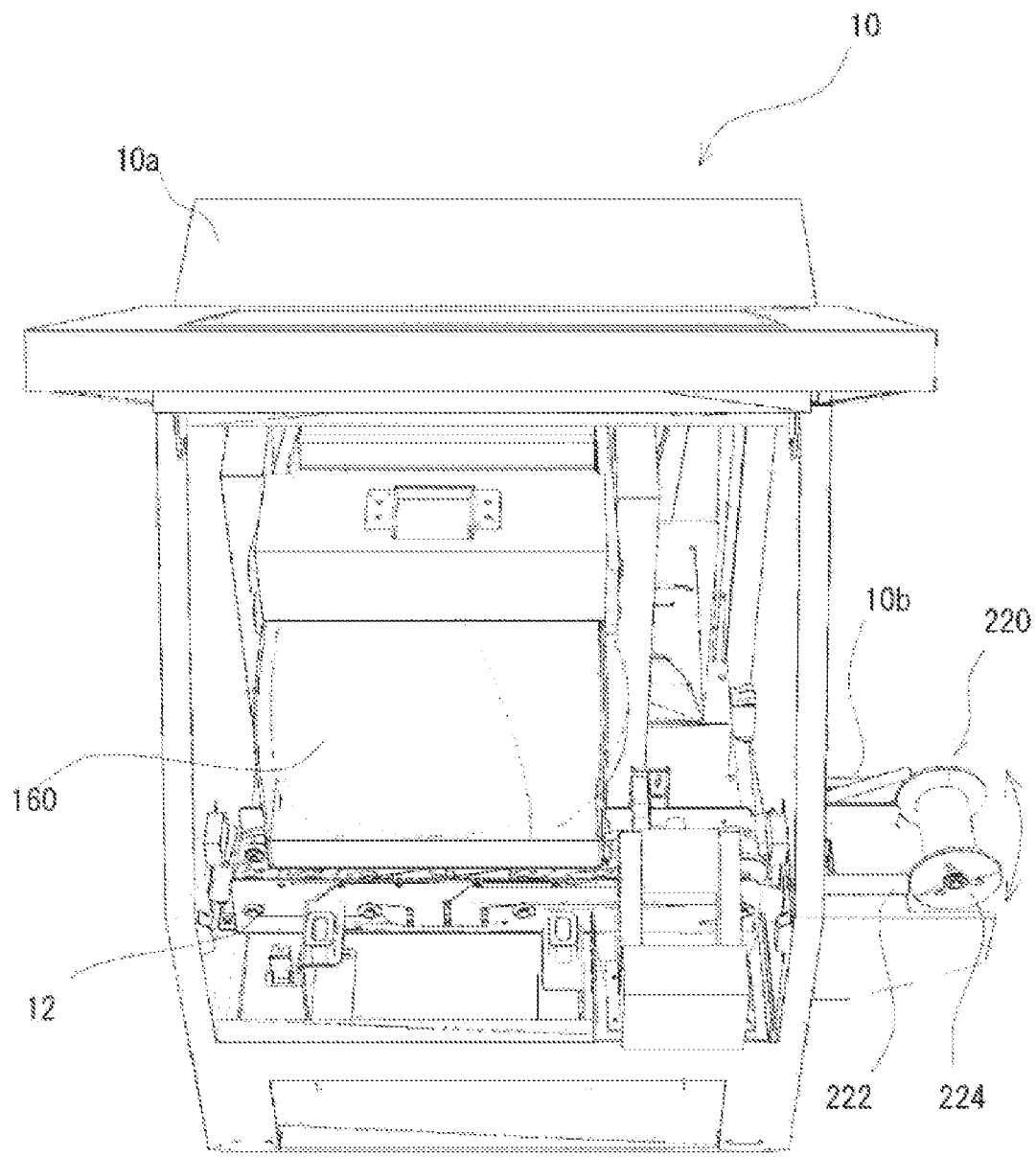
FIG. 14 is a perspective view of a medicine inspection device according to a modification example in a state wherein a front lid thereof is open.
Figure 15:
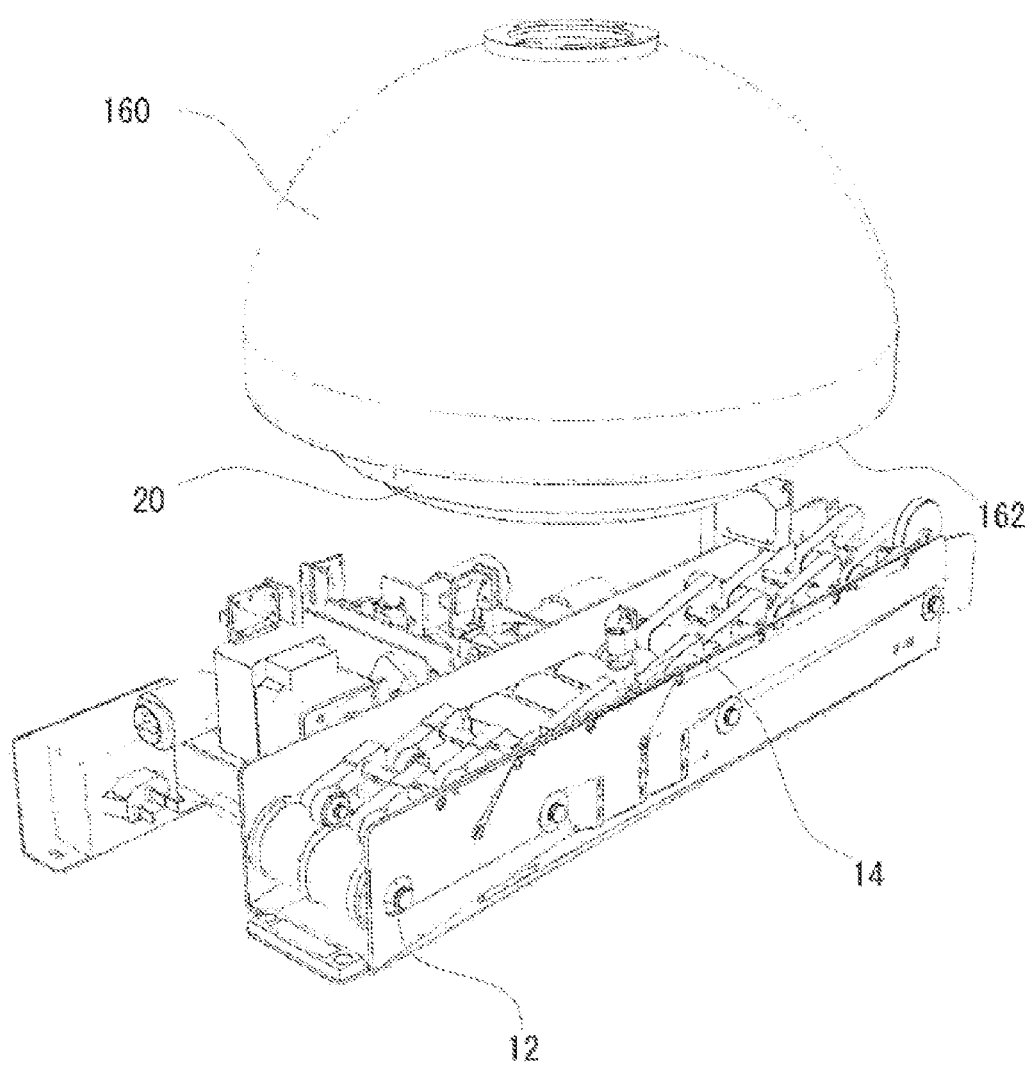
FIG. 15 is a perspective view showing the positional relationship between the lighting device and diffusion light emitting device and the transportation means used in the medicine inspection device shown in FIG. 14.

Although this embodiment showed a case of disposing an annular lighting device 20 above the inspection unit 14 to accurately capture the contour or color of a medicine disposed in the inspection unit 14, the present invention is not limited to this, and it is also possible to install above the inspection unit 14 a lighting device capable of generating diffused light such as a diffusion light emitting device 160 shown in FIG. 14 and FIG. 15 in addition to the lighting device 20, or by replacing the lighting device 20 with such an illumination device, for example.

Specifically, in the examples shown in FIG. 14 and FIG. 15, the diffusion light emitting device 160 is installed in addition to the lighting device 20. The diffusion light emitting device 160 has a hemispherical (so-called dome shape) exterior shape, and diffused light can be generated light in a circular light emitting surface 162 formed in the shape of a circular plane. The diffusion light emitting device 160 is mounted on an annular illumination device 20 such that the light emitting surface 162 is facing in the downward direction. The light emitting surface 162 is roughly parallel to the inspection unit 14, and it is possible to emit the diffused light toward the inspection unit 14 through the virtual area 40 enclosed by the lighting device 20.

By installing the diffusion light emitting device 160 as described above, a medicine disposed on the inspection unit 14 can be illuminated without any occurrence of shadows, and the contour of the medicine, the marking stamped on the surface or the printed characters etc., can be clearly captured. With this, the detection accuracy of the quantity or type of a medicine can be further improved.

Also, in the example shown in FIG. 14 and FIG. 15, although a diffusion light emitting device 160 is mounted on a lighting device 20, it is not necessary to mount it on the lighting device 20, and it may be positioned away from the lighting device 20. Moreover, the diffusion light emitting device 160 can be vertically movable or of an attachable/removable type as required.

In the medicine inspection device 10 of this embodiment, based on the prescription data, the prescription information acquisition means 68 acquires prescription information of the medicine to be inspected, and the collation means 70 collates this prescription information with the detection information acquired by the medicine information detector 66. Therefore, according to the medicine inspection device 10, it is possible to not only check the type and the quantity of medicines packed in a sachet b, but also to check whether a medicine packaged in a sachet b matches with the prescription data, and thus excels in usability. Moreover, although a configuration of collating prescription data and detection data by providing a collation means 70 was illustrated in this embodiment, the present invention is not limited to this, and a configuration without the collation means 70 is also possible. That is, the medicine inspection device 10 can be a device for just detecting the type and quantity of a medicine for the sake of inspection.

Also, in the medicine packaging device 100 of this embodiment, a connecting part 210 for connecting with the outlet 200 of the medicine packaging part 120 is provided on the medicine inspection device 10 side of the medicine inspection part 110. With this, by connecting the medicine inspection part 110 and medicine packaging part 120 through the connecting part 210 and operating both of them in cooperation integrally, the operation starting from packaging of the medicine till inspection can be conducted as a chain of tasks.

Although this embodiment illustrated a configuration incorporating the medicine inspection device 10 as a medicine inspection part 110 of the medicine packaging device 100, the present invention is not limited to this, and the medicine inspection device 10 may also be independently used. Further, although a configuration was illustrated wherein a medicine inspection part 110 including a medicine inspection device 10 was integrated with a medicine packaging part 120 by providing a connecting part 210, it is also possible to use the medicine packaging device 100 without integrating the medicine inspection part 110 and medicine packaging part 120. Even in this case, by enabling the medicine inspection part 110 and medicine packaging part 120 to operate in cooperation, the efficiency of a chain of operations starting from packaging of the medicine till inspection can be improved.

Although an example of inspecting a medicine packaged in a packaging paper was illustrated in this embodiment, the present invention is not limited to this, and it is also possible to dispose a medicine on the inspection unit 14 prior to packaging by a packaging paper and to carry out the inspection.

Although an example of inspecting both quantity and type of a medicine disposed on the inspection unit 14 was illustrated in this embodiment, the present invention is not limited to this, and it is also possible to inspect only the quantity or the type of a medicine.

Further, in the medicine inspection device 10, the sachet b formed by packaging medicines is supplied continuously as a continuous body of sachets B, and is disposed sequentially on the inspection unit 14. Therefore, in order to further improve the inspection accuracy, it is desirable to contemplate some measures to improve the positioning accuracy when conveying the continuous body of sachets B so that the center of each sachet b arrives at the center of the inspection unit 14. Specifically, for example, by having heat seal sections, or perforation formed between the adjacent sachets b in the continuous body of sachets B as a mark, and by using this mark as reference, it is possible to improve the positioning accuracy of a sachet b in the inspection unit 14. Also, if the length of a sachet b is known beforehand, it may be configured such that, after a section to be referenced such as the head section of a continuous body of sachets B is detected by a supply detection means 24a, the continuous body of sachets B is fed sequentially only by an extent equal to the length of the sachet b at a time, for example.

In the medicine inspection device 10 of this embodiment, the standing, overlap, contact and the like of medicines is eliminated by applying vibrations with leaf springs 28a to 28c to the sachets b that arrived at the inspection areas 26a to 26c, but it is also possible eliminate standing or the like of medicines by further providing separate vibrations.

Specifically, the medicine inspection device 10 illustrates an example of moving a continuous body of sachets B of packaged medicine by the transportation means 12 only at a certain direction towards the inspection unit 14, but instead of this, on the way from the upstream of transportation direction to the inspection unit 14, it is also possible to impart vibration (oscillation) to the medicine in the horizontal direction by reciprocating the continuous body of sachets B in small motions in the horizontal direction. In other words, by oscillating a continuous body of sachets B by alternately dispatching and retracting it, vibration in the horizontal direction may be imparted to the medicines inside each sachet b. By this, a medicine sealed inside a sachet b in an upright state will assume a fallen state by the time it reaches the inspection unit 14. Further, it also becomes possible to reliably part and separate medicines that are overlapped with or in contact with other medicines.

Furthermore, by oscillating a continuous body of sachets B (sachet b) in the horizontal direction on the way from the upstream of transportation direction to the inspection unit 14 as described above, it becomes possible to make the medicines in a fallen and dispersed state before they reach the inspection unit 14. Therefore, a possibility that the vibration needs to be applied by the leaf springs 28a to 28c in the inspection unit 14 can be reduced. With this, it becomes possible to further reduce the time required for the inspection operation.

In the modified example mentioned above, although an example was illustrated, wherein an overlap, contact or upright state of medicines is eliminated by vibrating a continuous body of sachets B (sachet b) in a horizontal direction in addition to imparting vibration in the inspection unit 14, it is also possible to combine other means with vibrating a continuous body of sachets B (sachet b) in the horizontal direction, or other means instead of vibrating the continuous body of sachets B (sachet b) in horizontal direction for solving the problem of overlap, contact, or upright state of the medicines. Specifically, as shown in FIG. 12, in the conveyance path of the packaging paper in which the medicine is packaged, an upright-state elimination means 110, which operates so as to follow the surface of the packaging paper, may also be provided in a place that is upstream of the inspection unit 14 in the conveyance direction.

Figure 12:
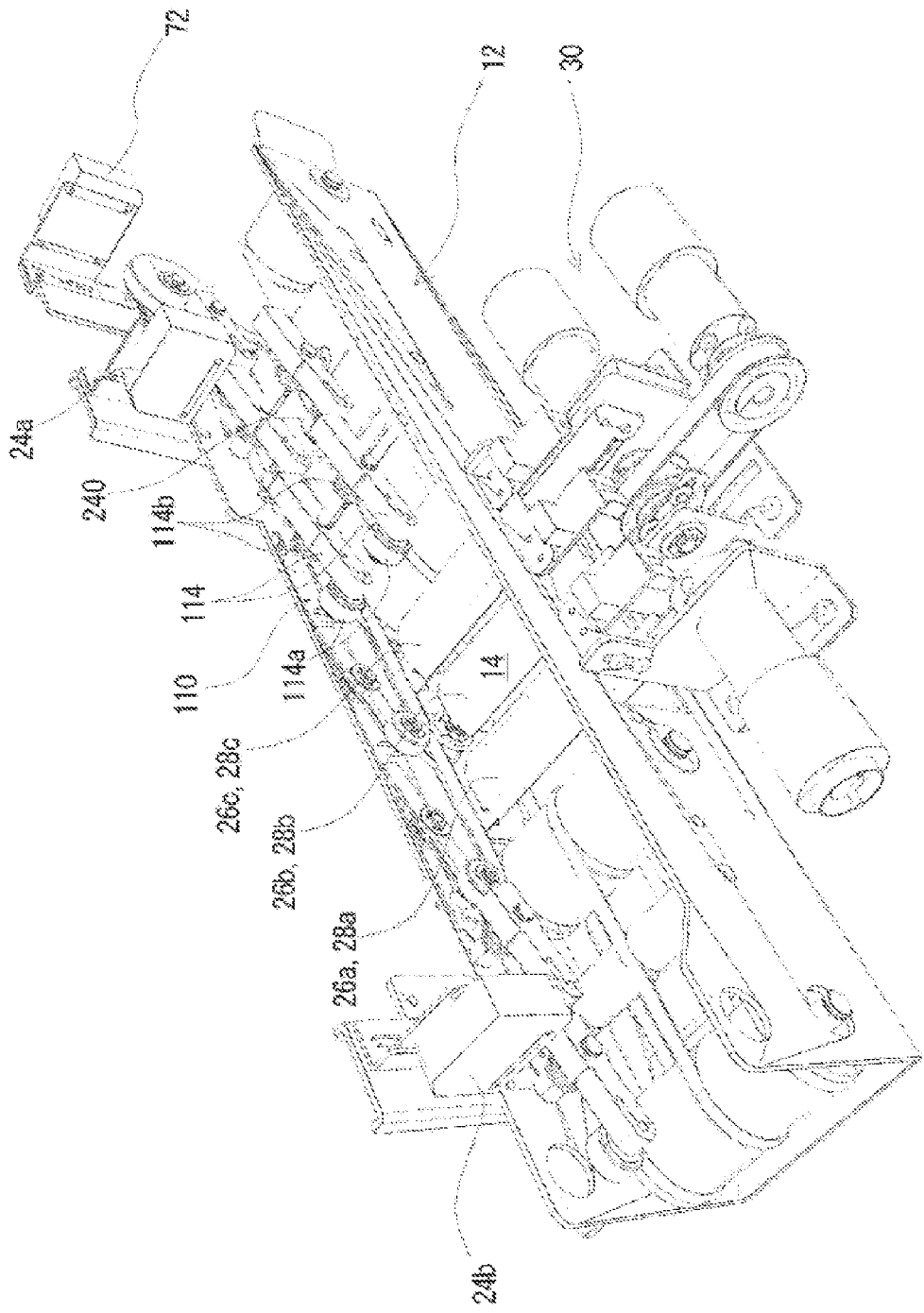
FIG. 12 is a perspective view showing an example of providing an upright-state elimination means shown in FIG. 13(a).

To explain more explicitly, as shown in FIG. 12 and FIG. 13, the upright-state elimination means 110 is comprised of a spindle 112 provided so as to across the conveyance path of the packaging paper, and arms 114 mounted so as to freely rotate with respect to the spindle 112. A plurality of arms 114 are provided along the axial direction of the spindle 112, that is, in the width direction of the conveyance path. A roller 114a is attached to the tip of an arm 114. Also, the arms 114 are biased towards the conveyance path by springs 114b. By this, with respect to the surface of the packaging paper traveling through the conveying path, a roller 114a can contact the packaging paper with appropriate strength that does not to damage the packaging paper or the medicine. Therefore, when the packaging paper travels through the conveyance path, the rollers 114a roll along the surface of the packaging paper, and the arms 114 rotate around the spindle 112 so as to follow the surface of the packaging paper. Moreover, the material of the rollers 114a can be resin, metal, or etc. like the arms 114, or may also be an elastic body like sponge, rubber etc., or a soft material. If the rollers 114a are formed of a resin or metal, it is less likely to have deformation or wear-out even on prolonged use, and a stable performance can be maintained. Further, if an elastic material such as sponge or rubber etc. or a soft material is used for the rollers 114a, the shock applied to medicines can be suppressed to a minimum level, and breakage or damage of the medicine can be prevented.

When an upright-state elimination means 110 as described above is provided, during the period the packaging paper is conveyed towards the inspection unit 14, the rollers 114a contact the packaged medicine through the packaging paper. With this, medicines packaged in the packaging paper are pushed down, and an overlap or contact of the medicines is eliminated. Further, a medicine contained in an upright state is pushed down by contacting the arms 114 (rollers 114a) through the packaging paper.

When an upright-state elimination means 110 described above is provided, it becomes possible to disperse the medicine before the sachet b for inspection reaches the inspection unit 14, and also overturn a medicine that was packaged in an upright state. Thus, the frequency of occasions in which medicines need to be dispersed by imparting vibration at the inspection unit 14 can be minimized. With this, it is possible to further decrease the time required for the inspection operation.

Figure 13A:
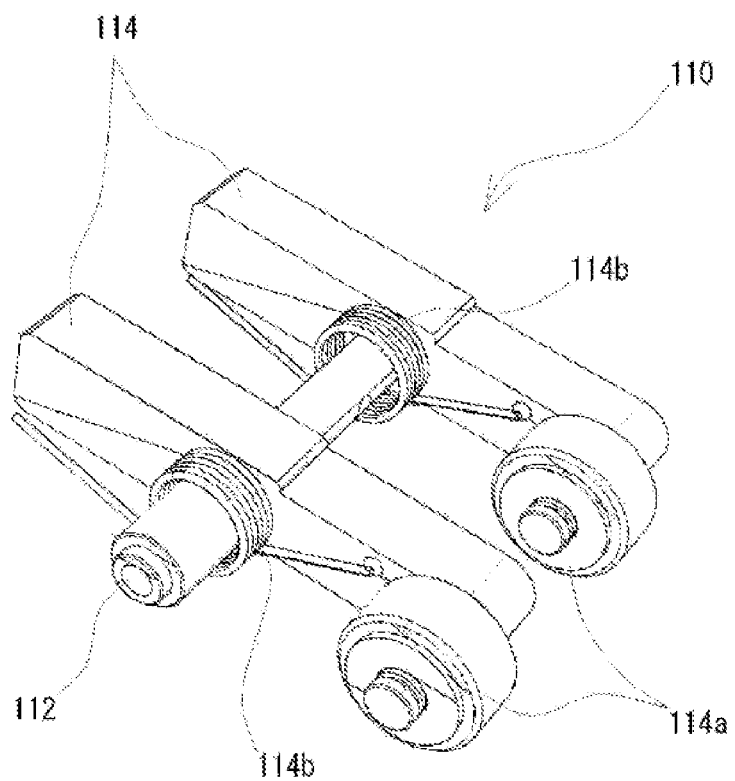
FIGS. 13A and 13B are perspective views showing an example of an upright-state elimination means.
Figure 13B:
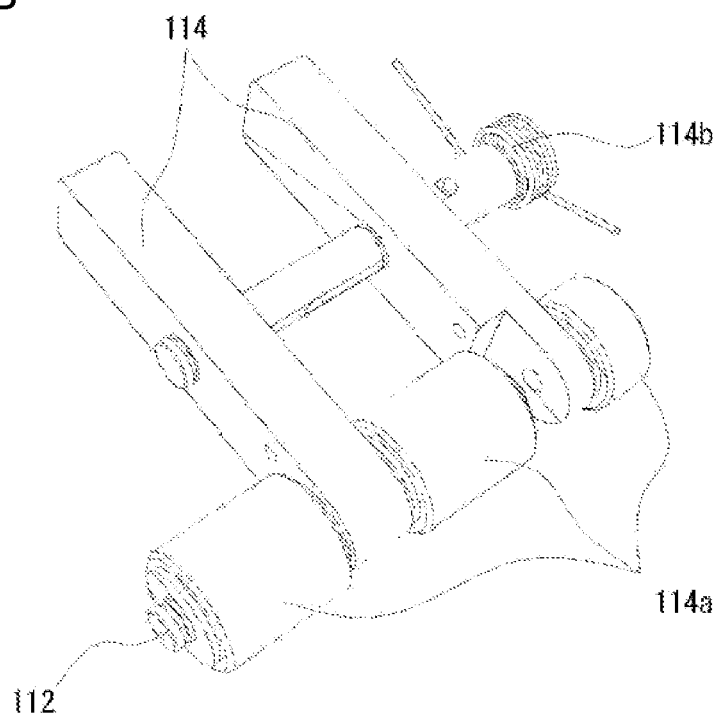

In the upright-state elimination means 110 described above, the rollers 114a may be provided in an area that is a part of the width direction of the conveyance path formed by the transportation means 12 as shown in FIG. 12, or the rollers 114a may be provided over the entire width of the conveyance path as shown in FIG. 13B by using rollers 114a that are wider than the ones shown in FIG. 13A. When such a configuration is used, since the entire surface region of each sachet b is traced by rollers 114a, it becomes possible to more reliably overturn a medicine that was packaged in an upright state in sachet b. With this, by analyzing using an image taken by the shooting means 18, the type and quantity of a medicine can be identified with certainty, and the inspection accuracy can be further improved.

As explained above, reciprocating a continuous body of sachets B (sachet b) in small motions in the horizontal direction to oscillate the continuous body of sachets B in the horizontal direction and overturning a medicine packaged in an upright state by providing an upright-state elimination means 110 are both effective measures for improving the medicine inspection accuracy and improving the inspection speed by reducing the frequency of vibration generation in the inspection unit 14. In the medicine inspection device 10, though it is possible to adopt these measures individually, it is preferable to use both measures in tandem. By coupling the oscillation of a continuous body of sachets B with the upright-state elimination means 110, it is possible to achieve further improvements in the inspection accuracy and inspection speed by combining the effects of both.

In the medicine inspection device 10, a continuous body of sachets B is supplied in the form of being linked to each other as a strip, and therefore, the medicine inspection operation can be continuously carried out and the speed of inspection operation can be improved. On the contrary, the packaging paper forming the sachet b is formed of a paper or a thin film etc., and it is assumed that the packaging paper is prone to damage even without applying a force that is not so large. Also, many of the continuous body of sachets B are provided with perforations in the boundary region of each sachet b so that a patient or the like can easily cut off each sachet b. Therefore, there is a possibility that, when introducing a continuous body of sachets B from the introduction unit 10b, the action of a tension exceeding the strength of the continuous body of sachets B may occur due to the influence of the force trying to pull the continuous body of sachets B into the device and a force acting to the outside of the inspection device due to the continuous body of sachets B hanging or the like, and the continuous body of sachets is damaged or broken. Therefore, in the medicine inspection device 10, it is desirable to provide a protection mechanism or the like of the continuous body of sachets B so that damage etc. of the continuous body of sachets B will not occur when introducing the sachets into the device.

Specifically, it is desirable to provide a protection mechanism comprising an introduction unit oscillating member 220 in the introduction unit 10b of the medicine inspection device 10 as shown in FIG. 14, for example. The introduction unit oscillating member 220 is provided with an introduction unit oscillating arm 224 and a roller 226. The introduction unit oscillating arm 224 is installed such that it can oscillate in a vertical direction as shown by the arrow in the diagram, and is biased towards the upper direction by a spring or the like, which is not illustrated. The roller 226 is fixed such that it can rotate freely with respect to the introduction unit oscillating arm 224.

A continuous body of sachets B supplied to the medicine inspection device 10 travels over the roller 226 of the introduction unit oscillating member 222, and is introduced into the medicine inspection device 10. When there is an action of forces such as a pulling force acting when a continuous body of sachets B is conveyed towards the inspection unit 14, and a force acting when a continuous body of sachets B is dangling, etc., the introduction unit oscillating arm 224 that is normally biased upwards will oscillate in the lower direction, and this prevents an excessively large force from acting on a continuous body of sachets B. With this, a damage or breakage of a continuous body of sachets B can be prevented. On the other hand, if there is an excess in a tension of the continuous body of sachets B itself, the roller of the introduction unit oscillating member 222 naturally rises due to an upward bias of spring etc., and because the continuous body of sachets B will also be hauled up with this, it becomes possible to impart beforehand the excess tension to this part.

In the medicine inspection device 10 shown in this embodiment, in order to properly inspect the medicines that have been packaged one dose each in sachet b, it is necessary to dispose a sachet b in a suitable position on the inspection unit 14. That is, if the position of the sachet b containing a medicine for inspection deviates from the inspection unit 14, the medicine in sachet b to be inspected may come in a position away from the inspection unit 14, and accurate inspection may not be possible.

When sequentially supplying sachets b in the form of a continuous body of sachets B, even if the deviation between the sachets b and inspection unit 14 is very small in the initial stages, there is a possibility that the deviation may accumulate in the inspection of several sachets b, and before long the positional deviation between the inspection unit 14 and sachets b may become large enough to lead to inspection failure. Therefore, it is desirable that positioning of each sachet b on the inspection unit 14 is possible with high positioning accuracy, and especially, when medicine to be inspected is packaged and supplied in the form of a continuous body of sachets B, it is necessary to position a sachet b on the inspection unit 14 with a high positioning accuracy.

Here, most of the continuous bodies of sachets B to be supplied to the medicine inspection device 10 are forming sachets b by folding a strip-shaped packaging paper into two substantially in the middle in the width direction and by sealing with longitudinal sealing parts s1 extending in the width direction of continuous body of sachets B, and a lateral sealing part s2 extending in the length direction of the continuous body of sachets. Further, between two sachets b and b that are continuous in the length direction of the continuous body of sachets B, the longitudinal sealing parts s1 and s1 are formed with a slight gap therebetween, and a boundary d of perforation or the like is formed between the sachets. Therefore, if it is possible to properly identify the position of the boundary d, then the position of sachet b (continuous body of sachets B) can be fine-tuned based on this result and the positioning accuracy between the sachets b and the inspection unit 14 can be improved.

However, it is not likely that the perforations or the like forming the boundary d can be accurately identified by imaging etc. Also, if the image resolution is enhanced to the point that the boundary d can be identified, it is likely that the processing speed will decline because of image processing speed etc. Therefore, if directly deriving the position of boundary d is difficult or if it is likely that the processing speed or the like will decrease because of the direct derivation etc., the positional information of the boundary d can be determined based on the positional information of the longitudinal sealing part s1 such as the positioning control means 230 shown below.

Figure 18:
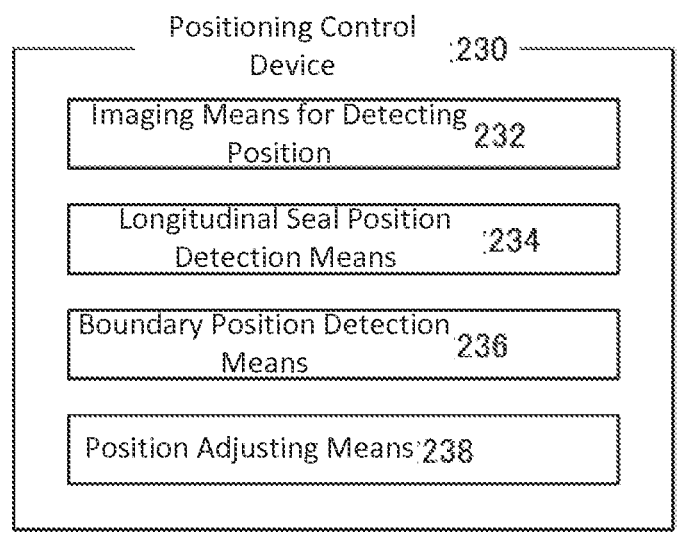
FIG. 18 is a block diagram showing a configuration of a positioning control means.

Specifically, the positioning control device 230 shown in FIG. 18 includes a position detection shooting means 232 for taking an image of longitudinal sealing parts s1, and a longitudinal seal position detecting means 234 to derive the position of the longitudinal sealing part s1 by analyzing the image obtained by the position detection shooting means 232. Also, the positioning control means 230 is provided with a boundary position detection means 236 for deriving the position of the boundary d based on the position of the vertical seals s1 derived by the longitudinal seal position detecting means 234, and a position adjusting means 238 for fine tuning the position of the continuous body of sachets B by operating the transportation means 12 based on the detection result of the boundary d.

With regard to two sachets b and b that are continuous in the longitudinal direction of a continuous body of sachets B, the position detection shooting means 232 is capable of setting a vertical seal position detection region that includes at least a part of the two longitudinal sealing parts s1 and s1 positioned next to each other with the boundary d therebetween, and taking an image of that region. Specifically, the x coordinate of the seal marks (for example, marks of knurling points of the welding rollers (not illustrated)) formed in the longitudinal sealing parts s1 and s1 in the said region and its total number can be determined from the image, and by adding all the coordinates and dividing by the total number, the boundary position can be derived. Or, by measuring the leftmost and rightmost x coordinates of the seal marks of the said longitudinal sealing position detection region and deriving its intermediate value, the coordinates of the position of the boundary d can be derived. The position adjusting means 238 compares the position of the boundary d derived from the boundary position detection means 236 and the position where the boundary d should be positioned, and operates the transportation means 12 so that the boundary d comes to the normal position.

By providing a positioning control device 230 as described above, even if the boundary d of the sachets b and b is perforations or the like, which is difficult to accurately identify by just taking a photograph of it, it is possible to accurately determine the position of the boundary d of a sachet b, and based on this result, the sachet b to be inspected can be accurately positioned with respect to the inspection unit 14. With this, the inspection accuracy and inspection speed of the medicine inspection device 10 can be further improved.

In the above-mentioned medicine inspection device 10, it is desirable to prevent the transportation errors of the continuous body of sachets B in order to accurately position a sachet b with respect to the inspection unit 14. Here, in order to improve the reliability of transportation of the continuous body of sachets B, it is preferable to provide a pushing mechanism for pushing the continuous body of sachets B onto the conveyance surface of the transportation means 12. Therefore, as shown in FIG. 12, in the medicine inspection device 10, it is desirable to provide one or a plurality of pushing rollers 240 in the middle of the conveyance path formed by the transportation means 12 to push the continuous body of sachets B on the conveyance surface with the help of these pushing rollers 240.

≪≪ Second Embodiment ≫≫

Next, a medicine inspection device 300 according to the second embodiment of the present invention will be explained in detail while referring to diagrams. Moreover, in the medicine inspection device 300 of this embodiment, the same referential numbers are used for the parts that are common to the medicine inspection device 10 described above, and their detailed description may be omitted.

Figure 19:
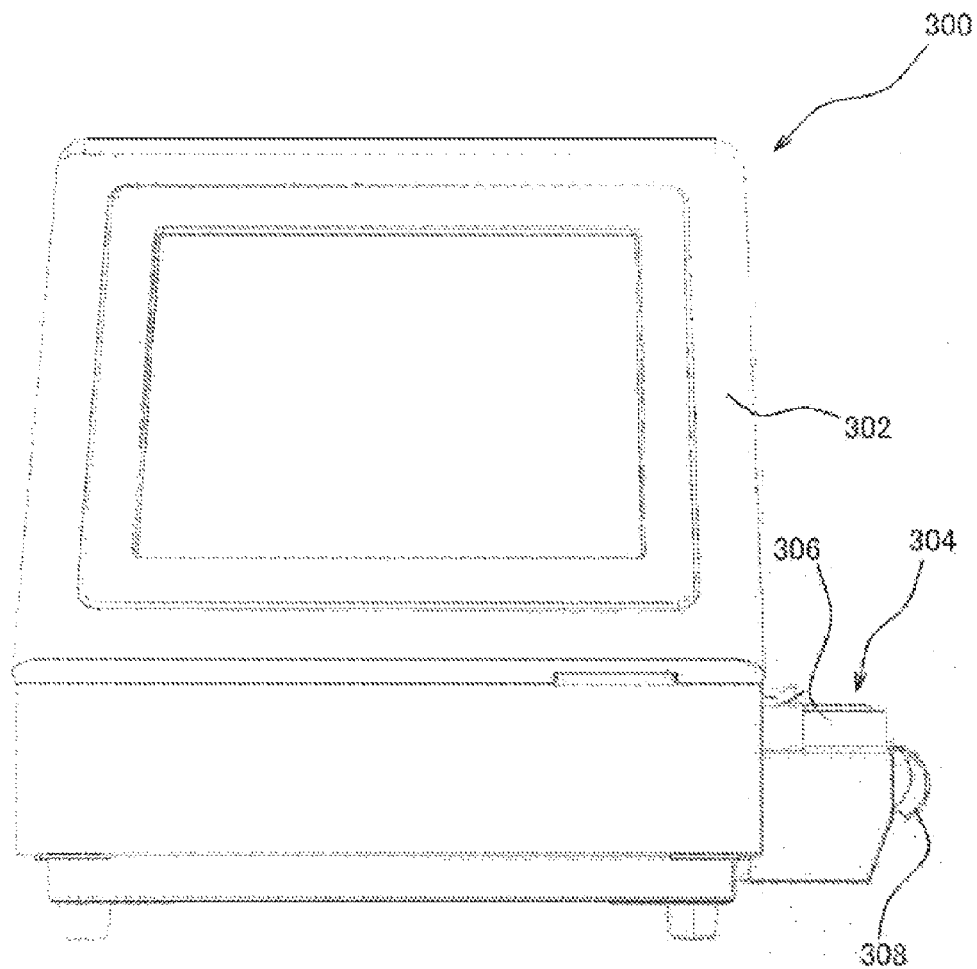
FIG. 19 is a front view showing a medicine inspection device according to the second embodiment of the present invention.
Figure 20:
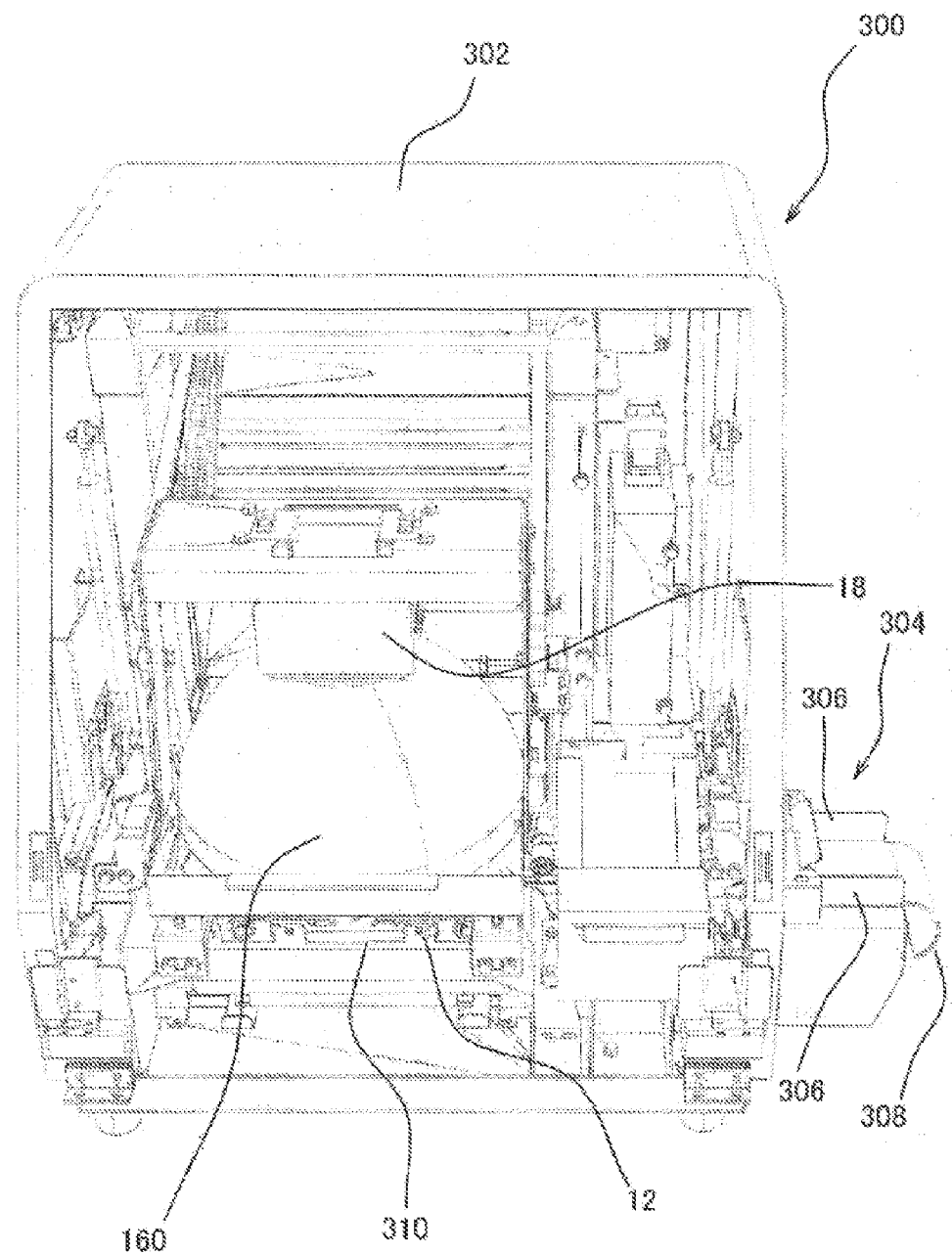
FIG. 20 is a perspective view showing the internal structure of the medicine inspection device shown in FIG. 19.

As shown in FIG. 19, the medicine inspection device 300 has approximately the same exterior as the above-mentioned medicine inspection device 10. As shown in FIG. 20, the medicine inspection device 300 is provided with the medicine inspection device 10 described above, a similar transportation means 12, and a shooting means 18 in the casing 302. Further, the medicine inspection device 300 is provided with a diffusion light emitting device 160 used in the modified example shown in FIG. 14. On the other hand, the configuration of the medicine inspection device 300 differs from the medicine inspection device 10 in that the vibrator 16 and the annular lighting device 20 are excluded. The configuration of the medicine inspection device 300 also differs from that of the medicine inspection device 10 in that an inspection unit 310 instead of inspection unit 14, a control device 330 instead of control device 22 (see FIG. 25), and an introduction unit 304 instead of introduction unit 10b are provided. The medicine inspection device 300 is described below with a focus on the characteristic configuration.

The introduction unit 304 is provided on the side surface of the casing 302 for introducing medicines for inspection. The introduction unit 304 has guide pieces 306 provided on both sides in order to guide a sachet b or a continuous body of sachets B so that it does not incline when supplied to the inside of the casing 302. Moreover, the end section of a plate that constitutes the bottom surface 308 of the introduction unit 304 is downwardly-bent in an arc shape so that a continuous body of sachets B does not get caught when the continuous body of sachets B is supplied.

Figure 21:
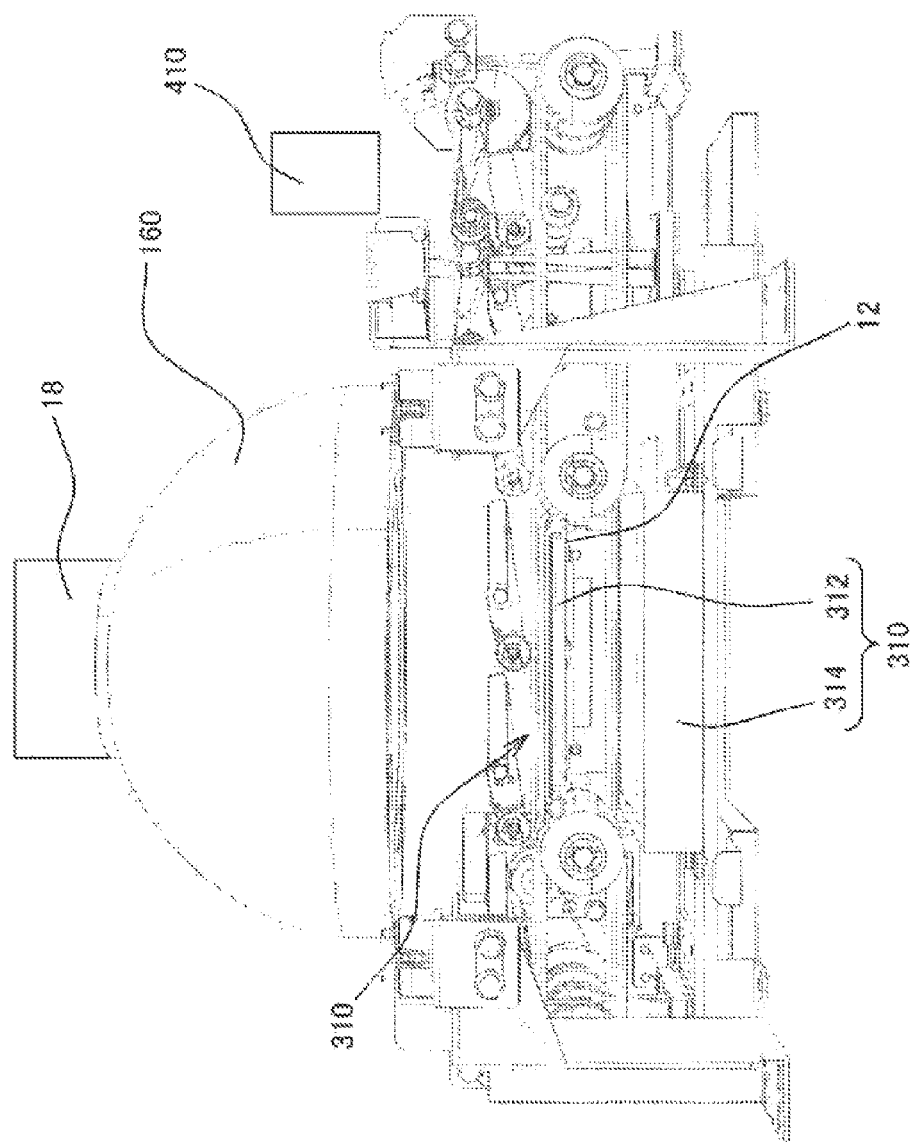
FIG. 21 is a side view showing the main configuration of the medicine inspection device shown in FIG. 19.
Figure 22:
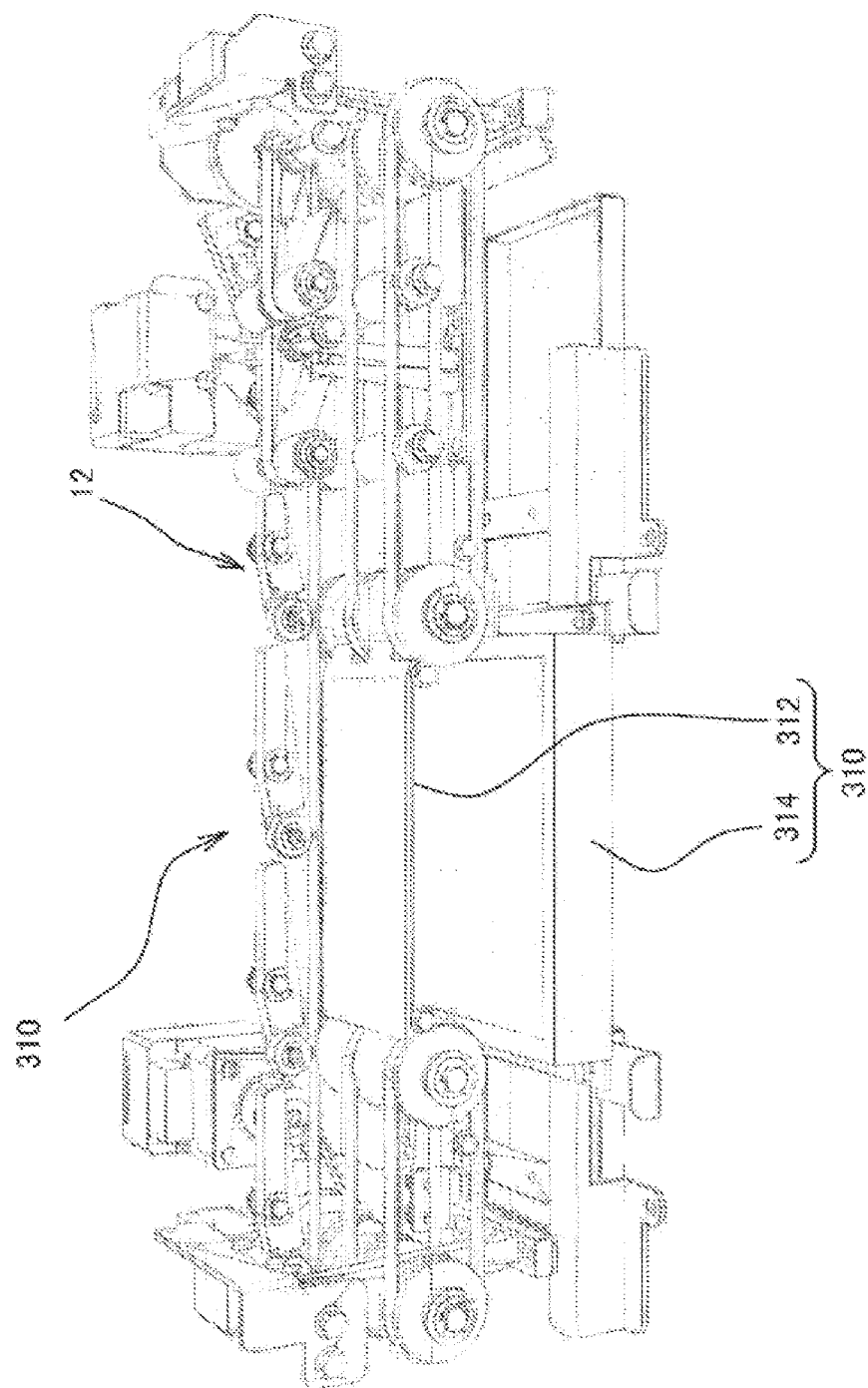
FIG. 22 is a perspective view showing the configuration of the inspection unit and near rear/front means of the medicine inspection device shown in FIG. 19.
Figure 23:
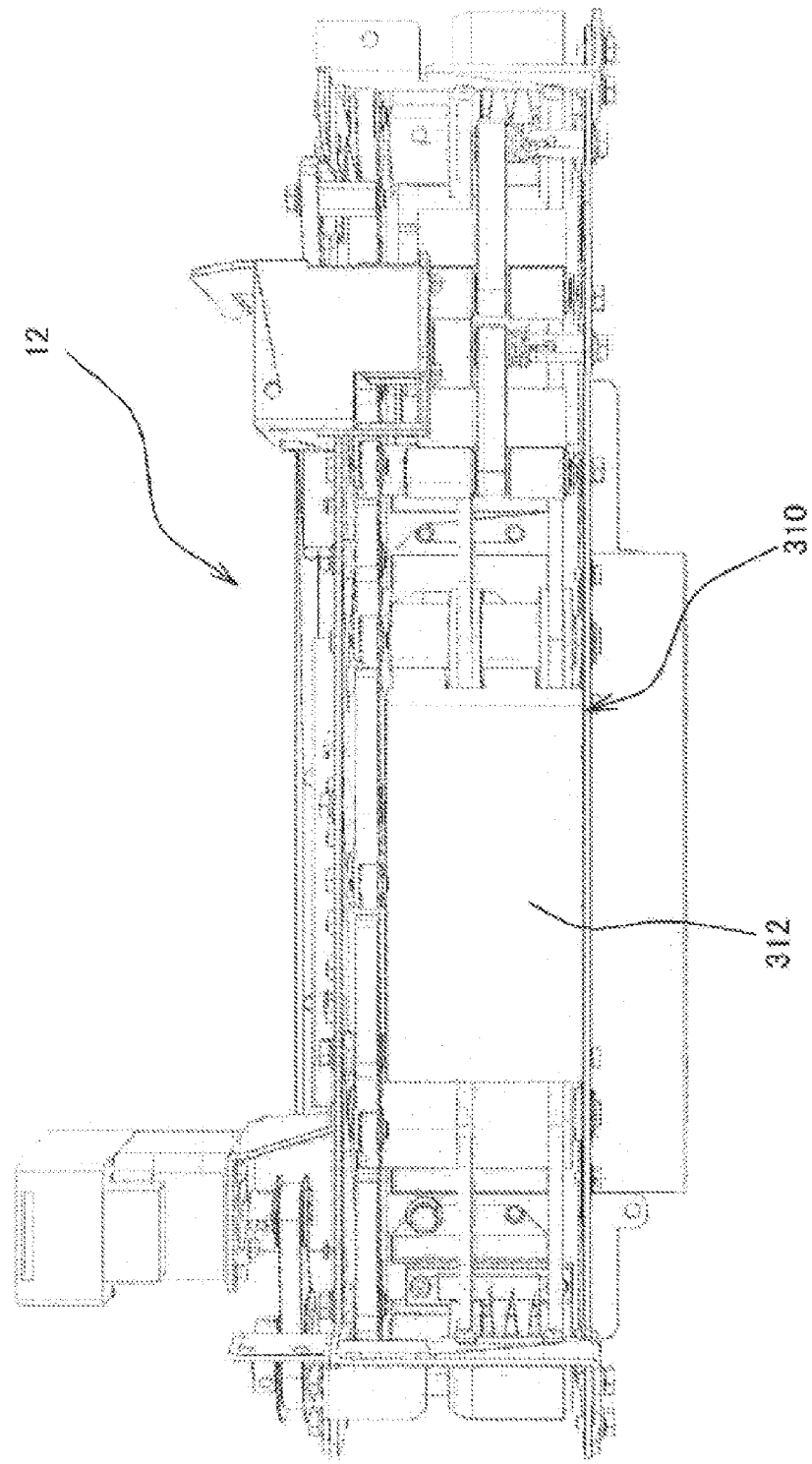
FIG. 23 is a plane view showing the configuration near the inspection unit of the medicine inspection device shown in FIG. 19.

The inspection unit 310, similar to the inspection unit 14 of the first embodiment described above, is a section where medicine for inspection packaged in a sachet b is disposed. As shown in FIG. 20 and FIG. 21, the inspection unit 310 is disposed directly below the shooting means 18 and the diffusion light emitting device 160 in the same way as the inspection unit 14. As shown in FIG. 20 through FIG. 23, the inspection unit 310 is provided with an imaging stage 312 for disposing a sachet b, and a backlight 314 to irradiate a sachet b disposed on the imaging stage 312 from the back side.

The imaging stage 312 is fabricated from a transparent plate, and has a size that is large enough for one sachet b to be mounted thereon. The backlight 314 is provided on the rear side (lower direction in the diagram) of the imaging stage 312, that is, in a region opposite to the shooting means 18 through the imaging stage 312. The backlight 314 is intended for illuminating substantially the entire area of the imaging stage 312, and can illuminate the whole sachet b mounted on the imaging stage 312 from the back side.

Figure 24A:
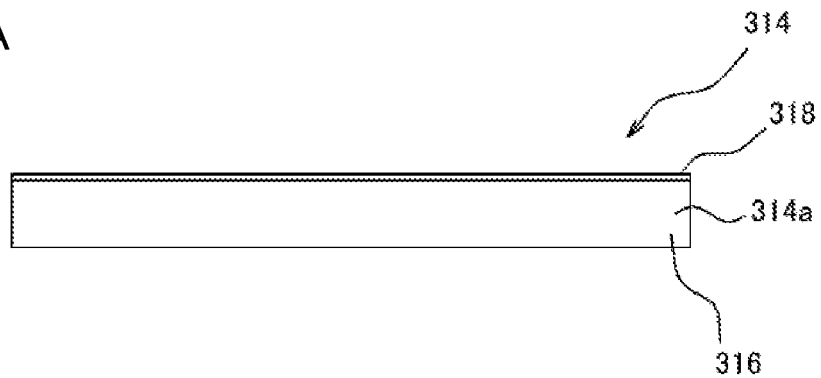
FIGS. 24A and 24B are, respectively, a side view conceptually showing a configuration of the rear/front means and a plane view of mesh materials.

The backlight 314 can emit light in a dot shape at each predetermined pitch to substantially the entire illumination region of the imaging stage 312. Specifically, as shown in FIG. 24, the backlight 314 is provided with a light source part 316 housed inside a casing 314a, and a mesh member 318 provided on the top surface of the casing 314a. The casing 314a is configured from a box with its top open. The light source part 316 is provided with light emitting diodes as light source. Further, the light source part 316 is designed to generate a light of a wavelength same as or longer than red. In this embodiment, light emitting diodes capable of generating red color light is used as the light source of the light source part 316. Further, the optical axis of the light emitting diodes provided in the light source part 316 is directed in substantially the perpendicular direction of the imaging stage 312.

Figure 24B:
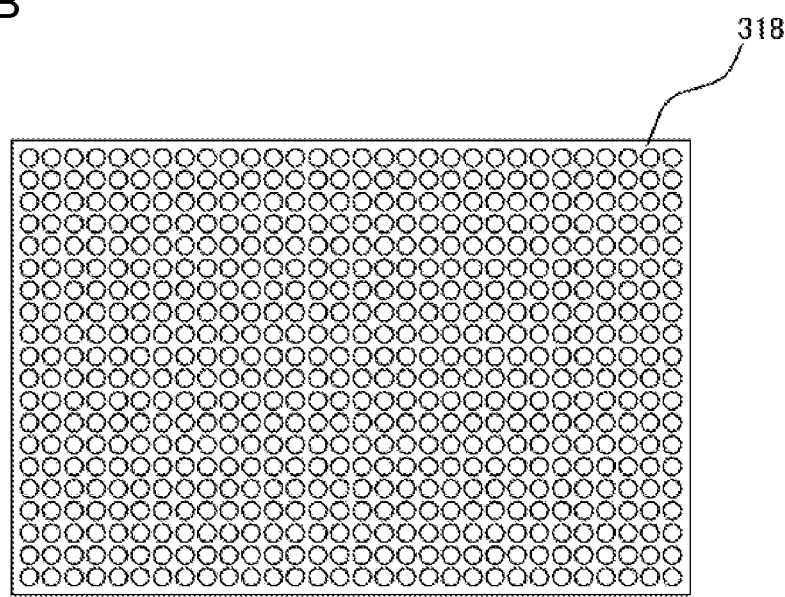

A dot forming part 318 is provided between the light source part 316 and the imaging stage 312 on which a sachet b is to be disposed. As shown in FIG. 24B, the dot forming part 318 is configured from a mesh having grids (openings) of predetermined pitch. Accordingly, when the light source part 316 emits light, the light will pass through the dot forming part 318, and light in a dot pattern is emitted onto the imaging stage 312.

The control device 330 used in this embodiment is implemented on a computer by installing a software to the computer. The control device 330 has a configuration shown in FIG. 25, and is capable of executing a medicine inspection process to check whether medicine packaged in each sachet b is as per prescription, and a foreign object detection process to find out whether there is a foreign object other than the medicine in each sachet b.

≪Medicine Inspection Process≫

Figure 25:
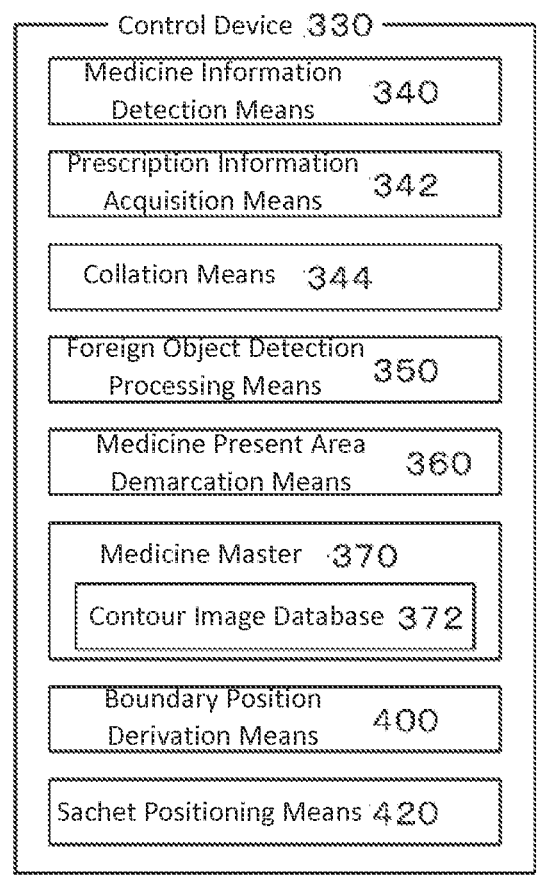
FIG. 25 is a block diagram showing the configuration of the control unit employed in the medicine inspection device shown in FIG. 19.
Figure 26:
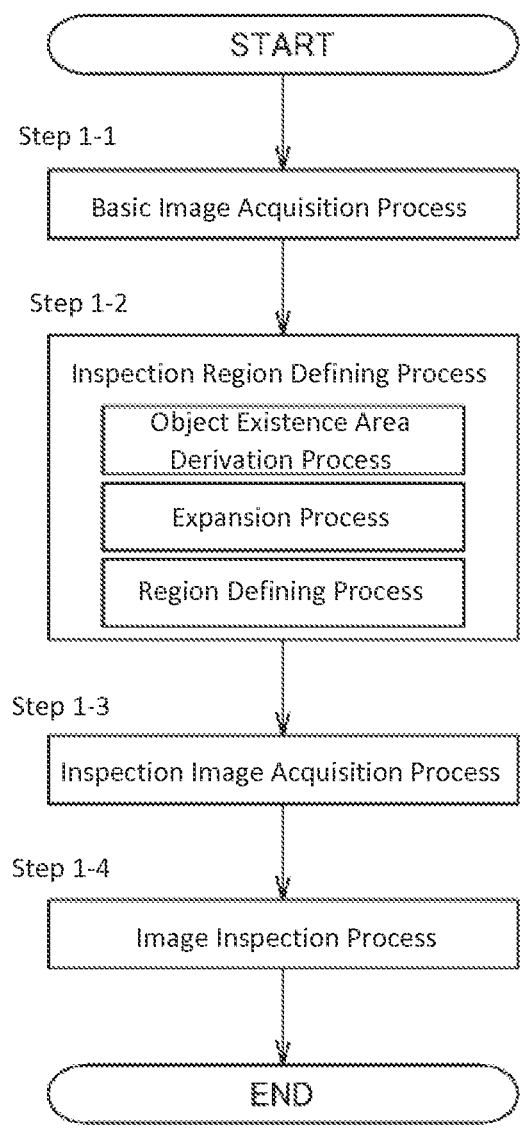
FIG. 26 is a flowchart describing the execution flow of the medicine inspection process performed in the medicine inspection device of FIG. 19.

As shown in FIG. 25, the control device 330, as an inspection process execution means for executing the medicine inspection process, includes a medicine information detector 340 and a prescription information acquisition means 342, and verification means 344. The medicine information detector 340 performs identification of medicine type as well as counting of medicine based on an image photographed by the shooting means 18. As shown in FIG. 26, the medicine information detector 340 can detect the information (type, quantity) about the medicine by sequentially executing an image processing that is roughly categorized into three steps that are a basic image acquisition process, inspection area defining process, and image inspection process.

Figure 27A:
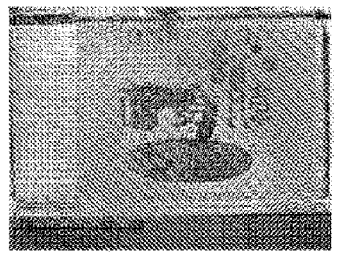
FIGS. 27A, 27B, 27C, 27D, 27E, 27F, 27G, and 27H are images showing the images taken during the execution of medicine inspection process in the medicine inspection device of FIG. 19.

Specifically, the medicine information detector 340 acquires an image (hereafter also referred to as 'back lit image') obtained by the shooting means 18 by illuminating a sachet, which is disposed on the imaging stage 312, from the back side (the lower side in the diagram) by the above-mentioned backlight 314 in the basic image acquisition process of step 1-1, as the basic image for medicine inspection. With this, a basic image shown in FIG. 27A is obtained.

Here, when printing or the like is not provided on the sachet b, substantially the whole section imaged in black color or dark color in the basic image (back lit image) is assumed to be due to objects such as medicine etc. However, if printing is provided on the sachet b, the printed area is also imaged in a black color or a dark color similarly to objects such as a medicine etc. Therefore, it is likely that a section that is imaged in black color or a dark color in the basic image described above includes an area in which printing is provided (print area). Accordingly, in order to accurately determine the medicine type or quantity by an image inspection, it is necessary to identify and exclude a print area from a region imaged in the black color or a dark color in the basic image obtained in the basic image acquisition process.

Figure 28:
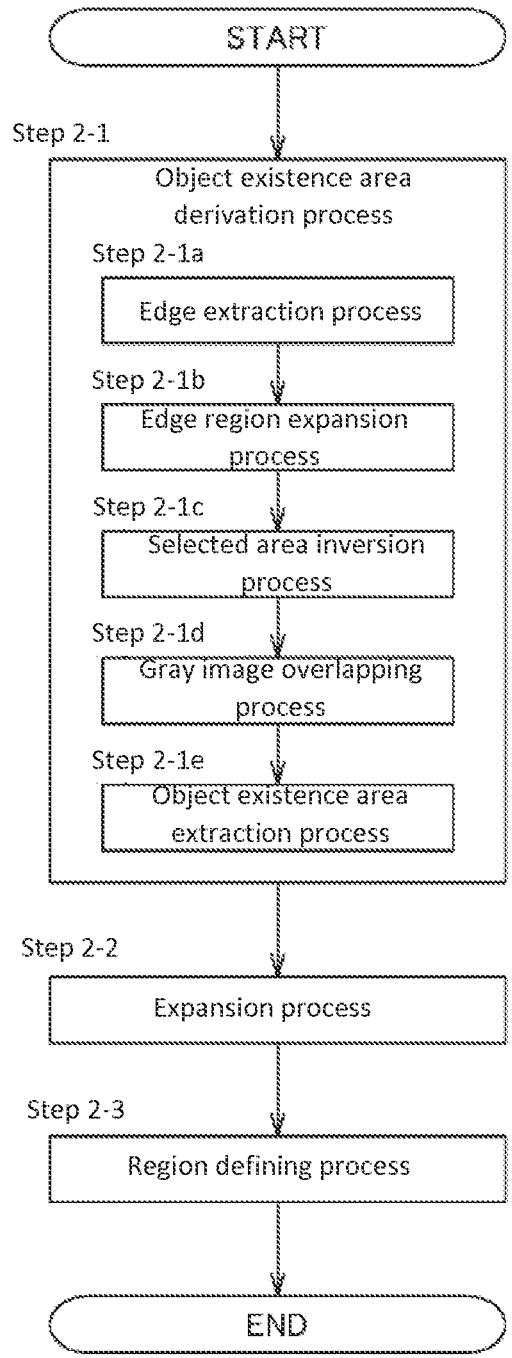
FIG. 28 is a flowchart describing the execution flow of the medicine inspection process performed in the medicine inspection device of FIG. 19.

In the inspection area defining process executed in step 1-2, the region wherein an object such as medicine exists is extracted by removing the print area from the said basic image, and with this extracted region as a reference, a process for defining an appropriate area for image inspection is executed. Specifically, in the inspection area defining process, a process comprised of three processes that are an object existence area derivation process, an expansion process and a region defining process is executed by the medicine information detector 340. The inspection area defining process is executed as per the flowchart shown in FIG. 28.

First, in the step 2-1, an object existence area derivation process is executed. The object existence area derivation process is a process for extracting a region wherein objects such as medicine are thought to exist (hereafter also referred to as 'object existence area') from the basic image. The object existence area derivation process is executed by deriving dot shaped translucent region due to emission of light by the backlight 314 and the print area due to printing provided on the sachet b as the regions to be excluded, and deleting those from the image area of the basic image.

Figure 27E:
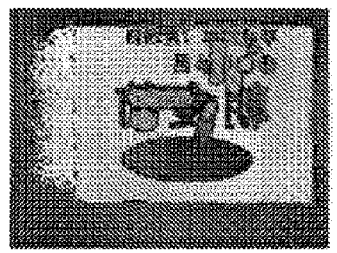
Figure 27B:
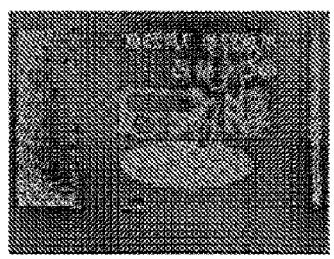

That is, in step 2-1a, an edge detecting process, which is a process for detecting edges included in the basic image, is executed. Specifically, in step 2-1a, by processing with an edge extraction filter such as the conventionally well-known Sobel filter, an edge included in the basic image is extracted (see FIG. 27B). Then, in step 2-1b, the region enclosed by the edge extracted in step 2-1a (hereafter also referred to as 'edge surrounding region') is selected, and an image processing of enlarging the edge surrounding region is performed. The expansion width of the edge surrounding region can be suitably determined based on the results of previous experiments, or by deriving based on a predetermined formula etc.

Here, regarding the section of the sachet b with printing, the dot shaped light from the backlight 314 passes through the packaging paper and is photographed. In other words, although substantially the entire area of the print area is black color or dark color in the basic image, a section through which dot shaped light is transmitted is hollow. On the other hand, regarding a section wherein an object such as medicine exists, the light emitted from backlight 314 does not pass through, and it is photographed in totally black or dark color in the basic image.

Regarding the expansion width of the edge surrounding region in step 2-1b, considering the relevant characteristics, it is desirable that the expansion width be set such that the edge surrounding regions corresponding to adjacent dot-shaped translucent regions are connected by expansion of the edge surrounding region. Further, regarding the expansion width of the edge surrounding region, it is desirable to set to the degree of expansion width so as to paint out a region inside the outline forming the outer edge of the print area by expanding the edge surrounding regions corresponding to dot-shaped translucent regions formed by transmission through the print area. In this embodiment, the expansion width of an edge surrounding region is set so as to comply with these conditions. When the image processing of expanding an edge surrounding region is finished as described above, as shown in FIG. 27C, the print area present in the basic image will assume a state wherein a region of continuous edge surrounding regions corresponding to the translucent region is generated. On the other hand, in the object existence area in which objects such as medicine etc., are present, since an edge surrounding region is not formed by the light emitted from the backlight 314, a region of continuous edge surrounding regions is not generated.

Figure 27F:
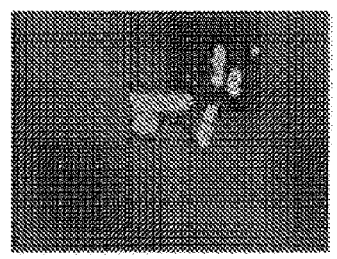
Figure 27C:
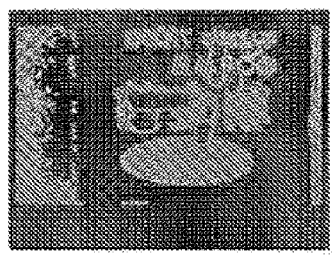

When the image processing of step 2-1b described above is finished, a process to invert a selected area (selected area inversion process) is executed in step 2-1c. With this, as shown in FIG. 27D, a region including a print area selected as an edge surrounding region is inverted to a non-selected state. Subsequently, in step 2-1d, an image processing is executed in which a separately selected gray color image (hereafter also referred to as 'gray image') is overlapped in the lower layer of the image prepared by the processes up to step 2-1c (see FIG. 27E). This gray image has a size substantially matching the size of the sachet b, and is a completely monochrome image. In the basic image that was processed up to step 2-1c, the gray image is disposed in the lower layer of the area where a sachet b to be inspected exists.

The image that was obtained from image processing of the step 2-1d described above is binarized in step 2-1e, and subjected to a process to extract sections that are darker than other regions (object existence area derivation process). Here, when the image obtained in step 2-1d is binarized, an object existence area where objects such as medicine are thought to be present is forming an area darker than the print area. Therefore, in step 2-1e, an object existence area as shown in FIG. 27F is extracted. By a sequence of processes according to step 2-1a through step 2-1e described above, the object existence area derivation process is completed.

Figure 27G:
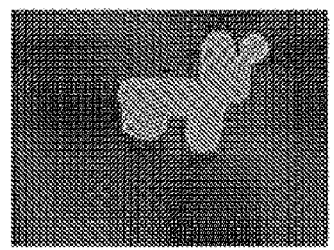
Figure 27D:
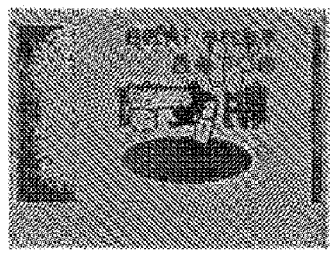
Figure 27H:
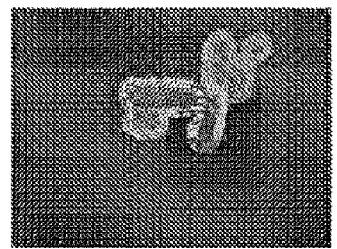

When object existence area derivation process is finished as described above, in step 2-2, a process of outwardly expanding the object existence area is executed (FIG. 27G). Subsequently, in step 2-3, an area demarcation process for creating a filter to exclude regions other than the areas expanded by the expansion process is executed in step 2-3 (FIG. 27H). With this, it is possible to set a filter for masking so that loss of mapping of objects such as medicines is not caused. Once setting of the filter is finished in 2-3, the inspection area defining process pertaining to step 1-2 is completed.

Once the inspection area defining process is completed, the control flow proceeds to the inspection image acquisition process according to step 1-3 of FIG. 26. In the inspection image acquisition process, an inspection image for carrying out inspection of medicine from the image limited to within the inspection area demarcated by the sequence described above is acquired. Specifically, in the image inspection process, by applying the above-mentioned filter acquired in the inspection area defining process to the image obtained separately from the back lit image used for the basic image acquisition process described above (hereafter also referred to as 'back unlit image'), an image for inspection in which the inspection area is narrowed to minimum will be obtained.

Here, the back unlit image used in the inspection image acquisition process is obtained by photographing a sachet b disposed in the inspection unit 310 with the backlight 314 in an unlit state by the shooting means 18. When the back unlit image is photographed, the diffusion light emitting device 160 is set in a lit state. The back unlit image can be acquired at an optional timing before the inspection of medicine is carried out in the image inspection process. Specifically, it is possible to photograph the back unlit image after acquiring the back lit image and while executing a process up to the inspection area defining process. With this, it becomes possible to effectively use the execution period of the inspection area defining process for photographing the back unlit image, and to speed up a series of inspection operations.

In the inspection image acquisition process of step 1-3, masking is performed by applying the above-mentioned filter to the back unlit image in order to prevent a loss of mapping of items such as medicine in the back unlit image. Thereafter, in step 1-4, an image inspection is performed to detect the quantity and type of the medicine in the image of the inside of the inspection area (image for inspection) narrowed down by masking in the inspection image acquisition process. In step 1-4, matching is performed by referring to the database in which shape information (edge information) and color information of the medicine to be inspected have been previously registered, and it is checked whether the prescribed medicine is packaged in the sachet b or not.

Figure 29A:
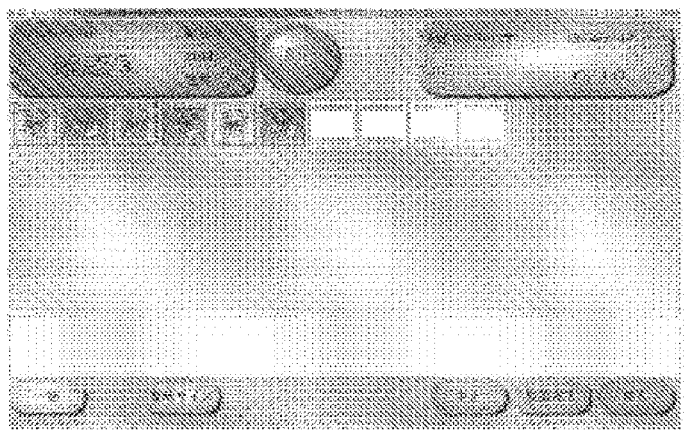
FIGS. 29A, 29B, and 29C are images respectively showing the display examples of the results of inspection by the medicine inspection process.
Figure 29B:
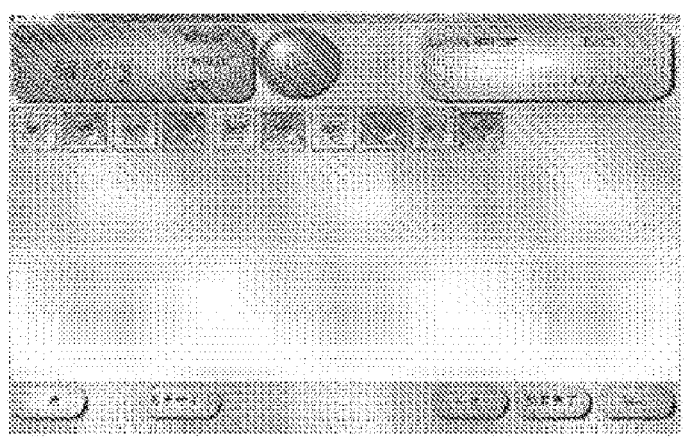

The inspection result of the medicine inspection process explained above is displayed in a display format as shown in FIG. 29, for example, on a display device such as a monitor of a personal computer of a control device 330. Specifically, during execution of the medicine inspection process, among the respective sachets b of a continuous body of sachets B supplied for inspection, the back unlit image for each sachet b will be displayed as a thumbnail in the order of completion of inspection, as shown in FIG. 29A. After the medicine inspection process is completed, if there is a sachet b containing excess or deficient quantity of medicine, the overall judgment is displayed as NG as shown in FIG. 29B. In this state, upon selecting (clicking) the inspection completion button, a log showing the inspection result is printed by a printer, which is not illustrated.

Figure 29C:
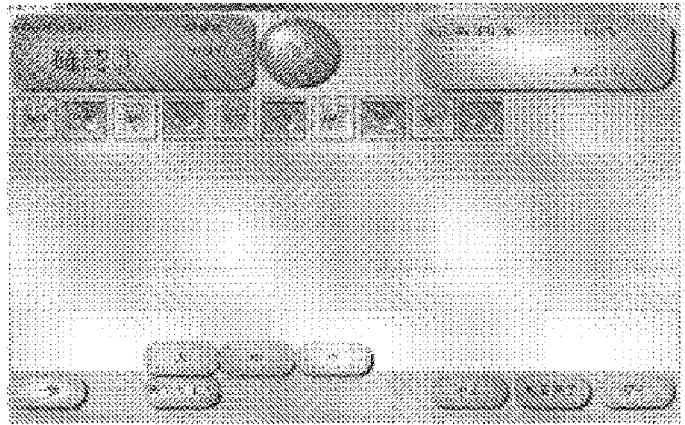

In a display state shown in FIG. 29B, upon selecting the display size button, it is possible to switch the display size of the thumbnail images showing each sachet b as shown in FIG. 29C. Further, by clicking the thumbnail image showing each sachet b, the inspection result of each sachet b can be checked individually as shown in FIG. 30.

Figure 30A:
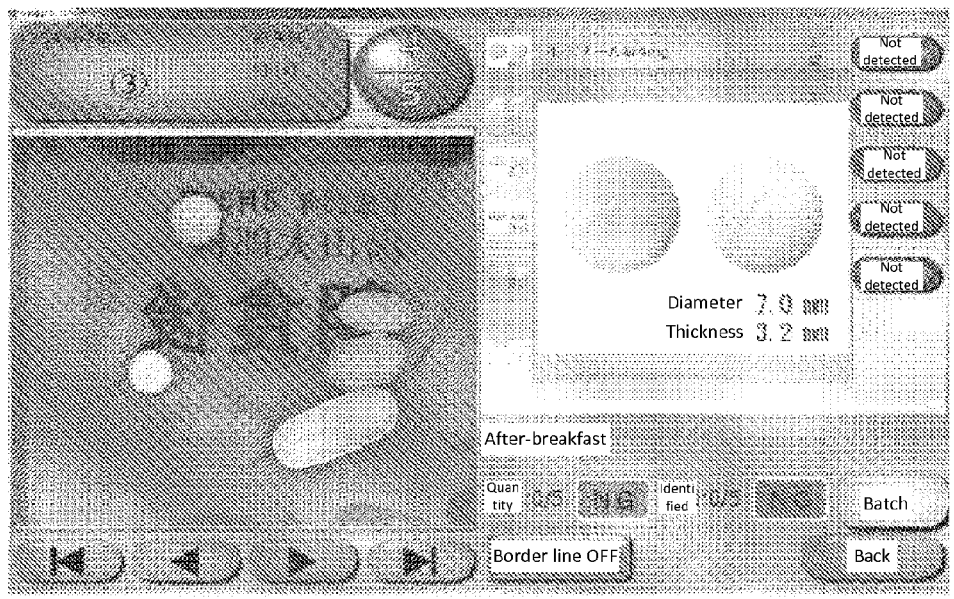
FIGS. 30A and 30B are images respectively showing the display examples individually confirming the inspection result of the sachets.
Figure 30B:
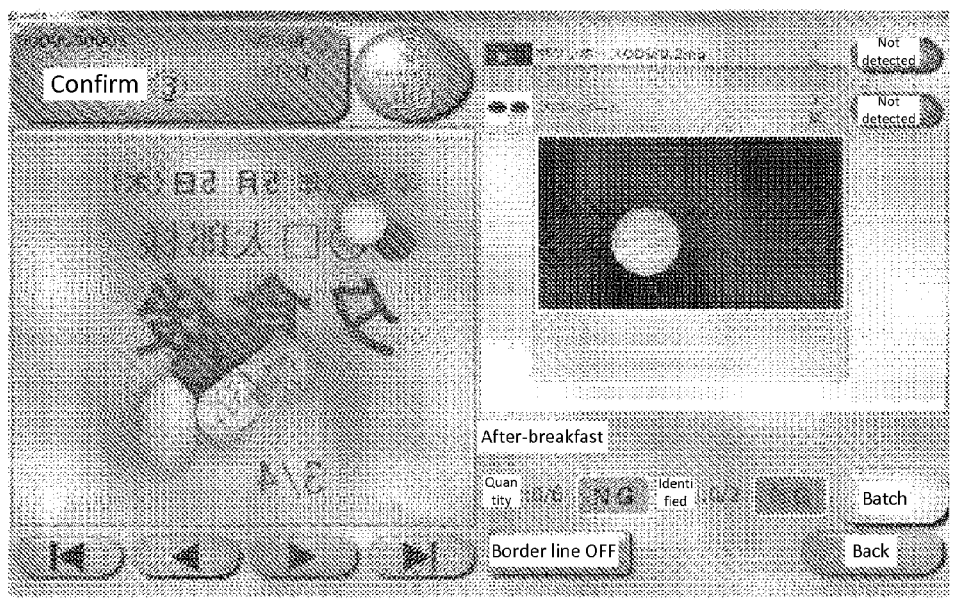

Specifically, upon clicking the thumbnail images showing each sachet b in the display state shown in FIG. 29, an individual display window of inspection result is displayed as shown in FIG. 30. In the individual display window of inspection results, in addition to displaying the name, image, and quantity of the prescribed medicine, the detection result of each medicine is also displayed. Further, upon selecting the image of medicine in the window, an enlarged image of that medicine is displayed as shown in FIG. 30, and information regarding the size is also displayed. In addition, when displaying the individual display window of inspection results, in case a medicine for which the image depicting the contour is not yet registered in the database is prescribed, an image cut out from the back unlit image used in the medicine inspection process will be displayed along with the medicine list (see FIG. 30B).

Figure 31A:
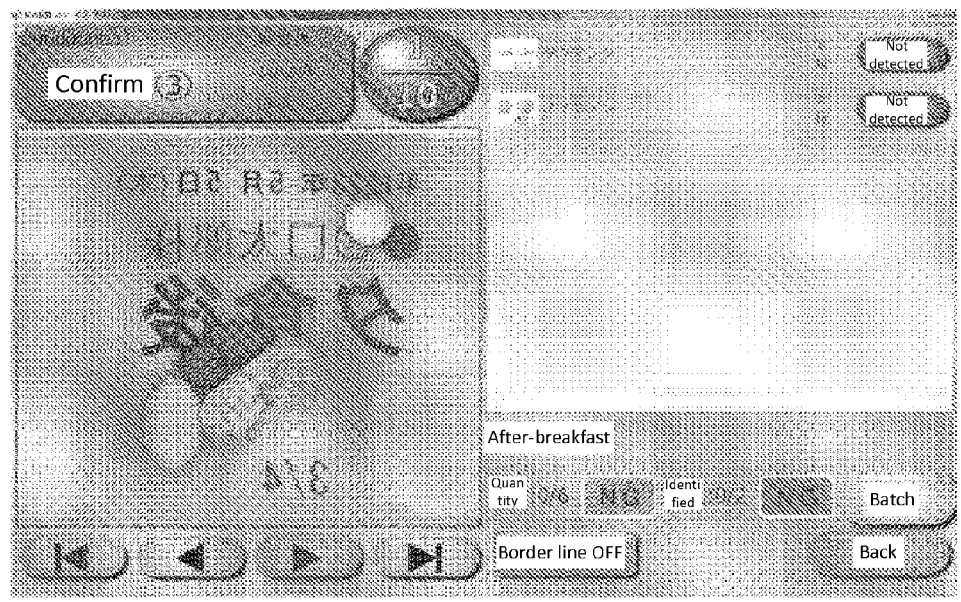
FIGS. 31A and 31B are images respectively showing the display examples individually confirming the inspection results of the sachets.
Figure 31B:
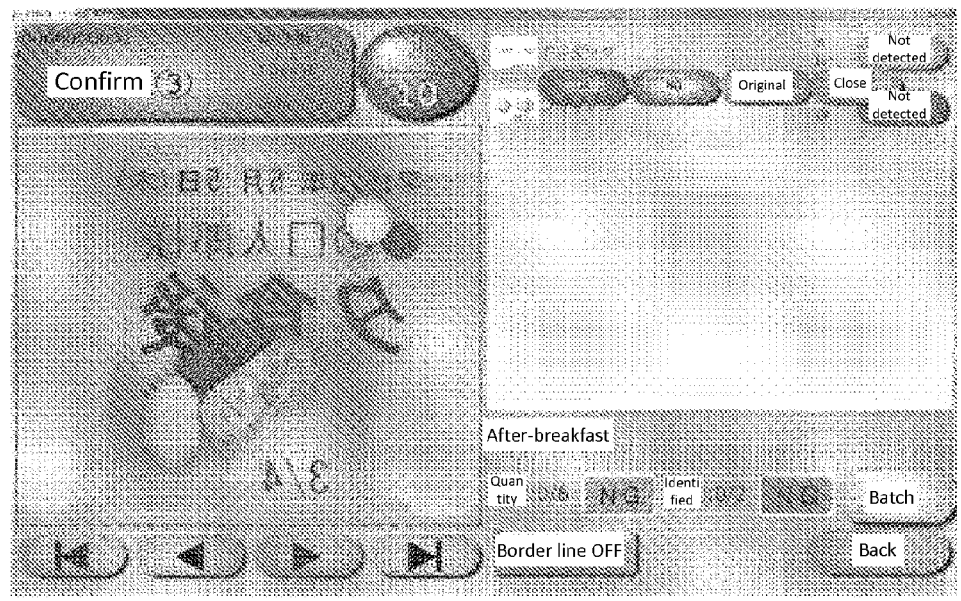

As a result of medicine inspection process, if there is a medicine that is included in the prescription information but not detected by the inspection, as shown in FIG. 31A, a button indicating that it was not detected is displayed in the medicines list column of inspection results individual display window. Upon selecting the button indicating that a medicine was not detected, a button by which an operator can determine by himself/herself whether a prescription drug is packaged in the sachet b or not is displayed as shown in FIG. 31B.

An operator can check whether the medicine has been packaged or not by using the back unlit image of the sachet b displayed in the left column of the individual display window of inspection results. Upon selecting the OK button in a state shown in FIG. 31B, it is determined that the operator made a judgment that the medicine is packaged in the sachet b in accordance with prescription, and the inspection result is determined. Upon selecting the NG button, it will be assumed that the operator made a judgment that the prescribed medicine is not packaged in sachet b, and the inspection results is determined. Further, upon selecting the original button, the decision of the operator made earlier by selecting the OK button or the NG button is retracted, and the inspection result will be restored to the judgment results of the medicine inspection process.

Figure 32A:
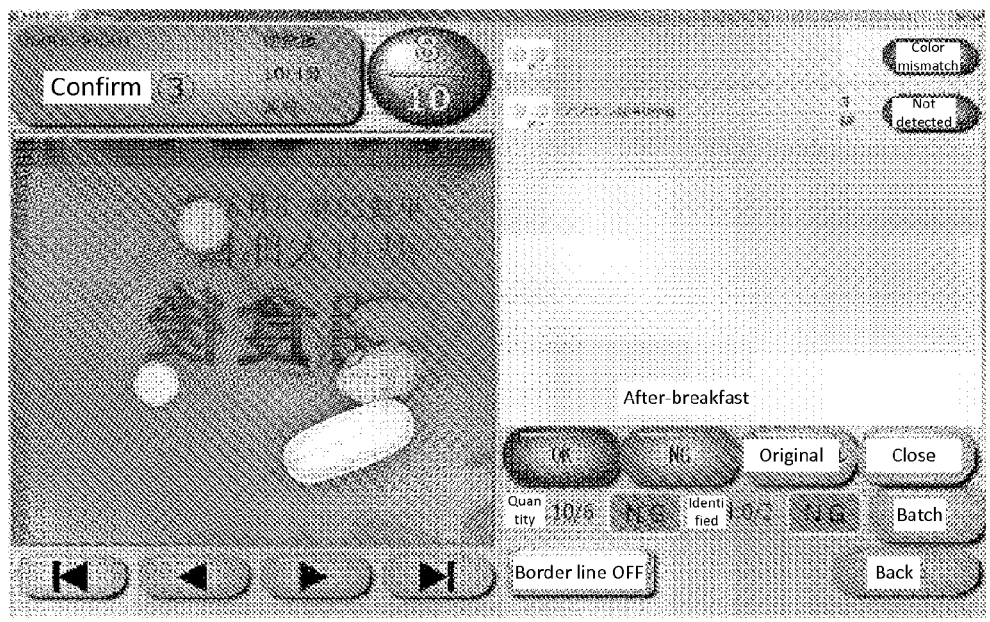
FIGS. 32A and 32B are images respectively showing the display examples individually confirming the inspection results of the sachets.
Figure 32B:
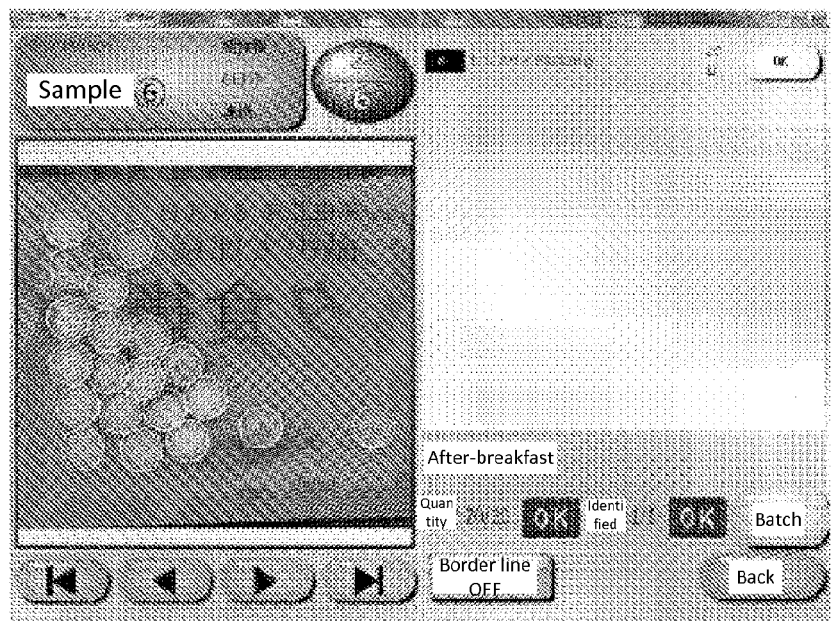

Further, as shown in FIG. 31 and FIG. 32, in the quantity display section provided at bottom right column of the individual display window of inspection results, the quantity of a medicine that should be packaged in sachet b, and the quantity of the medicine detected by the medicine inspection process are displayed in the form of a fraction, as well as the determined result of whether the medicine is properly packaged will be displayed. Specifically, if the quantity of medicine that should be contained in sachet b is 6, and the medicine detected by the medicine inspection process is 10, a display as illustrated in FIG. 32A will be displayed. In this case, because it cannot be said that the medicine is properly packaged, NG is displayed as a determined result. On the other hand, if the quantity of a medicine that should be present in the sachet b and the quantity of the medicine detected by the medicine inspection process are same, OK is displayed as in FIG. 32B.

As shown in the respective FIG. 31 and FIG. 32, in the identification result display section at bottom right column in the individual display window of inspection results, the inspection result based on the contour shape and color of a medicine determined by the medicine inspection process is shown. This identification result field also displays the quantity of a medicine that should be packaged in sachet b and the quantity of the medicine detected by medicine inspection process in the form of a fraction, and a determined result whether the medicine has been properly packaged.

As explained above, in the medicine inspection device 300, a basic image for medicine inspection is acquired based on a back lit image photographed by illuminating the sachet b, which is disposed in the inspection unit 310, by the backlight 314 in the basic image acquisition process. In the basic image, the inspection area is refined considering the characteristics that the region where the medicine is assumed to exist is photographed as a shadow and the other region is photographed as a translucent region emitting light in a dot pattern. That is, the translucent region emitting light in a dot pattern in the basic image is excluded from the inspection area. Therefore, it is possible to minimize the load of the control device 330 at the time of executing the inspection of a medicine in the image inspection process, and to enhance the inspection accuracy and the execution speed of image inspection.

In the medicine inspection device 300 of this embodiment, by effectively utilizing a characteristic wherein a difference of whether a continuous region is formed or not occurs in the basic image by changing a region enclosed by the outline only by a predetermined amount based on the difference whether it is a printed area where printing is done on sachet b or it is a region where the medicine is present, a printing area exclusion process (in this embodiment, equivalent to object existence region derivation process described above) for excluding the printing area from inspection area is executed. Therefore, in the medicine inspection device 300 of this embodiment, even if a sachet b with characters or the like printed thereon is fed, it becomes possible to accurately and rapidly derive the quantity and/or type of a medicine without receiving the influence of printing.

In the medicine inspection device 300 of this embodiment, an example in which a light source 316 and a mesh member 318, which is disposed between the light source 316 and sachet b and has translucent holes at each predetermined pitch, are provided as a backlight 314, but the present invention is not limited to this. That is, it can be anything as long as it is possible to emit light in a dot pattern at each predetermined pitch over the entire illumination area by the backlight 314, and it may be a configuration wherein light is emitted at each predetermined pitch by disposing light emitting diodes in a dot matrix pattern, for example. Also, the backlight 314 may also be a material capable of generating infrared laser light.

Further, the backlight 314 described above uses a light source capable of generating a light whose wavelength is same as or longer than that of red light as a light source 316, and the linearity of the generated light is high. With this, in the back lit image photographed by shooting means 18, a region where medicine exists and the outline of the medicine can be clearly identified in the basic image. Furthermore, the dot-patterned light emitted from the backlight 314 is also transmitted reliably in the printed region of sachet b, and the printed region can be clearly identified in the back lit image. With this, it becomes possible to not only improve the image processing accuracy when eliminating the printed area from the inspection area, but also to improve the accuracy of medicine inspection. Moreover, from the viewpoint of translucency, it is preferable that the backlight 314 is capable of generating a light whose wavelength is same as or longer than that of red light, but it may generate a light whose wavelength is less than that of red light.

Moreover, in the medicine inspection device 300 of this embodiment, elimination of a medicine-existing-region from the inspection area is prevented by executing the object existence region derivation process (elimination process) to expand the remained region by only a predetermined amount towards the outside in the expansion process in the inspection area defining process. With this, the accuracy of medicine inspection by the medicine inspection device 300 can be further enhanced.

≪ Foreign Object Detection Process≫

Figure 33:
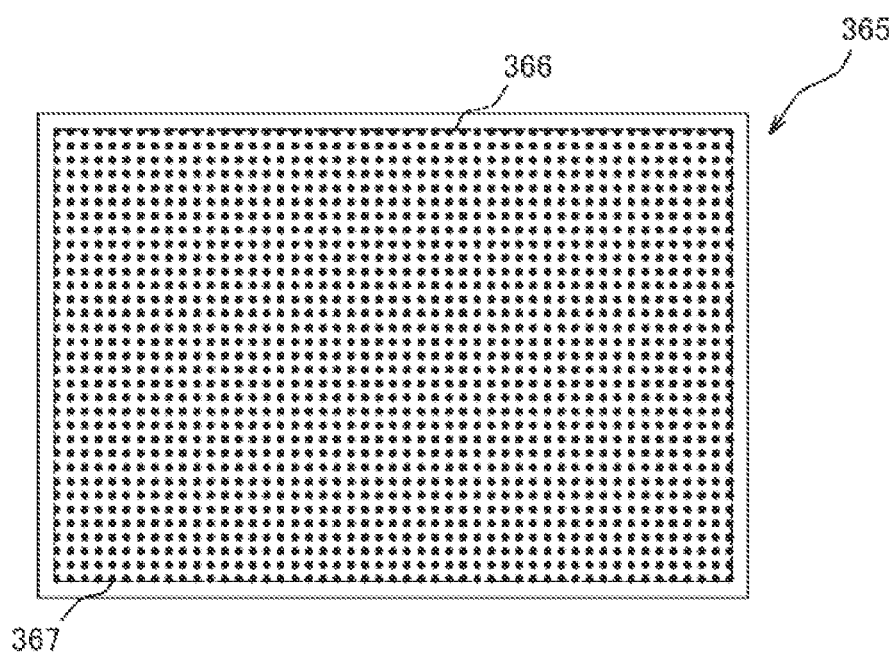
FIG. 33 is an image showing one example of an image for position recognition used in a foreign object detection process.

As an execution means for executing the foreign object detection process described above, a foreign object detection process means 350 is provided. In addition, a medicine present area demarcation means 360 is provided for demarcation of an area in which medicine is present in the sachet b that is disposed in the inspection unit 310. The foreign object detection process means 350 is provided in order to run the foreign object detection process for detecting whether a sachet b contains objects (foreign object) other than the medicine for inspection or not. In the foreign object detection process, in addition to a basic image acquired by the medicine information detector 340 described above, a separately prepared image for position recognition 365 is used. As shown in FIG. 33, the image for position recognition 365 has a position recognition area 366 having a size corresponding to the basic image. All of the position recognition area 366 is provided with dot-patterned position indicators 367 at a predetermined pitch. In addition, each position indicator 367 has coordinates.

By overlapping the position recognition area 366 of an image for position recognition 365 and a basic image, the foreign object detection processing means 350 can find out the position of mapping included in the basic image from the coordinates assigned to position indicators 367. Specifically, the foreign object detection processing means 350 can identify the position of the mapping of the object by overlapping a basic image and an image for position recognition 365 and by extracting the positional coordinates of a section in which the mapping of an object such as medicine or the like present in the basic image and the demarcated area are overlapped.

The medicine present area demarcation means 360 executes the process of demarcation of the area where the medicine exists in an image of a sachet b containing medicine. The medicine present area defining means 360 demarcates the area of medicine by a matching method such as a so-called shape base pattern matching or a gray pattern matching etc. In this embodiment, the medicine present area defining means 360 can execute a shape base pattern matching and demarcate the medicine existing area by carrying out a matching based on the information of external shape (contour) already registered for a medicine of inspection (edge information).

Figure 34:
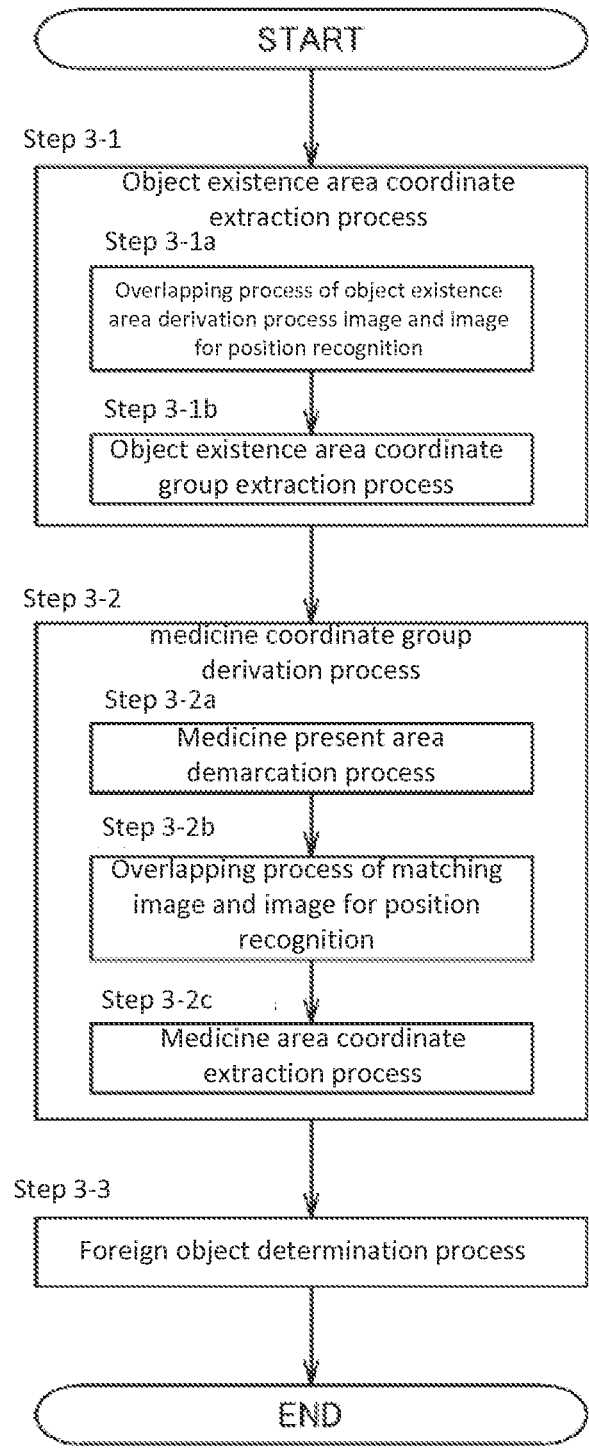
FIG. 34 is a flowchart showing the execution flow of the foreign object detection process performed in the medicine inspection device of FIG. 19.

Next, the foreign object detection process executed by a foreign object detection processing means 350 and medicine present area defining means 360 is described in detail. As shown in FIG. 34, the steps of the foreign object detection process can be largely classified into three steps that are an object existence area coordinate extraction process, a medicine coordinates group derivation process, and a foreign object determination process. The object existence area coordinate extraction process of step 3-1 is a step in which the positional coordinate group, which exists within the area enclosed by the outline in the basic image obtained by the medicine information detector 340 during medicine inspection process described above, is derived as the object existence area coordinate group.

Figure 35A:
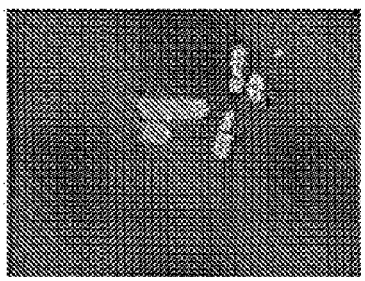
FIGS. 35A, 35B, 35C, 35D, and 35E are images respectively showing the images taken during the execution of foreign object detection process in the medicine inspection device of FIG. 19.
Figure 35E:
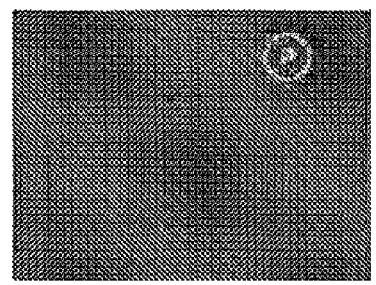
Figure 35B:
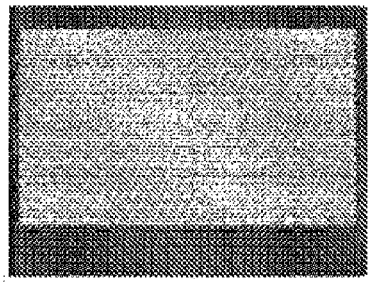
Figure 35C:
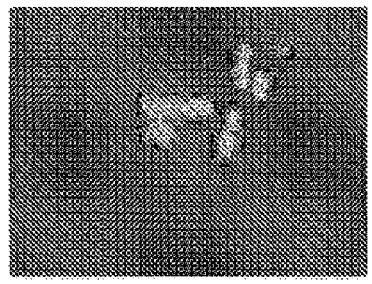

In the object existence area extraction process, as the first step 3-1a, an image processing is performed by overlapping an image (see FIG. 35A) obtained from the object existence area derivation process executed in the inspection area defining process of the medicine inspection process, and an image for position recognition 365 (see FIG. 33 and FIG. 35B) described above. As a result, an image as shown in FIG. 35C is obtained. Then, in step 3-1b, the foreign object detection processing means 350 executes a process in which, from the dot-patterned positional coordinates formed in the image for position recognition 365, the positional coordinates included in the object existing area defined by the object existence area derivation process are extracted as an object existence area coordinates group.

Figure 35D:
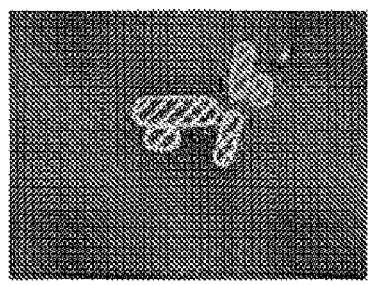

Once the object existence area extraction process of step 3-1 is completed as described above, the medicine coordinate group derivation process of step 3-2 is executed. In the medicine coordinates group derivation process, as the first step 3-2a, an image of a medicine-filled sachet b disposed in the inspection unit 310, which is photographed by the shooting means 18, is used to perform a shape base pattern matching by the medicine present area demarcation means 360. Used for the image used in this process (hereafter also referred to as 'matching image') is an image same as the back unlit image used in the image inspection process of medicine inspection process described above, or an image photographed in a situation similar to the back unlit image, which is a situation in which the backlight 314 is switched off and the diffusion light emitting device 160 is switched on. In the medicine coordinates group derivation process, the shape pattern matching mentioned above is carried out for the matching image, and the area in which medicine exists (medicine present area) is demarcated as in FIG. 35D.

Once the demarcation of the medicine present area in the image for matching is completed as described above, an image processing for overlapping the above-mentioned matching image and the above-mentioned image for position recognition 365 is implemented in step 3-2b. In step 3-2c, a process is executed in which, among the dot-patterned positional coordinates formed in the image for position recognition 365, the positional coordinates included in the medicine present area demarcated in step 3-2a are extracted as medicine area coordinates. With this, the medicine coordinates group derivation process is completed, and proceeds to the foreign object determination process in step 3-3.

In the foreign object determination process, whether a foreign object is mixed in sachet b or not is determined on the basis of the results of the object existence area coordinate extraction process and medicine coordinates group derivation process. That is, in the foreign object determination process, the object existence area coordinates group derived in step 3-1 described above and the medicine area coordinates group derived in step 3-2 are cross-checked by foreign object detection processing means 350, and the dot-patterned positional coordinates located in the matching coordinates in both are erased from the image. As a result, if the positional coordinates that are not present in the object existence area coordinates group exist in medicine area coordinates group, it is possible to retain the dots showing the positional coordinates as shown in FIG. 35E, and infer the presence of a foreign object in that coordination position.

As described above, in the medicine inspection device 300, by executing an object existence area coordinates group extraction process, the region wherein objects such as medicine etc. exist can be obtained from the outline present in the basic image as a form of object existence area coordinates group. Further, by a medicine coordinates group derivation process that is separately executed, a medicine-existing region can be obtained as a form of medicine area coordinates group. In the medicine inspection device 300, it is possible to determine whether a foreign object other than medicine is present in a sachet b or not based on whether the object existence area coordinates group and medicine area coordinates group match each other. Therefore, according to the medicine inspection device 300, it is possible to not only check the medicine quantity or type, but also detect the contamination of a foreign object other than medicine with certainty.

《Medicine Master Construction Process》

In addition to the medicine inspection process and the foreign object detection process described above, the control device 330 can also execute a process for constructing a medicine master 370 (medicine master construction process) in which the master information of the medicine to be inspected is registered in the computer. The medicine master 370 includes a contour image database 372 in which the contour image of a medicine is registered for review. In the contour image database 372, the contour image of a medicine is registered by classifying into each constituting surface (front, rear and side).

Figure 36A:
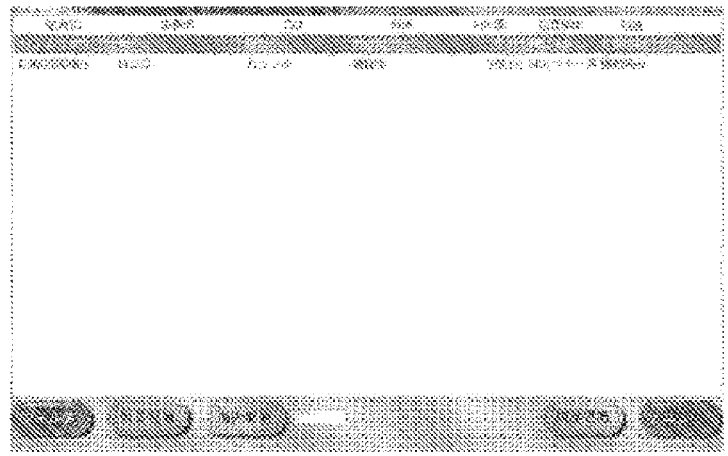
FIGS. 36A, 36B, and 36C are, respectively, an image showing one example of operational image used when displaying a medicine master, an image showing a list of medicines having similar contour, and an image showing the display example of master information about medicine.
Figure 36B:
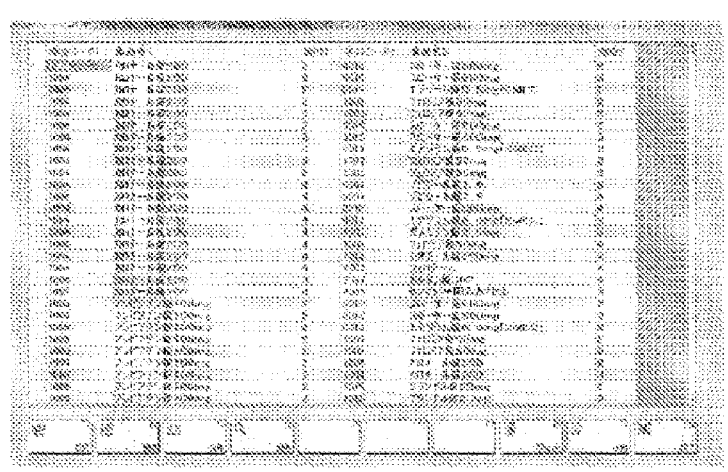

Here, in the medicine inspection device 300 of this embodiment, the medicine master can be displayed by selecting (clicking) the medicine master button that is displayed by selecting the menu button, in a state where the operational screen as shown in FIG. 36A is displayed on the monitor of the computer of the control device 330. Further, upon clicking the analogous medicine master button in the same screen, a list of medicines having a similar appearance can be listed as shown in FIG. 36B.

Figure 36C:
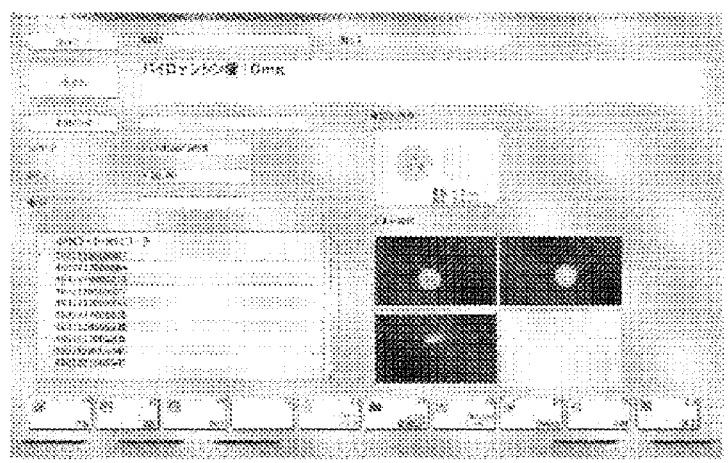
Figure 37A:
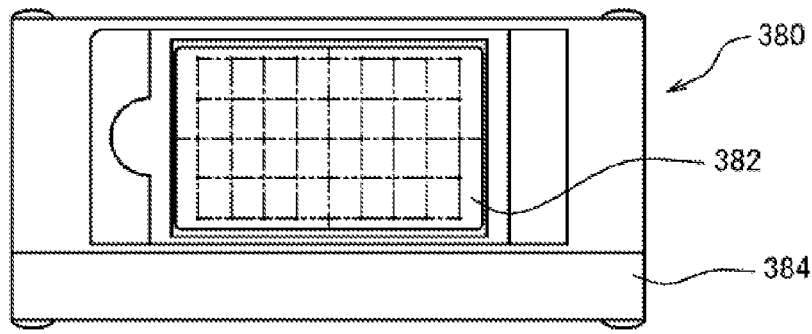
FIGS. 37A, 37B, 37C, 37D, and 37E show a photographing jig.
Figure 37B:
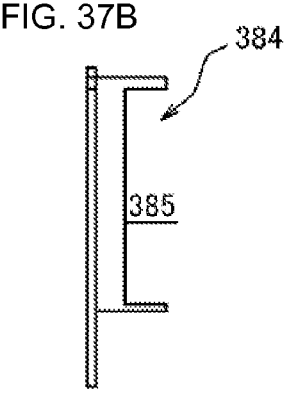
Figure 37C:
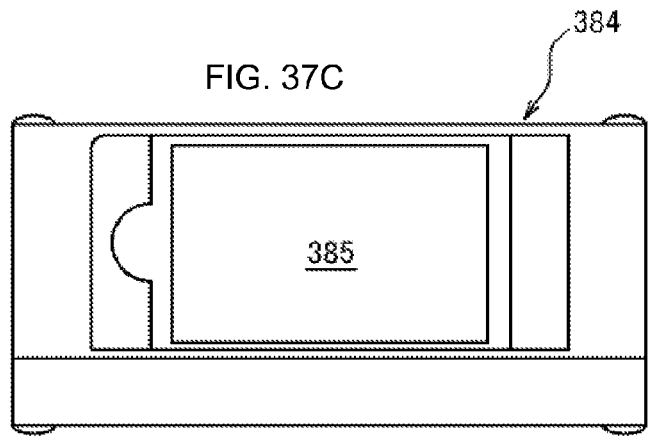
Figure 37D:
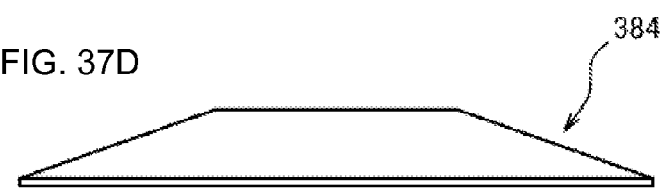
Figure 37E:
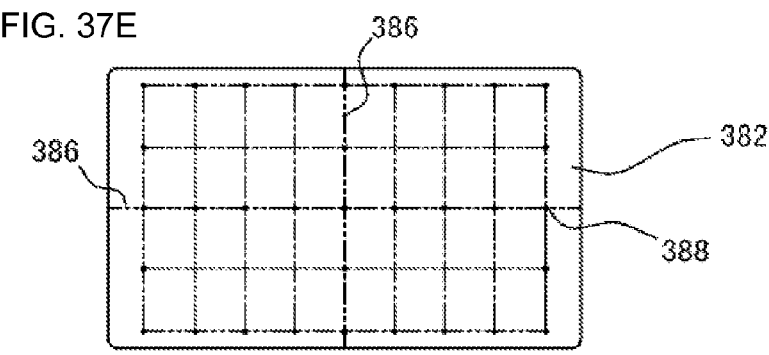

If the medicine master button is clicked in the operation screen of FIG. 36A, the master information for each medicine can be displayed as shown in FIG. 36C. In this master display screen, in addition to the medicine-related information such as name and code number of a medicine, the contour image of the medicine described above is displayed for each constituting surface.

When executing the medicine master construction process, a photographing jig 380 shown in FIG. 37 is employed. The photographing jig 380 includes a stage 382 for mounting a medicine, and a pedestal 384. Stage 382 is formed from a white-colored translucent resin. Stage 382 is divided into four regions by a central line 386 formed so as to extend in the vertical direction and the lateral direction in the center of the region. Each region formed in the sage 382 functions as an imaging zone associated with each side of the medicine to be photographed. In stage 382, positioning guide 388 is provided in each region to help dispose a medicine at a predetermined location. The positioning guide 388 is formed of dot-patterned marks drawn on the resin plate of the stage 382. The size of each dot of positioning guide 388 is smaller than the expected size of the medicine and foreign object being supplied for inspection.

The pedestal 384 is of a size that can be mounted on a transportation means 12 that is provided for conveying a sachet b to the inspection unit 310. A stage installation part 385 is provided in the middle of the pedestal 384 for fixing the resin plate of the stage 382. Therefore, by laying a medicine with its side associated with each imaging area facing upwards (towards shooting means 18) in each imaging zone formed in stage 382, and moving the stage 382 mounted on the pedestal 384 to the inspection unit 310 by the transportation means 12, the image of each surface of the medicine can be taken at the same time under the same conditions.

Further, all four sides of the stage installation part 385 are enclosed by a black colored or dark colored resin of the pedestal, and allow passage of light in the vertical direction. Therefore, when the photographing jig 380 is moved to the inspection unit 310 and photographed by the shooting means 18, a medicine can be vividly imaged. If imaging is performed with the backlight 314, which is disposed on the back of (below) the inspection unit 310, switched on, a medicine placed on the stage 382 is photographed with a clearly distinct contour.

Figure 39:
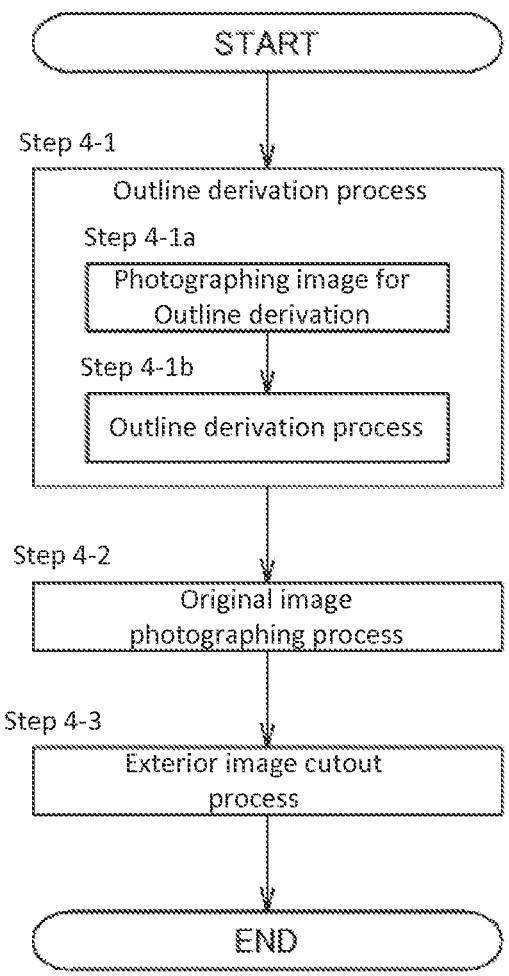
FIG. 39 is a flowchart describing the execution flow of the medicine master creation process performed in the medicine inspection device of FIG. 19.

Next, the method of executing the medicine master construction process is explained step-by-step. As shown in FIG. 39, the medicine master construction process is executed through the following three steps: outline derivation process, original image photographing process and contour image cutout process. The outline derivation process according to step 4-1 is a process involving photographing a medicine placed on stage 382 with the backlight 314 switched on, and deriving the outline of the medicine from that image. Specifically, in the outline derivation process, first, in step 4-1a, the photographing jig 380 with the medicine to be imaged placed on stage 382 is moved to the inspection unit 310. Then, stage 382 is irradiated by the backlight 314, and the medicine placed on stage 382 is photographed to obtain an outline derivation image. Subsequently, in step 4-1b, based on the outline derivation image, an imaging processing for deriving an outline for each surface of the medicine is executed.

Figure 38A:
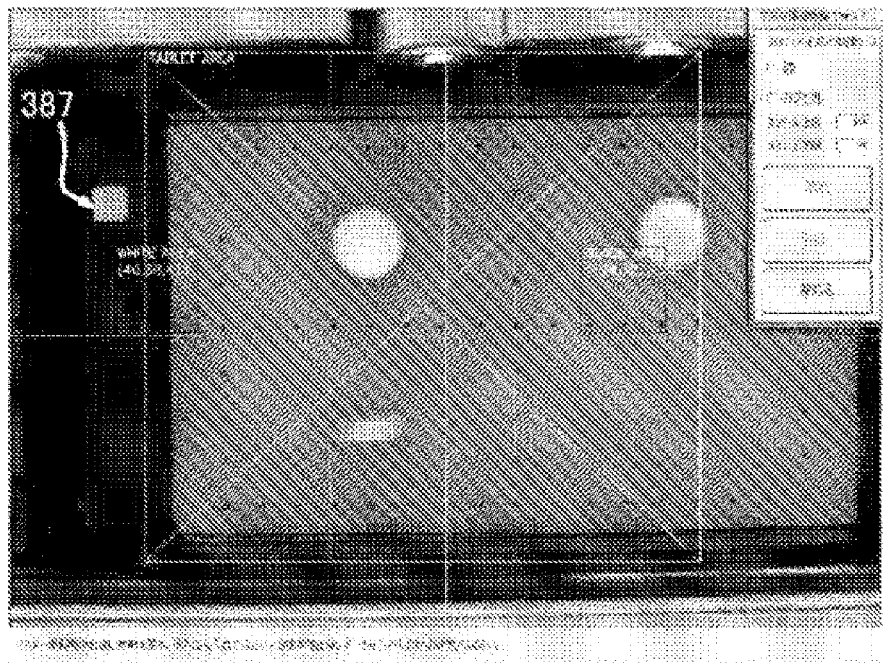
FIGS. 38A and 38B are images showing a state wherein each face of a medicine is photographed using the photographing jig.
Figure 38B:
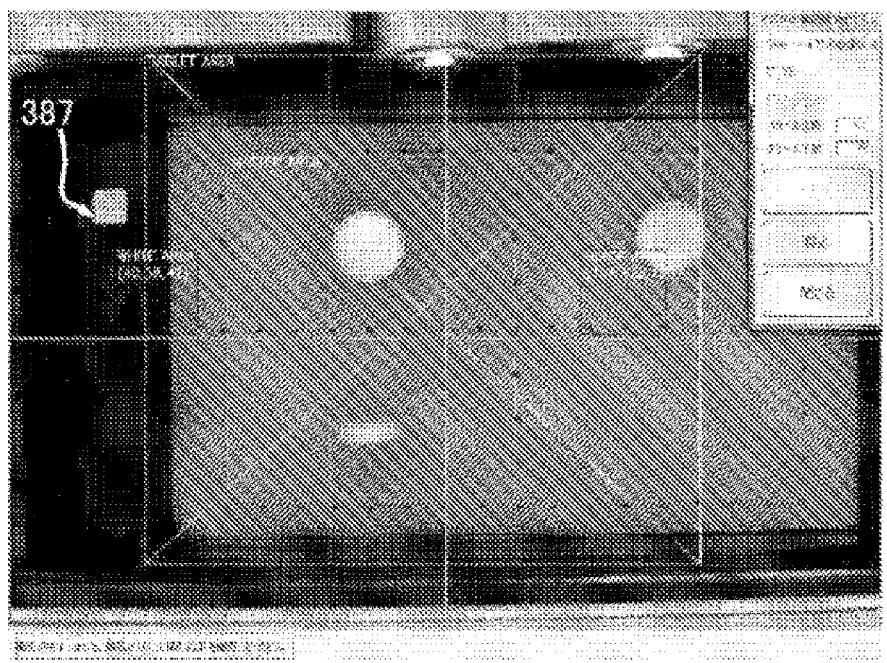

When the outline of the medicine is derived in step 4-1, an original image that serves as the base of a contour image of the medicine is photographed in the original image photographing process in step 4-2. That is, in step 4-2, the imaging is done by the shooting means 18 with the backlight 314 switched off, and the diffusion light emitting device 160 switched on to irradiate the stage 382. With this, as shown in FIG. 38, an index 387 is displayed along with stage 382 and medicine. Index 387 is displayed on a side of the stage 382, and is used for position identification of stage 382 and a medicine disposed on stage 382 from a relation with the positioning guide 388 provided on stage 382. Index 387 is also used as an index for recognizing the size of a medicine.

Once the original image for creating a contour image is acquired in step 4-2, it will proceed to the contour image cutout process in step 4-3. In step 4-3, in a state wherein the outline derivation image obtained in step 4-1 and the original image obtained in step 4-2 are overlapped, an image processing is executed to cut out an area corresponding to the area surrounded by the outline of the medicine from the original image. With this, contour image for each surface of the medicine is obtained.

A contour image obtained as described above is classified for each constituting surface of the medicine, and registered in a contour image database 372. The images of the contour image database 372 that was constructed in such a manner are used for displaying for browsing when displaying the inspection results of medicine inspection process, etc., mentioned above.

As described above, in the medicine inspection device 300, a region for cutting out the image of the medicine is identified by an outline on the basis of a back lit image (irradiated image) that includes a medicine as shadow, and from a back unlit image (back non-irradiated image) in which the medicine is vividly included, a section corresponding to the area enclosed by the outline is cut out. With this, a region of the back unlit image where a medicine is included can be cut out properly. Accordingly, in the medicine inspection device 300, a vivid contour image of a medicine can be obtained easily and with high accuracy, and a contour image database 372 can be constructed.

In this embodiment, stage 382 used for photographing the image of a medicine has a plurality of imaging zones corresponding to each constituting face of a medicine, and it is possible to place a medicine in each imaging zone such that the face associated with each imaging region is oriented towards the shooting means 18. Therefore, if an image is taken in a state wherein the stage 382 mounted with a medicine is placed on the pedestal 384 and reached the inspection unit 310, the contour image of each face of the medicine can be acquired at the same time and under the identical conditions. This allows minimizing the efforts and time required for acquisition of contour image of the medicine, and it is possible to homogenize the shade or the like of the contour image of each surface.

Further, as described above, the stage 382 is provided with positioning guides 388 for positioning a medicine at a predetermined position. With this, a medicine can be guided to be in a suitable position when the medicine is photographed for construction of a contour image database. Moreover, because the size of the positioning guide 388 is made adequately smaller than the expected size of a medicine or foreign object, it is possible to easily and accurately distinguish between the positioning guide 388 and medicine or the like in the image photographed for constructing a contour image database 372, and by erasing the positioning guides 388 from the image or the like, it becomes possible to prevent the positioning guides 388 from getting imaged in the contour image of the medicine. Moreover, this embodiment illustrated an example having a configuration of providing positioning guides 388 and making the positioning guides 388 very small, but the present invention is not limited to this. In other words, a configuration having no positioning guides 388, or making them of about the same size as medicine etc., is also possible. If positioning guides 388 are not provided, it is desirable to provide some mark or the like for guiding the placing position of the medicine. In addition, if the size of a positioning guide 388 is made almost the same as the medicine or the like, it is desirable to provide a configuration capable of reliably distinguishing the contour image of the medicine and the positioning guides 388.

In this embodiment, since the stage 382 is made of white color, even for medicines of dark colors such as green, black, or etc., for example, it is possible to clearly distinguish between the stage 382 and a medicine in the image taken for contour image acquisition. Thus, a contour image of a medicine can be acquired easily and accurately, and the accuracy of the contour image database can be improved. Moreover, stage 382 is not necessarily required to be white, and it may also be of other colors. In addition, in order to enable easy identification of black or dark-colored medicines, it is desirable that stage 382 is of a light color shade.

The medicine inspection device 300 of this embodiment described above illustrated an example of a configuration in which the shooting means 18 is used as a shooting means for a back lit image for photographing the image of a medicine in an irradiated state, and also as a shooting means for back unlit image for photographing a medicine wherein the rear side of the inspection unit is not irradiated, however, the present invention is not limited to this, and it is also possible to provide a configuration in which the shooting means for back lit image and the shooting means for back unlit image are configured from different imaging devices.

Specifically, it is possible to provide a configuration wherein a separate imaging device is provided in a place where space is available such as the upstream of the diffusion light emitting device 160, and to use this imaging device as a shooting means for back unlit image and use the shooting means as the shooting means for back lit image. It is also possible to provide a separate imaging device in an obliquely upward direction with respect to the diffusion light emitting device 160, and to use this imaging device as a shooting means for back unlit image and use the shooting means as the shooting means for back lit image. In such case, because the image taken by the shooting means for back unlit image is an image in which a medicine on the inspection unit 310 is photographed obliquely from above, it is preferable to consider measures such as compensating the image so as to become similar to that photographed from the front side.

Further, an imaging device of high pixel number capable of photographing the contour of a medicine vividly by imaging the medicine in an unlit state can be provided as a shooting means 18, and this shooting means 18 can be used as a shooting means for back unlit image and as a shooting means for back lit image at the same time. When such a configuration is adopted, an image obtained by photographing a medicine in the irradiated state is thought to be of excessive quality for the purpose of extracting the contour of the medicine. Therefore, when using an imaging device of high resolution as a shooting means 18, it is preferable to take measures such as image processing or the like to transform the image of the medicine photographed in an irradiated state into a lower quality image when extracting the outline of the medicine. Further, when providing a shooting means for back unlit image and a shooting means for back lit image separately as described above, the imaging conditions such as illumination degree may be changed when photographing by shooting means for back lit image and when photographing by shooting means for back unlit image.

《Modified Example of Medicine Master Construction Process》

Figure 70:
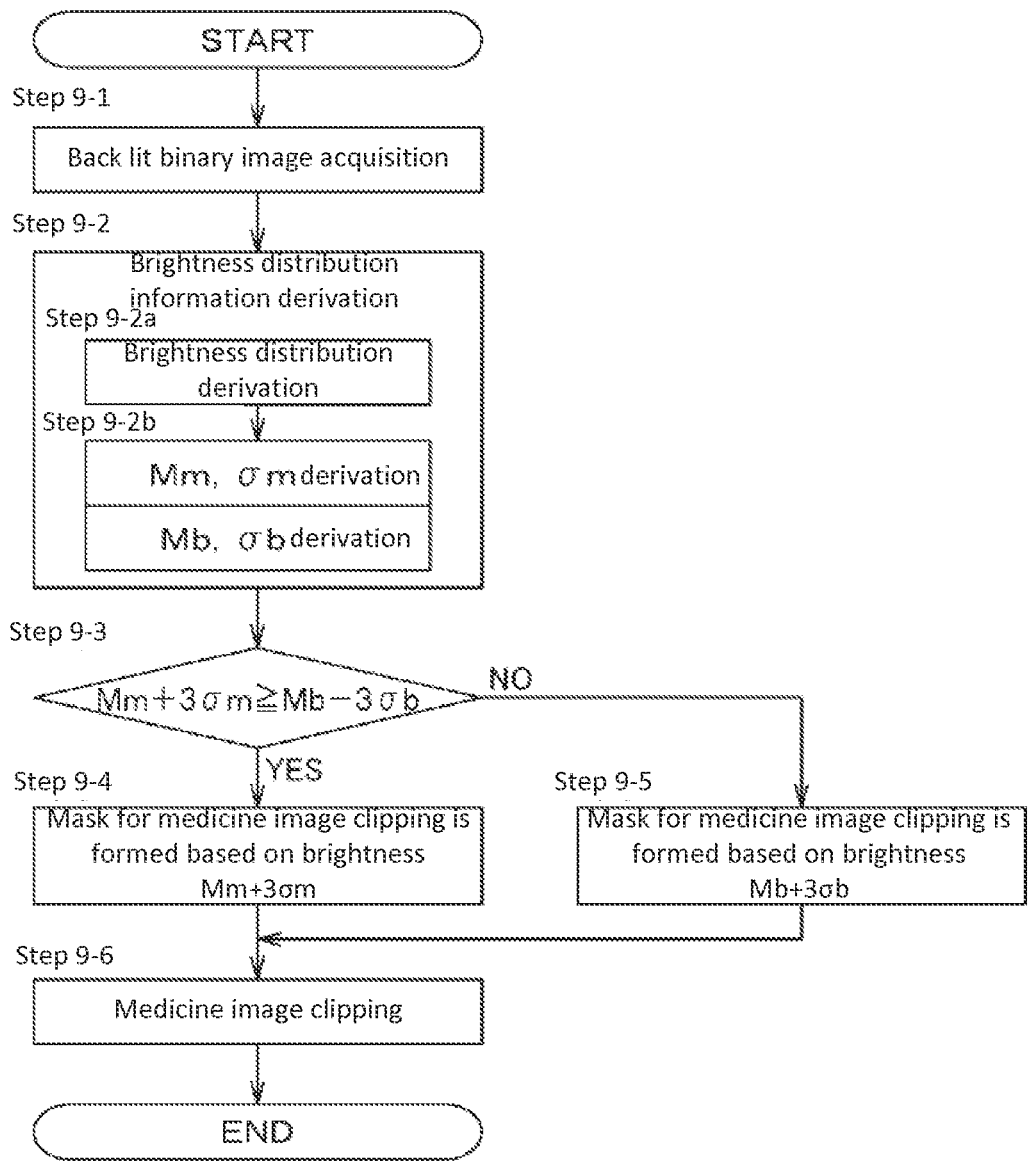
FIG. 70 is a flowchart showing a modification example of medicine master construction process according to one embodiment of the present invention.

The method of constructing a medicine master is not limited to the method described above, and it is also possible to construct a medicine master by using an image corresponding to medicine that was cut out as per the control flow shown in FIG. 70, for example. The method shown in FIG. 70 is described step-by-step below.

The image acquiring method for medicine master construction shown in FIG. 70 involves cutting out the image of a medicine placed in the inspection unit 310 by using a back lit image obtained by photographing with the shooting means 18 in an irradiated state in which the inspection unit 310 is irradiated by backlight 314, and a back unlit image obtained by photographing, without irradiating the inspection unit 310 by the backlight 314, by shooting means 18 in a back non-irradiated state by switching off the diffusion light emitting device 160. In the control flow shown in FIG. 70, in step 9-1, an image processing is first performed to obtain a back lit binarized image for later use. Specifically, in step 9-1, the back lit image is RGB resolved, and from among the obtained back lit R channel image, back lit G channel image, and back lit B channel image, at least one is selected as the back lit single channel image. Then, the selected back lit single channel image is subjected to binarizing image processing. In this embodiment, back lit R channel image is selected as the back lit single channel image, and this is subjected to binarizing image processing to get a back lit binarized image. The threshold value of binarization is determined from the minimum value of the brightness histogram, and an area of low brightness is assumed as a provisional medicine region, and an area of high brightness is considered as a provisional background region.

In step 9-2, the provisional medicine region and provisional background region acquired in step 9-1 are used for deriving the information related to brightness distribution in the back lit single channel image. Specifically, in step 9-2a, the brightness distributions of medicine and background images in the back lit single channel image is derived under the assumption that it is Gaussian distribution (normal distribution) (see FIGS. 71A and 71B). In step 9-2b, the mean value Mm and standard deviation σm for the brightness distribution of provisional medicine region and the mean value Mb and standard deviation σb for the brightness distribution of the provisional background region are derived.

Figure 71A:
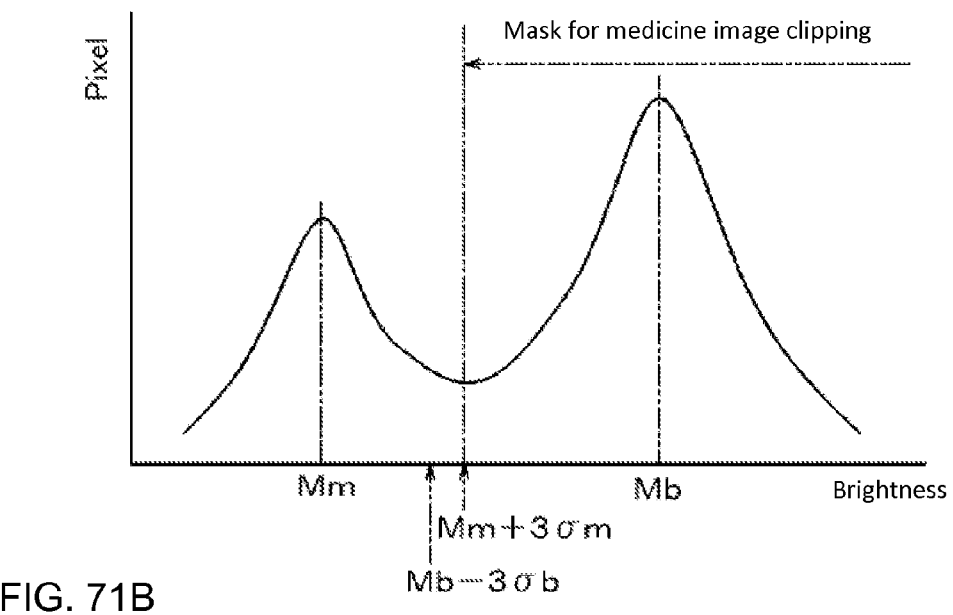
FIGS. 71A and 71B are graphs schematically showing the brightness distribution of medicine and background image in a back lit single channel image acquired in the control flow in FIG. 70.
Figure 71B:
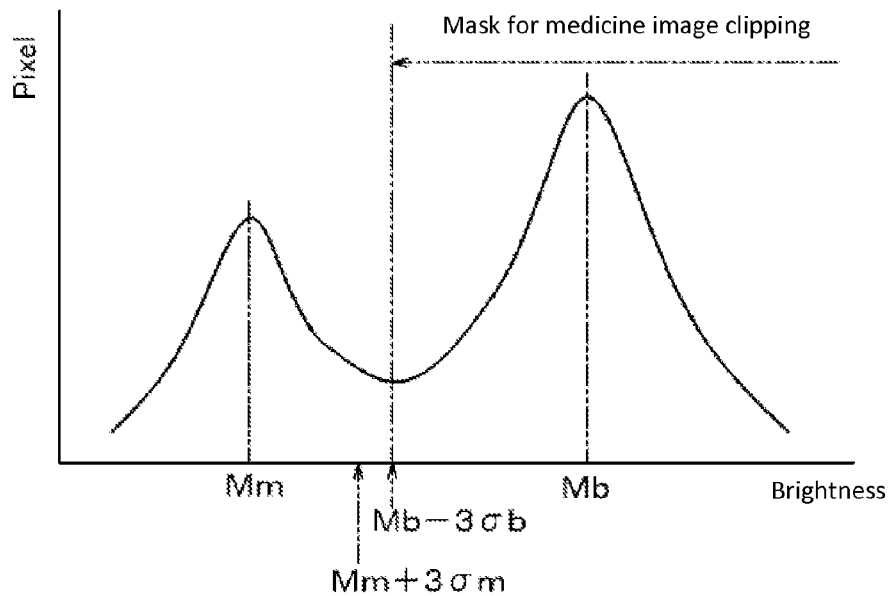

Specifically, the brightness of the region corresponding to the medicine is lower than the brightness of the region corresponding to the background, and they are mutually different. Therefore, as shown in the graphs of FIGS. 71A and 71B, as brightness distribution of back lit single channel image, two peaks substantially forming normal distribution appear. Of these two peaks, the peak of lower brightness shows the brightness distribution of a region corresponding to the medicine, and the peak of high brightness shows the brightness distribution of a region corresponding to the background. Therefore, in the graph of FIG. 71, the mean value of the lower brightness peak becomes the mean value Mm, and the mean value of the higher brightness peak becomes the mean value Mb. The standard deviations σm and σb can be derived from the graph of FIG. 71.

Once the information related to brightness distribution is derived as described above, the control flow proceeds to step 9-3. In step 9-3 through step 9-5, in order to suppress the selection omission of a region corresponding to medicine, under the concept shown in FIG. 71($b$), a medicine image cut-out mask, which is for providing a masking to the region corresponding to the background existing on the high brightness side, is formed on the basis of brightness. Brightness that becomes the reference for preparing a medicine image cut-out mask is determined based on magnitude relationship between brightness (Mm+3σm) and brightness (Mb−3σb).

Specifically, in step 9-3, as shown in FIG. 71A, it is checked whether a relation of Mm+3σm≥Mb−3σb is established or not. When this relationship is established, the Gaussian distribution corresponding to the medicine overlaps with the Gaussian distribution corresponding to the background, but if an image for the brightness range for the medicine is acquired by adding 3 σm to Mm, the probability of obtaining a region corresponding to the medicine without omission of image is thought to be high. Therefore, when a relationship of Mm+3 σm≥Mb−3 σb is established, the control flow proceeds to step 9-4, and with brightness Mm+3 σm as reference, a medicine image cut-out mask is formed for providing masking to a region with a brightness greater than reference brightness.

On the other hand, if the relationship of Mm+3σm Mb−3σb is not established in step 9-3, that is, in case of Mm+3 σm<Mb−3σb as in FIG. 71B, the Gaussian distribution corresponding to the medicine will be separated from the Gaussian distribution corresponding to the background. However, in order to select an image area corresponding to the medicine without omission, it is desirable to mask a region having a brightness greater than Mb−3σb located in the lower limit side of the brightness distribution of the background. Therefore, when the relation of Mm+3σm<Mb−3σb is established, the control flow proceeds to step 9-5, and a medicine image cut-out mask for masking a region brighter than Mb−3σb is formed.

If a medicine image cut-out mask is formed in step 9-4 or step 9-5 as described above, the control flow proceeds to step 9-6. In step 9-6, based on the medicine image cut-out mask, an image processing to cut out the back unlit image is executed. That is, the region set for masking by the medicine image cut-out mask is assumed to be a region where the medicine does not exist. Therefore, by applying a medicine image cut-out mask to the back unlit image, an image of the medicine can be obtained by cutting out a region that is not masked in the back unlit image.

By cutting out a back unlit image based on the medicine image cut-out mask that was set as described above, the image of a medicine disposed in the inspection unit 310 can be acquired without omission, and by this, the inspection accuracy of the medicine inspection device 300 can be further improved.

《Perforation Detection Process》

As explained above in the first embodiment, when supplying a sachet b to the inspection unit 310, it is necessary to dispose a sachet b in a suitable position with respect to the inspection unit 310 in order to prevent deterioration in the inspection accuracy of the medicine. When supplying sachet b in a form of a continuous body of sachets formed by a continuum of sachets b, even if the deviation between the sachet b and inspection unit 310 is considered to be extremely small in the initial stages, the deviation will accumulate by sending sachets b sequentially, and there is a possibility that the positional deviation of sachet b with respect to the inspection unit 14 becomes large enough to result in inspection failure. To overcome such problems, it is desirable to detect a boundary d (see FIG. 40) that is formed by perforations etc. between the longitudinal sealing parts s1 and s1 of two continuous sachets b and b in the length direction of the continuous body of sachets B, and to position a sachet b with respect to the inspection unit 310 on the basis of this boundary d.

Therefore, similarly to the medicine inspection device 10 of the above-mentioned first embodiment, the medicine inspection device 300 of this embodiment has a configuration that enables detecting the boundary d between adjacent sachets b. Specifically, the medicine inspection device 300 has a configuration in which a control device 330 is provided with a boundary position detection means 400. Below, the boundary position detection means 400 will be explained in detail.

Figure 41:
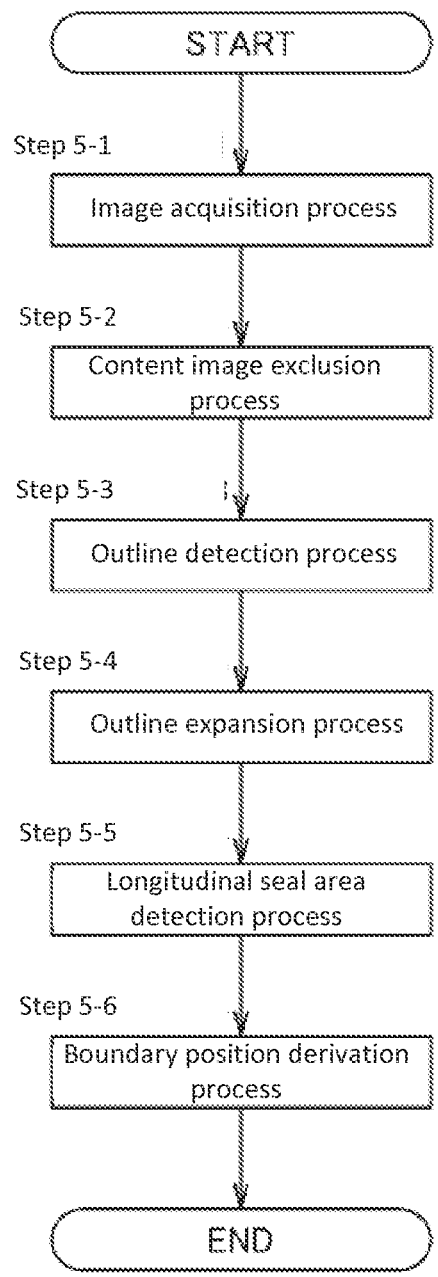
FIG. 41 is a flowchart showing the execution flow of the boundary position detection means performed in the medicine inspection device of FIG. 19.

The boundary position detection means 400 is capable of executing a boundary position derivation process for deriving a boundary d formed in a continuous body of sachets B based on an image obtained by photographing a continuous body of sachets B. As shown in FIG. 41, the boundary position derivation process is executed via the following processes: image acquisition process; content image exclusion process; outline detection process; outline expansion process; and longitudinal seal area detection process.

Specifically, when executing the boundary position derivation process, first, an image acquisition process to acquire an image (hereafter, called as 'original image for boundary derivation') of the continuous body of sachets B by shooting means 18 is executed in step 5-1. Then, in step 5-2, a content image exclusion process is executed to filter out a mapping of medicine or the like contained in sachet b from the original image for boundary derivation by image processing. Specifically, based on either one or both of brightness information or color information of the original image for boundary derivation, a content such as medicine packed in sachet b is identified, and the image information of a section corresponding to the content is removed. In this embodiment, based on the brightness information of the original image for boundary derivation, a content image exclusion process is executed. Here, the content image exclusion process does not need to be performed immediately after acquisition of original image for boundary derivation, and it may be executed in the operation stage before executing the longitudinal seal area detection process, which is described later in detail.

In step 5-3, the original image for boundary derivation, after the content image exclusion process, is subjected to outline detection process. The outline detection process is executed by matching using methods such as the so-called shape base pattern matching, or gray pattern matching etc. The boundary position detection means 400 of this embodiment can detect an outline included in the original image for boundary derivation by shape base pattern matching.

Once the step 5-3 is completed, the boundary position detection means 400 executes the outline expansion process in step 5-4. The contour line expansion process is an image processing for acquiring an image for vertical seal area detection by executing an image processing of expanding a region surrounded by the outline, which was detected by outline detection process, outwardly only by a predetermined amount.

Here, within a rectangular area in which longitudinal sealing is formed in the continuous body of sachets B, a large number of dot-patterned seal marks are formed in the shorthand direction (width direction) of the continuous body of sachets B. Therefore, if a region formed by an outline of the seal marks is expanded, each region mutually overlaps to form a region extending as a whole in the vertical seal direction (hereafter also referred to as 'vertical seal area').

In light of these characteristics, in step 5-5, the boundary position detection means 400 executes a process (the longitudinal seal area detection process) to detect an image region corresponding to the vertical seal area from the vertical seal detection image obtained in step 5-4. If the vertical seal area is detected by this, subsequently in step 5-6, a process is executed to derive the intermediate position of the vertical seal area as the position of the boundary d between the adjacent sachets b (boundary position derivation process).

As described above, in the medicine inspection device 300 of this embodiment, by expanding an outline towards the outside of a detection area by an outline expansion process to make a plurality of detection areas overlapped with one another, accuracy is improved to determine whether the detected outline and detection area in the outline detection process are due to dot-patterned seal marks of the longitudinal sealing part. Therefore, according to the medicine inspection device 300, identification of the position of the vertical seal applied to a continuous body of sachets B, and identification of the boundary position between adjacent sachets b can be performed with excellent accuracy.

Further, in the medicine inspection device 300 of this embodiment, by executing the content image exclusion process in an operation stage prior to executing the longitudinal seal area detection process, the item stored in a sachet b is identified based on the brightness information or color information of an image used for deriving the position of the boundary, and the image information of a section corresponding to the content is removed. This makes it possible to suppress the possibility of erroneously detecting the outline of content as the outline of the longitudinal sealing part, and to further improve the accuracy of detecting the perforations of boundary d.

Moreover, in this embodiment, the execution accuracy and execution speed of longitudinal seal area detection process is improved by previously removing the image information of a section corresponding to the content by executing the content image exclusion process, but the present invention is not limited to this, and it is also possible not to execute the content image exclusion process.

《 Modified Example of Perforation Detection Process》

Figure 69:
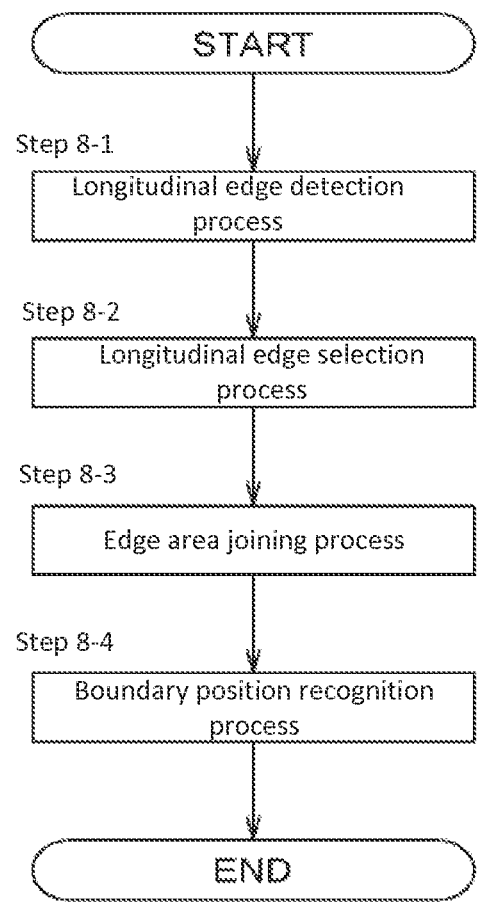
FIG. 69 is a flowchart showing a modification example of perforation detection process according to one embodiment of the present invention.

The method of executing perforation detection process by the boundary position detection means 400 is not limited to the method described above, and it may also be a method that is executed in accordance with the control flow shown in FIG. 69, for example. The control flow of FIG. 69 is described below.

In the boundary position detection means 400, it is possible to derive the position of boundary by executing each of the flowing processes. That is, in step 8-1, the longitudinal edge detection process is first executed. That is, an image analysis is performed for detecting edges from the image of sachet b photographed by shooting means 18 (original image for boundary derivation). Among the edges detected by this, the outline extending in the vertical direction is detected as a vertical edge.

Once detection of the vertical edge is completed in step 8-1, the control flow executes a longitudinal edge selection process in step 8-2. The longitudinal edge selection process is a process to select a vertical edge, among the vertical edges detected in step 8-1, that is likely to be a boundary d and the longitudinal sealing parts s1 and s1 adjacent to the boundary d. The longitudinal edge selection process selects edges, among the vertical edges detected in step 8-1, that is longer than a predetermined length as a candidate of boundary d and vertical edges corresponding to the longitudinal sealing part s1 and s1 adjacent to the boundary d. Next, the control flow proceeds to step 8-3.

In step 8-3, an edge area joining process is performed. The edge area joining process combines, among a plurality of vertical edges selected by the longitudinal edge selection process, the region in which the interval between vertical edges fits within a predetermined interval, which is set based on the width of longitudinal sealing part, as edge areas. That is, if the interval between vertical edges is larger than a predetermined error range with the interval between the longitudinal sealing parts s1 and s1 as reference, or if smaller than that, it is likely that the vertical edge selected in step 8-2 is not a boundary d or does not correspond to longitudinal sealing parts s1 and s1. Thereupon, the regions that fit within a predetermined interval, wherein the interval between the vertical edges is set using the width of the longitudinal sealing part as reference, are searched and joined as edge areas.

When the joining of edge areas is completed as described above, the control flow proceeds to step 8-4, and the boundary position recognition process is executed. A boundary position confirmation process is a process for checking whether the central portion of the edge area joined in the edge area joining process of step 8-3 is valid as a position of the boundary d between the longitudinal sealing parts. With this, the boundary d can be easily and accurately detected.

Moreover, when the processes of step 8-1 through step 8-4 cannot be properly executed (error state) in the perforation detection process according to this modification example, it may be configured to notify a user of a failure to detect boundary d, but it may also be configured to perform detection of perforations (boundary d), for example, by methods according to the control flow shown in FIG. 41, or by other methods.

In the method of perforation detection process described above, boundary d is to be derived by focusing on the features of a continuous body of sachets B in which longitudinal sealing parts s1, s1, and the boundary d formed between the longitudinal sealing parts s1 and s1 extend in the vertical direction and can be detected as a vertical edge that extends longer than a predetermined length, as well as the vertical edge corresponding to longitudinal sealing part and the boundary fit within a predetermined interval. Therefore, in the method of perforation detection process described above, the position of the boundary d can be derived easier and more accurately compared to a case of deriving the boundary by a simple image analysis.

《 Method of Aligning the Top Sachet Position at the Time of Continuous Prescription》

Figure 40:
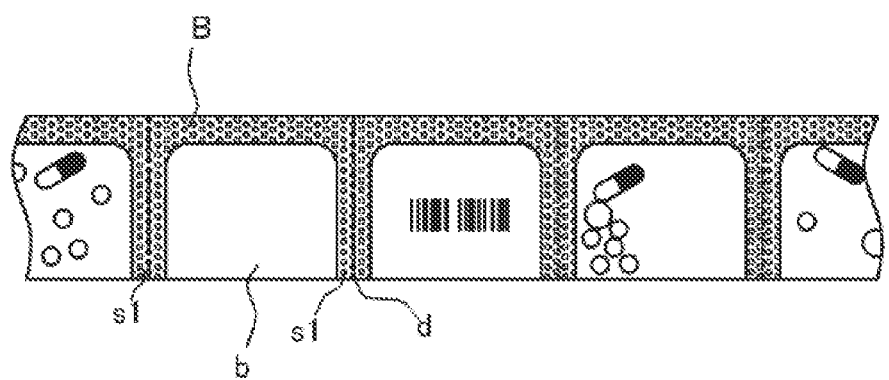
FIG. 40 is an explanatory drawing illustrating an example of a continuous body of sachets with an empty sachet formed midway.

In the medicine inspection device 300 of this embodiment, a continuous body of sachets B formed by a continuum of many sachets b can be supplied sequentially to inspection unit 310, and checked if a medicine has been packaged according to prescription. Here, when a medicine is packaged in the form of a continuous body of sachets B, in addition to forming different continuous body of sachets B for each prescription, a continuous body of sachets B may be also formed by a continuum of sachets b of multiple prescription doses. Thus, if sachets b of different prescriptions are present in one series of a continuous body of sachets B, one or a plurality of empty sachets are formed between the sachets b of the former prescription and sachets b of the latter prescription as shown in FIG. 40. Further, in a predetermined position of an empty sachet b, a bar code providing information such as prescription information (identification label) is added.

In the case of including a continuum of sachets b of different prescriptions is one series as described above, when sachets b of latter prescription following an empty sachet b is supplied to the inspection unit 310 after inspection of sachets b of the former prescription is carried out, it is necessary to position the sachet b precisely with respect to inspection unit 310 when performing inspection for the latter prescription. Therefore, when sachets b of multiple prescriptions are included in a single continuous body of sachets B, a medicine inspection device 300 is configured as described below in order to determine the position of a prescription sachet b (head feeding) that follows an empty sachet.

Specifically, the medicine inspection device 300 includes an identification mark recognition means 410 for recognizing the identification marks attached to an empty sachet b. In this embodiment, as an identification mark recognition means 410, a bar code reader capable of reading a bar code by generating laser light is used. In addition, the identification mark recognition means 410 is disposed in the upstream of the direction in which the continuous body of sachets B is conveyed by the transportation means 12 with respect to the inspection unit 310.

A sachet positioning means 420 is provided to the control device 330. The sachet positioning means 420 can determine the position of a medicine-containing sachet b existing in the downstream of the empty sachet b with respect to inspection unit 310 based on the recognized position where an identification mark (bar code) was recognized by identification mark recognition means 410, i.e. installation position of the identification mark recognition means 410. Specifically, at the instant when an identification mark is recognized by identification mark recognition means 410, the sachet positioning means 420 infers that an empty sachet b has reached directly below the identification mark recognition means 410.

Here, the interval between identification mark recognition means 410 and inspection unit 310, and the size of sachet b are previously determined by sachet positioning means 420. Therefore, at the instant when an empty sachet b has reached directly below the identification mark recognition means 410, the sachet positioning means 420 can derive how much a continuous body of sachets B should be moved towards the inspection unit 310 so that a sachet b of the next prescription can reach the inspection unit 310. Then, the sachet positioning means 420 sends the continuous body of sachets B towards the inspection unit 310 only by that length required for a sachet b of the next prescription to reach the inspection unit 310. Accordingly, a prescription sachet following an empty sachet b can be positioned with respect to the inspection unit 310 (head feeding). Therefore, in the medicine inspection device 300 of this embodiment, even for a case such as forming an empty sachet in the middle of a continuous body of sachets B for continuous prescription etc., as described above, with regard to a medicine-filled sachet b existing in the downstream of an empty sachet b, it becomes possible to avoid lowering of the inspection accuracy due to a decrease in the positioning accuracy with respect to the inspection unit 310.

In this embodiment, an example was presented in which a medicine inspection device 300 is capable of not only medicine inspection process, but also foreign object detection process, medicine master construction process, and perforation detection process, however, the present invention is not limited to this, and it may also exclude a function to perform all or part of processes except for the medicine inspection process.

It is also possible to use the medicine inspection device 300 of this embodiment instead of the medicine inspection device 10 in the medicine packaging device 100 of the first embodiment described above.

《《 Modification Examples 》》

Below, modification examples that can be applied to either one or both of the medicine inspection devices 10 and 300 shown in the embodiments above will be described in detail with reference to diagrams. In the description below, the modification examples applicable to either one or both of the medicine inspection devices 10 and 300 will be described taking the medicine inspection device 300 as an example unless otherwise restricted.

《 Fixing Device and Oscillation Operation 》

In both of the medicine inspection devices 10 and 300 described above, by vibrating a continuous body of sachets B (sachets b) in a horizontal direction on the way to the inspection units 14 and 310 from the upstream of conveying direction, it is possible to overturn and disperse a medicine by the time it reaches the inspection units 14 and 310. Here, if a sachet b is heavy because it contains many medicines or the like, the sachet b may slip in the conveyance path and may not be oscillated well even when the transportation means 12 is operated so as to perform an oscillating operation as described above. Consequently, it is possible that a sachet b is not correctly disposed in the inspection location after oscillation, and accurate imaging and inspection may not be performed. In order to avoid such a situation, it is preferable to temporarily secure the end of a continuous body of sachets B.

Figure 42:
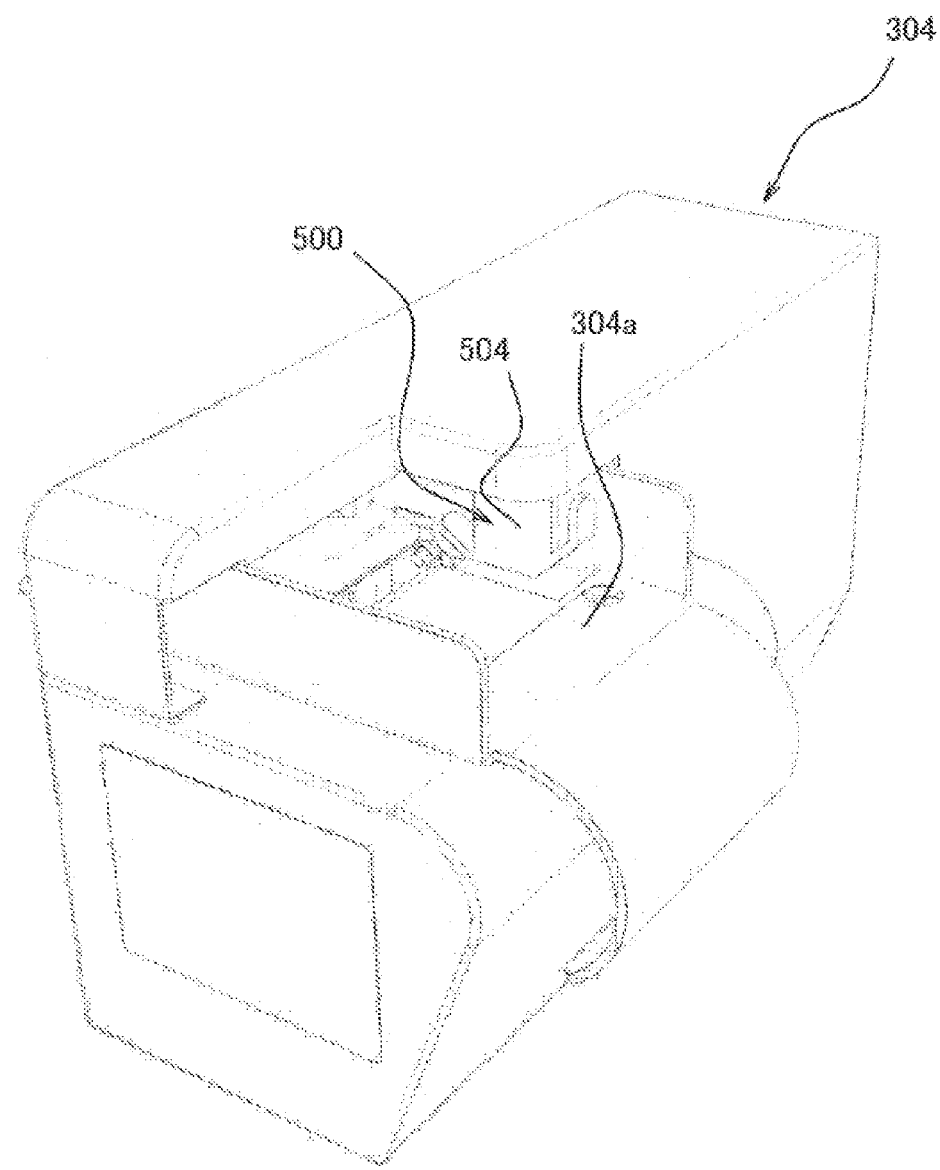
FIG. 42 is a perspective view of the appearance of an introduction unit.
Figure 43:
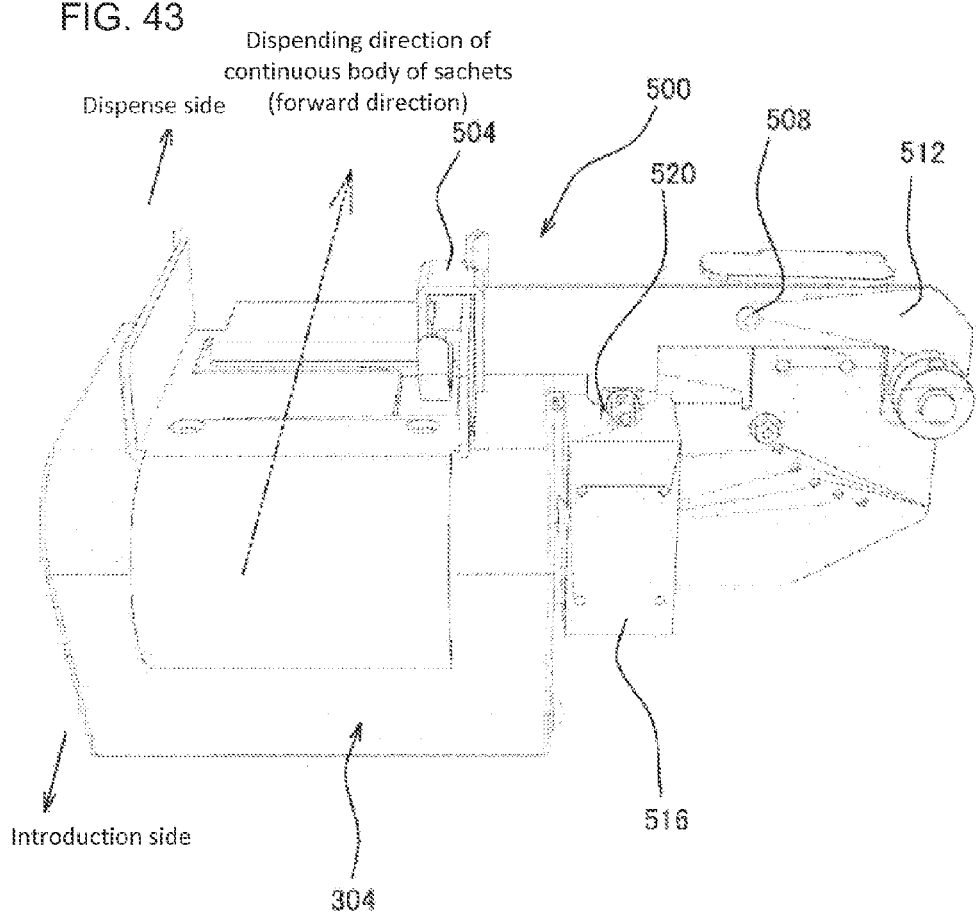
FIG. 43 is a perspective view of the internal structure of the introduction unit
Figure 44:
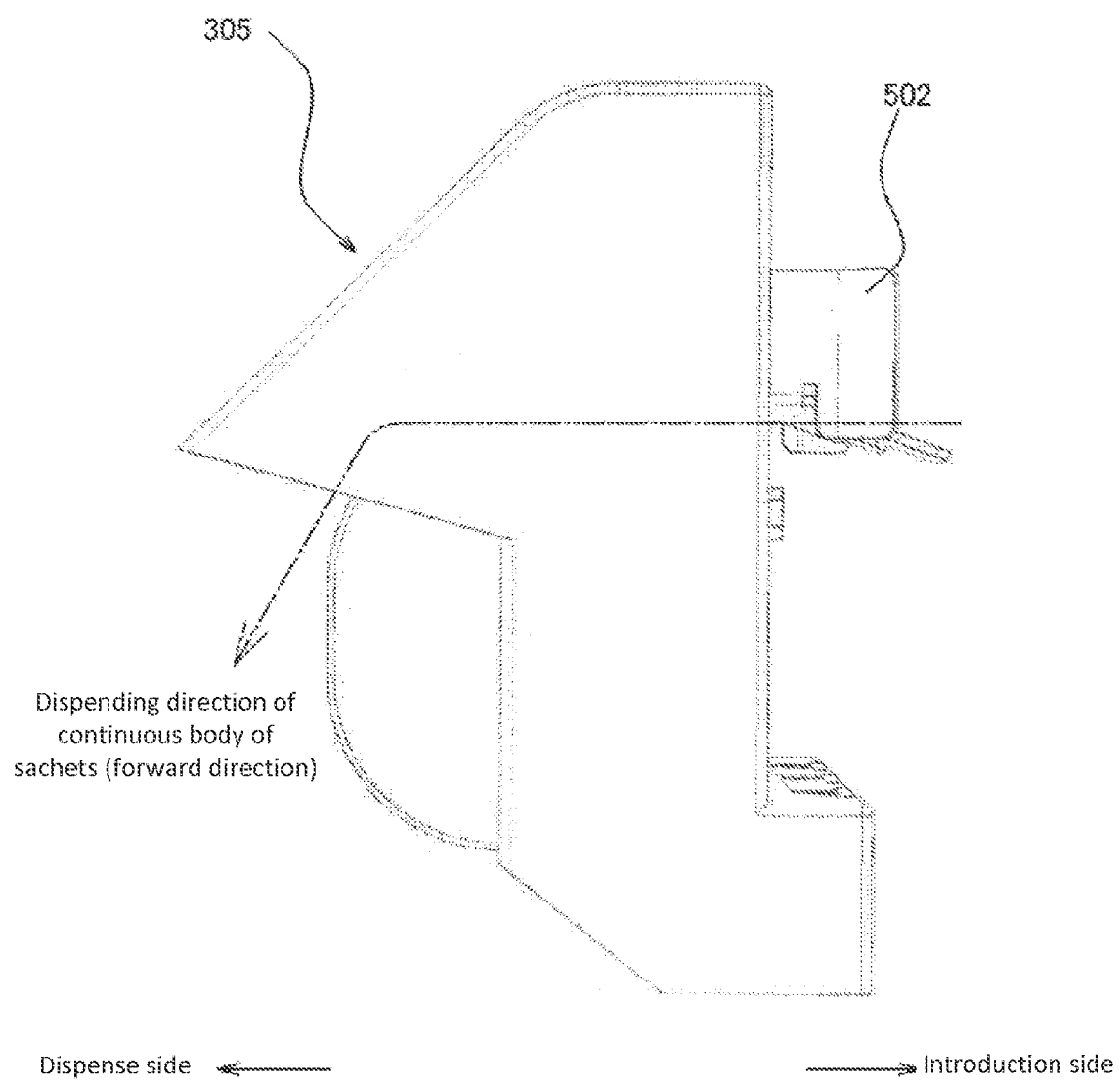
FIG. 44 is a side view showing the appearance of an ejection unit.
Figure 45:
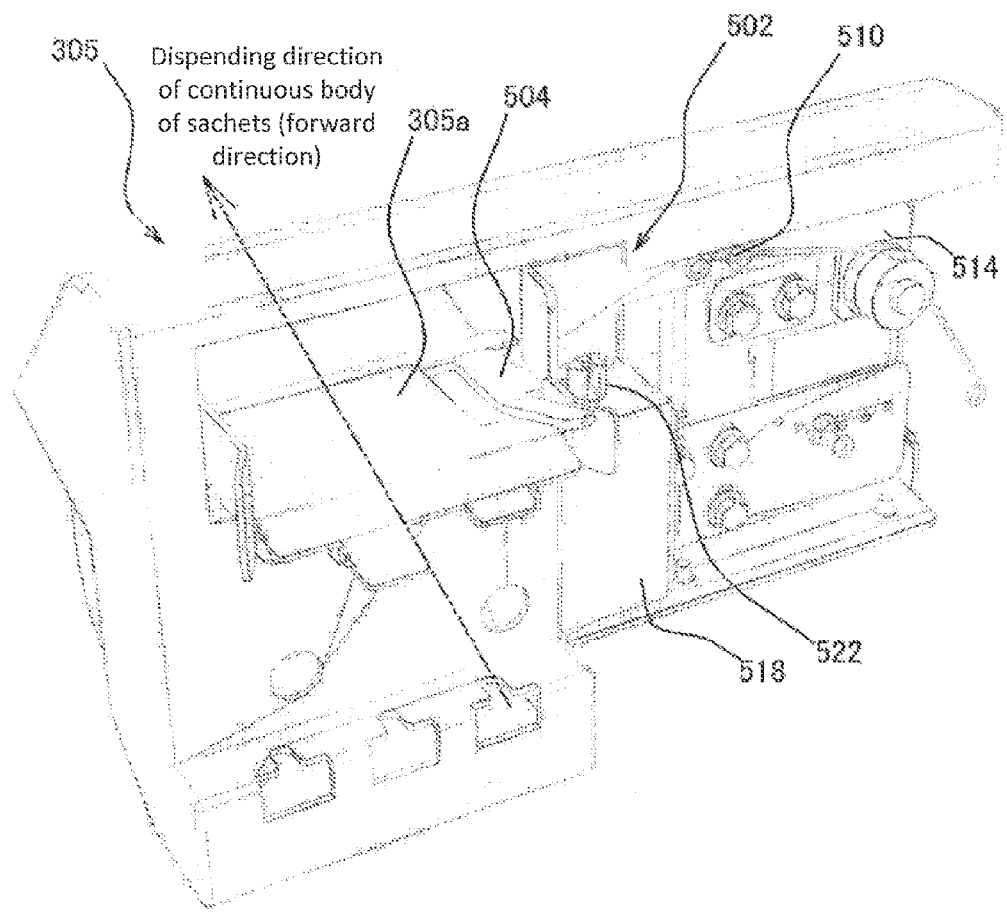
FIG. 45 is a perspective view showing an ejection unit when viewed from the inside of the medicine inspection device.
Figure 46:
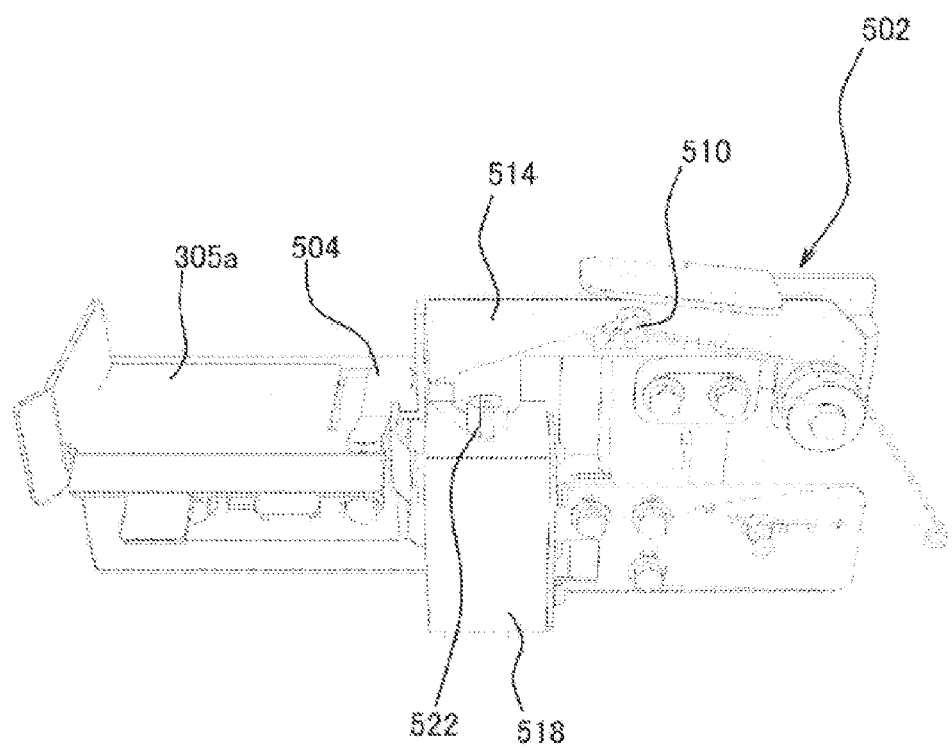
FIG. 46 is a perspective view of the structure of an ejection unit.

By further explaining with the medicine inspection device 300 as an example, a fixing device 500 as shown in FIG. 42 and FIG. 43 is provided to the introduction unit 304. As shown in FIG. 44 through FIG. 46, a fixing device 502 equipped with a driving mechanism similar to the fixing device 500 is also provided in the ejection unit 305. Fixing devices 500 and 502 are provided with pressing pieces 504 and 506 capable of moving up/down with respect to a horizontal surface 304a and 305a in which a continuous body of sachets B passes through in the introduction unit 304 and ejection unit 305. Usually, the pressing pieces 504 and 506 are located above the horizontal surfaces 304a and 305a with a clearance in which a continuous body of sachets B can pass through. When it is necessary to temporarily fix a continuous body of sachets B, the pressing pieces 504 and 506 are lowered and pressed against the horizontal surfaces 304a and 305a. With this, it becomes possible to hold and fix a continuous body of sachets B existing in the gap between the horizontal surfaces 304a, 305a and pressing pieces 504, 506.

It is possible to use any kind of operating mechanism and installation position of the fixing devices 500 and 502. That is, apart from the configuration to integrally hold the belt of the transportation means 12 and a continuous body of sachets B, the fixing devices 500 and 502 can be of type shown in FIG. 42 through FIG. 46, for example. Namely, the fixing devices 500 and 502, on the side of the horizontal surfaces 304a and 305a of the introduction unit 304 or ejection unit 305, have swinging pieces 512 and 514 supported so as to oscillate around the shaft body 508 and 510 such as bolt or pin. Pressing pieces 504 and 506 have been integrally formed in the tip section of the swinging pieces 512 and 514. Further, drive shafts 520 and 522 of solenoids 516 and 518 are connected to the swinging pieces 512 and 514. By moving the drive shafts 520 and 522 back and forth, the swinging pieces 512 and 514 can be oscillated, and the pressing pieces 504 and 506 provided in the tip section can be moved up and down.

Next, the oscillation operation for oscillating a continuous body of sachets B in the horizontal direction so as to disperse a medicine packaged in a continuous body of sachets B (sachet b), and coordinated operation with fixing devices 500 and 502 will be explained. For oscillation operation, an oscillation method P1 involving first oscillating a sachet toward the introduction unit 304 followed by oscillating it to return to the ejection unit 305, and a oscillation method P2 involving first oscillating a sachet to the ejection unit 305 followed by oscillating it to return to the introduction unit 304 may be considered. When oscillating a continuous body of sachets B by the oscillation method P1, the continuous body of sachets B is to be fixed by the fixing device 500 provided on the introduction unit 304 side, and the fixing by the fixing device 502 provided on the ejection unit 305 side is to be released. When oscillating a continuous body of sachets B by the oscillation method P2, the continuous body of sachets B is to be fixed by the fixing device 502 provided on the ejection unit 305 side, and the fixing by the fixing device 500 provided on the introduction unit 304 side is to be released. Thus, it is possible to oscillate a continuous body of sachets B without damaging it.

《 Upright-State Elimination Means 》

Figure 47:
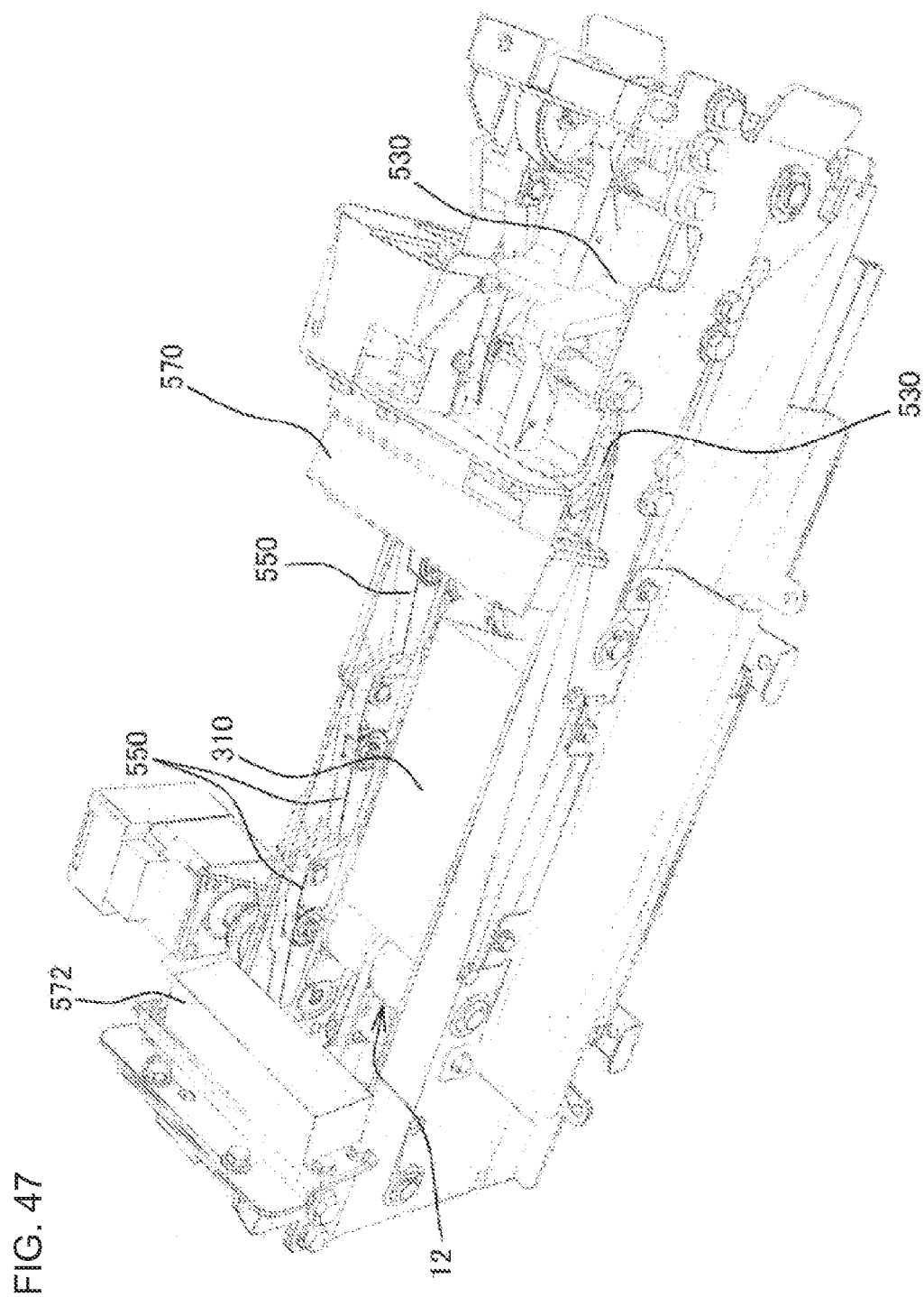
FIG. 47 is a perspective view showing the major parts of a structure according to a modification example.
Figure 48:
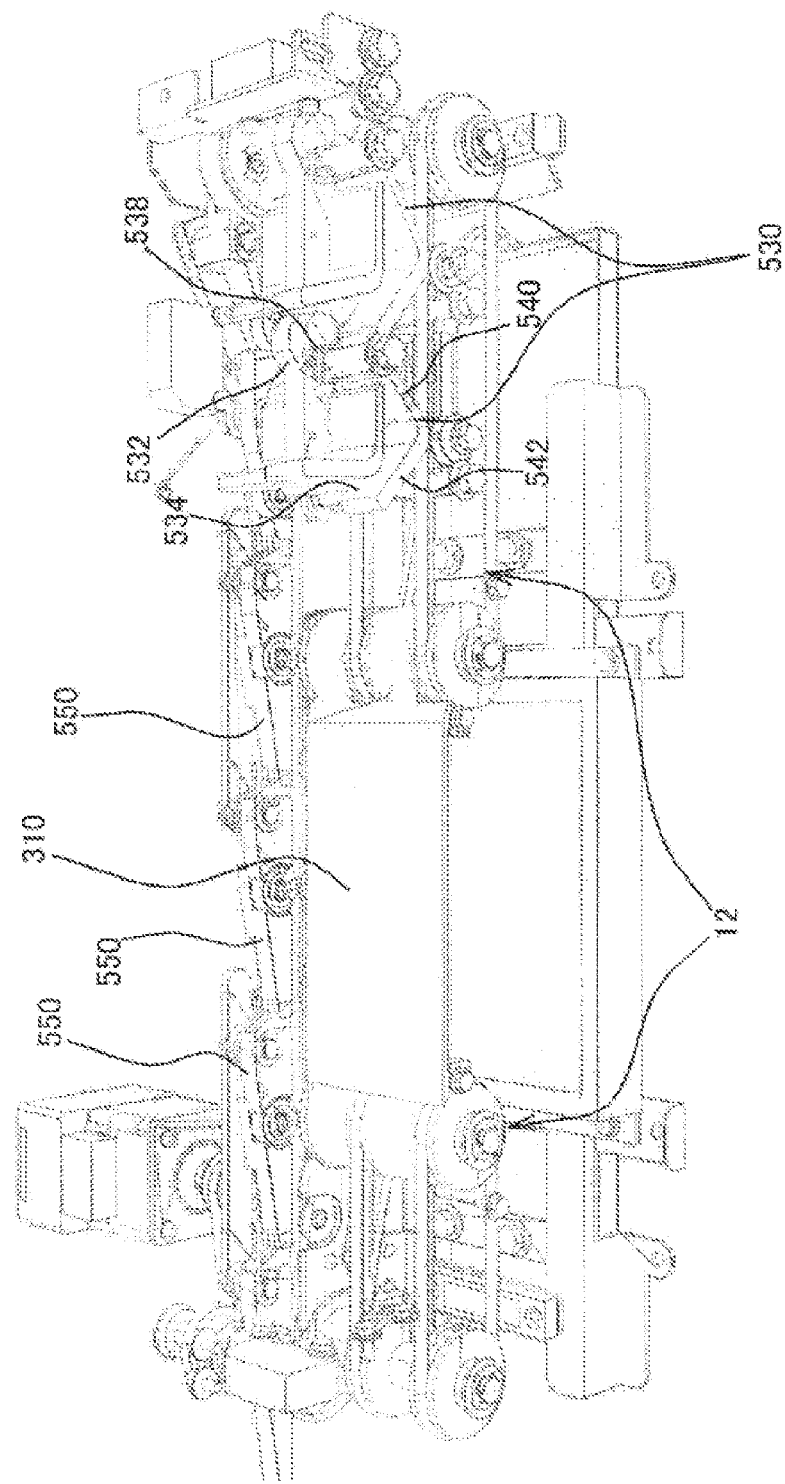
FIG. 48 is a perspective view showing the major parts of a structure according to a modification example.
Figure 49:
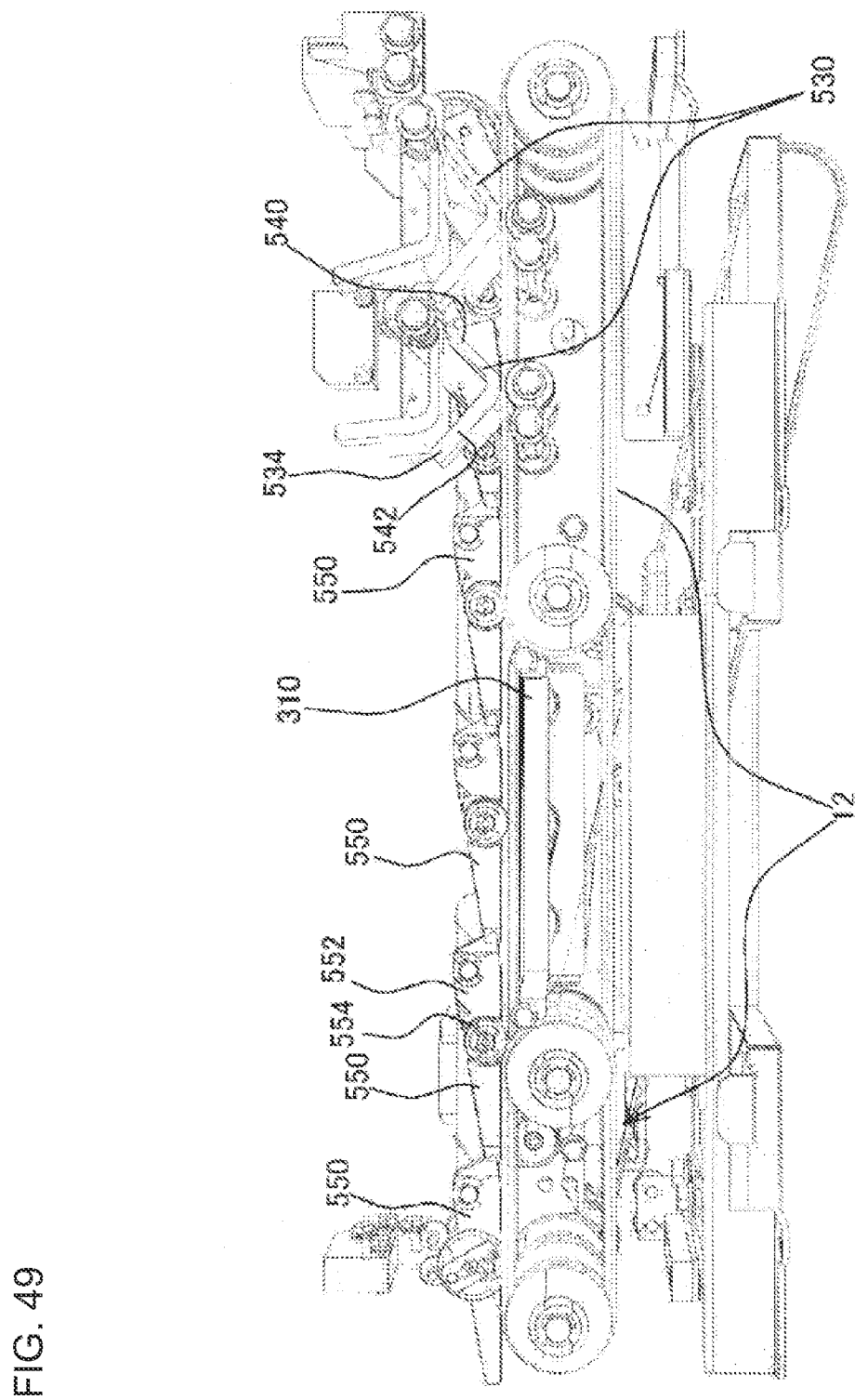
FIG. 49 is a side view showing the major parts of a structure according to a modification example.
Figure 50A:
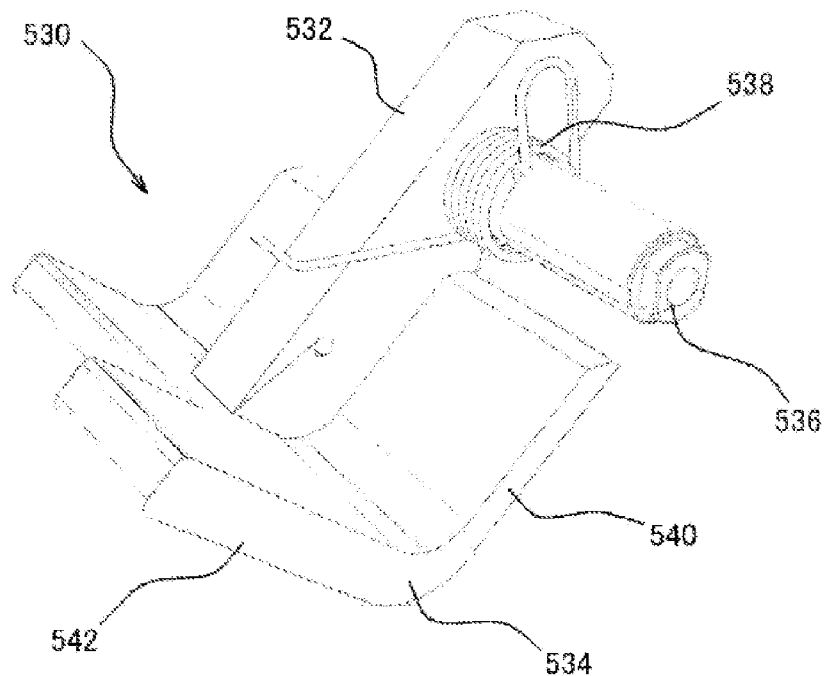
FIGS. 50A and 50B are, respectively, a perspective view and the side view of an upright-state elimination means.
Figure 50B:
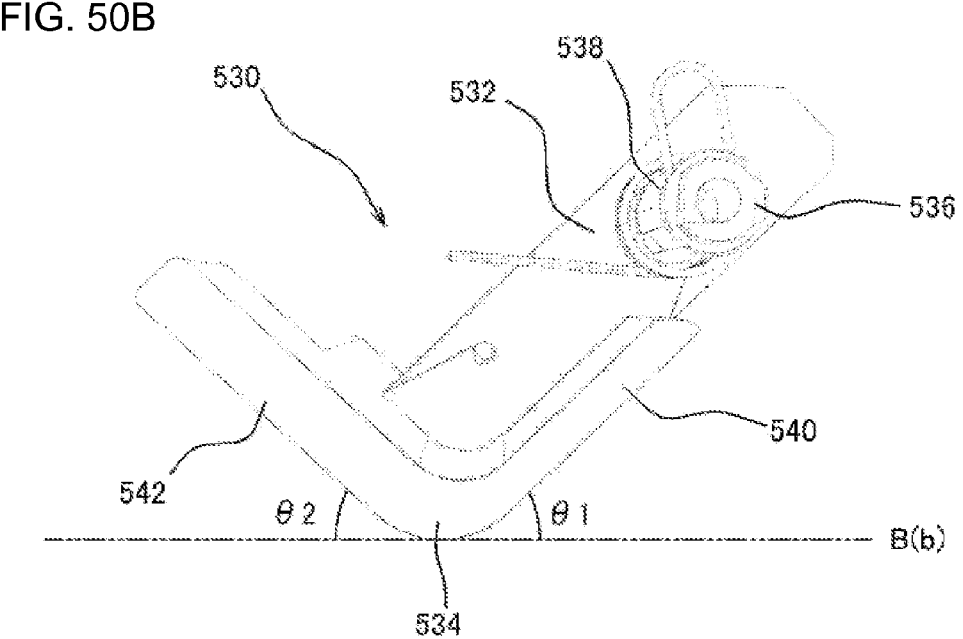

The above embodiment illustrated an example of providing an upright-state elimination means 110 provided with a roller 114*a* at the tip of an arm 114 for overturning an upright medicine in a sachet b, but it is not limited to the configuration described above, and it is also possible to have an upright-state elimination means 530 shown in FIG. 50, and one or more of it can be provided in the upstream of the inspection unit 310 as shown in FIG. 47 through FIG. 49. Specifically, the upright-state elimination means 530 consists of an arm 532, and a contact part 534 having an approximately 'V' shape in the side view is provided at the end of the arm 532. Similar to the arm 114 of the above-mentioned upright-state elimination means 530, the arm 532 is installed so as to freely rotate with respect to a spindle 536 that is provided so as to be transverse to the conveyance path of the packaging paper. Further, the arm 532 is biased towards the conveyance path by a spring 538. Accordingly, with respect to the surface of the packaging paper passing through the conveying path, the contact part 534 can be contacted with the packaging paper by an appropriate strength that does not damage the packaging paper and the medicine.

The contact part 534 consists of an introduction side sloping surface 540 inclining towards the introduction unit 304, and a dispense side sloping surface 542 inclining towards the ejection unit 305. The angle θ1 formed between the introduction side sloping surface 540 and the conveyance path formed by the transportation means 12 and a continuous body of sachets B (sachet b) traveling on this, and the angle θ2 formed between the conveyance path and dispense side sloping surface 542 are both acute angle.

《 Another Modified Example of Upright-State Elimination Means 》

The above-mentioned upright-state elimination means 110 and 530 are only one embodiment of the present invention, and it is also possible to have a different one. Specifically, an upright-state elimination means 700 shown in FIG. 75 is comprised of a contact part 702. The contact part 702 consists of an introduction side sloping surface 704 and dispense side sloping surface 706. The introduction side sloping surface 704 and dispense side sloping surface 706 have a configuration similar to the introduction side sloping surface 540 and dispense side sloping surface 542 respectively forming the contact part 534 of the upright-state elimination means 530 described above. Therefore, a detailed description will be omitted.

The upright-state elimination means 700 is characterized by being provided with a medicine leveling unit 708 in addition to the introduction side sloping surface 704 and the dispense side sloping surface 706 described above. The medicine leveling unit 708 is installed between the introduction side sloping surface 704 and dispense side sloping surface 706. The medicine leveling unit 708 is comprised of a spindle 710 and a bead member 712. Spindle 710 is a shaft body provided so as to extend along a ridge formed in the boundary section between the introduction side sloping surface 704 and dispense side sloping surface 706. That is, with respect to the installation condition of the upright-state elimination means 700, the spindle 710 is installed so as to be substantially orthogonal to the traveling direction of the continuous body of sachets B.

The bead member 712 is configured by such as abacus bead or pearl like beads. In this embodiment, a hexagonal cross-section-shaped or approximately diamond-shaped bead having an appearance as though bottom of two cones have been joined, such as an abacus bead, is used as a bead member 712. The bead member 712 is mounted so as to slide with respect to the spindle 710.

If such a configuration is adopted, by the reciprocation of a continuous body of sachets B, the bead member 712 will slide along the spindle 710 while contacting the medicine. The bead member 712, while moderately contacting the medicine while sliding in the axial direction in this manner, can overturn a medicine in an upright condition so that inspection can be done easily.

《 Introduction Operation of a Continuous Body of Sachets 》

By providing an upright-state elimination means 530 of a shape described above, not only the operation of sending a continuous body of sachets B from the introduction unit 304 towards the ejection unit 305 (forward operation), but also when performing an operation for sending the continuous body of sachets B in a direction opposite to this (reverse operation), the continuous body of sachets B flows smoothly without climbing onto the upright-state elimination means 530. Therefore, by providing the upright-state elimination means 530, the operations as follows can be executed without causing failure, for example.

That is, similarly to the medicine inspection device 10, it is possible to provide a configuration of the medicine inspection device 300 wherein a supply detection means 24*a* and a reading device 72 are provided in the upstream of conveyance path with respect to the inspection unit 14, and a dispense detection means 24*b* is provided in the downstream of conveyance path with respect to the inspection unit 14. Here, if normal, together with detecting a continuous body of sachets B by supply detection means 24*a*, by sending the continuous body of sachets B by executing the above-mentioned forward operation to move it only by a predetermined distance from the moment of recognizing by reading the bar code provided at the top section of the continuous body of sachets B with a reader device 72, it is possible to make a sachet b to be inspected to reach the inspection unit 310 and the position thereof can be determined.

However, when introducing a continuous body of sachets B, if an operator misses the timing of releasing a hand from the continuous body of sachets B or the like, it's rare but the continuous body of sachets B may not travel in the conveyance path as expected, and there is a possibility of sachet b cannot be positioned accurately with respect to the inspection unit 310. If such a problem is expected, it is desirable to operate by combination of forward and reverse operations, and introduce a continuous body of sachets B in the following manner.

That is, when introducing a continuous body of sachets B into the device, by first operating the transportation means 12 in the forward direction, a continuous body of sachets B is drawn through a path to reach the installation location of dispense detection means 24*b* via the installation location of the supply detection means 24*a* and inspection unit 310. With this, at the moment when the continuous body of sachets B is detected by dispense detection means 24*b*, the transportation means 12 is operated in reverse direction, and the sachet b to be inspected is reached to the inspection unit 310. The positional relationship between the dispense detection means 24*b* and inspection unit 310 is determined in advance, and cannot be changed. Therefore, by performing a reverse operation to move the continuous body of sachets B in the opposite direction only by a distance between dispense detection means 24*b* and inspection unit 310, a sachet b can be accurately positioned with respect to the inspection unit 310.

Also, if a continuous body of sachets B is introduced into the device as explained above, even if a continuous body of sachets B is assumed to be short, an upright-state elimination means 530 prevents a problem such as a continuous body of sachets B riding onto top of the upright-state elimination means 530 during reverse operation.

≪ Another Modification Example for Introduction Operation of a Continuous Body of Sachets ≫

If the above-mentioned upright-state elimination means 530 or upright-state elimination means 700 is provided, a continuous body of sachets B can be moved smoothly in forwards direction (forward operation) as well as in reverse direction (reverse operation). Therefore, when each sachet b of a continuous body of sachets B is inspected in the inspection unit 14, if the result of the inspection is determined to be different from the prescription, or if a potential foreign object is identified to be present in sachet b, it is possible to move the sachet b in the opposite direction up to the upright-state elimination means 530, 700, and to reciprocate the continuous body of sachets B within the range where the upright-state elimination means 530, 700 contacts the surface of the sachet b.

As described above, by moving the sachet b to the upright-state elimination means 530, 700 and reciprocating it in case the result of inspection is abnormal, a medicine contained in sachet b can be surely overturned, and made into a state in which an accurate inspection is possible. Thus, if the cause for abnormal inspection result is due to the upright state of the medicine contained in sachet b, this cause can be resolved.

As described above, by sending a continuous body of sachets B in opposite direction up to upright-state elimination means 530, 700 if the result of the inspection differs from the prescription information, an inspection failure due to upright state of a medicine can be resolved, and the inspection accuracy can be improved. As described above, by sending a continuous body of sachets B in opposite direction up to upright-state elimination means 530, 700 only if the result of the inspection differs from the prescription information, an inspection failure due to upright state of a medicine can be resolved, and the inspection accuracy can be improved.

≪ Conveyance Guide ≫

Figure 16:
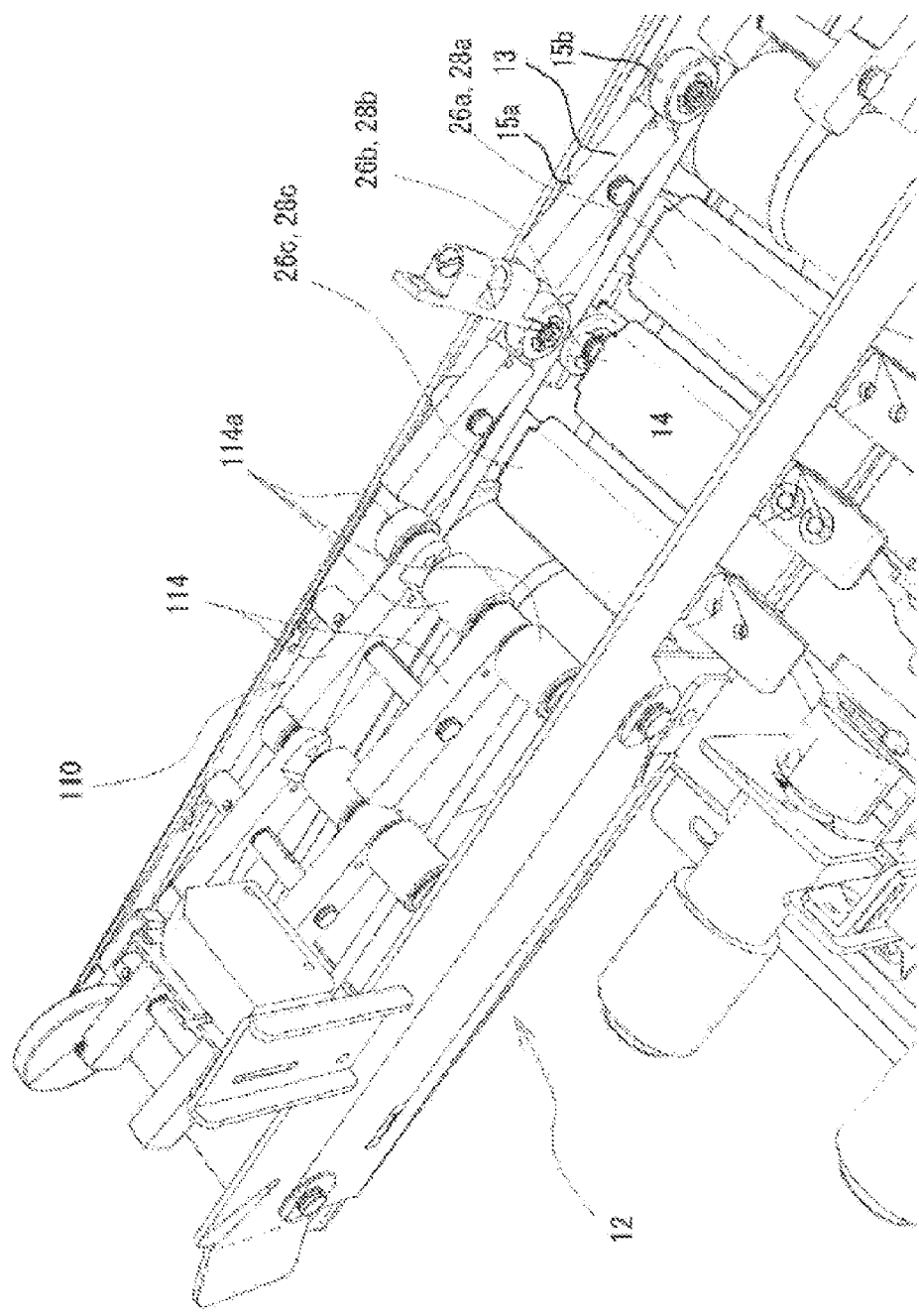
FIG. 16 is a perspective view showing an example of providing an upright-state elimination means shown in FIG. 13(b).
Figure 17:
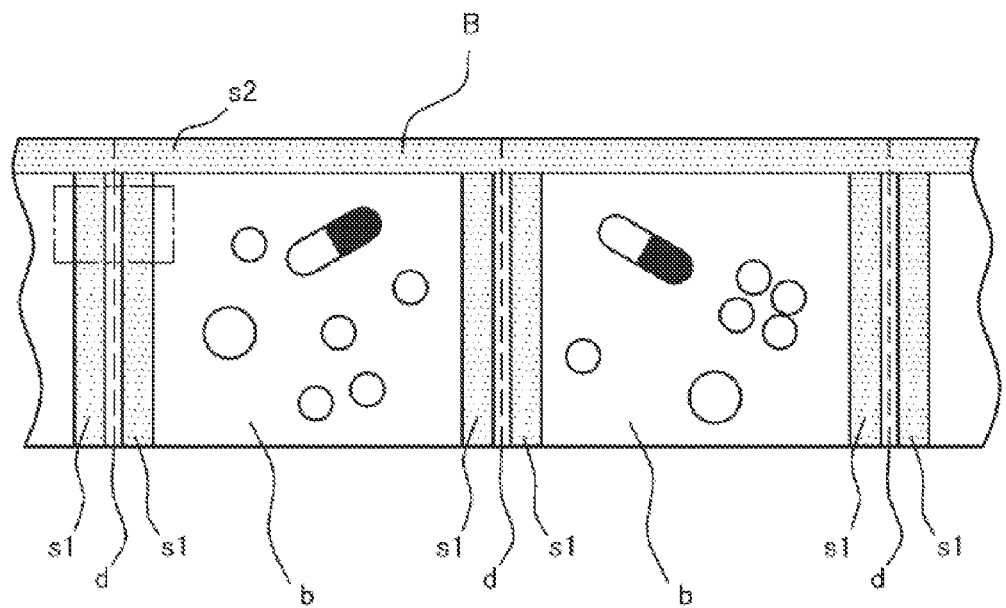
FIG. 17 is a front view showing one example of a continuous body of sachets.

In the medicine inspection devices 10, 300, a plurality of conveyance guides 13 are aligned in the conveyance direction on the side of the transportation means 12 for sending a continuous body of sachets B to inspection unit 310. As for the conveyance guides 13 shown in FIG. 5 and FIG. 16 etc., the guide roller 15*b* is attached rotatably at the tip of support arm 15*a*, which is biased towards conveyance path. The conveyance guide 13 can come in contact with the guide roller 15*b* in the section corresponding to the transverse seal part of a continuous body of sachet that travels on the conveyance path, and apply pressing force. Therefore, a continuous body of sachets B can be guided without need to apply pressing force to the medicine contained in each sachet b.

Figure 51A:
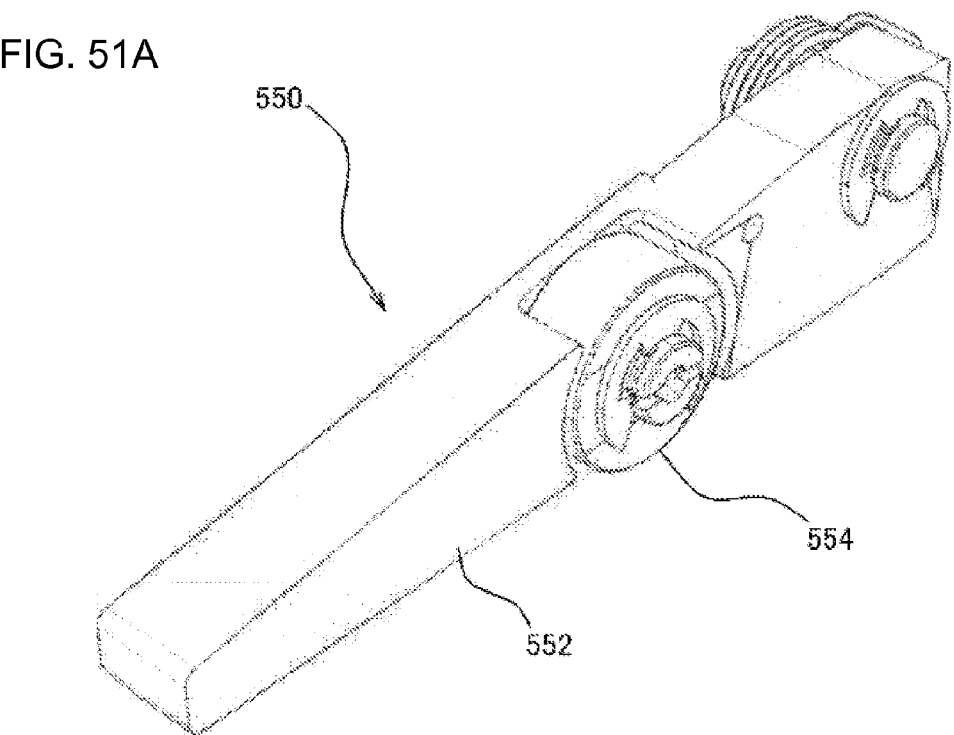
FIGS. 51A, 51B, and 51C are, respectively, a perspective view, a front view, and a rear view of a conveyance guide according to a modification example.
Figure 51B:
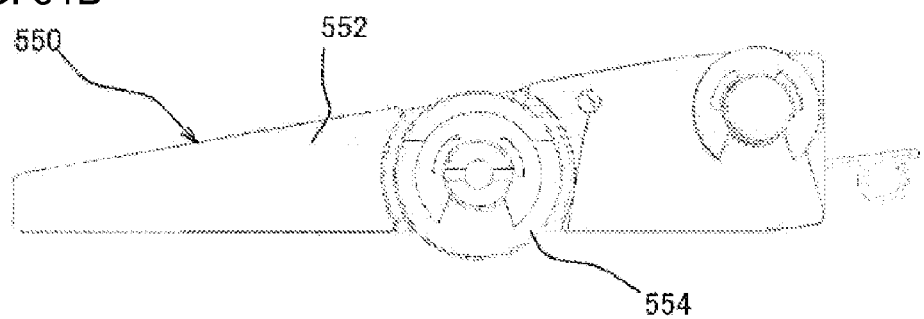
Figure 51C:
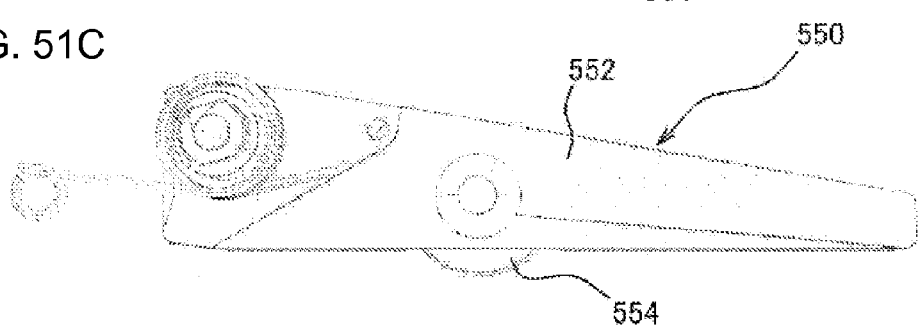

Here, in case the transportation means 12 is operated in forward and reverse directions as described above when introducing the above-mentioned continuous body of sachets B into the device, it is possible that the continuous body of sachets B may climb on the conveyance guides 13. If there is such a concern, it is desirable that, instead of the conveyance guides 13 shown in FIG. 5 and FIG. 16, etc. a conveyance guide 550 as shown in FIG. 51 be installed as shown in FIG. 47 through FIG. 49.

Specifically, the conveyance guide 550 is formed so as extend in the conveyance direction by the transportation means 12, and is provided with a support arm 552 that can surface-contact the surface of the continuous body of sachets B passing over the conveyance path. The conveyance guide 550 is installed at the side of the transportation means 12 so as to align with the support arm 552 without providing a gap for the passage of a sachet. Further, at the center in the longitudinal direction of the support arm 552, a guide roller 554 is attached.

By configuring the conveyance guide 550 as described above, irrespective of moving the continuous body of sachets B either in forward direction or reverse direction on the conveyance path, it is possible to prevent the continuous body of sachets B from climbing on the conveyance guide 550. Furthermore, because the guide roller 554 pass over the lateral sealing part of the continuous body of sachets B, the passing of the guide roller 554 on the medicine contained in each sachet b can be prevented.

≪ Edge Detection by Composite Image ≫

Next, a modification example of the image inspection method implemented in the medicine inspection device 300 shown in the above-mentioned second embodiment will be described. As described above, in the medicine inspection device 300, it is possible to identify the quantity and type of medicine packaged in a sachet b, and check whether they match the prescription information by following the flow shown in FIG. 26 or FIG. 66. Here, when executing the image inspection process in step 1-4 or step 6-6 of the flow shown in FIG. 26 or FIG. 66, a matching process is performed on the image (basic image processed image) obtained by processing the basic image via the respective processes of step 1-1 through step 1-3, or step 6-1 through step 6-5.

Here, when performing the matching process in step 1-4 or step 6-6, a process is executed wherein the outer contour that is thought to be the image of the medicine is extracted from the basic image processed image as an edge. When the color of a medicine included in the basic image processed image is not same as the background color of the image, the outer contour of the medicine can be extracted easily and accurately. However, in case the color of a medicine is same as the background color, extraction of the outer contour of the medicine is considered to be extremely difficult. Therefore, when the extraction of the outer contour of the medicine is difficult because the color of a medicine is same as the background color or the like, a composite image edge extraction process described below can be executed using a control device 330.

The composite image edge extraction process is executed by using a brightness map image created based on back unlit image and a saturation map image, in addition to the basic image processed image obtained via the respective processes in step 1-1 through step 1-3, or step 6-1 through step 6-5 described above. A brightness map image is an image represented by the brightness component constituting a back unlit image. Also, a saturation map image is an image represented by saturation component constituting a back unlit image. In the composite image edge extraction process, a process for extracting an edge present in a composite image is executed using a composite image created by overlapping a basic image processed image, a brightness map image, and a saturation map image. With this, it becomes possible to easily and accurately extract the outer contour of a medicine that was difficult to extract with only a basic image processed image.

The composite image edge extraction process described above may be executed regardless of the difference or similarity between the background color and the color of a medicine, but it is preferable to execute the process only in the case wherein the background color of a basic image processed image and the color of a medicine are of the same color. If the composite image edge extraction process is only performed in the case where the background color and the color of the medicine are same, the decrease in the processing speed of matching process can be minimized.

≪ Modification Example of Edge Detection by Composite Image ≫

In order to enhance the processing accuracy when executing the matching process for the image (basic image processed image) obtained by processing the basic image via each process of step 1-1 through step 1-3, or step 6-1 through step 6-5, there may be cases where it is preferable to detect the edges of medicine based on the composite image that was processed based on the basic image as described above and to perform the matching process rather than using the basic image processed image alone. In addition, even regarding the composite image used for edge detection, it is desirable to use the best one considering such as the color of the medicine to be inspected. The edge detection method based on this aspect is described below in detail with reference to the flowchart shown in FIG. 68.

Figure 68:
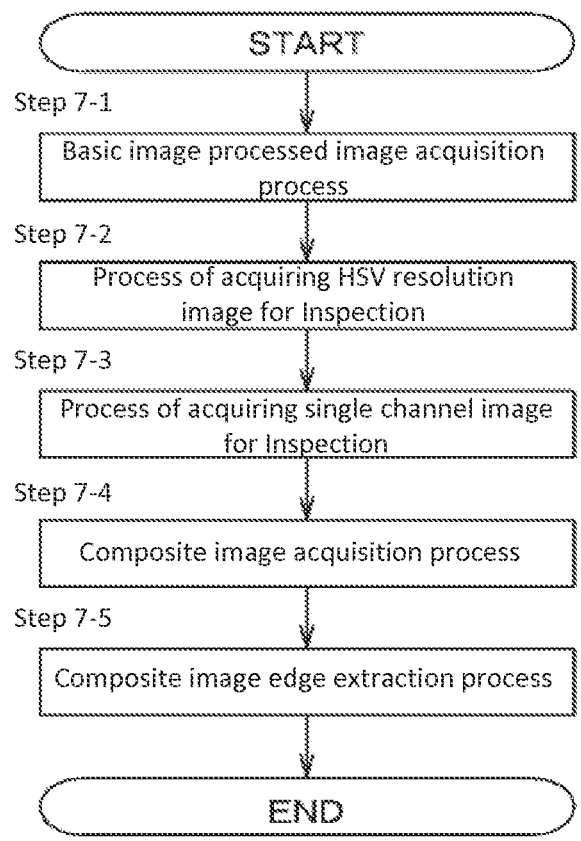
FIG. 68 is a flowchart showing a modification example of an edge detection method with a composite image according to one embodiment of the present invention.

In the control flow of FIG. 68, the region of inspection included in the basic image is first extracted in the basic image processed image acquisition process of the steps 7-1, and the process of acquiring basic image processed image is executed. Specifically, a basic image processed image is obtained, for example, by executing each of the processes of step 1-1 through step 1-3 of the control flow shown in FIG. 26, or step 6-1 through step 6-5 of the control flow shown in FIG. 66.

If the acquisition of basic image processed image is finished in step 7-1, the control flow will proceed to the inspection HSV resolution image acquisition process of step 7-2. In this process, the back unlit image obtained by taking an image in a state where the backlight 314 is in an unlit state and the diffusion light emitting device 160 is in an illuminated state is subjected to HSV resolution. One of the back unlit H channel image, back unlit S channel image and back unlit V channel image obtained is used as a HSV resolution image for inspection.

Here, in obtaining the HSV image for inspection, a predetermined one can be selected regardless of condition among the back unlit H channel image, back unlit S channel image and back unlit V channel image regardless of condition, but it is desirable to differentiate a channel image selected based on whether the background color of a sachet and the color of the medicine that is contained in the sachet b are of same color or not at the time of acquisition of basic image or back unlit image. Specifically, in case the background color of sachet b and the color of the medicine accommodated in the sachet b are of same color, it is desirable to select the back unlit H channel image as a HSV resolution image for inspection. Moreover, in case the background color of the sachet b and the color of the medicine that is contained in the sachet b are different, it is desirable to select the back unlit S channel image as a HSV resolution image for inspection.

If the process of HSV resolution image acquisition for inspection of step 7-2 is completed as described above, the control flow proceeds to the process of single channel image acquisition for inspection of step 7-3. In this process, one among the back unlit R channel image, back unlit G channel image and back unlit B channel image obtained by RGB-resolving the back unlit image is acquired as a single channel image for inspection. Even regarding the selection method of a single channel image for inspection, a pre-specified one can be selected regardless of condition as described in connection with the selection method of HSV resolution image for inspection, it is desirable to perform the selection as follows. That is, utilizing the fact that the position of the inspection area and area other than the inspection area have been determined in advance in the basic image processed image that was acquired in step 7-1, among the back unlit R channel image, back unlit G channel image and back unlit B channel image, one having the largest contrast between inspection area and area other than the inspection area is selected as the single channel image for inspection.

Once the acquisition of single channel image for inspection of step 7-3 is completed as described above, the control flow will proceed to composite image edge extraction process of step 7-4. In this process, a composite image is obtained by combining the basic image processed image acquired in step 7-1, HSV resolution image for inspection acquired in step 7-2, and single channel image for inspection acquired in step 7-3 as a three channel image.

When a composite image is obtained as described above, the control flow proceeds to the composite image edge extraction process of step 7-5, and an image processing is carried out for extracting edges included in the composite image. With this, the contour of a medicine inside a sachet b can be identified.

As described above, if the contour of the medicine is identified by using the composite image obtained by combining the basic image processed image and HSV resolution image for inspection and single channel image for inspection as a three channel image, it is possible to add a perspective of HSV color space and perspective of RGB color model as a perspective for extracting the edge corresponding to the outer edge of the medicine. With this, it becomes possible to further improve the identification accuracy of the contour of a medicine, and to execute the inspection of the medicine quickly with high accuracy.

In the control flow explained above, a relation between the color of the medicine and background color is considered when selecting the HSV resolution image for inspection, and whether the medicine is of same color as the background color is taken into account. That is, if the color of a medicine is same as the background color, the back unlit H channel image is chosen as the HSV resolution image for inspection by taking into consideration that there is a high possibility of strong manifestation of a difference in the color phase between medicine and background. If a medicine is of a color that is different from the background color, the back unlit S channel image is chosen as a HSV resolution image for inspection by taking into consideration that there is a high possibility of strong manifestation of a difference in saturation. By this, the identification accuracy of the contour of a medicine and inspection accuracy of the medicine can be improved.

Further, in the control flow described above, because one having the largest contrast between inspection area and area other than the inspection area is selected among the back unlit R channel image, back unlit G channel image and back unlit B channel image, accuracy in extracting the edge corresponding to the outer edge of a medicine is improved. With this, it is possible to further improve the identification accuracy of the contour of a medicine and inspection accuracy of the medicine.

《Medicine Database for Inspection and Contour Image Database of Divided Medicine》

Figure 52:
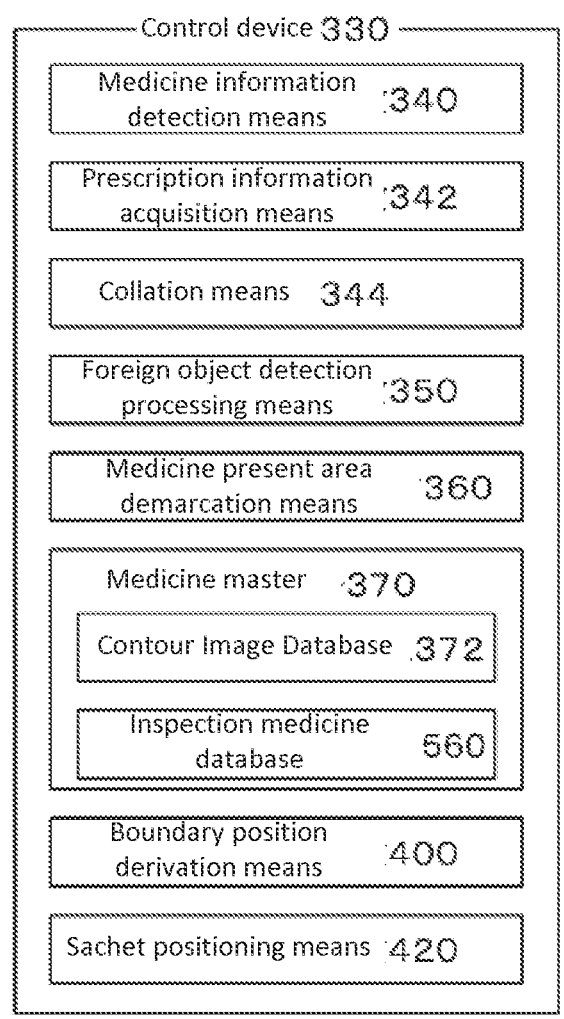
FIG. 52 is a block diagram showing a structure of a control device according to a modification example.

Both the medicine inspection devices 10 and 300 described above identify the type and quantity of a medicine and perform the inspection by image inspection. Here, when performing image inspection, as shown in FIG. 52, as a part of the medicine master 370, a database (inspection medicine database 560) will be required in which information such as the appearance image, size, type, color etc., of a medicine have been stored as master data for matching. In other words, image inspection can be performed by the medicine inspection devices 10 and 300 for a medicine whose master data has been registered in the inspection medicine database 560. Further, though the medicine packaged in sachet b may be a tablet that has been divided into two or more parts (divided medicine), if information such as contour image etc., of the divided medicine is registered in the inspection medicine database 560, precise inspection with the medicine inspection devices 10 and 300 will be possible.

Here, when registering the contour image of a divided medicine in the inspection medicine database 560, actual photographs of divided medicine can be used. However, the types of medicines that can be registered in the inspection medicine database 560 are enormous and it is an extremely complicated task to separately photograph one by one and register them. Therefore, it is desirable to register the contour image of undivided medicine (whole tablet master contour image) in the inspection medicine database 560, and to generate contour images of the divided medicine (divided tablet master contour image) by image processing whole tablet master contour image, and to register them in the inspection medicine database 560.

Figure 53A:
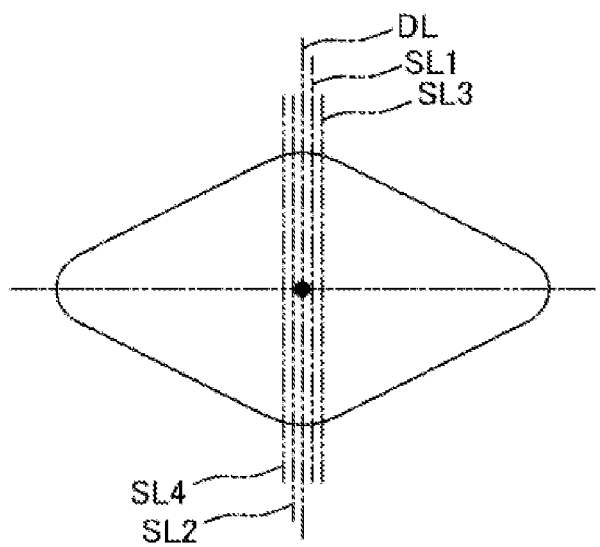
FIGS. 53A and 53B are explanatory drawings to illustrate the method of acquiring a divided tablet master image.

As a means of creating a divided tablet master contour image from a whole tablet master contour image, although various methods can be used, the following means can be used, for example. That is, as shown in FIG. 53A, by dividing the whole tablet master contour image at a boundary of a dividing line DL passing through the center of the medicine region corresponding to the medicine, a divided tablet master contour image for the divided medicine can be obtained.

Further, when a medicine is actually divided, it is possible that the medicine may get split in a position slightly deviating from the center of the medicine. In such a case, the matching accuracy of the divided medicine may decrease because of the divided tablet master contour image obtained by dividing the whole tablet master contour image at the dividing line DL. Therefore, when creating a divided tablet master contour image by image processing, as shown in FIG. 53A, it is desirable that in addition to an image obtained by dividing the whole tablet master contour image with the DL line as the boundary, a quasi-dividing line SL is assumed at a position away by a predetermined distance from the dividing line D, and an image obtained by cutting out the whole tablet master contour image with this quasi-dividing line SL as a boundary is added as one of the divided tablet master contour images to the inspection medicine database 560.

Figure 53B:
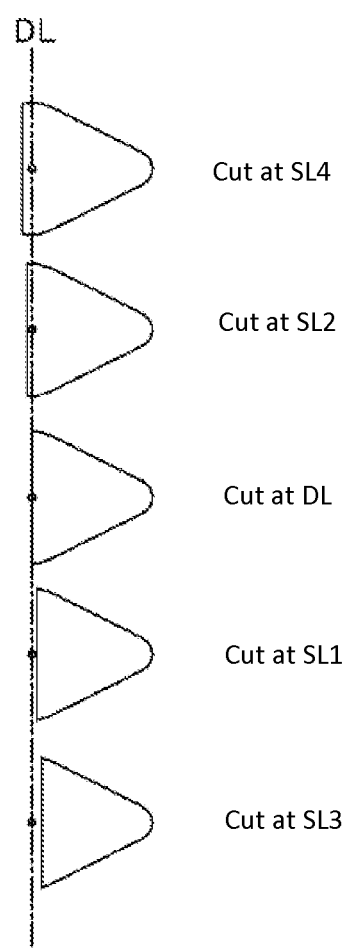

It is further desirable to set multiple quasi-dividing lines SL, and to prepare several types of divided tablet master contour images. Specifically, in the example shown in FIG. 53A, it is desirable to set quasi-dividing lines SL1 and SL2 that are away from the dividing line DL by a distance d in left and right directions respectively, and quasi-dividing lines SL3 and SL4 that are away from the dividing line DL by a distance 2d in left and right directions respectively, and images obtained by dividing the whole tablet master contour image at these quasi-dividing lines SL1 to SL4 (see FIG. 53B) are added as divided tablet master contour images to the inspection medicine database 560. More specifically, it is desirable to perform the aforementioned image processing to acquire divided tablet master contour images by assuming the quasi-dividing lines SL1 to SL4 at locations away from the dividing line DL by predetermined pixels in left and right directions. By doing so, even for a case wherein a medicine is broken at a position slightly away from the center of the medicine, it becomes possible to carry out image inspection on a divided medicine with excellent accuracy.

Figure 54A:
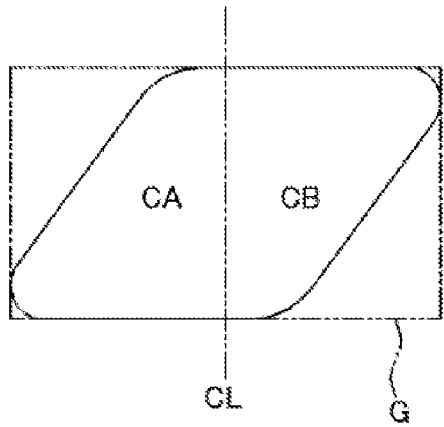
FIGS. 54A, 54B, 54C, and 54D are explanatory drawings to illustrate the method of defining a dividing line used for acquiring a divided tablet master image.
Figure 54B:
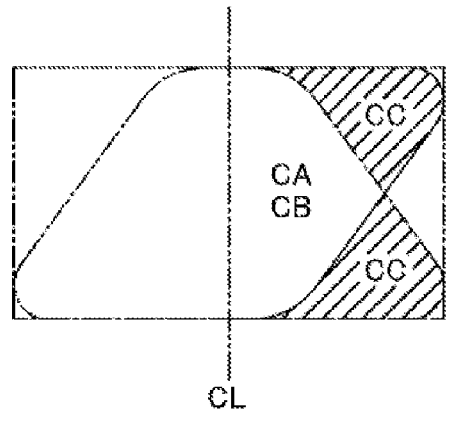
Figure 54C:
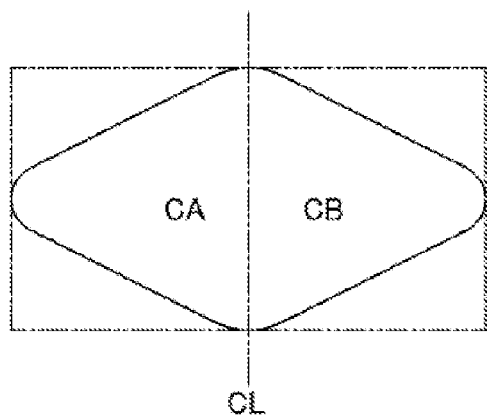
Figure 54D:
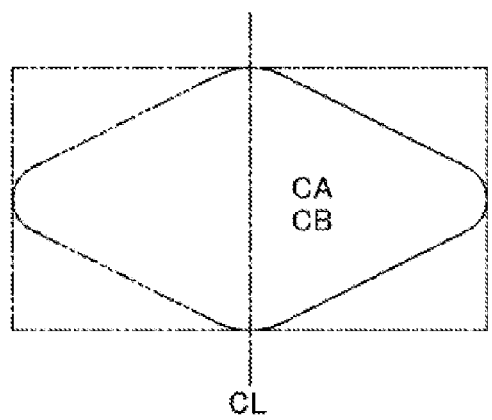

Here, when creating divided tablet master contour images for a divided medicine by specifying a dividing line DL as described above, it may be difficult, depending on the shape of the medicine, to specify the dividing line DL that can divide a medicine into exactly two halves. Specifically, in case of medicines having shapes as shown in FIG. 53 and FIG. 54, it is normal to specify a dividing line DL as shown in FIG. 53A and FIG. 54B, but a dividing line DL may be specified as shown in FIG. 54A. Therefore, it is desirable to specify a dividing line DL by following the procedure shown below so that an appropriate dividing line DL can be specified for medicines of any shape.

Namely, as shown in FIG. 54, a rectangular guide G for setting division line that is in contact with the medicine region externally is assumed in the contour image for inspection. Thereupon, as shown in FIGS. 54A and 54C, a division candidate line CL that passes through the center of the guide G for setting division line and that forms a line perpendicular to the length side of a rectangle forming a vertical line setting guide is specified. The medicine region existing on one side of this division candidate line CL is defined as CA, while the medicine region existing on the other side is defined as CB. Then, as shown in FIGS. 54B and 54D, the size of a region that is not overlapped (non-overlapping region CC) when the medicine region CA is inverted on the medicine region CB with the division candidate line CL as boundary (for example, when CA and CB are overlapped) is derived. Such a process of deriving a non-overlapping region CC by rotating the rectangular region constituting the guide G for setting division line by various predetermined angles is performed for the entire perimeter of the medicine region. As a result, the division candidate line CL when the non-overlapping region CC is smallest is defined as dividing line DL. With this, appropriate dividing lines DL can be specified for medicines of any shape.

As for a divided tablet master contour image for the inspection medicine database 560 obtained as described above, a contour image of medicine can also be registered in the contour image database 372 for reference. With this, a contour image of a divided medicine can also be displayed to an operator.

Next, the work flow for registering a divided tablet master contour image into an inspection medicine database 560 is illustrated. Here, regarding the example described below, it can be also used for registration of colors of medicines in order to accommodate edge detection by the composite image described above. Therefore, when the medicine inspection devices 10 and 300 do not accommodate edge detection by composite images, the registration of colors of medicines can be omitted.

Figure 55A:
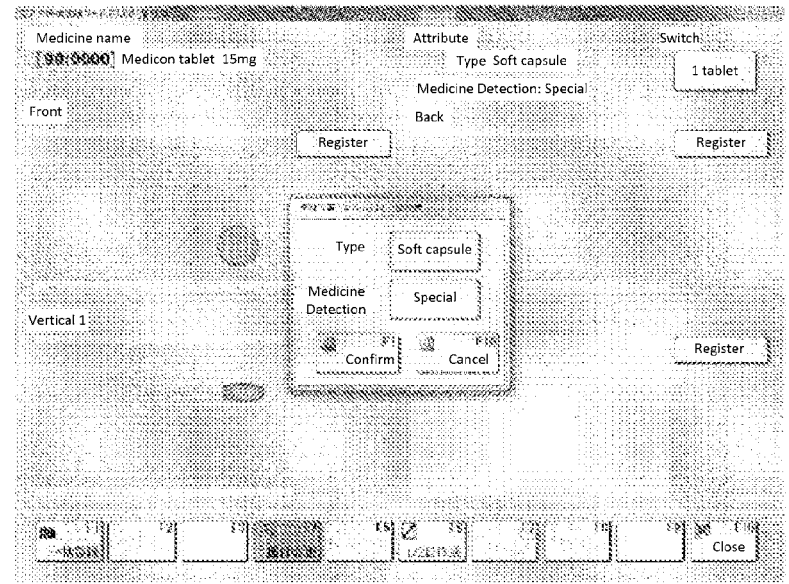
FIGS. 55A and 55B are images showing one example of an operational image that is displayed when registering a divided tablet master contour image in an inspection medicine database.
Figure 55B:
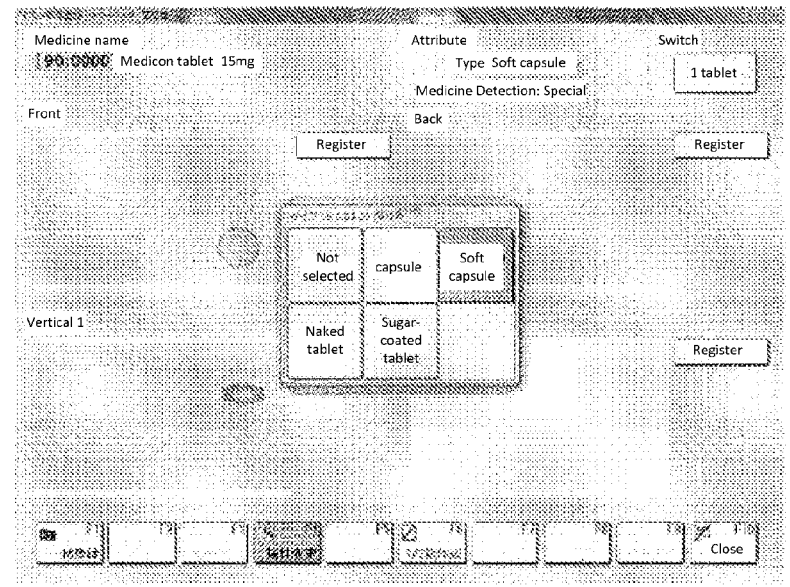

When registering a divided tablet master contour image in the inspection medicine database 560, a window as shown in FIG. 55A is displayed on the operation screen of the operator. In this window, upon selecting the button (displayed as 'Soft Capsule' in the illustrated example) located next to "type", a window as shown in FIG. 55B is displayed, and by selecting a type of the medicine, input becomes possible. In this example, a type of medicine can be selected from four types that are capsule, soft capsule, naked tablet, and sugar-coated tablet. If naked tablet is selected, for example, as shown in FIG. 56, a display corresponding to the type selected is shown (in this example, 'Soft Capsule') on the button located next to "type".

Figure 56:
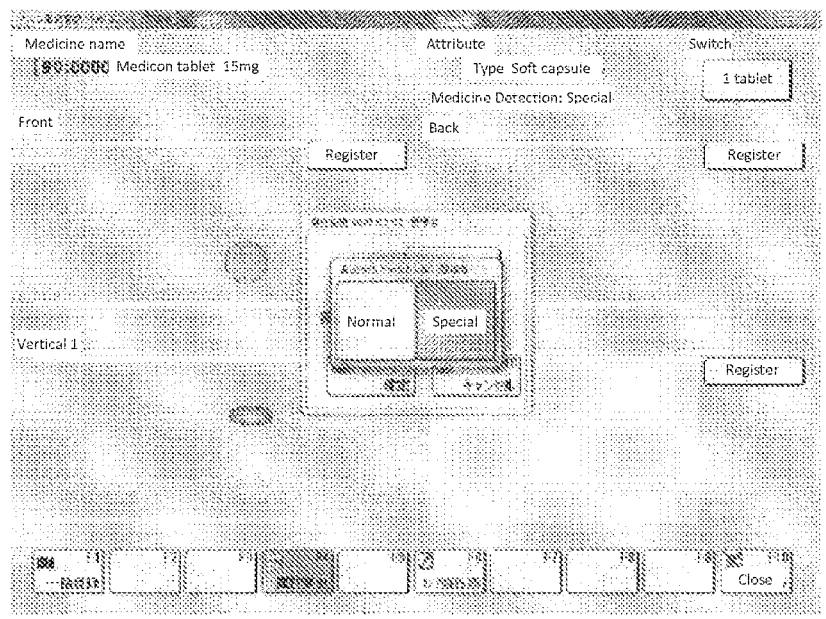
FIG. 56 is an image showing one example of an operational image that is displayed when registering a divided tablet master contour image in an inspection medicine database.

Also, in the window shown in FIG. 55A, if the button located next to 'Medicine Detection' is selected, a window shown in FIG. 56 is displayed. In the window of FIG. 56, it is possible to select whether to perform medicine detection by the detection method for carrying out edge detection with composite image (mentioned as 'Special' in the illustrated example), or by normal detection method (mentioned as "Normal" in the illustrated example). If "Special" button is selected in this window, for example, it will return to the window shown in FIG. 55A, and the selection is appended to the button.

Figure 57A:
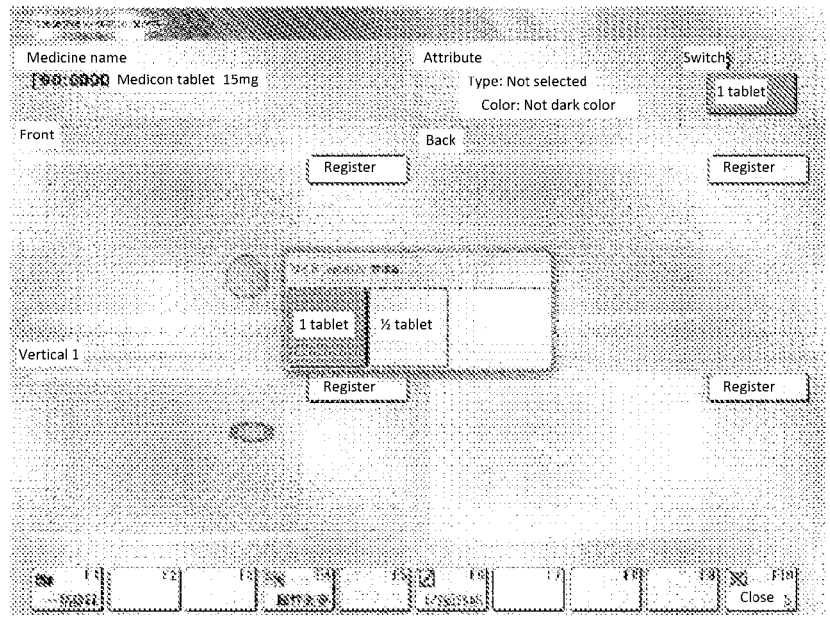
FIGS. 57A and 57B are images showing one example of an operational image that is displayed when registering a divided tablet master contour image in an inspection medicine database.
Figure 57B:
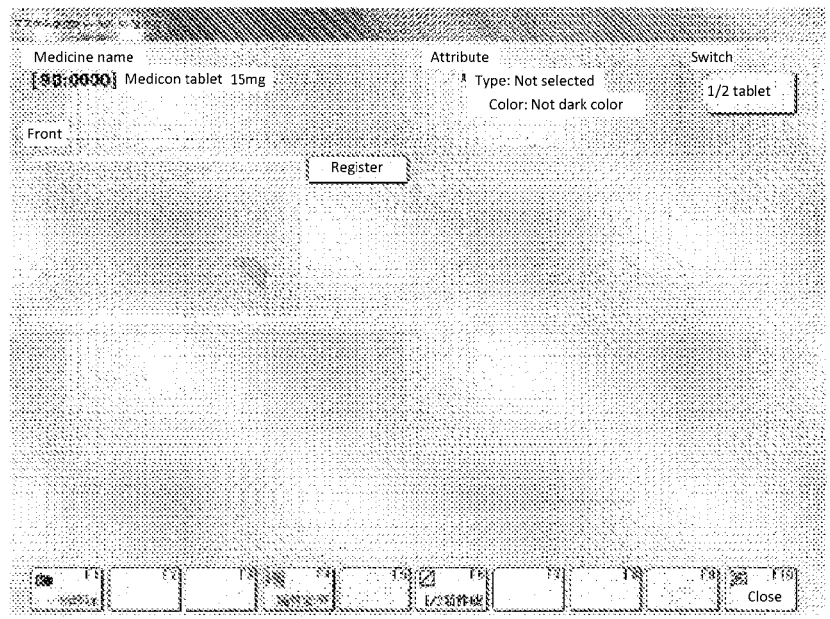

In the window shown in FIG. 55A, if the button located in switch column at top right is selected, a window as shown in FIG. 57A is displayed, and it is possible to choose whether the medicine to be registered in the inspection medicine database 560 is a divided medicine or not. Here, by selecting the button of ½ tablet, the image corresponding to half-tablet as shown in FIG. 57B will be registered as a divided tablet master contour image.

≪ Modified Example of a Construction Method of Inspection Medicine Database and Contour Image Database of Divided Medicine≫

The method of constructing inspection medicine database and contour image database of divided medicine is not limited to the above-mentioned method, and other methods may also be used. Specifically, in many of the medications prescribed in a divided state, for the purpose of easy split or the purpose of split position index, a groove (drug division groove) is formed in the surface of the medicine. Therefore, when a medicine division groove is present in a medicine included in the whole tablet master contour image, by setting the dividing line DL having this medicine division groove as an indicator, it is expected that a divided tablet master contour image for constructing the inspection medicine database and contour image database of divided medicine can be acquired easily and with high accuracy. In light of such finding, the method of acquiring a divided tablet master contour image is described according to the control flow shown in FIG. 72.

Figure 72:
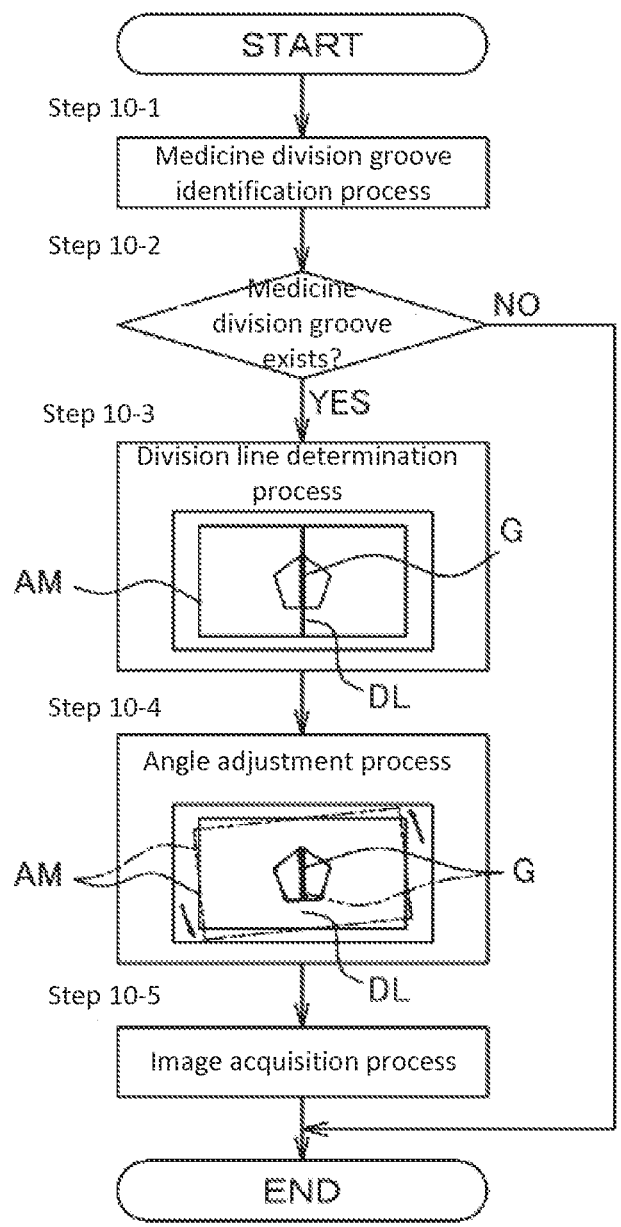
FIG. 72 is a flow chart showing a modification example of a method of constructing an inspection medicine database and a contour image database for a divided medicine according to one embodiment of the present invention.

In the control flow shown in FIG. 72, first, in the medicine division groove identification process of step 10-1, the whole tablet master contour image is subjected to image analysis, and the medicine division groove of the medicine is searched. Subsequently, in step 10-2, whether a medicine division groove was detected or not is verified. Here, in case the medicine division groove was not detected, the dividing line DL cannot be set based on the medicine division groove according to this control flow, and therefore, the control flow ends. In this case, a divided tablet master contour image is acquired by a method for setting the dividing line DL without having the medicine division groove as an indication as described above.

On the other hand, in case the detection of a medicine division groove was confirmed in step 10-2, the control flow proceeds to division line determination process of step 10-3. In the division line determination process, a dividing line DL passing through the medicine division groove imaged in the whole tablet master contour image (shown by the symbol AM in FIG. 72) is determined.

When a dividing line DL is set in step 10-3, the control flow proceeds to an angle adjustment process of step 10-4. In the angle adjustment process, together with fixing the dividing line DL determined in the division line setting process of step 10-3, a process is executed in which, with the dividing line DL as reference, the whole tablet master contour image AM is rotated around the center of gravity of the medicine at each predetermined angle in positive and negative directions, and checking whether the medicine regions existing on either sides of the dividing line DL are symmetrical or not. When the medicine regions on both sides of the dividing line DL become symmetrical, the rotation of the whole tablet master contour image AM is stopped at that location. This completes the angle adjustment of the whole tablet master contour image AM.

Once the angle adjustment of the whole tablet master contour image AM is completed as described above, the control flow moves to image acquisition process of step 10-5. In the image acquisition process, the whole tablet master contour image in which an angle thereof has been adjusted in step 10-4 is divided with reference to the dividing line DL set in step 10-3 to obtain a divided tablet master contour image. By using such a method, a divided tablet master contour image of high accuracy can be acquired.

≪ Side Illumination≫

When taking images configuring a contour image database 372, it is desirable to take an image by irradiating light with as much brightness as possible and from a suitable direction in order to obtain a vivid image. Therefore, as shown in FIG. 47, it is possible to have a configuration of providing side illuminations 570, 572 for irradiating the inspection unit 310 in locations adjacent to upstream and downstream of the inspection unit 310.

Any side illumination 570, 572 may be used as long as it is possible to acquire a vivid image, and a bar-shaped lighting as shown in FIG. 47, etc. can be used. Also, conventionally known light bulbs, fluorescent lights, LEDs or the like may be used as a light source of side illuminations 570, 572. In this embodiment, LED is built-in as a light source of the side illuminations 570, 572, and is installed such that their optical axis is directed towards the inspection unit 310 and oriented towards horizontal direction or upward of horizontal direction. By installing in this manner, a vivid image for configuring contour image database 372 etc. can be obtained.

≪ Image Drawings≫

In the medicine inspection device 10, 300, although an image displayed to the operator in each stage of operation can be suitably modified, it is also possible to use something like those shown in FIG. 58 through FIG. 64, for example. Specifically, when showing the result of inspection by displaying the back unlit images of each sachet b in a thumbnail format, apart from using a display format shown in FIG. 29A, a number in the sequence of inspection for an inspected sachet b may also be included adjacent to a thumbnail image as shown in FIGS. 58A and 58B. Thus, identification of a sachet b and distinguishability of inspection result is further improved. Also, the distinguishability can be further improved by changing the color etc. of the border line around thumbnail images according to the determined result.

Figure 58A:
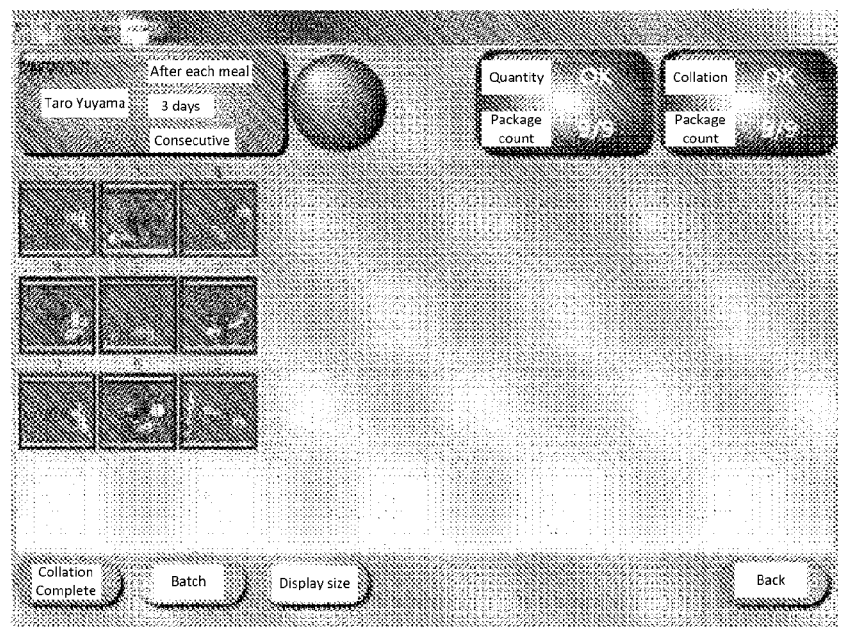
FIGS. 58A and 58B are image showing one example of images shown to an operator in each stage of operation.
Figure 58B:
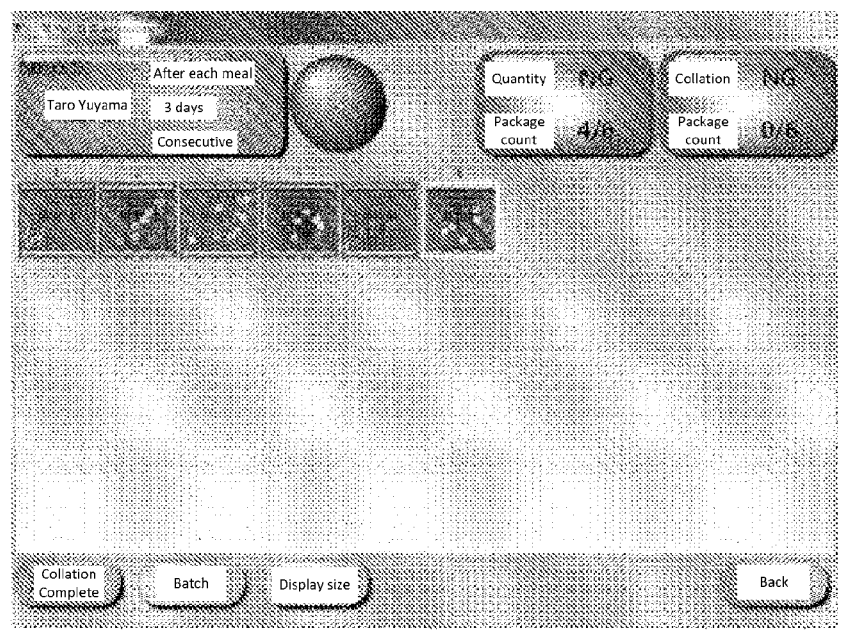

Also, as shown in FIGS. 58A and 58B, the result of inspection is displayed at top right for quantity and external appearance separately. Specifically, in the column displaying 'Quantity', in addition to displaying the inspection results for quantity as either 'OK' or 'NG', the package count is also displayed. Also, in the 'Collation' display column, in addition to displaying the inspection result based on external appearance as either 'OK' or 'NG', the package count is also displayed.

Figure 59:
FIG. 59 is an image showing one example of an image shown to an operator in each stage of operation.

When displaying a list of collation results in the medicine inspection device 10, 300, it may be displayed by an image drawing as shown in FIG. 59, for example. When the result is display by such an image drawing, if the color of display column is varied based on the OK/NG of the result of collation, the distinguishability can be further improved.

Instead of image drawings shown in FIG. 30 through FIG. 32, it is also possible to use image drawings shown in FIG. 60 through FIG. 64. Specifically, in image drawings shown in FIG. 60 through FIG. 64, all of the followings are included in a single image drawing: (1) attribute display part 580, (2) package count display part 582, (3) image display part 584, (4) details display part 586, (5) dosing time display part 588, (6) inference display part 590, and (7) button display part 592.

Figure 60A:
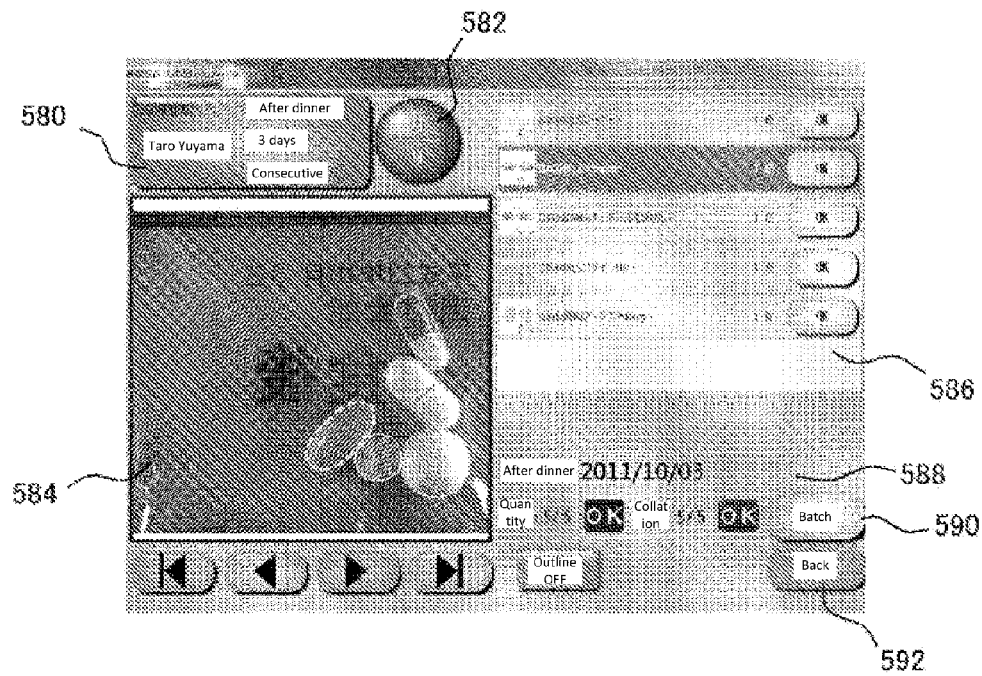
FIGS. 60A and 60B are illustrating one example of images shown to an operator in each stage of operation.

The attribute display part 580 is a region for displaying attribute information such as patient name, ID no., and dosing time of the medicine contained in an inspected sachet b. The package count display part 582 is a region for displaying the quantity of sachets b of a continuous body of sachets B, and the number that the displayed sachet b was inspected in the form of a fraction or the like. The image display part 584 is a region for displaying the image of an inspected sachet b. In the image display part 584, an image can be displayed by including the outline of the medicine. The show/hide of the outline can be switched by pressing the button provided in the button display part 592. Further, as shown in FIG. 60A, by selecting medicine etc. listed in the details display part 586, which is described later in detail, it becomes a state wherein the outline corresponding to that medicine etc. is identifiable from others (active state). In the example of FIG. 60A, a display is shown wherein the outline of a selected medicine is displayed by a dotted line, and as if the dotted line is revolving in the circumferential direction of the medicine, but it is also possible to make it to an active state by blinking the outline, for example.

The details display part 586 lists the prescription data and inspection result. In the details display part 586, image for checking, medicine name, prescription quantity, and inspection result for each medicine will be displayed side-by-side in a line. Although any appropriate method of displaying inspection results can be adopted, if a medicine is packaged as per the prescription, an 'OK' will be displayed in the column corresponding to the medicine in the examples of FIG. 60 through FIG. 64 (see FIG. 60B). Also, if there are similar medicines, "similar exist" will display as a reminder (see FIG. 61A). Further, if a medicine is not packaged in accordance with the prescription data, the reason for the result will also be mentioned.

Figure 60B:
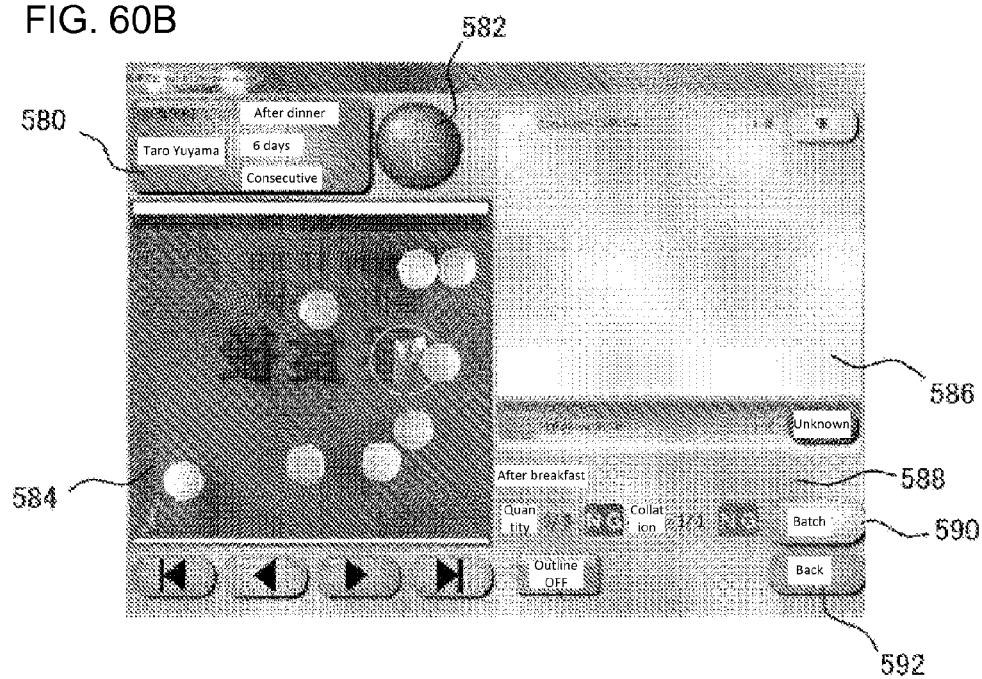
Figure 61A:
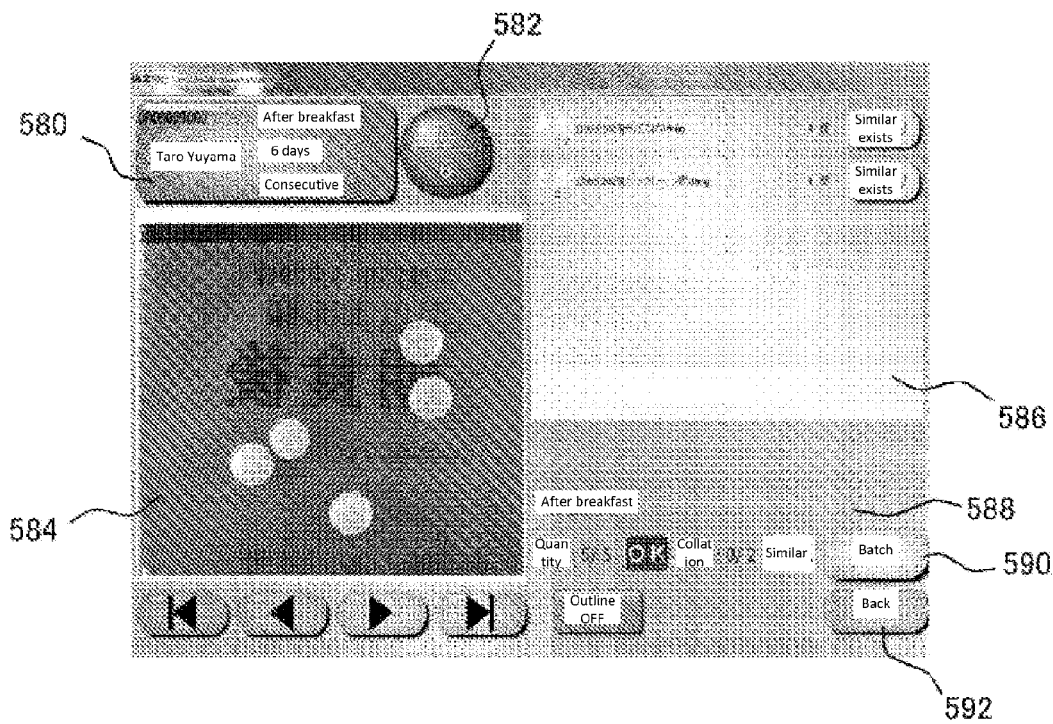
FIGS. 61A and 61B are illustrating one example of images shown to an operator in each stage of operation.
Figure 61B:
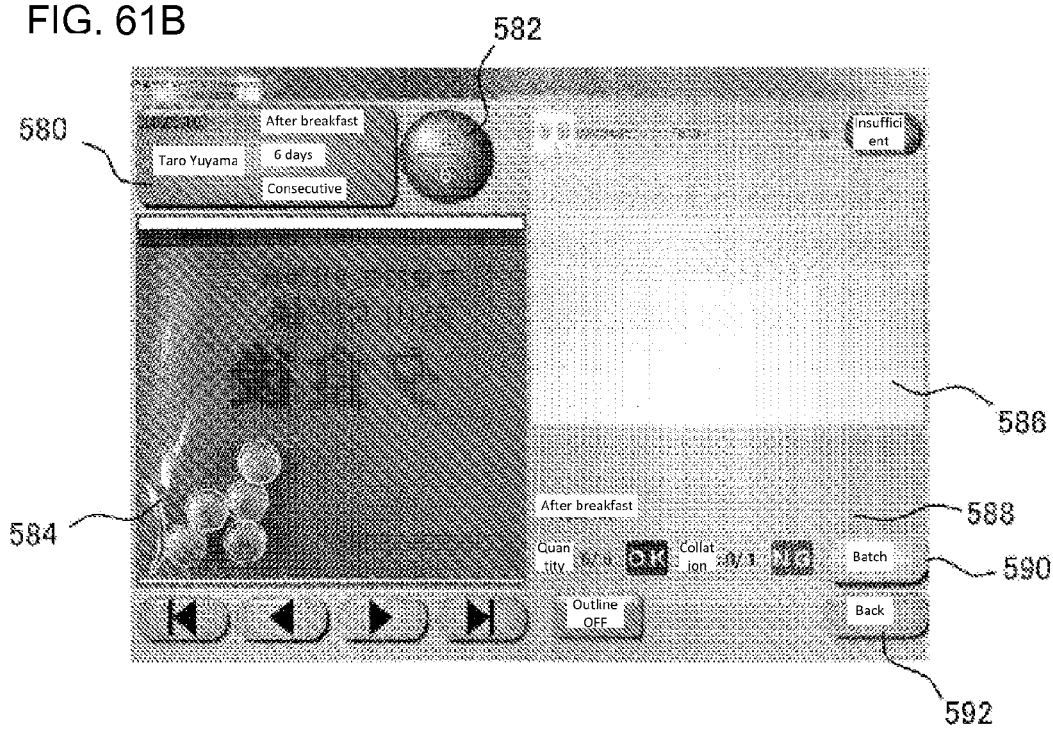
Figure 62A:
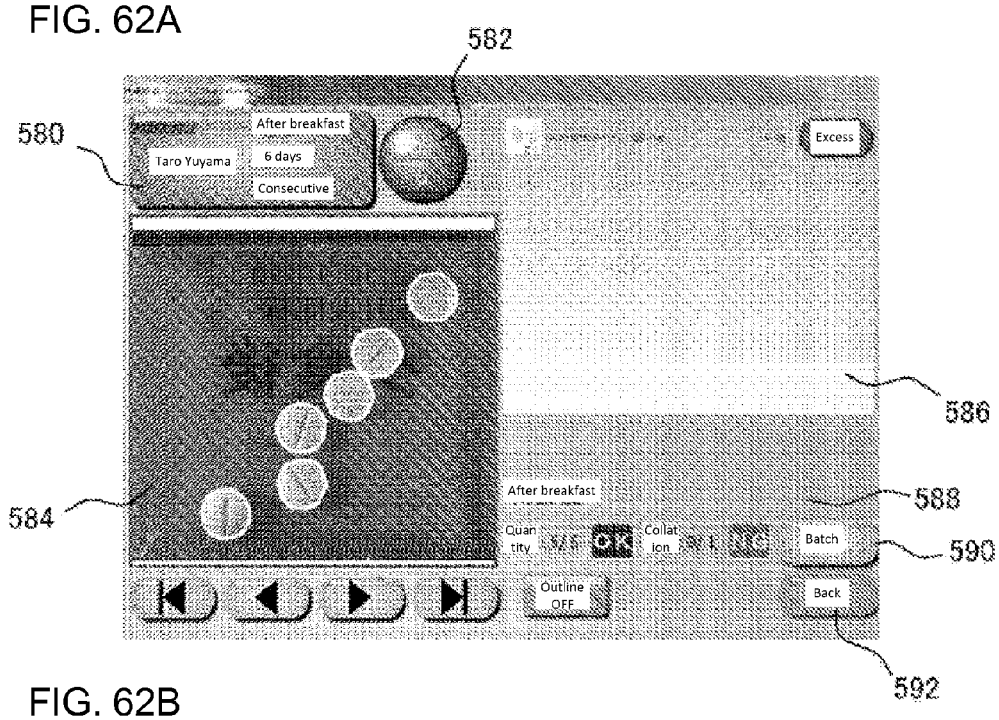
FIGS. 62A and 62B are illustrating one example of images shown to an operator in each stage of operation.
Figure 62B:
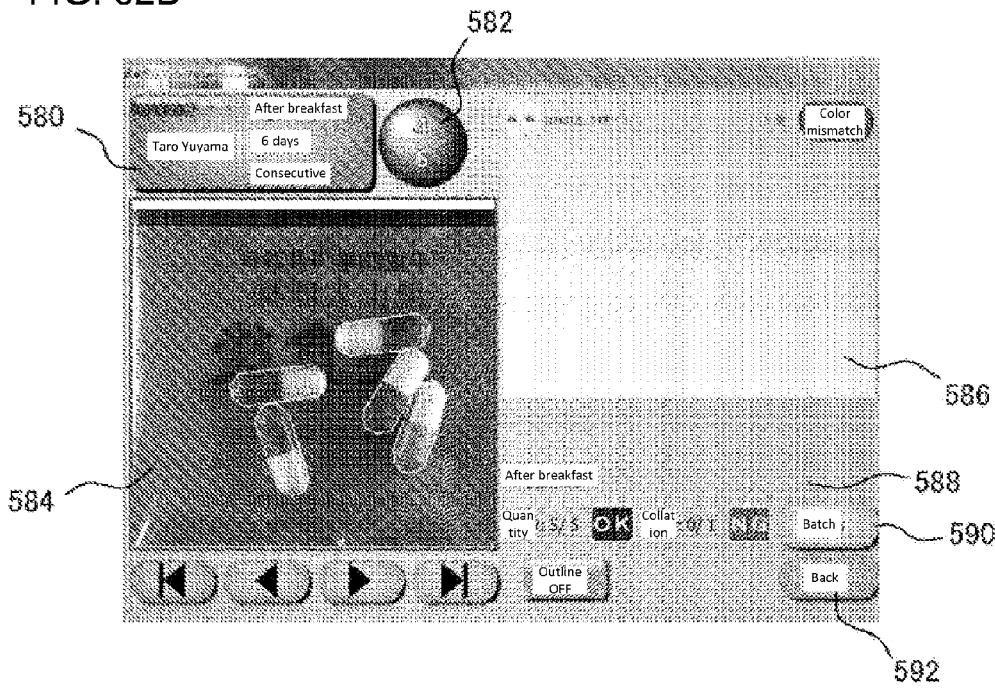

Specifically, in FIG. 61B, 'insufficient' is displayed since the quantity of the medicine is insufficient. In the example shown in FIG. 62A, 'Excess' is displayed since the quantity of the medicine larger than the prescribed quantity is packaged. In the example shown in FIG. 60B, because a foreign object is coexisting in sachet b, this matter is displayed. Regarding a display notifying the foreign object contamination, though it is possible to display in continuation with the medicine list display or coexist within the medicine list, it is desirable to display in a location away from the medicine list such as in the bottommost column etc. as shown in FIG. 60B in order to improve the distinguishability. In the example shown in FIG. 60B, an object identified as a foreign object in the image of image display part 584 is enclosed by a circular mark and displayed. In the example shown in FIG. 62B, because a medicine with a different color exists, it is displayed as 'Color mismatch'.

Figure 63:
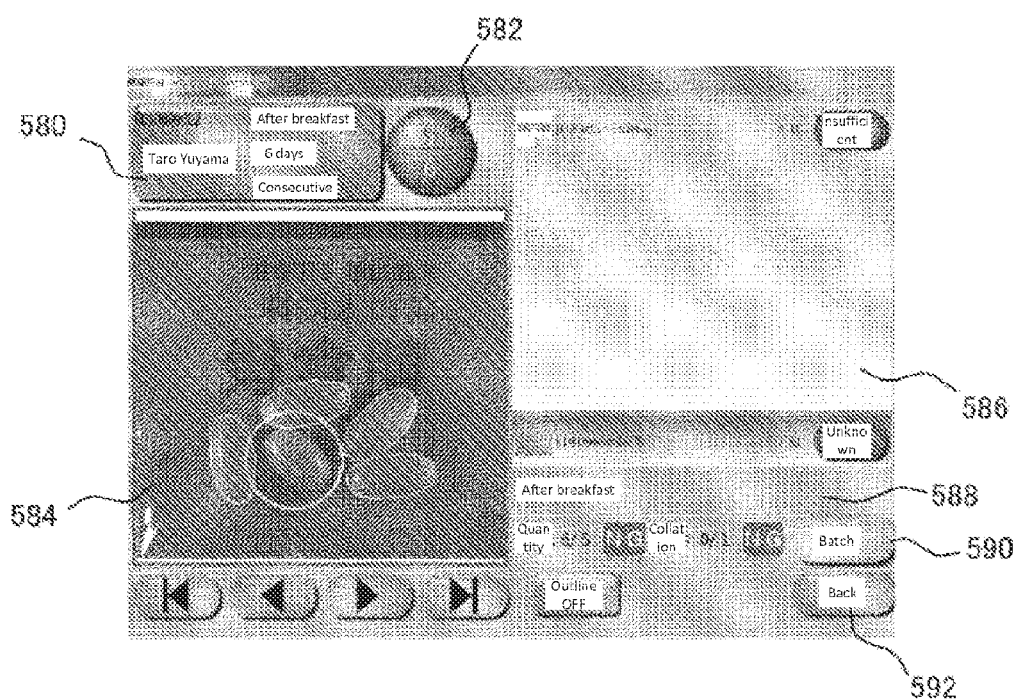
FIG. 63 is an image showing one example of an image shown to an operator in each stage of operation.

In the example shown in FIG. 63, since the medicine quantity is less than the prescribed quantity, it is displayed as 'Insufficient'. Further, since an unknown medicine exists, this fact is displayed similarly to foreign object contamination of FIG. 60B. An object that was identified as an unknown medicine in the image of image display part 584 is enclosed by a circular mark. It is desirable to make the enclosed line prominent by changing the color at certain time intervals, or by blinking etc. In the examples shown in FIG. 60 through FIG. 64, it is desirable to change the color of the outline of the medicine in the image displayed in the image display part 584 according to the result of inspection.

Figure 64A:
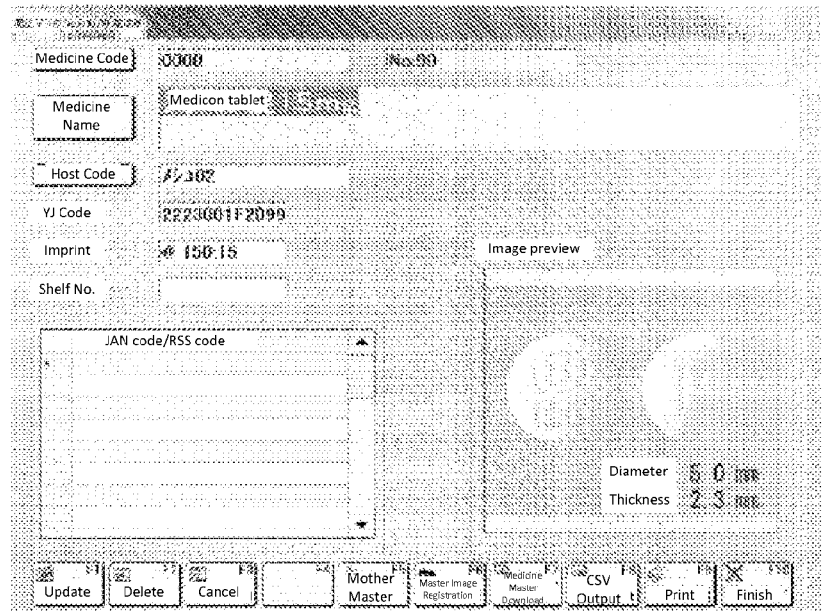
FIGS. 64A and 64B are illustrating one example of images shown to an operator in each stage of operation.
Figure 64B:
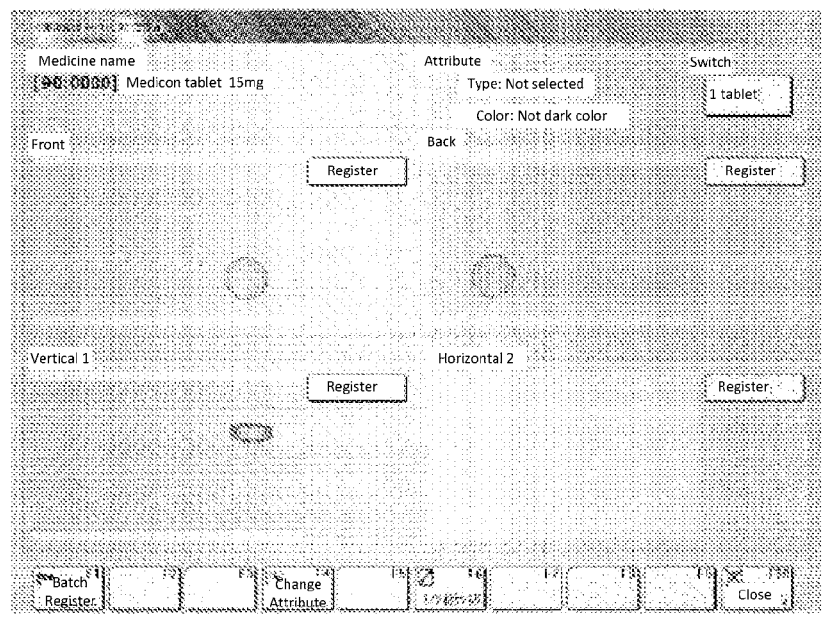

When displaying the master information for each medicine, apart from displaying as in FIG. 36C, it is also possible to display it as shown in FIG. 64A. When registering master information, as shown in FIG. 64B, in addition to displaying textual information such as medicine product name and attributes, it is desirable to display front, rear and side surface images etc. of the medicine.

Figure 74A:
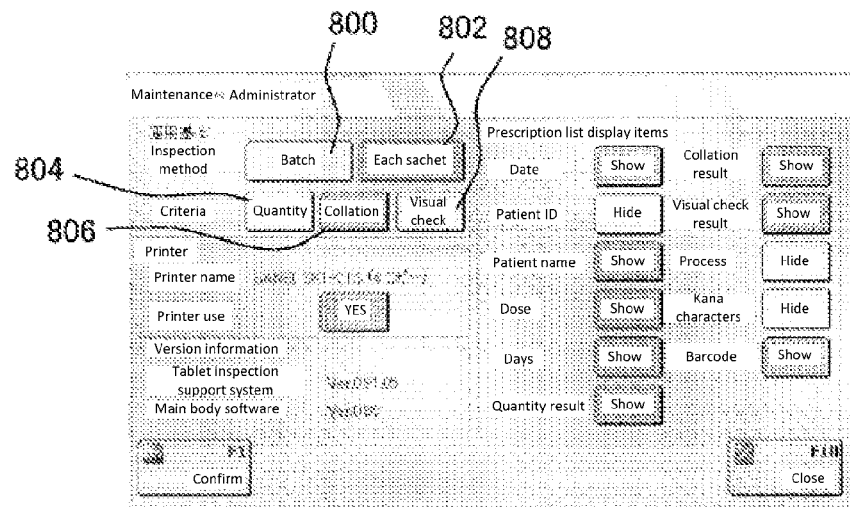
FIGS. 74A and 74B are illustrating, respectively, one example of operation condition setting screen displayed in the medicine inspection device in one embodiment of the present invention and an image showing one example of a display method of the inspection result.

It is possible to have a configuration in which, by providing an operation condition setting screen for medicine inspection devices 10, 300 as shown in FIG. 74A, various settings for the operation method can be made in the operation screen. Specifically, as for inspection method, it is possible to have a configuration wherein buttons 800, 802 is provided to enable selecting whether the respective sachets b of a continuous body of sachets B is collectively inspected, or each sachet is inspected one by one. As a criteria for judging the inspection result, it is possible to provide a quantity button 804 to set the operation so as to check whether or not the quantity of the medicine is matching the prescription information and not to check the type of a medicine, a collate button 806 for setting the operation to perform inspection by collating both the quantity and type of medicine with the prescription information, and a visual button 808 that enables visual inspection by health care providers such as pharmacists and doctors is also possible.

Figure 74B:
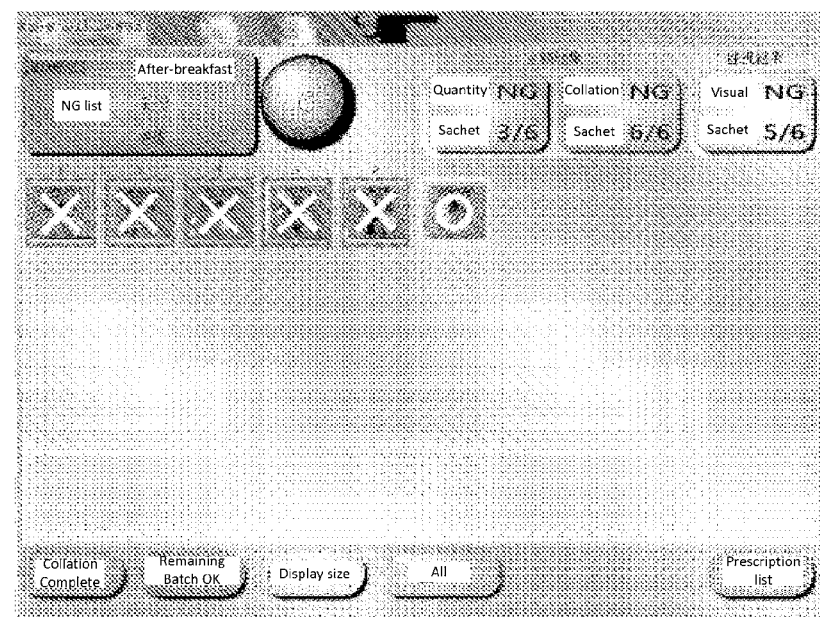
Figure 75B:
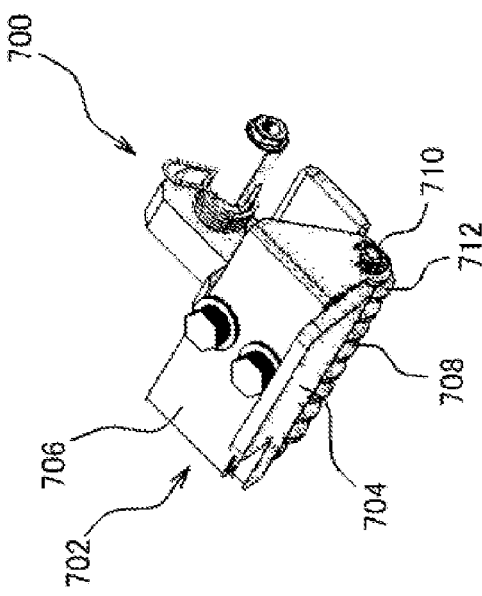
FIGS. 75A, 75B, 75C, and 75D show, respectively, a modification example of an upright-state elimination means in a plan view, perspective view, front view, and side view.
Figure 75D:
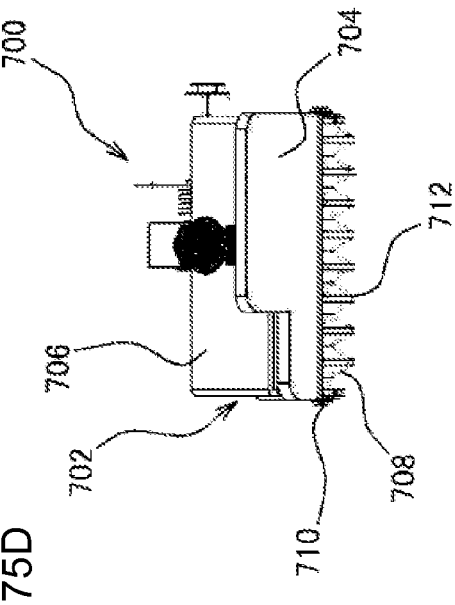
Figure 75A:
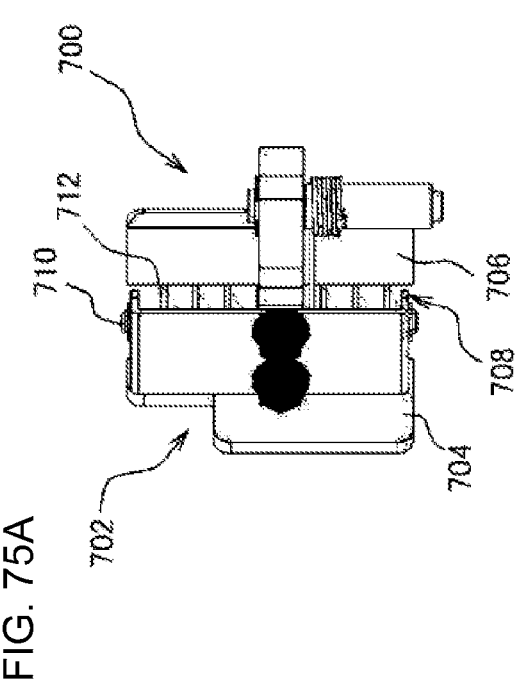
Figure 75C:
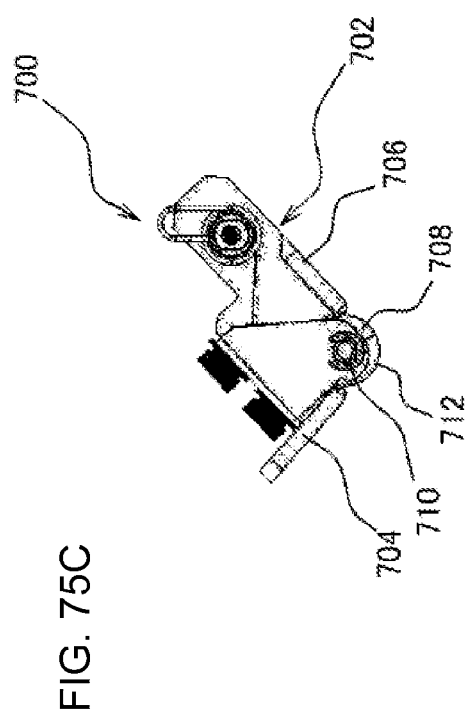

It is possible to suitably vary the display method of inspection results using the medicine inspection device 10, 300, but one shown in FIG. 74B can be used, for example. Specifically, regarding the inspection results obtained by the medicine inspection device 10, 300, a different display format can be shown for when the packaged medicine is a complete mismatch with the prescription, when an item resembling the prescribed medicine is contained, and when the medicine is a complete match with the prescription. In the example shown in FIG. 74B, in case of a complete mismatch, the thumbnail image depicting the sachet b is enclosed by a red border line, and by a yellow border line in case a similar medicine is contained, and by a blue border line in case of a complete match. When using the results of visual inspection by health care providers such as pharmacists and doctors, such results are displayed with symbols such as ○ or X etc., and are displayed by a display method that is different from the display of inspection results by the medicine inspection devices 10, 300.

《Data Linkage with Medicine Packaging Device》

It is desirable to execute the image inspection based on the prescription data acquired from a medicine packaging device 100 by connecting the above-mentioned medicine inspection devices 10, 300 to a medicine packaging device 100 such that data communication is possible. With this, a series of operations starting from packaging operation of medicine till inspection operation can be performed without a hitch, speedily and accurately.

《Journal》

In the medicine inspection devices 10, 300, it is desirable to be able to output printing (Journal) showing the inspection results. Although the output format of the journal can be of any format, it is possible to print as shown in FIG. 65, for example. Specifically, if the inspection result is good, it is possible to print as shown in FIG. 65A. If there is a sachet b for which the inspection result has a problem, it is preferable to print so as to identify the sachet b having a problematic inspection result, and to print the reason for the problem as shown in FIG. 65B. If necessary, it is also possible to include an identification indicator such as bar code as shown in FIG. 65C.

《Modified Example of Medicine Inspection Process》

In the above-mentioned embodiment, an example of carrying out an inspection process while acquiring various types of images as shown in FIG. 27 as per the control flow shown in FIG. 26, but the present invention is not limited to this. Specifically, it is possible to carry out the inspection process while acquiring various types of images as shown in FIG. 67 as per the control flow shown in FIG. 66. Below, a method of executing a medicine inspection process according to this modification example will be described in detail with reference to the drawings. Here, in the following description, duplicate descriptions will be omitted for sections to perform identical processes as the control flow shown in FIG. 26 or the like in the above embodiment.

Figure 66:
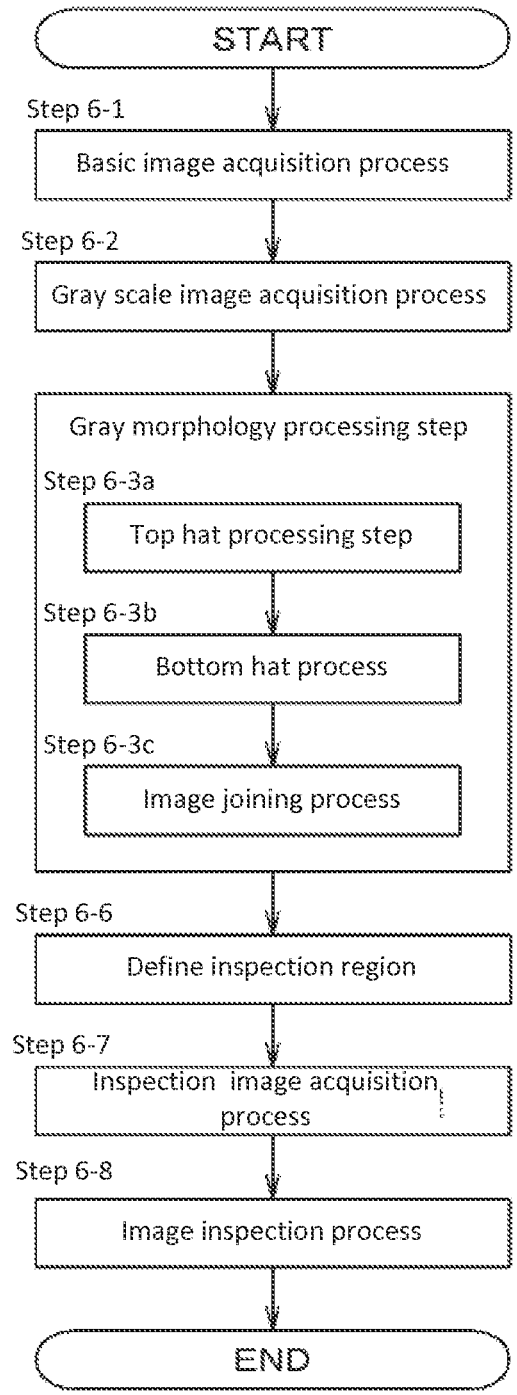
FIG. 66 is a flowchart showing the edge detection method with a composite image in one embodiment of the present invention.
Figure 67A:
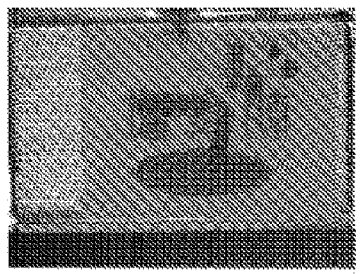
FIGS. 67A, 67B, 67C, 67D, 67E, 67F, 67G, and 67H are illustrating images acquired in each stage of a modification example of medicine inspection process according to one embodiment of the present invention.
Figure 67B:
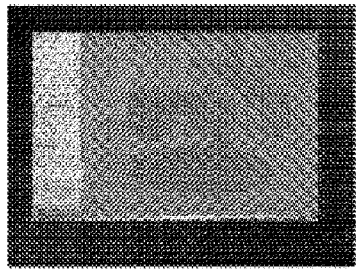

In the control flow shown in FIG. 66, first, in the basic image acquisition process of step 6-1, a basic image for medicine inspection is acquired based on the back lit image photographed with the packaging paper illuminated from back by the backlight 314 (see FIG. 67A). Then, in the gray scale image acquisition process of step 6-2, a gray scale image is acquired by gray-scaling the basic image acquired in step 6-1 (see FIG. 67B).

Figure 67C:
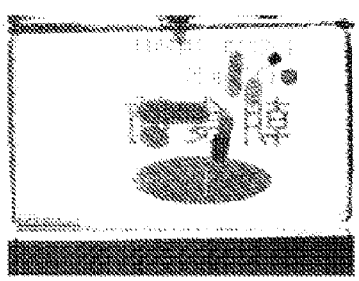

Once the gray scale image acquisition is completed in step 6-2, the control flow proceeds to the gray morphology treatment process of step 6-3. In this process, a top hat treatment, bottom-hat process, and image joining process, which will be described later in detail, are carried out in order. That is, in the gray morphological process, first, the top hat treatment is executed in step 6-3a. In the execution of the top hat process, the basic image acquired in step 6-1 is subjected to RGB resolution. In this manner, an R channel image (basic R channel image) as shown in FIG. 67C is obtained.

Figure 67D:
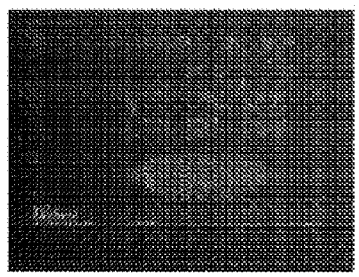

In step 6-3a, the basic R channel image is subjected to top hat treatment. By this, a top hat image as shown in FIG. 67D is obtained. A top hat image shown in FIG. 67D is an image that selectively shows, in the gray-scale image, a dot-patterned section corresponding to the transmitted light passing through the print area on sachet b.

Figure 67E:
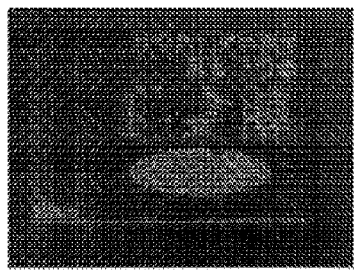

In the bottom-hat process of step 6-3b, the basic R channel image is subjected to bottom hat process. By this, a bottom hat image as shown in FIG. 67E is obtained. A bottom hat image shown in FIG. 67E is an image in which, among the print section on sachet b included in the gray scale image, a region excluding the dot-patterned section corresponding to the transmitted light described above is selectively shown.

Figure 67F:
Figure 67G:
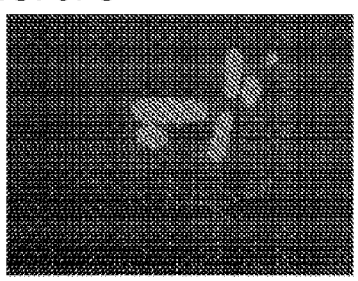
Figure 67H:
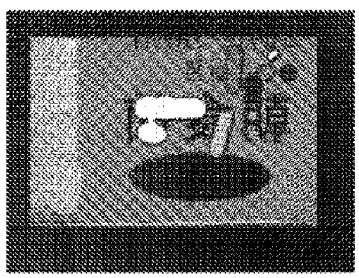

Once the top hat image and bottom hat image are acquired as described above, the control flow proceeds to the image joining process of step 6-3c. In this process, by combining the top hat image and bottom hat image, an exclusion area identification image as shown in FIG. 67F is obtained. This exclusion area identification image is a combination of the dot-patterned area corresponding to transmitted light passed through print section of the sachet b and a region excluding the dot-patterned section. Therefore, the exclusion area identification image is an image showing the print area on sachet b.

Once the exclusion area identification image is acquired as described above, the control flow proceeds to inspection area determination process of step 6-4. In this process, by obtaining the difference between the gray scale image obtained in step 6-2, and the exclusion area identification image obtained in step 6-3, the region for inspection is identified. That is, in step 6-4, a process of excluding the printing area on sachet b from the entire region of the gray scale image is performed. By this, it is possible to form a filter for identifying the area to be inspected (inspection area) in the regions included in the gray scale image.

Once the identification of the inspection area is completed as described above, the control flow proceeds to inspection image acquisition process of step 6-6. This is a process executed for the purpose similar to that of step 1-3 shown in FIG. 26 described above. That is, from a back unlit image wherein the region same as the back lit image was photographed with the backlight 314 switched off, an image of the area corresponding to the inspection area determined in step 6-5 is acquired as the image for inspection. In other words, the filter for inspection area identification obtained in step 6-5 is applied to the back unlit image to narrow down the area for inspection and to exclude the print area on the sachet b.

Once the image for inspection is acquired in step 6-5, the control flow proceeds to image inspection process of step 6-6. In this process, based on the image for inspection acquired in step 6-5, an inspection process is executed for detecting either the medicine quantity or type or both. The inspection process in step 6-5 is carried out in the similar manner as in step 1-4 of the control flow shown in FIG. 26 described above.

If the image for inspection is acquired as described above, it is possible to separate a region containing text or symbols etc. printed on sachet b from a region containing medicine with even higher accuracy, and to determine the image for inspection. With this, the speed of inspection process can be improved while further improving the medicine inspection accuracy.

《Detecting Introduction Failure of Continuous Body of Sachets》

As described above, in the medicine inspection devices 10, 300, a strip of continuous body of sachets B in which each dose is packaged in a sachet b is supplied sequentially to inspection units 14, 310, and inspected. Here, if a continuous body of sachets B is a long body, introduction failure is likely to occur due to distortion in the introduction units 10b, 304. Therefore, it is desirable that the medicine inspection devices 10, 300 have a configuration in which introduction failures at the introduction units 10b, 304 can be detected. To deal with such problems, the following configuration can be adopted, for example. In the following explanation, of the introduction units 10b, 304, explanation is made using 304 as an example.

As shown in FIG. 42 and FIG. 43, the introduction unit 304 is comprised of a horizontal surface 304a for facilitating, at the time of feeding a continuous body of sachets B into casing 302, to dispose the continuous body of sachets B in a flat state and help pass through. On both sides of the horizontal surface 304*a*, guide pieces 306 and 306 are provided so as to guide a continuous body of sachets B without tilting. Further, in a position that is on both sides of the horizontal surface 304*a* and that is adjacent to the guide pieces 306, 306, that is, on both sides of the horizontal surface 304*a* based on the passage direction of the continuous body of sachets, sachet detecting sensors 304*b* and 304*b* for detecting a continuous body of sachets B passing on the horizontal surface 304*a* are provided. The sachet detecting sensors 304*b* and 304*b* are connected to a control device 330 to facilitate information communication.

The control device 330 functions as an introduction failure determining means for determining an introduction failure of a continuous body of sachets B at the introduction unit 304. Specifically, the gap between the guide pieces 306 and 306 in the introduction unit 304 is made to be of a size similar to the width of the continuous body of sachets B (sachet b) for preventing a tilted introduction etc. of the continuous body of sachets B (sachet b). Therefore, when a continuous body of sachets B (sachet b) is fed without distortion, both of the sachet detecting sensors 304*b* and 304*b* installed near the guide pieces 306 and 306 will detect the continuous body of sachets B (sachet b). On the other hand, if a continuous body of sachets B (sachet b) is distorted, only one of the two sachet detecting sensors 304*b* and 304*b* will detect the continuous body of sachets B (sachet b), and there will be no detection by the other sensor. Therefore, with a condition that a continuous body of sachets B is detected by only one of the two sachet detecting sensors 304*b*, 304*b* provided on both sides, the control device 330 determines that a continuous body of sachets is distorted and having an introduction failure in the introduction unit, and notifies.

If the distortion of a continuous body of sachets B (sachet b) can be detected as described above, an inspection failure accompanying the introduction failure of a continuous body of sachets B (sachet b) can be prevented. In addition, damage etc. due to introduction of a continuous body of sachets B (sachet b) in distorted state can be prevented.

≪ Shape of Introduction Unit ≫

Figure 73:
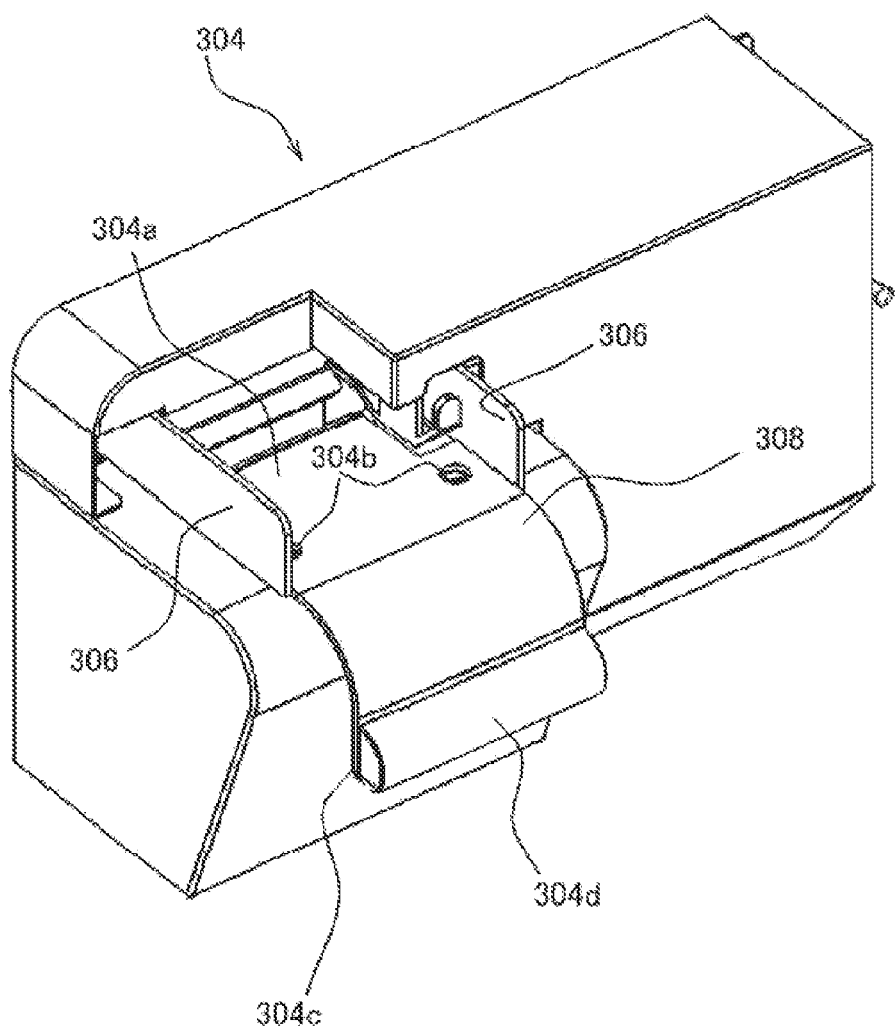
FIG. 73 is a perspective view showing a modification example of an introduction unit of a medicine inspection device according to one embodiment of the present invention.

As shown in FIG. 42 and FIG. 43, the introduction unit 304 has a shape wherein the end section of a plate that forms the bottom surface 308 of the introduction unit 304 is bent in the form of an arc in the lower direction in order to prevent a continuous body of sachets B from getting stuck, but the present invention is not limited to this, and a configuration for example shown in FIG. 73 is also possible. That is, the end section of a plate that forms the bottom surface 308 of the introduction unit 304 is bent to form a drooping part 304*c* extending roughly vertically downward. A bulging part 304*d* that is bulging on the surface (the side where a continuous body of sachets B passes) is provided in the drooping part 304*c*. Although it is possible to form the bulging part 304*d* by further looping back the end part of the drooping part 304*c*, in this embodiment, the bulging part 304*d* is formed by fixing a separately fabricated member of semicircular cross-section in the width direction of the introduction unit 304.

When such a bulging part 304*d* as described above is provided, a continuous body of sachets B will contact the bulging part 304*d* when flowing along a plate forming the bottom plate 308, and the medicine contained in each sachet b is subjected to a light vibration. This could help getting rid of an upright state of medicine if the medicine was packaged in an upright state in sachet b.

≪ Sampling Inspection Mode ≫

In the above-mentioned medicine inspection devices 10 and 300, all sachets b of a continuous body of sachets B introduced for inspection are inspected, however, the present invention is not limited to this, and it is also possible operate in a sampling inspection mode by sampling a part, and display in a state where the inspection results can be visually checked. As for the method of implementing sampling inspection mode, though it is possible to use any suitable method, it is also possible to use the one described below, for example.

Figure 76A:
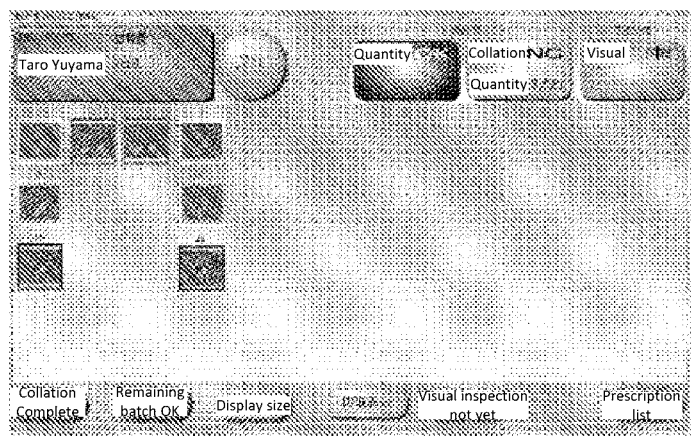
FIGS. 76A, 76B, and 76C are respective images showing one example of an image displayed when executing a sampling inspection mode in the medicine inspection device according to one embodiment of the present invention.
Figure 76B:
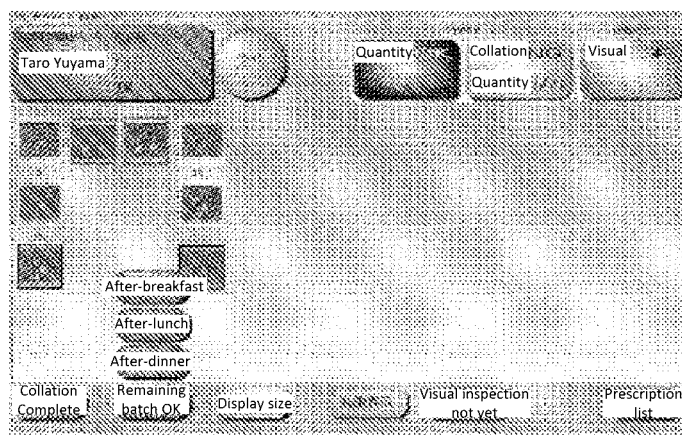

Specifically, in the example shown in FIG. 76, an operation by sampling inspection mode becomes possible by pressing the 'Sampling display' button. In this example, when a continuous body of sachets B includes after-breakfast dose, after-lunch dose and after-dinner dose that are formed continuously, among multiple sachets b corresponding to each dosage time, the inspection result is sampled for the first and last sachets and displayed. In the example shown in FIG. 76, the inspection results for after-breakfast dose, after-lunch dose and after-dinner dose are vertically classified according to the dosage time and displayed. In this example, the inspection results for after-breakfast dose are shown in the upper row, after-lunch dose in the middle row and after-dinner dose in the bottom row.

In the sampling inspection mode, in addition to the first sachet and last sachet of each dosage period, the result of inspection where the inspection result does not match the prescription data, or a questionable inspection result where there is a possibility of presence of a similar medicine are also displayed. For each case of a case where the inspection results are consistent with the prescription data, a case where the inspection results are inconsistent, and a case where caution is required because of a possibility of existence of an analogous medicine, display is done by different method. In the example shown in FIG. 76, the color of the border surrounding a thumbnail showing each sachet b is changed in accordance with the inspection result. Specifically, the result is displayed by blue border if the inspection result is consistent with the prescription data, by red border if inconsistent, and by yellow border if caution is required. As examples of an inspection result requiring caution can include a case where an analogous medicine is present, or medicines causing high risk to humans, or medicine in which packaging operation includes manual operation by pharmacists, etc.

In the example shown in FIG. 76, a result that a pharmacist or the like visually checked and confirmed whether the inspection result is correct can be displayed. Specifically, in the example shown in FIG. 76, upon pressing the 'Remaining lot OK' button, it will be possible to reflect a judgment by pharmacists or the like that all of the inspection result is error-free. Further, by pressing 'After breakfast' button, 'After lunch' button, or 'After dinner' button, it is possible to reflect a judgment by pharmacists or the like that there is no error with regard to the sachet b of after-breakfast dose, sachet b of after-lunch dose, or sachet b of after-dinner dose. In addition, in the example of FIG. 76, by pressing the 'Visual inspection not yet' button, only the thumbnails of sachets b that have not been subjected to visual inspection can be displayed.

Figure 76C:
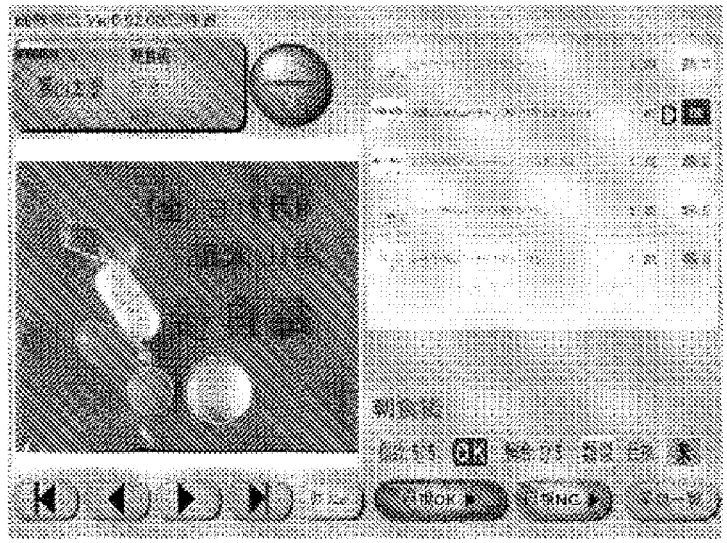

Moreover, when pressed a thumbnail that corresponds to each sachet b shown in FIG. 76C, the detailed information for this sachet b is displayed as shown in FIG. 76. In this display screen, by pressing the button 'Visual inspection OK' button, or 'Visual inspection NG', it becomes possible to set the confirmation result by visual inspection by a pharmacist or the like.

By facilitating an operation as per the above-mentioned sampling inspection mode, it becomes possible to address a demand for selectively checking, among the inspection results, only an optional item. With this, the operation of checking inspection result by a doctor or pharmacist can be further simplified.

Moreover, when the thumbnail corresponding to a sachet b for which inspection is to be carried out is pressed (selected) in a state shown in FIG. 76A and the detailed information as in FIG. 76C is displayed, after setting the confirmation result of visual inspection by such as a pharmacist by pressing the 'Visual inspection OK' button, or 'Visual inspection NG', the subsequent operations can be suitably decided. That is, after setting the confirmation result of visual inspection in the state of FIG. 76C, the display may return to the thumbnail view of FIG. 76A or sequentially switch to images showing the detailed information for other sachets b that were selected for sampling display. As in the latter case, by making it possible to sequentially switch displays of the detailed information for other sachets b that were selected for sampling display, the inspection operation by visual inspection can be easier and faster.

Further, when there is an inspection result requiring caution such as when there is a medicine of high risk to human body (hereinafter also referred to as 'high risk medicine'), or when there is a medicine wherein the packaging of the medicine is also done by manual operation by a pharmacist or the like (hereafter also referred to as 'manually distributed medicine') etc. in the group of prescribed medicines or in the medicine group judged to be analogous by the result of inspection, it is desirable to display alerts in various places of the display screen of FIG. 76C. Specifically, regarding the names of high risk medicines, it is desirable to make the display format distinct by displaying the medicine name in a color different from normal (e.g. red color) or the like. Further, also regarding the judgment result of a high risk medicine, it is desirable that the display format be distinct by displaying the medicine name in a color different from normal. Further, based on the result of inspection, if a medicine of high risk is included in the group of medicines judged to be analogous, it is desirable to clearly display the fact that a high risk medicine exists among the candidates of analogous medicines by displaying the judgment result by a color that is different from normal (e.g. red color), etc., for example. As the symbol 'D' was assigned to a manually distributed medicine in FIG. 76C, for example, it is desirable to indicate that it is a manually distributed medicine by symbols etc., so that it can be distinguished from others.

《Display of Visual Inspection Result》

Figure 77A:
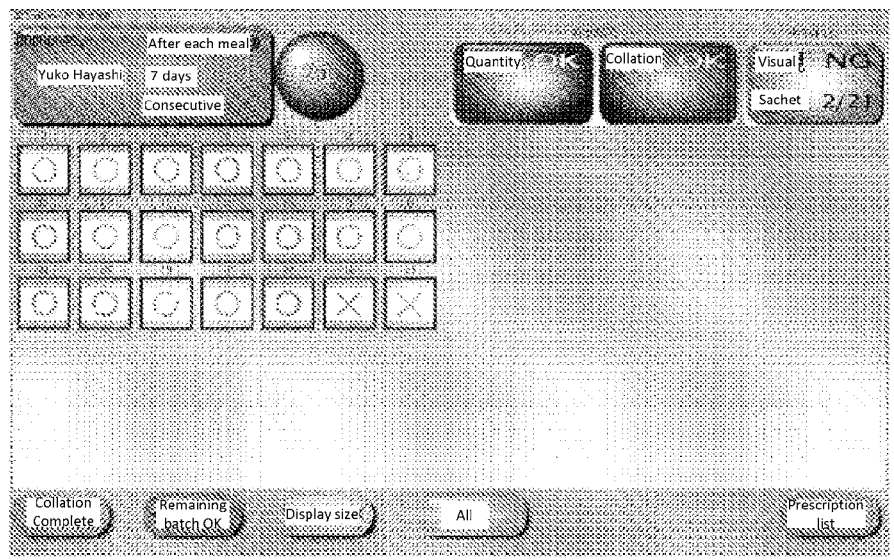
FIGS. 77A and 77B are images respectively showing one example of a method of displaying the results by visual inspection.
Figure 77B:
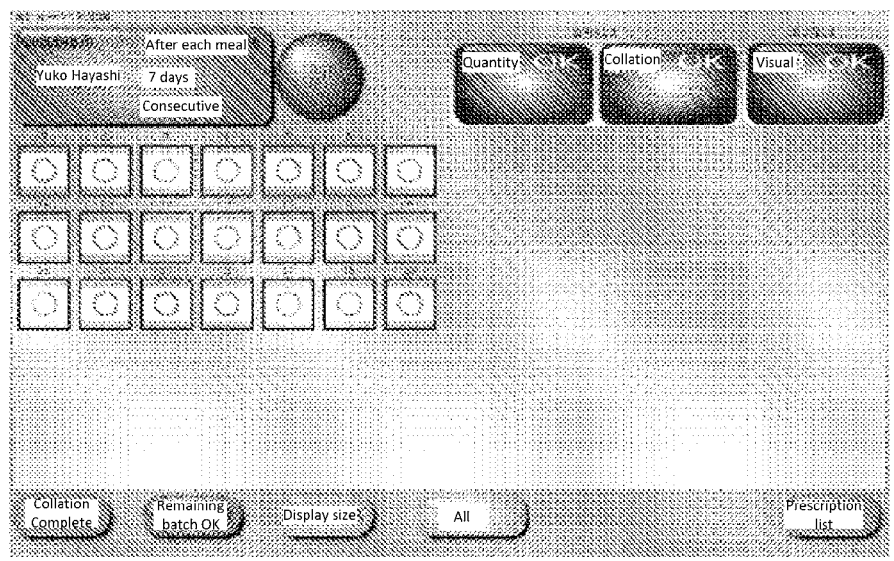

The medicine inspection devices 10 and 300 may have a configuration in which, in addition to the inspection by the said devices, visual inspection by a doctor or a pharmacist is also possible. If such a configuration is adopted, by displaying an interface as shown in FIGS. 77A and 77B, for example, the ability to discern inspection results by visual inspection can be improved. Specifically, as shown in FIGS. 77A and 77B, an inspection result by visual inspection can be displayed by using a symbol such as 'O' mark or 'X' mark for the thumbnail provided for each sachet b so that the result is intuitively distinguishable. Also, it is possible to display the inspection result by visual inspection for an entire continuous body of sachets B comprised of a collection of sachets b in a predetermined format. Specifically, if there is a sachet b for which the inspection result by visual inspection has a problem, the indication that the inspection result for an entire continuous body of sachets B has a problem can be displayed in the display column of inspection result provided at top right in FIG. 77A (in the example illustrated, displayed as 'Visual inspection NG'). Likewise, if the inspection result by visual inspection for an entire continuous body of sachets B is good, the indication that the inspection result for an entire continuous body of sachets B is good can be displayed as in FIG. 77B (in the example illustrated, displayed as 'Visual inspection OK'). In this way, it becomes possible to distinguish the result of visual inspection at a glance, and to further improve the user-friendliness.

The present invention is not limited to the embodiments illustrated as first embodiment and second embodiment, and various modifications of each embodiment described above, and those skilled in the art may easily understand that other modifications may be also obtained from the teaching and spirit within the scope of the claims.

The invention claimed is:

1. A medicine inspection device, comprising:
    an inspection unit on which a medicine for inspection is disposed, the medicine being contained in a sachet;
    an imaging unit capable of photographing the sachet disposed on the inspection unit; and
    a medicine information detector capable of detecting at least either of a quantity or type of the medicine based on an image obtained by the imaging unit;
    wherein the inspection unit comprises a backlight capable of illuminating the sachet from backside when photographing, the backlight comprising illumination areas located dottedly per predetermined pitch, and
    wherein the medicine information detector is configured to implement:
    a basic image acquisition process for acquiring a basic image for medicine inspection based on a back lit image photographed by illuminating a packaging paper from behind by the backlight;
    an inspection area defining process for defining an area for inspection by executing an exclusion process of excluding a dot-shaped translucent region contained in the basic image obtained in the basic image acquisition process;
    an inspection image acquisition process for acquiring an inspection image by extracting an area corresponding to the area for inspection from a back unlit image obtained by photographing same region as the back lit image in a state where the backlight is unlit; and
    an image inspection process for performing image inspection to detect the medicine quantity or type or both based on the inspection image.

2. The medicine inspection device according to claim 1, wherein the backlight comprises a light source, and a mesh member disposed between the light source and the sachet and having perforations through which light passes through at each predetermined pitch.

3. The medicine inspection device according to claim 2, wherein the backlight is configured to generate red light or a light of a longer wavelength than red.

4. The medicine inspection device according to claim 2, further comprising:
    a medicine present area defining unit for determining a medicine present area in a medicine region identification image obtained by photographing a sachet disposed in the inspection unit with the imaging unit; and
    a foreign object detection process for detecting a foreign object existing in the sachet based on an image for position recognition containing position signs provided with coordinates for each predetermined pitch, and a basic image acquired by the medicine information detector;
    wherein the foreign object detection process is configured to implement:
    an object existence area coordinate extraction process for extracting position coordinates existing in a region determined by the inspection area defining process by superposing the image for position recognition and basic image, a medicine coordinates group derivation process for extracting position coordinates existing inside a medicine-existing area defined by the medicine present area defining unit by superposing an image for medicine area determination and the basic image; and a foreign object determination process for judging a presence of a foreign object in coordinate position on condition that coordinates that are different from the medicine area coordinates group are existing in the object existence area coordinates group.

5. The medicine inspection device according to claim 2, wherein in the inspection area defining process, an expansion process is executed for expanding an area remaining after an execution of elimination process by a predetermined amount towards outside.

6. The medicine inspection device according to claim 2, wherein an image of a medicine provided on the inspection unit is able to be clipped by use of a back lit image obtained by photographing with the imaging unit in a irradiated state wherein the inspection unit is irradiated by the backlight and a back unlit image obtained by photographing by the imaging unit in a back non-irradiated state wherein the inspection unit is not irradiated by the backlight, and an image of medicine provided on an inspection unit is able to be obtained by:

acquiring a back lit binary image by binarization of a back lit RGB resolution image comprising at least one from among the back lit R channel image, back lit G channel image and back lit B channel image obtained from the RGB resolution of the back lit image, assuming an intensity distribution of medicine and the back lit image in the said back lit binary image to be a Gaussian distribution, deriving mean value Mm and standard deviation σm of the intensity distribution corresponding to the medicine, and mean value Mb and standard deviation σb of the intensity distribution corresponding to the back image;

creating a mask for medicine image clipping for masking a region of an intensity higher than an intensity Mm+3σm on condition that Mm+3σm≥Mb-3σb;

creating a mask for medicine image clipping for masking a region of an intensity higher than an intensity Mb-3σb on condition that Mm+3σm<Mb-3σb; and clipping a back unlit image based on the mask for medicine image clipping.

7. The medicine inspection device according to claim 2, further comprising a photographing jig comprising a translucent stage, wherein the photographing jig with the medicine to be photographed disposed on the stage is moved to the inspection unit, an outline of the medicine is derived based on the back lit image obtained by photographing with the imaging unit in an irradiation state where the stage is irradiated by the backlight, in the back unlit image obtained by photographing the jig disposed in the inspection unit by the imaging unit in a non-irradiated state wherein the stage is not irradiated by the backlight, the device is able to construct a contour image database by accumulating appearance images showing external appearance of the medicine obtained by clipping a region corresponding to a region surrounded by the outline of the medicine derived based on the back lit image.

8. The medicine inspection device according to claim 7, wherein the stage comprises a plurality of imaging zones associated with each side of a medicine, and a medicine is arranged in each imaging area such that a side associated with each imaging area is orienting towards the imaging unit, and by using a back lit image and back unlit image obtained when the photographing jig is moved to the inspection unit, a database is created by storing a contour image of each side of the medicine.

9. The medicine inspection device according to claim 7, wherein an installation guide is provided in the stage to facilitate disposing a medicine in a predetermined location, and size of the installation guide is smaller than presumed size of a medicine and foreign object.

10. The medicine inspection device according to claim 7, wherein a color of the stage is white.

11. The medicine inspection device according to claim 7, further comprising a backlit imaging unit for photographing a back lit image, and a back unlit imaging unit for photographing a back unlit image.

12. The medicine inspection device according to claim 1, wherein a medicine packaged in a printed packaging paper is able to be supplied for the inspection unit as a medicine for inspection, and the medicine information detector is capable of executing an image processing to vary size of a region surrounded by outline in the basic image, and as a result of such image processing if a continuous region is formed wherein a region surrounded by the outline is contiguous, the medicine information detector is capable of executing a printed area exclusion process for excluding an area containing the said continuous region as printed area from the inspection area.

13. The medicine inspection device according to claim 1, wherein in the image inspection process, a contour of a medicine existing in a sachet is able to be identified by executing a composite image edge extraction process to extract an edge contained in a composite image formed by superposing a basic image processed image in which an inspection area contained in the basic image has been extracted, a brightness map showing a distribution of brightness in the back unlit image, and a saturation map showing a distribution of the saturation component in the back unlit image that were obtained in the image inspection process.

14. The medicine inspection device according to claim 13, wherein the composite image edge extraction process is executed if a background color of the sachet during acquisition of the basic image and a color of the medicine packaged in the sachet are similar.

15. The medicine inspection device according to claim 1, wherein the image inspection process is configured to execute:

an acquisition of a basic image processed image wherein an inspection area contained in the basic image has been extracted;

an acquisition of a HSV resolution image for inspection comprising at least one from among a back unlit H channel image, a back unlit S channel image and a back unlit V channel image that were obtained by a HSV resolution of the back unlit image; and an acquisition of a single channel image for inspection comprising at least one from among a back unlit R channel image, a back unlit G channel image and a back unlit B channel image that were obtained by a RGB resolution of the back unlit image, wherein the image inspection process is also configured to execute composite image edge extraction process to extract an edge contained in a composite image formed by superposing the basic image processed image, the HSV resolution image for inspection and the single channel image for inspection in order to identify a contour of a medicine existing in a sachet.

16. The medicine inspection device according to claim 15, wherein when acquiring the HSV resolution image for inspection, a back unlit H channel image is selected as a HSV resolution image for inspection on a condition that a background color of the sachet during acquisition of the basic image and a color of the medicine packaged in the sachet are similar, and a back unlit S channel image is selected as a HSV resolution image for inspection on a condition that a background color of the sachet and a color of the medicine packaged in the sachet are different.

17. The medicine inspection device according to claim 15, wherein when acquiring the single channel image for inspection, from among a back unlit R channel image, back unlit G channel image and back unlit B channel image that were obtained by RGB resolution of the back unlit image, the image having highest contrast between the inspection area and a non-inspection area is selected as a single channel image for inspection.

18. The medicine inspection device according to claim 1, further comprising a medicine database for inspection in which master contour images showing at least shapes of medicines that is able to be inspected are stored, wherein
the device is capable of carrying out image inspection by matching an outside shape inspection image with a contour image of the medicine present in a sachet, and
among the master contour images registered in the medicine database for inspection, by dividing a master contour image showing a complete shape of the medicine by a dividing line passing through middle of the medicine area corresponding to the medicine as boundary, a master contour image is able to be acquired for a divided medicine obtained by dividing the medicine, and registered in the medicine database for inspection.

19. The medicine inspection device according to claim 18, wherein with the dividing line as reference, an image obtained by dividing a master contour image with an imaginary quasi-dividing line as boundary at a location separated by a predetermined interval, is able to be added as a master contour image for the divided medicine.

20. The medicine inspection device according to claim 18, wherein medicine division groove included in a medicine is identified in the master contour image, and a dividing line is determined on the basis of the medicine division groove contained in the master contour image.

21. The medicine inspection device according to claim 20, wherein after determining the dividing line with reference to the medicine division groove contained in the master contour image, the master contour image is rotated around a center of gravity of a medicine region with reference to said dividing line, and in a situation where a shape of a medicine region present on one side and a shape of a region that is present on the other side with respect to the dividing line are symmetrical, by dividing the master contour image with the dividing line as reference, a master contour image of the divided medicine is obtained.

22. The medicine inspection device according to claim 18, wherein by dividing a master contour image depicting a full shape of a medicine by a dividing line as boundary, a master contour image of a divided medicine obtained by dividing the medicine is registered as a contour image of the contour of a divided medicine in a contour image database.

23. The medicine inspection device according to claim 18, wherein:

a rectangular guide for setting a divisional line circumscribing a medicine area in an outside shape inspection image is assumed all over the medicine area,
passing through a center of the rectangular guide for setting a divisional line and perpendicular to a length side of the rectangular guide for setting a divisional line is specified as division candidate line, and a medicine region present on one side with the said division candidate line as boundary is defined as medicine region CA, and a medicine region present on the other side is defined as medicine region CB, and a non-overlapping region, formed by flipping the medicine region CA over the medicine region CB with the said division candidate line as boundary, is defined as non-overlapping region CC, and
the division candidate line when the said non-overlapping region CC is smallest is specified as a dividing line.

24. The medicine inspection device according to claim 18, further comprising a side illumination on a side of the inspection unit and away at a location higher than the inspection unit, wherein an optical axis of the side illumination is directed towards the inspection unit in a horizontal direction or higher than the horizontal direction.

25. The medicine inspection device according to claim 1, wherein medicines are supplied as a continuous array of sachets formed by packaging one dose of the medicine per sachet in a packaging paper and aligning the sachets in form of a strip, and each sachet is able to be inspected one by one,
the medicine inspection device further comprising an introduction unit for introducing the continuous array of sachets,
wherein the introduction unit comprises:
a horizontal portion wherein a continuous body of sachets is able to be disposed in a horizontal state,
a sachet detecting sensor capable of detecting a continuous body of sachets present on the horizontal portion, and
an introduction failure determining unit for determining introduction failure of a continuous body of sachets in the introduction unit,
and wherein the sachet detecting sensor is provided in both directions with the direction of passage of the continuous body of sachets in the horizontal portion as reference,
and on condition that the continuous body of sachets is detected by one of the sachet detecting sensors that are provided on both sides, the introduction failure determining unit is configured to judge that an introduction failure of the continuous body of sachets has occurred.

26. The medicine inspection device according to claim 1, wherein medicines are supplied as a continuous array of sachets formed by packaging one dose of the medicine per sachet in a packaging paper and aligning the sachets in form of a strip, and each sachet is able to be inspected one by one, and is able to show an inspection result,
wherein a sachet of the continuous body of sachets is able to be classified based on dosing time, and
among a plurality of sachets corresponding to each doing time, a result of inspection for desired sachet is able to be selectively displayed.

27. The medicine inspection device according to claim 1, wherein medicines are supplied as a continuous array of sachets formed by packaging one dose of the medicine per sachet in a packaging paper and aligning the sachets in form of a strip, and each sachet is able to be inspected one by one,
wherein each of the sachets is sealed with a longitudinal seal part along a width direction of the continuous array of sachets and a lateral seal part along a longer direction of the continuous array of sachets, and a boundary is formed between longitudinal seal parts of neighboring sachets in the continuous array of sachets, the medicine inspection device further comprising:
a detecting position imaging unit is provided so as to be able to photograph the longitudinal seal part located at both sides of the boundary in a longer direction of the continuous array of sachets, the detecting position imaging unit is capable of photographing the supplied continuous array of sachets in a predetermined position:
a longitudinal seal position detecting unit capable of obtaining a location information of each longitudinal seal part appearing in an image area photographed by the detecting position imaging unit;
a boundary position detection unit capable of deriving position of the boundary by calculating an intermediate value of position information of each of longitudinal seal parts detected by the longitudinal seal position detecting unit; and
a position identification unit for identifying position of sachet with respect to the inspection unit based on position of the boundary derived by the boundary position detection unit.

28. The medicine inspection device according to claim 1, wherein a medicine is supplied in form of continuous array of sachets in which a plurality of sachets are aligned in form of a strip and each of the sachets is formed by sealing packaging paper, and a longitudinal seal part is provided at least between neighboring sachets, and a dot-shaped seal trace is formed in the longitudinal seal part, and each sachet is able to be inspected one by one,
the medicine inspection device further comprising a boundary position detection unit capable of deriving a position of the boundary,
wherein the boundary position detection unit is configured to derive the position of the boundary by implementing:
an outline detection process for detecting an outline present in an image area of the sachets photographed by the imaging unit;
an outline expansion process for expanding a detected area surrounded by an outline detected by the outline detection process toward outside in a predetermined amount;
a longitudinal seal area detection process for detecting a longitudinal area, the longitudinal area being an area comprising a plurality of detected areas which is mutually overlapped by expansion in an image after the outline expansion process, and the longitudinal area elongating along a longitudinal seal direction; and
a boundary position derivation process for deriving an intermediate position of the longitudinal seal area as a position of the boundary.

29. The medicine inspection device according to claim 28, wherein a content image removal process is implemented before the longitudinal seal area detection process and content packaged in packaging paper is recognized based on luminance information and/or color information of an image for deriving a position of the boundary and image information corresponding to the content is removed.

30. The medicine inspection device according to claim 1, wherein medicines are supplied as a continuous array of sachets formed by packaging one dose of the medicine per sachet in a packaging paper and aligning the sachets in form of a strip, and each sachet is able to be inspected one by one,
wherein each of the sachets is sealed with a longitudinal seal part along a width direction of the continuous array of sachets and a lateral seal part along a longer direction of the continuous array of sachets, and a boundary is formed between longitudinal seal parts of neighboring sachets in the continuous array of sachets,
the medicine inspection device further comprising a boundary position detection unit capable of deriving position of the boundary, wherein the boundary position detection unit is configured to implement:
a longitudinal edge detection process for detecting the longitudinal edge, the longitudinal edge being an outline elongating longitudinally in an image area of the sachets photographed by the imaging unit;
a longitudinal edge selection process for selecting a longitudinal edge longer than a predetermined length from the longitudinal edge derived from the longitudinal edge detection process;
an edge area recognition process for recognizing an area where a distance between longitudinal edges selected by the longitudinal edge selection process is equal to or shorter than a predetermined distance set based on a width of longitudinal seal part; and
a boundary position recognition process for recognizing a central part of the edge area recognized by the edge area recognition process as a boundary position between the longitudinal seal parts.

31. The medicine inspection device according to claim 1, wherein medicines are supplied as a continuous array of sachets formed by packaging one dose of the medicine per sachet in a packaging paper and aligning the sachets in form of a strip; a vacant sachet not containing medicine is provided in an intermediate part of the continuous array of sachets; an identification mark is put on a predetermined position of the vacant sachet; and each sachet is able to be inspected one by one,
the medicine inspection device further comprising an identification mark recognition unit capable of recognizing the identification mark having arrived at a predetermined readout position present in the inspection unit or an upstream side of supply direction of the continuous array of sachets from the inspection unit,
wherein a sachet containing medicine and positioned in a downstream side of the vacant sachet is locatable against the inspection unit based on the recognition position where the identification mark is recognized by the identification mark recognition unit.

32. A medicine packaging device comprising:
the medicine inspection device described in claim 1;
a medicine supplier capable of supplying a medicine according to a prescription; and
a medication preparation station for gathering the medicine supplied from the medicine supplier for each package and dispensing the medicine;
wherein a quantity of medicine dispensed from the medication preparation station is able to be inspected by the medicine inspection device.

33. A medicine inspection device, comprising:
an inspection unit on which a medicine for inspection is disposed, the medicine being contained in a sachet;
an imaging unit capable of photographing the sachet disposed on the inspection unit; and
a medicine information detector capable of detecting at least either of a quantity or type of the medicine based on an image obtained by the imaging unit;
wherein the inspection unit comprises a backlight capable of illuminating the sachet from backside when photographing, the backlight comprising illumination areas located dottedly per predetermined pitch, and
wherein the medicine information detector is configured to implement:

a basic image acquisition process for acquiring a basic image for medicine inspection based on a back lit image photographed by illuminating a packaging paper from behind by the backlight;

a gray scale image acquisition process for acquiring a gray scale image by gray-scaling the basic image;

a top hat treatment process in which at least one channel image from among basic R channel image, basic G channel image and basic B channel image that were obtained by RGB resolution of the basic image is subjected to top hat treatment to obtain a top hat image;

a gray morphology treatment process, wherein at least one channel image from among the basic R channel image, basic G channel image and basic B channel image is subjected to a gray morphology treatment to be acquired as an image for identifying a region for exclusion;

an inspection area defining process for defining an area for inspection by executing an exclusion process of excluding a region for exclusion determined by the image for identifying a region for exclusion to the gray scale image;

an inspection image acquisition process for acquiring an inspection image by extracting an area corresponding to the area for inspection from a back unlit image obtained by photographing same region as the back lit image in a state where the backlight is unlit; and an image inspection process for performing image inspection to detect the medicine quantity or type or both based on the inspection image.

* * * * *